(12) United States Patent
Cabrera Aquino et al.

(10) Patent No.: US 11,364,032 B2
(45) Date of Patent: Jun. 21, 2022

(54) CLAMP DEVICE FOR MINIMALLY INVASIVE PROCEDURES AND USES THEREOF

(71) Applicants: Jose Gustavo Cabrera Aquino, Mexico City (MX); Blanca Angelica Segura Pacheco, Mexico City (MX); Steven Masterson, Encinitas, CA (US); Allan Rozenberg, San Diego, CA (US); Paul Faucher, Escondido, CA (US); John Hoffman, Poway, CA (US)

(72) Inventors: Jose Gustavo Cabrera Aquino, Mexico City (MX); Blanca Angelica Segura Pacheco, Mexico City (MX); Steven Masterson, Encinitas, CA (US); Allan Rozenberg, San Diego, CA (US); Paul Faucher, Escondido, CA (US); John Hoffman, Poway, CA (US)

(73) Assignee: Global Bio Therapeutics, Inc., San Diego, CA (US)

( * ) Notice: Subject to any disclaimer, the term of this patent is extended or adjusted under 35 U.S.C. 154(b) by 1333 days.

(21) Appl. No.: 14/455,871

(22) Filed: Aug. 8, 2014

(65) Prior Publication Data
US 2015/0066056 A1  Mar. 5, 2015

Related U.S. Application Data

(60) Provisional application No. 61/863,903, filed on Aug. 8, 2013.

(51) Int. Cl.
*A61B 17/12* (2006.01)
*A61B 17/00* (2006.01)

(52) U.S. Cl.
CPC ............ *A61B 17/12013* (2013.01); *A61B 2017/00407* (2013.01); *A61B 2017/00557* (2013.01);
(Continued)

(58) Field of Classification Search
CPC .... A61B 17/12013; A61B 2017/12004; A61B 2017/00862; A61B 2017/00407; A61B 2017/00557
See application file for complete search history.

(56) References Cited

U.S. PATENT DOCUMENTS

| 928,011 A | * | 7/1909 | Whitlock ....... A61B 17/320708 |
| | | | 606/160 |
| 3,538,917 A | | 11/1970 | Selker .......................... 128/326 |

(Continued)

FOREIGN PATENT DOCUMENTS

| EP | 282 185 | 9/1988 |
| EP | 1 049 487 | 11/2000 |

(Continued)

OTHER PUBLICATIONS

U.S. Appl. No. 13/815,206, filed Feb. 7, 2013, 2013/0211380, Aug. 15, 2013.

(Continued)

*Primary Examiner* — Elizabeth Houston
*Assistant Examiner* — Michael G Mendoza
(74) *Attorney, Agent, or Firm* — Dentons US LLP; Stephanie Seidman

(57) ABSTRACT

Provided herein is a clamp device that can be used in minimally invasive procedures, including surgeries such as laparoscopic surgeries, for clamping a tissue or an organ or a portion of a tissue or organ. Also provided herein are methods of clamping a tissue or an organ or a portion thereof during minimally invasive surgery using the clamp device provided herein. Also provided are systems for performing a minimally invasive surgery that include the clamp device for minimally invasive surgery provided herein and an
(Continued)

injection device configured to access an endoscopic port for the minimally invasive surgery.

32 Claims, 32 Drawing Sheets

Specification includes a Sequence Listing.

(52) U.S. Cl.
CPC ............... *A61B 2017/00862* (2013.01); *A61B 2017/12004* (2013.01)

(56) References Cited

U.S. PATENT DOCUMENTS

| | | | |
|---|---|---|---|
| 3,667,471 A * | 6/1972 | Doty ..................... A61B 17/12 24/280 | |
| 3,993,076 A | 11/1976 | Fogarty ........................ 128/325 | |
| 4,311,146 A * | 1/1982 | Wonder ........... A61B 17/12109 264/264 | |
| 4,342,832 A | 8/1982 | Goeddel et al. ........... 435/91.41 |
| 4,431,740 A | 2/1984 | Bell et al. ................. 435/252.33 |
| 4,517,295 A | 5/1985 | Brack et al. .................. 435/101 |
| 4,522,811 A | 6/1985 | Eppstein et al. ............... 514/2.4 |
| 4,531,519 A | 7/1985 | Dunn et al. .................... 128/325 |
| 4,652,525 A | 3/1987 | Rutter et al. ............. 435/252.33 |
| 4,703,008 A | 10/1987 | Lin ................................ 435/360 |
| 4,708,140 A | 11/1987 | Baron ........................... 128/325 |
| 4,718,419 A | 1/1988 | Okada ...................... 128/303.15 |
| 4,738,927 A | 4/1988 | Taniguchi et al. ............. 435/243 |
| 4,763,667 A | 8/1988 | Manzo .......................... 600/563 |
| 4,965,195 A | 10/1990 | Namen et al. ............. 435/69.52 |
| 5,139,941 A | 8/1992 | Muzyczka et al. ........... 435/456 |
| 5,188,597 A | 2/1993 | Sweeney et al. ............. 604/110 |
| 5,203,786 A | 4/1993 | Vernick .......................... 606/151 |
| 5,229,127 A | 7/1993 | McKinzie ...................... 424/427 |
| 5,236,437 A | 8/1993 | Wilk ............................... 606/158 |
| 5,273,056 A | 12/1993 | McLaughlin et al. ......... 128/898 |
| 5,282,851 A | 2/1994 | LaBarre ......................... 623/6.56 |
| 5,292,362 A | 3/1994 | Bass et al. ................. 106/173.01 |
| 5,300,041 A | 4/1994 | Haber et al. ................... 604/207 |
| 5,304,188 A | 4/1994 | Marogil ......................... 606/157 |
| 5,328,470 A | 7/1994 | Nabel et al. .................... 604/101 |
| 5,486,183 A | 1/1996 | Middleman et al. .......... 606/127 |
| 5,496,333 A | 3/1996 | Sackier et al. ................. 227/901 |
| 5,543,328 A | 8/1996 | McClelland et al. ....... 435/320.1 |
| 5,622,856 A | 4/1997 | Natsoulis ....................... 435/325 |
| 5,670,488 A | 9/1997 | Gregory et al. ............. 514/44 R |
| 5,685,853 A | 11/1997 | Bonnet .......................... 604/164 |
| 5,756,086 A | 5/1998 | McClelland et al. ........ 424/93.2 |
| 5,782,839 A | 7/1998 | Hart et al. ...................... 606/110 |
| 5,785,689 A | 7/1998 | Alvarez de Toledo et al. ............ 604/158 |
| 5,792,453 A | 8/1998 | Hammond et al. ......... 424/93.21 |
| 5,801,029 A | 9/1998 | McCormick ................ 424/93.2 |
| 5,882,887 A | 3/1999 | Noeske et al. ............. 435/69.1 |
| 5,993,418 A | 10/1999 | Alexander ..................... 604/110 |
| 5,994,106 A | 11/1999 | Kovesdi et al. .............. 435/91.4 |
| 5,994,128 A | 11/1999 | Fallaux et al. ................. 435/325 |
| 5,998,205 A | 12/1999 | Hallenbeck et al. .......... 435/325 |
| 6,001,650 A | 12/1999 | Colosi ............................ 435/369 |
| 6,004,295 A | 12/1999 | Langer et al. ............. 604/164.01 |
| 6,057,155 A | 5/2000 | Wickham et al. ............. 435/325 |
| 6,127,175 A | 10/2000 | Vigne et al. ................... 435/325 |
| 6,142,088 A | 11/2000 | Beyer ............................ 112/222 |
| 6,218,186 B1 | 4/2001 | Choi et al. ..................... 435/456 |
| 6,309,375 B1 | 10/2001 | Glines et al. .................. 604/187 |
| 6,322,536 B1 | 11/2001 | Rosengart et al. ....... 604/164.01 |
| 6,464,711 B1 * | 10/2002 | Emans ............. A61B 17/32002 606/167 |
| 6,579,855 B1 | 6/2003 | Yla Herttuala et al. ..... 514/44 R |
| 6,723,082 B1 | 4/2004 | Payne et al. ................... 604/528 |
| 6,743,206 B1 | 6/2004 | Smith et al. ............. 604/164.01 |
| 6,821,264 B1 | 11/2004 | Khurana et al. ................ 604/46 |
| 7,094,604 B2 | 8/2006 | Snyder et al. ................. 435/457 |
| 7,462,592 B2 | 12/2008 | Zuckermann et al. ........... 514/2 |
| 7,645,285 B2 | 1/2010 | Cosgrove et al. ............. 606/142 |
| 8,337,468 B1 | 5/2012 | Reis et al. ..................... 604/181 |
| 8,328,560 B2 | 12/2012 | Niblock et al. ............... 434/262 |
| 2002/0168714 A1 | 11/2002 | Barbas et al. ................ 435/69.1 |
| 2003/0104625 A1 | 6/2003 | Cheng et al. .................. 435/456 |
| 2004/0053875 A1 | 3/2004 | Kreutzer ......................... 514/44 |
| 2005/0129660 A1 | 6/2005 | Hagstrom et al. ........... 424/93.2 |
| 2005/0149069 A1 | 7/2005 | Bertolero et al. ............. 606/151 |
| 2005/0261634 A1 | 11/2005 | Karlsson ....................... 604/197 |
| 2006/0025749 A1 | 2/2006 | Moenning ..................... 604/506 |
| 2006/0200083 A1 | 9/2006 | Freyman et al. ............. 604/181 |
| 2008/0009823 A1 | 1/2008 | McKay .......................... 604/500 |
| 2008/0025952 A1 | 1/2008 | Scheule et al. .............. 424/93.2 |
| 2008/0119880 A1 | 5/2008 | Chu ............................... 606/157 |
| 2008/0243152 A1 | 10/2008 | Paganon et al. .............. 606/157 |
| 2008/0281248 A1 | 11/2008 | Anheloiu et al. ............. 604/523 |
| 2009/0149876 A1 | 6/2009 | Patel et al. ..................... 128/898 |
| 2009/0270806 A1 | 10/2009 | Macaulay et al. ............ 604/117 |
| 2010/0048990 A1 | 2/2010 | Bakos ........................... 600/106 |
| 2010/0217073 A1 | 8/2010 | Fischer et al. ................ 600/104 |
| 2010/0234862 A1 | 9/2010 | Patel et al. ..................... 606/151 |
| 2010/0312173 A1 | 12/2010 | McKay et al. .................. 604/28 |
| 2011/0152895 A1 | 6/2011 | Nyuli et al. ................... 606/151 |
| 2011/0160533 A1 | 6/2011 | Sampson ...................... 600/106 |
| 2011/0218485 A1 | 9/2011 | Tran et al. ...................... 604/26 |
| 2011/0226646 A1 | 9/2011 | Wyrick ......................... 206/365 |
| 2011/0262399 A1 | 10/2011 | Fontanellas Romá et al. ............ 424/93.2 |
| 2011/0288482 A1 | 11/2011 | Farrell et al. ............. 604/164.04 |
| 2012/0009268 A1 | 1/2012 | Asokan et al. ................ 424/499 |
| 2012/0308522 A1 | 12/2012 | Martin et al. ................ 424/93.2 |
| 2013/0068224 A1 | 3/2013 | Srinivasan ............... 128/203.26 |
| 2013/0211380 A1 | 8/2013 | Cabrera-Aquino et al. .. 604/187 |
| 2014/0081213 A1 | 3/2014 | Chevallier et al. ........... 604/198 |
| 2014/0323991 A1 | 10/2014 | Tang et al. ..................... 604/272 |
| 2015/0045769 A1 | 2/2015 | Cabrera-Aquino et al. .. 604/506 |
| 2015/0352293 A9 | 12/2015 | Cabrera-Aquino et al. .. 606/140 |

FOREIGN PATENT DOCUMENTS

| | | |
|---|---|---|
| EP | 1 928 504 | 8/2006 |
| EP | 1 718 254 | 11/2006 |
| EP | 2 489 380 | 8/2012 |
| JP | S62-32944 | 2/1987 |
| JP | 2003-502101 | 1/2003 |
| JP | 6297692 | 3/2018 |
| WO | WO 1993/014778 | 8/1993 |
| WO | WO 1995/026411 | 10/1995 |
| WO | WO 1995/029993 | 11/1995 |
| WO | WO 1995/034671 | 12/1995 |
| WO | WO 1996/022378 | 7/1996 |
| WO | WO 1996/040955 | 12/1996 |
| WO | WO 1997/000326 | 1/1997 |
| WO | WO 1997/025466 | 7/1997 |
| WO | WO 1999/025860 | 5/1999 |
| WO | WO 2000/044895 | 8/2000 |
| WO | WO 2000/078235 | 12/2000 |
| WO | WO 2001/029058 | 4/2001 |
| WO | WO 2001/030843 | 5/2001 |
| WO | WO 2001/075164 | 10/2001 |
| WO | WO 2001/092513 | 12/2001 |
| WO | WO 2005/049094 | 6/2005 |
| WO | WO 2007/019646 | 2/2007 |
| WO | WO 2010/134806 | 11/2010 |
| WO | WO 2013/034651 | 3/2013 |
| WO | WO 2013/107068 | 7/2013 |
| WO | WO 2015/021443 | 2/2015 |

OTHER PUBLICATIONS

U.S. Appl. No. 14/455,865, filed Aug. 8, 2014.
Letter/Written Disclosure of the Information Disclosure Statement for the above-referenced application, dated Nov. 24, 2014, 3 pages.
Abdalla et al., "Hepatic vascular occlusion: which technique?" Surg. Clin. N. Am., 84:563-585 (2004).

(56) References Cited

OTHER PUBLICATIONS

Adenovirus Wiki, "Human adenovirus genome sequences and annotations," Published on Dec. 1, 2010 [online][retrieved on Mar. 21, 2013] Retrieved from:<URL:binf.gmu.edu/wiki/index.php [1 page].
Assil et al., "Multivesicular liposomes. Sustained release of the antimetabolite cytarabine in the eye," Arch Ophthalmol. 105:400-403 (1987).
Barakat, M. and P. Kaiser, "VEGF inhibitors for the treatment of neovascular age-related macular degeneration," Expert Opin. Investig. Drugs 18(5):637-646 (2009).
Baxley, S. and R. Serra, "Inhibiting breast cancer progression by exploiting TGFbeta signaling," Curr. Drug Targets 11(9):1089-1102 (2010).
Belghiti et al., "Continuous versus intermittent portal triad clamping for liver resection: a controlled study," Annals of Surgery, 229:369-375 (1999).
Bergelson et al., "Isolation of a common receptor for Coxsackie B viruses and adenoviruses 2 and 5," Science 275:1320-1323 (1997).
Berkner et al., "Abundant expression of polyomavirus middle T antigen and dihydrofolate reductase in an adenovirus recombinant," J. Virol. 61:1213-1220 (1987).
Berkner et al., "Expression of heterologous sequences in adenoviral vectors," Curr. Top. Micro. Immunol., 158:39-66 (1992).
Berkner et al., "Generation of adenovirus by transfection of plasmids," Nuc. Acids Res. 11:6003-6020 (1983).
Best et al. "Assessment of renal oxygenation during partial nephrectomy using DLP hyperspectral imaging." Proc. SPIE, 7932, Emerging Digital Micromirror Device Based Systems and Applications III, 793202, 8 pages (2011).
Blaisdell et al., "The pathophysiology of skeletal muscle ischemia and the reperfusion syndrome: a review," Cardiovascular Surgery, 10:620-630 (2002).
Blomer et al., "Highly efficient and sustained gene transfer in adult neurons with a lentivirus vector," J. Virol., 71:6641-6449 (1997).
Blume et al., "Formulated collagen gel accelerates healing rate immediately after application in patients with diabetic neuropathic foot ulcers," Wound Repair Regen., 19:302-308 (2011).
Brekke, O. and I. Sandlie, "Therapeutic antibodies for human diseases at the dawn of the twenty-first century," Nat. Rev. Drug. Discov. 2(1):52-62 and Correction (2003).
Breyer et al., "Adenoviral vector-mediated gene transfer for human gene therapy," Current Gene Therapy, 1:149-162 (2001).
Brooks et al., "Specific organ gene transfer in vivo by regional organ perfusion with herpes viral amplicon vectors: implications for local gene therapy," Surgery 129(3):324-334 (2001).
Buchshacher, G. and F. Wong-Staal, "Development of lentiviral vectors for gene therapy for human diseases," Blood, 95:2499-2504 (2000).
Buell et al., "Is any method of vascular control superior in hepatic resection of metastatic cancers? Longmire clamping, pringle maneuver, and total vascular isolation,"Arch. Surg., 136:569-575 (2001).
Burger et al., "Recombinant AAV viral vectors pseudotyped with viral capsids from serotypes 1, 2, and 5 display differential efficiency and cell tropism after delivery to different regions of the central nervous system," Mol. Ther., 10:302-317 (2004).
Campos et al., "Current advances and future challenges in Adenoviral vector biology and targeting," Curr. Gene Ther., 7:189-204 (2007).
Cantrell et al., "Cloning, sequence, and expression of a human granulocyte/macrophage colony-stimulating factor," Proc. Natl. Acad. Sci, 82:6250-6254 (1985).
Cassani et al., "Integration of retroviral vectors induces minor changes in the transcriptional activity of T cells from ADA-SCID patients treated with gene therapy," Blood, 114:3546-3556 (2009).
Cerullo et al., "Oncolytic adenovirus coding for granulocyte macrophage colony-stimulating factor induces antitumoral immunity in cancer patients," Cancer Res., 70:4297-4309 (2010).
Chillon et al. "Group D adenoviruses infect primary central nervous system cells more efficiently than those from group C," J. Virol., 73:2537-2540 (1999).
Chiorini et al., "Cloning and characterization of adeno-associated virus type 5," J. Virol., 73:1309-1319 (1999).
Chiorini et al., "Cloning of adeno-associated virus type 4 (AAV4) and generation of recombinant AAV4 particles," J. Virol., 71:6823-6833 (1997).
Cho et al., "Therapeutic nanoparticles for drug delivery in cancer," Clin. Cancer. Res., 14:1310-1316 (2008).
Choi et al., "Hybrid HIV/MSCV LTR enhances transgene expression of lentiviral vectors in human CD34(+) hematopoietic cells," Stem Cells, 19:236-246 (2001).
Chroboczek et al., "The sequence of the genome of adenovirus type 5 and its comparison with the genome of adenovirus type 2," Virology, 186:280-285 (1992).
Clowes et al., "Long-term biological response of injured rat carotid artery seeded with smooth muscle cells expressing retrovirally introduced human genes," J. Clin. Invest. 93:644-651 (1994).
Curcio et al., "Oligonucleotides as modulators of cancer gene expression," Pharmacol Therapy, 74:317-332 (1997).
Curiel, D., "Strategies to adapt adenoviral vectors for targeted delivery," Ann NY Acad. Sci., 886:158-171 (1999).
Czubayko et al., "Adenovirus-mediated transduction of ribozymes abrogates HER-2/neu and pleiotrophin expression and inhibits tumor cell proliferation," Gene Therapy, 4:943-949 (1997).
Darcin et al. "Pressure-controlled vascular clamp: a novel device for atraumatic vessel occlusion," Ann Vasc Surg. 18(2):254-256 (2004).
David et al., "Gene therapy for the fetus: is there a future?" Best Pract Res Clin Obstet Gynaecol. 22(1):203-218 (2008).
Davidson et al., "Overproduction of polyomavirus middle T antigen in mammalian cells through the use of an adenovirus vector," J. Virol. 61:1226-1239 (1987).
Davison et al., "The DNA sequence of adenovirus type 40," J. Mol. Biol., 234:1308-1316 (1993).
Denardi et al., "Nephron-sparing surgery for renal tumours using selective renal parenchymal clamping," BJU Int. 2005 96:1036-1039 (2005).
Dmitriev et al., "An adenovirus vector with genetically modified fibers demonstrates expanded tropism via utilization of a coxsackievirus and adenovirus receptor-independent cell entry mechanism," J. Virol., 72:9706-9712 (1998).
Duque et al., "Intravenous administration of self-complementary AAV9 enables transgene delivery to adult motor neurons," Mol. Ther., 17:1187-1196 (2009).
Eastman et al., "Development of catheter-based procedures for transducing the isolated rabbit liver plasmid DNA," Human Gene Therapy 13:2065-2077 (2002).
Eto et al., "Development of PEGylated adenovirus vector with targeting ligand," Int. J. Pharm., 354:3-8 (2008).
Fabre et al., "Hydrodynamic gene delivery to the pig liver via an isolated segment of the inferior vena cava," Gene Ther., 15:452-462 (2008).
Fallaux et al., "New helper cells and matched early region 1-deleted adenovirus vectors prevent generation of replication-competent adenoviruses," Hum. Gene Ther. 9:1909-1907(1998).
Faraji, A. and P. Wipf, "Nanoparticles in cellular drug delivery," Bioorg. Med. Chem. 17(8):2950-2962 (2009).
Finch, P. and J. Rubin, "Keratinocyte growth factor expression and activity in cancer: implications for use in patients with solid tumors," J. Natl. Cancer Inst. 98(12):812-824 (2006).
Fisher et al., "Recombinant adenovirus deleted of all viral genes for gene therapy of cystic fibrosis," J. Virol., 217:11-22 (1996).
Foust et al., "Intravascular AAV9 preferentially targets neonatal neurons and adult astrocytes," Nature Biotechnology, 27:59-65 (2009).
Franzen, S., "A comparison of peptide and folate receptor targeting of cancer cells: from single agent to nanoparticle," Expert Opin. Drug. Deliv. 8(3):281-298 (2011).
Fu et al., "Correction of neurological disease of mucopolysaccharidosis IIIB in adult mice by rAAV9 trans-blood-brain barrier gene delivery," Mol. Ther., 19:1025-1033 (2011).
Fujita et al., "Sendai virus-mediated gene delivery into hepatocytes via isolated hepatic perfusion," Biological & Pharmaceutical Bulletin, 29:1728-1734 (2006).

(56) References Cited

OTHER PUBLICATIONS

Gagner et al., "Laparoscopic liver resection: benefits and controversies." Surg Clin North Am. 84(2):451-462 (2004).
Gao et al., "Clades of Adeno-associated viruses are widely disseminated in human tissues," J. Virol., 78:6381-6388 (2004).
Gao et al., "Novel adeno-associated viruses from rhesus monkeys as vectors for human gene therapy," Proc Natl. Acad. Sci., 99:11854-11859 (2002).
GenBank Accession No. AB685372.1, "Human adenovirus 5 gene hexon, partial cds, strain: 11_02402/Mongolia/hexon," Published on Oct. 8, 2013 [online][retrieved on Aug. 22, 2014] Retrieved from:<URL:ncbi.nlm.nih.gov/nuccore/AB685372.1 [2 pages].
Genbank Accession No. AY530629.1, "Adeno-associated virus isolate hu.9 capsid protein VP1 (cap) gene, complete cds," Published on Jun. 24, 2004 [online][retrieved on Mar. 19, 2013] Retrieved from:<URL:ncbi.nlm.nih.gov/nuccore/AY530629.1[2 pages].
Genbank accession No. AF517770.1, "Sus scrofa alpha-fetoprotein precursor, mRNA, complete cds," Published on Dec. 30, 2002 [online][retrieved on Aug. 22, 2014] Retrieved from:<URL: http://www.ncbi.nlm.nih.gov/nuccore/AF517770.1[2 pages].
Genbank accession No. AY033476.1, "Sus scrofa serum albumin gene, promoter region," Published on May 5, 2002 [online][retrieved on Aug. 22, 2014] Retrieved from:<URL:ncbi.nlm.nih.gov/nuccore/AY033476.1 [2 pages].
Generx, "FGF-4 gene therapy GENERX—Collateral Therapeutics," BioDrugs 16:75-76 (2002).
George, D., "Receptor tyrosine kinases as rational targets for prostate cancer treatment: platelet-derived growth factor receptor and imatinib mesylate," Urology 60(3 Suppl. 1):115-121 (2002).
Ghosh-Choudhury et al., "Stable transfer of a mouse dihydrofolate reductase gene into a deficient cell line using human adenovirus vector," Biochem. Biophys. Res. Commun., 147:964-973 (1987).
Gilardi et al., "Expression of human alpha 1-antitrypsin using a recombinant adenovirus vector," FEBS Lett.267:60-62 (1990).
Gondi, C. and J. Rao, "Concepts in in vivo siRNA delivery for cancer therapy," J. Cell Physiol. 220(2):285-291. (2009).
Gong et al., "Thirteen UDPglucuronosyltransferase genes are encoded at the human UGT1 gene complex locus," Pharmacogentics, 11:357-368 (2001).
Gorziglia et al., "Elimination of both E1 and E2 from adenovirus vectors further improves prospects for in vivo human gene therapy," J. Virology 70:4173-4178 (1996).
Graham et al., "Characteristics of a human cell line transformed by DNA from human adenovirus Type 5," J. Gen. Virol. 36:59-72 (1977).
Graham, F., "Covalently closed circles of human adenovirus DNA are infectious," EMBO J. 3:2917-2922 (1984).
Grimm, D. and M. Kay, "From virus evolution to vector revolution: use of naturally occurring serotypes of adeno-associated virus (AAV) as novel vectors for human gene therapy," Current Gene Therapy, 3:281-304 (2003).
Groskreutz et al., "Genetically engineered proinsulin constitutively processed and secreted as mature, active insulin." J. Biol. Chem., 269:6241-6245 (1994).
Grossman, M. and J. Wilson, "Retroviruses: delivery vehicle to the liver," Curr. Opin. in Genetics and Devel. 3:110-114 (1993).
Haj-Ahmad et al., "Development of a helper-independent human adenovirus vector and its use in the transfer of the herpes simplex virus thymidine kinase gene," J. Virol. 57:267-274 (1986).
Hampel, A., "The hairpin ribozyme: discovery, two-dimensional model, and development for gene therapy," Prog. Nucleic Acid Res. Mol. Biol., 58:1-39 (1998).
Harris et al., "Tissue-specific gene delivery via nanoparticle coating," Biomaterials, 31:998-1006 (2010).
Hodges et al., "Local delivery of viral vector mitigates neutralization by antiviral antibodies and results in efficient transduction of rabbit liver," Mol. Ther. 12:1043-1051 (2005).
Hoffman et al., "Renal ischemic tolerance," AMA Arch. Surg., 109:550-551 (1974).

Invalidity Search Report prepared by a third-party, "Invalidity Search—Provisional Application—Clamping Device, Global Bio Therapeutics," redacted, dated May 21, 2014, 13 pages.
Invalidity Search Report prepared by a third-party, "Invalidity Search—Provisional Application—Injectcion Device, Global Bio Therapeutics," redacted, dated May 21, 2014, 10 pages.
James, H. and I. Gibson, "The therapeutic potential of ribozymes," Blood, 91:371-382 (1998).
Jiao et al., "Clinical short-term results of radiofrequency ablation in primary and secondary liver tumors," Am J Surg. 177(4):303-306 (1999).
Jimeno, A. and M. Hidalgo, "Pharmacogenomics of epidermal growth factor receptor (EGFR) tyrosine kinase inhibitors," Biochim. Biophys. Acta 1766(2):217-229 (2006).
Jin et al., "Nanoparticle-mediated drug delivery and gene therapy," Biotechnol. Prog., 23:32-41 (2007).
Jolly et al., "Viral vector systems for gene therapy," Cancer Gene Therapy, 1:51-64 (1994).
Joung et al., "Partial nephrectomy using parenchymal compression without renal pedicle clamping," Korean J. Urol., 28:265-269 (2007).
Kanematsu et al., "A newly designed clamp facilitates hepatic resection," Jpn. J. Surg., 14:432-423 (1984).
Kay et al., "Evidence for gene transfer and expression of factor IX in haemophilia B patients treated with an AAV vector," Nat Genet. 24(3):257-261 (2000).
Kiem et al., "Retrovirus-mediated gene transduction into canine peripheral blood repopulating cells," Blood 83:1467-1473 (1994).
Kim et al., "Preparation of multivesicular liposomes," Bioch. Bioph. Acta 728:339-348 (1983).
Kinoshita et al., "Targeted gene delivery to selected liver segments via isolated hepatic perfusion with clamping of the portal vein," Molecular Therapy 9: S119 (2004).
Kinoshita et al., "Targeted gene delivery to selected liver segments via isolated hepatic perfusion," J Surg. Res., 160:47-51 (2010).
Ko et al., "Efficacy of parenchymal compression in open partial nephrectomies: a comparison with conventional vascular clamping," Korean J. Urol., 51:8-14 (2010).
Kochanek et al., "A new adenoviral vector: Replacement of all viral coding sequences with 28 kb of DNA independently expressing both full-length dystrophin and beta-galactosidase," Proc. Natl. Acad. Sci., 93:5731-5736 (1996).
Kota et al., "Follistatin gene delivery enhances muscle growth and strength in nonhuman primates." Sci Transl Med. 1(6):6ra15, 8 pages (2009).
Kotin et al., "Site-specific integration by adeno-associated virus," Proc. Natl. Acad. Sci., 87:2211-2215 (1990).
Kotin, R., "Prospects for the use of adeno-associated virus as a vector for human gene therapy," Human Gene Therapy, 5:793-801 (1994).
Krasnykh et al., "Genetic targeting of adenoviral vectors," Mol. Ther., 1:391-405 (2000).
Lee et al., "Laboratory evaluation of laparoscopic vascular clamps using a load-cell device—are all clamps the same?" J. Urol. 180:1267-1272 (2008).
Lesurtel et al. (2009) "Clamping techniques and protecting strategies in liver surgery," HPB (Oxford). 11:290-295.
Levrero et al., Defective and nondefective adenovirus vectors for expressing foreign genes in vitro and in vivo, Gene 101:195-202 (1991).
Lewis, P. and F. Emerman, "Passage through mitosis is required for oncoretroviruses but not for the human immunodeficiency virus," J. Virol., 68:510-516 (1996).
Li, S. and L. Huang, "Gene therapy progress and prospects: non-viral gene therapy by systemic delivery," Gene Therapy, 13:1313-1319 (2006).
Lieber et al., "Recombinant adenoviruses with large deletions generated by Cre-mediated excision exhibit different biological properties compared with first-generation vectors in vitro and in vivo," J. Virol., 70:8944-8960 (1996).
Lo et al., "EGFR signaling pathway in breast cancers: from traditional signal transduction to direct nuclear translocalization," Breast Canc. Res. Treat. 95(3):211-218 (2006).

(56) References Cited

OTHER PUBLICATIONS

Lo, H., "EGFR-targeted therapy in malignant glioma: novel aspects and mechanisms of drug resistance," Curr. Mol. Pharmacol. 3(1):37-52 (2010).
Manilla et al., "Regulatory considerations for novel gene therapy products: a review of the process leading to the first clinical lentiviral vector," Human Gene Therapy, 16:17-25 and Corrections (2005).
Massie et al., "Construction of a helper-free recombinant adenovirus that expresses polyomavirus large T antigen," Mol. Cell. Biol. 6:2872-2883 (1986).
Mellstedt, H., "Monoclonal antibodies in human cancer," Drugs Today 39(Supl. C):1-16 (2003).
Miller, A, "Human gene therapy comes of age," Nature 357(6378):455-460 (1992).
Mittal et al., "Monitoring foreign gene expression by a human adenovirus-based vector using the firefly luciferase gene as a reporter," Virus Res. 28:67-90 (1993).
Mizuguchi et al., "Targeted adenovirus vectors," Hum. Gene Ther., 15:1034-1044 (2004).
Morral et al., "High doses of a helper-dependent adenoviral vector yield supraphysiological levels of alpha1-antitrypsin with negligible toxicity," Hum. Gene Ther., 10:2709-2716 (1998).
Muramatsu et al., "Nucleotide sequencing and generation of an infectious clone of adeno-associated virus 3," Virol., 221:208-217 (1996).
Muzyczka, N., "Use of adeno-associated virus as a general transduction vector for mammalian cells," Curr. Top. Micro. Immunol., 1 58:97-129 (1992).
Naldini et al., "In vivo gene delivery and stable transduction of nondividing cells by a lentiviral vector," Science, 272:263-267 (1996).
Nathwani et al., "Sustained high-level expression of human factor IX (hFIX) after liver-targeted delivery of recombinant adeno-associated virus encoding the hFIX gene in rhesus macaques," Blood, 100:1662-1669 (2002).
Nemerow, G., "Cell receptors involved in adenovirus entry," Virology 274:1-4 (2000).
Oh, Y. and T. Park, "siRNA delivery systems for cancer treatment," Adv. Drug. Deliv. Rev. 61(10):850-862 (2009).
Ohashi et al., "Modified infusion procedures affect recombinant adeno-associated virus vector type 2 transduction in the liver," Human Gene Therapy 16:299-306 (2005).
Papadakis et al., "Promoters and control elements: designing expression cassettes for gene therapy." Curr Gene Ther. 4(1):89-113 (2004).
Parks et al., "A helper-dependent adenovirus vector system: removal of helper virus by Cre-mediated excision of the viral packaging signal," Proc. Natl. Acad. Sci., 93:13565-13570 (1996).
Pathak et al., "Nano-vectors for efficient liver specific gene transfer," Int. J. Nanomedicine, 3:31-49 (2008).
Podevin et al., "Factors influencing immune response after in vivo retrovirus-mediated gene transfer to the liver," J Gene Med. 6(1):16-21 (2004).
Qi et al., "The clinical effect of recombinant human ad p53 agent-Gendicine in advanced cancer patients in 23 cases," Modern Oncology, 14:1295-1297 (2006) [Article in Chinese with abstract in the English language].
Rasmussen et al., "TNFerade Biologic: preclinical toxicology of a novel adenovector with a radiation-inducible promoter, carrying the human tumor necrosis factor alpha gene," Cancer Gene Ther., 9:951-957 (2002).
Roberts et al., "DNA sequences from the adenovirus 2 genome," J. Biol. Chem., 259:13968-13975 (1984).
Roelvink et al., "The coxsackievirus-adenovirus receptor protein can function as a cellular attachment protein for adenovirus serotypes from subgroups A, C, D, E, and F," J. Virol. 72:7909-7915 (1998).
Rossi, J., "Therapeutic applications of catalytic antisense RNAs (ribozymes)," Ciba Found. Symp., 209:195-204 (1997).
Russell et al., "Oncolytic virotherapy," Nature Biotechnology, 30:658-670 (2012).
Russell, W., "Adenoviruses: update on structure and function," J Gen. Virol. 90:1-20 (2009).
Rutledge et al., "Infectious clones and vectors derived from adeno-associated virus (AAV) serotypes other than AAV type 2," J. Virol, 72:309-319 (1998).
Sachdeva et al., "Chimeric HIV-1 and HIV-2 lentiviral vectors with added safety insurance," Journal of Medical Virology, 79:118-126 (2007).
Sajja et al., "Development of multifunctional nanoparticles for targeted drug delivery and noninvasive imaging of therapeutic effect," Curr. Drug. Discov. Technol. 6(1):43-51(2009).
Salmons, B. and W. Gunzberg, "Targeting of retroviral vectors for gene therapy," Human Gene Therapy 4:129-141 (1993).
Schiffelers et al., "Cancer siRNA therapy by tumor selective delivery with ligand-targeted sterically stabilized nanoparticle," Nucleic Acids Res.32(19):e149, 10 pages (2004).
Schilephake, H., "Bone growth factors in maxillofacial skeletal reconstruction," Int. J. Oral Maxillofac. Surg. 31(5):469-484 (2002).
Segura-Pancheco et al., "HDAC inhibitor valproic acid upregulates CAR in vitro and in vivo," Genet. Vaccines Ther.5:10, 8 pages (2007).
Shayakhmetov et al., "Adenovirus binding to blood factors results in liver cell infection and hepatotoxicity," J. Virol. 79:7478-7491 (2005).
Sheridan, C., "Gene therapy finds its niche," Nature Biotechnology, 29:121-128 and errata (2011).
Shirakawa, T., "Clinical trial design for adenoviral gene therapy products," Drugs News Perspectives, 22(3):140-145 (2009).
Sprengel et al., "Nucleotide sequence of human adenovirus type 12 DNA: comparative functional analysis," J. Virol., 68:379-389 (1994).
Sterman et al., "A phase I trial of repeated intrapleural adenoviral-mediated interferon-beta gene transfer for mesothelioma and metastatic pleural effusions," Mol. Ther., 18:852-860 (2010).
Storm et al. "A simplified clamp for hepatic resection," Surg Gynecol Obstet.133(1):103-104 (1971).
Sullenger "Revising messages traveling along the cellular information superhighway," Chem. Biol., 2:249-253 (1995).
Sullenger, B., "Ribozyme-mediated repair of RNAs encoding mutant tumor suppressors," Cytokines Mol. Ther., 2:201-205 (1996).
Thompson et al., "The impact of ischemia time during open nephron sparing surgery on solitary kidneys: a multi-institutional study," J. Urology, 177:471-476 (2006).
Toren et al., "Use of a novel parenchymal clamp for laparoscopic and open partial nephrectomy," Can. Urol. Assoc., 4:E133-E136 (2010).
Trojanowska, M and J. Varga, "Molecular pathways as novel therapeutic targets in systemic sclerosis," Curr. Opin. Rheumatol. 19(6):568-573 (2007).
Uniprot Accession No. P00451, "Coagulation factor VIII," Last Modified on Mar. 6, 2013 [online][retrieved on Mar. 19, 2013] Retrieved from:<URL:uniprot.org/uniprot/P00451 [22 pages].
Uniprot Accession No. P00740, "Coagulation factor IX," Last Modified on Jul. 9, 2014 [online][retrieved on Aug. 22, 2014] Retrieved from:<URL:uniprot.org/uniprot/P00740 [17 pages].
Uniprot Accession No. P00749, "Urokinase-type plasminogen activator," Last Modified on Jul. 9, 2014 [online][retrieved on Aug. 22, 2014] Retrieved from:<URL:uniprot.org/uniprot/P00749 [12 pages].
Uniprot Accession No. P00750, "Tissue-type plasminogen activator," Last Modified on Mar. 6, 2013 [online][retrieved on Mar. 19, 2013] Retrieved from:<URL:uniprot.org/uniprot/P00750 [10 pages].
Uniprot Accession No. P01241, "Somatotropin," Last Modified on Mar. 6, 2013 [online][retrieved on Mar. 19, 2013] Retrieved from:<URL:uniprot.org/uniprot/P01241 [9 pages].
Uniprot Accession No. P01242, "Growth hormone variant," Last Modified on Mar. 6, 2013 [online] [retrieved on Mar. 19, 2013] Retrieved from:<URL:uniprot.org/uniprot/P01242[6 pages].
Uniprot Accession No. P01308, "Insulin," Last Modified on Mar. 6, 2013 [online][retrieved on Mar. 19, 2013] Retrieved from:<URL:uniprot.org/uniprot/P01308[11 pages].

(56) References Cited

OTHER PUBLICATIONS

Uniprot Accession No. P01583, "Interleukin-1 alpha," Last Modified on Mar. 6, 2013 [online][retrieved on Mar. 19, 2013] Retrieved from:<URL:uniprot.org/uniprot/P01583[6 pages].
Uniprot Accession No. P01584, "Interleukin-1 beta," Last Modified on Mar. 6, 2013 [online][retrieved on Mar. 19, 2013] Retrieved from:<URL:uniprot.org/uniprot/P01584 [14 pages].
Uniprot Accession No. P01588, "Erythropoietin," Last Modified on Mar. 6, 2013 [online][retrieved on Mar. 19, 2013] Retrieved from:<URL:uniprot.org/uniprot/P01588 [6 pages].
Uniprot Accession No. P04141, "Granulocyte-macrophage colony-stimulating factor," Last Modified on Mar. 6, 2013 [online][retrieved on Mar. 19, 2013] Retrieved from:<URL:uniprot.org/uniprot/P04141 [5 pages].
Uniprot Accession No. P04275, "von Willebrand factor," Last Modified on Mar. 6, 2013 [online][retrieved on Mar. 19, 2013] Retrieved from:<URL:uniprot.org/uniprot/P04275 [12 pages].
Uniprot Accession No. P05112, "Interleukin-4," Last Modified on Mar. 6, 2013 [online][retrieved on Mar. 19, 2013] Retrieved from:<URL:uniprot.org/uniprot/P05112 [7 pages].
Uniprot Accession No. P08700, "Interleukin-3," Last Modified on Mar. 6, 2013 [online][retrieved on Mar. 19, 2013] Retrieved from:<URL:uniprot.org/uniprot/P08700 [5 pages].
Uniprot Accession No. P09919, "Granulocyte colony-stimulating factor," Last Modified on Mar. 6, 2013 [online][retrieved on Mar. 19, 2013] Retrieved from:<URL:uniprot.org/uniprot/P09919 [6 pages].
Uniprot Accession No. P13232, "Interleukin-7," Last Modified on Mar. 6, 2013 [online][retrieved on Mar. 19, 2013] Retrieved from:<URL:uniprot.org/uniprot/P13232 [5 pages].
Uniprot Accession No. P60568, "Interleukin-2," Last Modified on Mar. 6, 2013 [online][retrieved on Mar. 19, 2013] Retrieved from:<URL:uniprot.org/uniprot/P60568 [6 pages].
Von Seggern et al., "Complementation of a fibre mutant adenovirus by packaging cell lines stably expressing the adenovirus type 5 fibre protein," J. Gen. Virol. 79:1461-1468 (1998).
Vorburger, S. and K. Hunt, "Adenoviral gene therapy," The Oncologist, 7:46-59 (2002).
Wang et al., "Adenoviral vector systems for gene therapy," Gene Therapy and Mol. Biology, 9:291-300 (2005).
Whitehead et al., "Knocking down barriers: advances in siRNA delivery," Nat. Rev. Drug. Discov. 8(2):129-138 including corrigendum and errata (2009).
Wickham et al., "Increased in vitro and in vivo gene transfer by adenovirus vectors containing chimeric fiber proteins," J. Virol., 71:8221-8229 (1997).
Wickham, T., "Targeting adenovirus," Gene Ther., 7:110-114 (2000).
Xiao et al., "Gene therapy vectors based on adeno-associated virus type 1," J. Virol., 73:3994-4003 (1999).
Yang et al., "An approach for treating the hepatobiliary disease of cystic fibrosis by somatic gene transfer," Proc. Natl. Acad. Sci. USA 90:4601-4605 (1993).
Yla-Herttuala, S., "Endgame: glybera finally recommended for approval as the first gene therapy drug in the European union," Mol. Ther., 20:1831-1832 (2012).
Yoshino et al., "Naked plasmid DNA transfers to the porcine liver using rapid injection with large volume," Gene Ther.13:1696-1702 (2006).
Zhang et al., "Generation and identification of recombinant adenovirus by liposome-mediated transfection and PCR analysis," BioTechniques 15(5):868-872 (1993).
Zheng et al., "Antibody gene therapy: an attractive approach for the treatment of cancers and other chronic diseases, " Cell Research, 17:303-306 (2007).
Zhou et al. "A comparative study assessing a new tool for occluding parenchymal blood flow during liver resection for hepatocellular carcinoma," S Afr J Surg. 51(1):12-15 (2013).
International Search Report and Written Opinion, dated May 23, 2013, in connection with International Patent Application No. PCT/US2013/025234, 24 pages.

Restriction Requirement, dated Sep. 19, 2013, in connection with U.S. Appl. No. 13/815,206, 6 pages.
Response to Restriction Requirement, dated Oct. 21, 2013, in connection with U.S. Appl. No. 13/815,206, 13 pages.
Response to International Search Report and Written Opinion, dated Dec. 9, 2013, in connection with International Patent Application No. PCT/US2013/025234, 49 pages.
Written Opinion, dated Jan. 27, 2014, in connection with International Patent Application No. PCT/US2013/025234, 9 pages.
Response to Written Opinion, dated Mar. 27, 2014, in connection with International Patent Application No. PCT/US2013/025234, 45 pages.
Office Action, dated Apr. 22, 2014, in connection with U.S. Appl. No. 13/815,206, 47 pages.
International Preliminary Report on Patentability, dated May 6, 2014, in connection with International Patent Application No. PCT/US2013/025234, 10 pages.
Response to Office Action, dated Oct. 22, 2014, in connection with U.S. Appl. No. 13/815,206, 31 pages.
Letter/Written Disclosure of the Information Disclosure Statement for the above-referenced application, dated Oct. 26, 2015, 2 pages.
International Search Report and Written Opinion, dated Nov. 5, 2014, in connection with corresponding International Patent Application No. PCT/US2014/050441, 15 pages.
International Search Report and Written Opinion, dated Mar. 30, 2015, in connection with International Patent Application No. PCT/US2014/050446, 15 pages.
Final Office Action, dated Apr. 28, 2015, in connection with U.S. Appl. No. 13/815,206, 54 pages.
Response to International Search Report and Written Opinion, dated Jun. 8, 2015, in connection with corresponding International Patent Application No. PCT/US2014/050441, 49 pages.
Response to International Search Report and Written Opinion, dated Jun. 30, 2015, in connection with International Patent Application No. PCT/US2014/050446, 43 pages.
Written Opinion, dated Jul. 7, 2015, in connection with corresponding International Patent Application No. PCT/US2014/050441, 9 pages.
Response, dated Sep. 7, 2015, to the second Written Opinion, dated Jul. 7, 2015, in connection with corresponding International Patent Application No. PCT/US2014/050441, 40 pages.
International Report on Patentability, dated Sep. 29, 2015, in connection with International Patent Application No. PCT/US2014/050446, 35 pages.
Letter/Written Disclosure of the Supplemental Information Disclosure Statement for the above-referenced application, filed herewith on Aug. 10, 2017, 2 pages.
News Article, "Spotlight: Global BioTherapeutics—Cultivating Entrepreneurship in Gene Therapy," Published Sep. 30, 2015 [online] Retrieved on May 25, 2016 from: <URL:mexicosalud.com/spotlight-global-biotherapeutics-cultivating-entrepreneurship-in-gene-therapy/, 6 pages.
Examiner's Report, dated Oct. 21, 2016, in connection with corresponding Canadian Patent Application No. 2920261, 4 pages.
Reponse, filed Jan. 19, 2017, Examiner's Report, dated Oct. 21, 2016, in connection with corresponding Canadian Patent Application No. 2920261, 36 pages.
Examiner's Report, dated Feb. 9, 2017, in connection with corresponding Canadian Patent Application No. 2920261, 3 pages.
Response, filed Aug. 3, 2017, to Examiner's Report, dated Feb. 9, 2017, in connection with corresponding Canadian Patent Application No. 2920261, 33 pages.
Communication pursuant to Article 94(3) EPC (Examination Report), dated May 3, 2017, in connection with corresponding European Patent Application No. 14 752 772.5, 5 pages.
U.S. Appl. No. 14/455,865, filed Aug. 8, 2014, 2015/0045769, Feb. 12, 2015.
Letter/Written Disclosure of the Supplemental Information Disclosure Statement for the above-referenced application, filed herewith on Apr. 28, 2016, 2 pages.
International Preliminary Report on Patentability, dated Nov. 12, 2015, in connection with International Patent Application No. PCT/US2014/050441, 36 pages.

(56) References Cited

OTHER PUBLICATIONS

Letter/Written Disclosure of the Supplemental Information Disclosure Statement for the above-referenced application, filed herewith on Apr. 23, 2018, 2 pages.
Machine-generated English language translation of Japanese Patent No. JP S62-32944 (A), published on Feb. 12, 1987, generated from Espacenet on Jan. 3, 2018, 6 pages.
Notice of Allowance, dated Aug. 16, 2017, in connection with corresponding Canadian Patent Application No. 2,920,261, 1 page.
Office Action, dated Nov. 17, 2017, in connection with corresponding Chinese Patent Application No. 201480055532.3 [English translation and original document in Chinese], 7 pages.
Response, filed Jan. 24, 2018, to Office Action, dated Nov. 17, 2017, in connection with corresponding Chinese Patent Application No. 201480055532.3 [English instructions, original document as filed in Chinese and amended claims in English], 29 pages.
Office Action, dated Aug. 8, 2017, in connection with corresponding Eurasian Patent Application No. 201600138 [English reporting letter with translation and original document in Russian], 4 pages.
Response, filed Dec. 7, 2017, to Office Action, dated Aug. 8, 2017, in connection with corresponding Eurasian Patent Application No. 201600138 [English instructions with original document as filed in Russian], 51 pages.
Response, filed Aug. 25, 2017, to Examination Report, dated May 3, 2017, in connection with corresponding European Patent Application No. 14752772.5, 42 pages.
Office Action, dated Sep. 26, 2017, in connection with corresponding Japanese Patent Application No. 2016-533483 [English summary, English translation and original document in Japanese], 10 pages.
Response, filed Dec. 11, 2017, to Office Action, dated Sep. 26, 2017, in connection with corresponding Japanese Patent Application No. 2016-533483 [English instructions, original document in Japanese and English translation of marked-up and clean amended claims], 41 pages.
Decision to Grant, dated Jan. 23, 2018, in connection with Japanese Patent Application No. 2016-533483 [English reporting letter with original document in Japanese], 4 pages.
Office Action, dated Mar. 1, 2018, in connection with corresponding Eurasian Patent Application No. 201600138 [English reporting letter with translation and original document in Russian; D1 = U.S. Pat. No. 3,667,471], 6 pages.
Letter/Written Disclosure of the Supplemental Information Disclosure Statement for the above-referenced application, filed herewith on Aug. 27, 2018, 3 pages.
Communication Under Rule 71(3) EPC (Intention to Grant), dated May 31, 2018, in connection with corresponding European Patent Application No. 14 752 772.5, 7 pages.
Office Action, dated Jun. 1, 2018, in connection with corresponding Chinese Patent Application No. 201480055532.3 [English translation and original document in Chinese], 19 pages.
Letter/Written Disclosure of the Supplemental Information Disclosure Statement for the above-referenced application, filed herewith on Jun. 28, 2019, 2 pages.
Response, filed Oct. 16, 2018, to Office Action, dated Jun. 1, 2018, in connection with corresponding Chinese Patent Application No. 201480055532.3 [English instructions, original document as filed in Chinese, and English translation of amended claims], 45 pages.
Notice of Granting Patent Right for Invention (Notice of Allowance), dated Feb. 25, 2019, in connection with corresponding Chinese Patent Application No. 201480055532.3 [English translation and original document in Chinese], 4 pages.
Certificate of Grant, dated May 7, 2019, in connection with corresponding Chinese Patent Application No. 201480055532.3 [English translation and original document in Chinese], 4 pages.
Response, filed Dec. 6, 2018, to Office Action, dated Mar. 1, 2018, in connection with corresponding Eurasian Patent Application No. 201600138 [English instructions and original document as filed in Russian], 63 pages.
Office Action, dated Feb. 7, 2019, in connection with corresponding Eurasian Patent Application No. 201600138 [English reporting letter with translation and original document in Russian], 4 pages.
Response, filed Jun. 7, 2019, to Office Action, dated Feb. 7, 2019, in connection with corresponding Eurasian Patent Application No. 201600138 [English instructions and original document as filed in Russian], 37 pages.
Response, filed Jun. 19, 2018, to the Communication Under Rule 71(3) EPC (Intention to Grant), dated May 31, 2018, in connection with corresponding European Patent Application No. 14752772.5, 16 pages.
Communication Under Rule 71(3) EPC (Intention to Grant), dated Sep. 25, 2018, in connection with corresponding European Patent Application No. 14752772.5, 267 pages.
Decision to Grant, dated Feb. 21, 2019, in connection with corresponding European Patent Application No. 14752772.5, 2 pages.
Office Action, dated Jan. 22, 2019, in connection with corresponding Japanese Patent Application No. 2018-028509 [English summary, English translation, and original document in Japanese], 6 pages.
Office Action, dated Feb. 14, 2019, in connection with corresponding Mexican Patent Application No. MX/a/2016/001667 [English translation and original document in Spanish], 7 pages.
Letter/Written Disclosure of the Supplemental Information Disclosure Statement for the above-referenced application, filed herewith on Sep. 8, 2020, 2 pages.
Letters Patent, dated Apr. 3, 2018, in connection with corresponding Canadian Patent Application No. 2,920,261, 1 page.
Office Action, dated Jul. 19, 2019, in connection with corresponding Eurasian Patent Application No. 201600138 [English reporting letter with translation and original document in Russian], 4 pages.
Response, filed Nov. 22, 2019, to Office Action, dated Jul. 19, 2019, in connection with corresponding Eurasian Patent Application No. 201600138 [English instructions and original document as filed in Russian], 27 pages.
Certificate of Grant, dated Mar. 20, 2019, in connection with corresponding European Patent Application No. 14752772.5, 1 page.
Certificate of Grant, dated Nov. 15, 2019, in connection with corresponding Hong Kong Patent Application No. 16113718.6, 2 pages.
Examination Report, dated Jul. 26, 2019, in connection with corresponding Indian Patent Application No. 201617006126, 6 pages.
Response, filed Jan. 24, 2020 to the Examination Report, dated Jul. 26, 2019, in connection with corresponding Indian Patent Application No. 201617006126, 44 pages.
Letters Patent, dated Mar. 2, 2018, in connection with corresponding Japanese Patent Application No. 2016-533483 [English reporting letter and original document in Japanese], 4 pages.
Response, filed Jul. 17, 2019, to Office Action, dated Jan. 22, 2019, in connection with corresponding Japanese Patent Application No. 2018-028509 [English instructions and original document as filed in Japanese], 10 pages.
Decision to Grant, dated Aug. 20, 2019, in connection with corresponding Japanese Patent Application No. 2018-028509 [English reporting letter and original document in Japanese], 4 pages.
Letters Patent, dated Sep. 27, 2019, in connection with corresponding Japanese Patent Application No. 2018-028509 [English reporting letter and original document in Japanese], 4 pages.
Response, filed Jul. 5, 2019, to Office Action, dated Feb. 14, 2019, in connection with corresponding Mexican Patent Application No. MX/a/2016/001667 [English instructions and original document as filed in Spanish], 27 pages.
Office Action, dated Sep. 3, 2019, in connection with corresponding Mexican Patent Application No. MX/a/2016/001667 [English translation and original document in Spanish], 7 pages.
Response, filed Nov. 26, 2019, to Office Action, dated Sep. 3, 2019, in connection with corresponding Mexican Patent Application No. MX/a/2016/001667 [English instructions and original document as filed in Spanish], 497 pages.
Letter/Written Disclosure of the Supplemental Information Disclosure Statement for the above-referenced application, filed herewith dated Feb. 14, 2022, 2 pages.

(56) References Cited

OTHER PUBLICATIONS

Notice of Allowance, published on Sep. 8, 2020, in connection with Mexican Patent Application No. MX/a/2016/001667 [English reporting letter and original document in Spanish], 6 pages.

Letters Patent, dated Jan. 6. 2021, in connection with Mexican Patent Application No. MX/a/2016/001667 [English translation of Letters Patent: and original document as issued in Spanish], 2 pages.

* cited by examiner

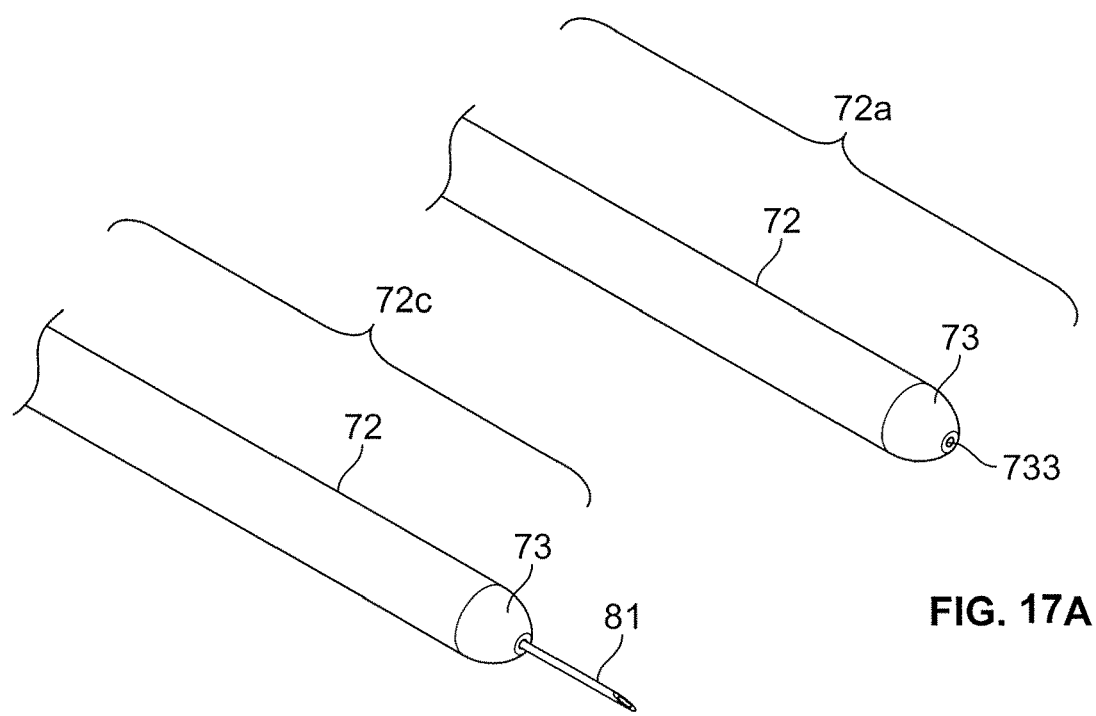
FIG. 17A
FIG. 17B
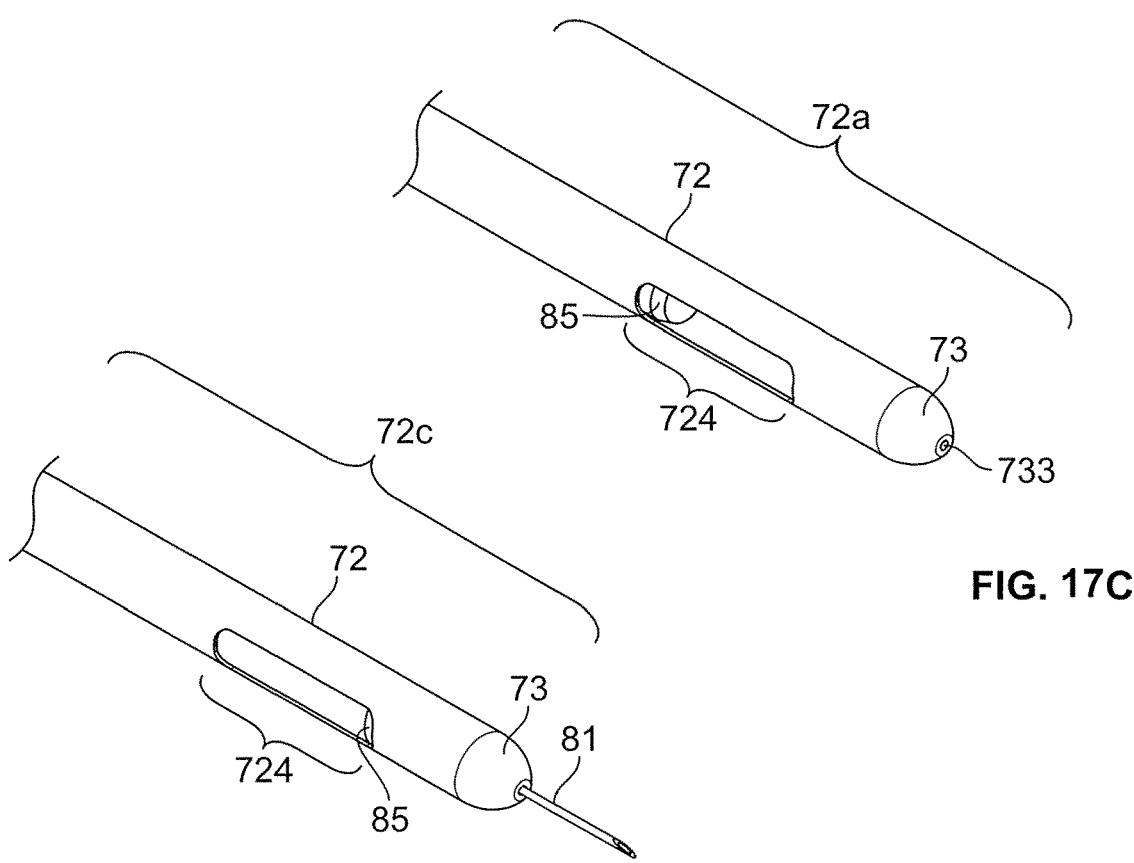
FIG. 17C
FIG. 17D

SEQUENCE LISTING

<160> NUMBER OF SEQ ID NOS: 2

<210> SEQ ID NO 1
<211> LENGTH: 18
<212> TYPE: DNA
<213> ORGANISM: Artificial Sequence
<220> FEATURE:
<223> OTHER INFORMATION: E4 human Adenoviral region primer - forward

<400> SEQUENCE: 1
ggagtgcgcc gagacaac                                                18

<210> SEQ ID NO 2
<211> LENGTH: 19
<212> TYPE: DNA
<213> ORGANISM: Artificial Sequence
<220> FEATURE:
<223> OTHER INFORMATION: E4 human Adenoviral region primer - reverse

<400> SEQUENCE: 2
actacgtccg gcgttccat                                               19

CLAMP DEVICE FOR MINIMALLY INVASIVE PROCEDURES AND USES THEREOF

RELATED APPLICATIONS

Benefit of priority is claimed to U.S. Provisional Application No. 61/863,903, filed Aug. 8, 2013, entitled "Clamp Device For Minimally Invasive Procedures And Uses Thereof."

This application is related to International PCT Application Serial No. PCT/US2014/050441, filed the same day herewith, entitled "Clamp Device For Minimally Invasive Procedures And Uses Thereof," which claims priority to U.S. Provisional Application No. 61/863,903.

This application also is related to U.S. application Ser. No. 14/455,865, filed the same day herewith, and International PCT Application No. PCT/US2014/050446, filed the same day herewith, each entitled "Injection Device for Minimally Invasive Procedures and Uses Thereof," both of which claim priority to U.S. Provisional Application Ser. No. 61/863,888, filed Aug. 8, 2013, entitled "Injection Device for Minimally Invasive Procedures and Uses Thereof."

This application also is related to U.S. application Ser. No. 13/815,206, filed Feb. 7, 2013, and International PCT Application No. PCT/US13/25234, filed Feb. 7, 2013, each entitled "Compartmentalized Method of Nucleic Acid Delivery and Compositions and Uses Thereof," both of which claim priority to U.S. Provisional Application Ser. No. 61/633,287, filed Feb. 7, 2012, entitled "Compartmentalized Method of Nucleic Acid Delivery and Compositions and Uses Thereof."

The subject matter of each of the above-noted applications is incorporated by reference in its entirety.

INCORPORATION BY REFERENCE OF SEQUENCE LISTING PROVIDED ELECTRONICALLY

An electronic version of the Sequence Listing is filed herewith, the contents of which are incorporated by reference in their entirety. The electronic file was created on Aug. 7, 2014, is 1 kilobyte in size, and is titled 552SEQ001.txt.

FIELD OF THE INVENTION

Provided herein is a clamp device that can be used in minimally invasive procedures, including surgeries such as laparoscopic surgeries, for clamping a tissue or an organ or a portion of a tissue or organ. Also provided herein are methods of clamping a tissue or an organ or a portion thereof during minimally invasive surgery using the clamp device provided herein. Also provided are systems for performing a minimally invasive surgery that include the clamp device for minimally invasive surgery provided herein and an injection device configured to access an endoscopic port for the minimally invasive surgery.

BACKGROUND

Many laparoscopic procedures, including laparoscopic surgeries, can require the clamping of a tissue or an organ or a portion of a tissue or organ to perform the procedure. Clamping of all or portions of a tissue or organ, such as the liver, kidney or other organs can be required in order to stop blood flow to the portion of tissue so that it can be observed without the presence of a significant amount of blood. Often it is difficult to achieve a clamping pressure around the tissue or organ that is sufficient to cut off the circulation while also leaving the tissue undamaged. Thus, there is a need for a clamp device that can be used during minimally invasive procedures that can achieve a clamping pressure that cuts off the circulation to the tissue while leaving the tissue without any damage.

REFERENCE NUMERALS LIST

The following list indicates the terms used and the corresponding reference numerals. Reference to each should be made with respect to the description below and the accompanying Drawings.

10—band clamp device
20—pistol grip handle portion
21—first band tensioning wheel (large)
22—second band tensioning wheel (small)
23—band tension/loosen switch
  23a—switch—down position
  23b—switch—up position
24—ratchet mechanism
  24a—ratchet mechanism—loosening position
  24b—ratchet mechanism—tensioning position
25—balloon inflation line
26—case
27—opening for switch (23)
30—sheath component
31—sheath adjustment knob
32—hollow sheath
33—screw mechanism to advance sheath
40—clamp portion
41—elongate surface member
42—flexible upper band
  42a—flexible upper band—flat position
  42b—flexible upper band—slack position
  42c—flexible upper band—tensioned position
4—biocompatible deformable article
43—balloon
  43a—balloon—deflated
  43b—balloon—inflated
44—notch
45—cradle
50—target tissue
51—injection device
501—liver
60, 60' or 60"—laparoscopic injection device
71 or 71'—needle sheath controller
  710—needle sheath controller housing
  711—positioner
    711a—positioner—forward position
    711b—positioner—intermediate position
    711c—positioner—rearward position
  712—lock and release element
  713—connection member
  715—distal sheath stop
  716—proximal sheath stop
  717—controller lumen
72, 72' or 72"—needle sheath
  72a—needle sheath—sheathed position
  72b—needle sheath—transitional position
  72c—needle sheath—unsheathed position
  720—proximal portion of needle sheath
  723—needle sheath lumen
  724—visibility window
  725—visibility window
  726—open cavity 73 or 73'—needle sheath distal tip
  733—needle channel
76—needle groove
81—injection needle
82—coupling member
83—injection tube
84—needle hub
85—needle coupler
900a—standard syringe—detached position
900b—standard syringe—connected position
910—dockable syringe
  910a—dockable syringe—undocked position
  910b—dockable syringe—docked position
91, 91' or 91"—syringe barrel
92, 92' or 92"—plunger
  920—auxiliary plunger
93—Luer fit adaptor
94—syringe barrel base
95 or 95'—plunger head
  951—plunger adaptor
96—syringe adaptor lining
  960—plunger rest cavity
  961—barrel dock
  962—barrel rest cavity
  963—barrel dock

SUMMARY

Provided herein is a clamp device for minimally invasive surgery that contains an elongate surface member that has a proximal end and a distal end; a biocompatible deformable article that rests on the surface member at the distal end of the surface member; and a flexible band that has a proximal end and a distal end, with the distal end of the flexible band connected to the distal end of the surface member and forming a closed loop with the biocompatible deformable article on the surface member, with the closed loop being able to fit a tissue or an organ or a portion thereof during minimally invasive surgery. The biocompatible deformable article is any material that can conform to the anatomy of a tissue or organ to assure even distribution of clamping force. For example, the biocompatible deformable article is a low or medium durometer material that is biocompatible. Exemplary of such materials include, but are not limited to, elastomeric foams, silicones (e.g. low durometer silicones), elastomers (e.g. low durometer elastomers), silicone rubbers, visco-elastic gels or hydrogels. In some examples, the biocompatible deformable article is an inflatable balloon where the balloon, when it is inflated, can conform to the anatomy. Thus, provided herein is a clamp device for minimally invasive surgery that contains an elongate surface member that has a proximal end and a distal end; an inflatable balloon that rests on the surface member at the distal end of the surface member; and a flexible band that has a proximal end and a distal end, with the distal end of the flexible band connected to the distal end of the surface member and forming a closed loop with the balloon on the surface member, with the closed loop being able to fit a tissue or an organ or a portion thereof during minimally invasive surgery. The proximal end of the flexible band is configured to be adjustably tensioned so that the portion of the flexible band that forms a closed loop with the biocompatible deformable article, such as a balloon, can be shortened or lengthened to allow the loop to clamp a tissue or an organ or a portion thereof during minimally invasive surgery.

In any of the examples provided herein, the device provided herein further contains a sheath having a lumen with a proximal end and a distal end. In examples of a clamp device provided herein that contains a balloon, the lumen of the sheath contains a balloon inflation line having a proximal end and a distal end, where the distal end is in communication with the proximal end of the inflatable balloon to control inflation of the balloon. The lumen of the sheath encloses a portion of the elongate surface member and flexible band, but, since the surface member is longer than the sheath, the lumen of the sheath does not enclose the biocompatible deformable article resting in the cradle at the distal end of the surface member. For example, in devices containing a balloon, the lumen of the sheath encloses a portion of the elongate surface member, flexible band and balloon inflation line, and the surface member is longer than the sheath, thus the lumen of the sheath does not enclose the inflatable balloon resting in the cradle at the distal end of the surface member. In some examples, the sheath of the clamp device is configured to be linearly movable along the surface member to shorten or lengthen the portion of the surface member that is not enclosed by the sheath.

In any of the examples herein, the device can further contain an adjustable knob operably connected to the sheath to control movement of the sheath linearly along the surface member. The adjustable knob is configured on the device so that axial rotation of the adjustable knob with respect to the sheath linearly moves the sheath with respect to the surface member to advance or retract the sheath into the adjustable knob, thus shortening or lengthening the portion of the surface member enclosed by the lumen of the sheath.

Any of the above devices provided herein can further contain a handle connected to the proximal end of the surface member. The handle includes a case having an inside and an outside, a first tensioning wheel mounted in the case for access by an operator to adjustably tension the flexible band, and the proximal end of the flexible band. The proximal end of the flexible band is operably engaged with the first tensioning wheel, and movement of the tensioning wheel shortens or lengthens the portion of the flexible band that forms a closed loop with the biocompatible deformable article, such as a balloon, in the distal end of the elongate surface member. The first tensioning wheel is operably connected to a second tensioning wheel so that movement of the first tensioning wheel effects simultaneous movement of the second tensioning wheel in the same direction. The second tensioning wheel is configured to hold the flexible band around its exterior circumference so that movement of the first tensioning wheel shortens or lengthens the portion of the flexible band that forms a closed loop with the biocompatible deformable article, such as a balloon, in the distal end of the elongate surface member.

In any of such examples, the handle of the band clamp device provided herein can further contain a movable switch mounted on the handle that controls the direction of movement of the first tensioning wheel. In some examples, the switch is mounted to have an a portion outside of the case that is accessible by an operator and a portion inside the that is operably coupled to a ratchet located in proximity to the switch, so that movement of the switch moves the ratchet and movement of the ratchet engages the first tensioning wheel. The ratchet position determines the direction the first tensioning wheel is able to move.

Provided herein is a clamp device for minimally invasive surgery that contains an elongate surface member; a biocompatible deformable article; a flexible band; a sheath containing a lumen that encloses a portion of the surface member and flexible band; an adjustable knob to control movement of the sheath; and a handle containing a case, a first tensioning wheel, a second tensioning wheel, a ratchet and a switch. In examples of the device, the biocompatible deformable article can contain an inflatable balloon that is controlled through a balloon inflation line. Hence, provided herein is a clamp device for minimally invasive surgery that contains an elongate surface member; an inflatable balloon; a flexible band; a sheath containing a lumen that contains a balloon inflation line in connection with the inflatable balloon, where the sheath encloses a portion of the surface member, flexible band and balloon inflation line; an adjustable knob to control movement of the sheath; and a handle containing a case, a first tensioning wheel, a second tensioning wheel, a ratchet and a switch. The elongate surface member of the device provided herein has a concave surface that has a proximal end and a distal end. The biocompatible deformable article, such as an inflatable balloon, has a proximal end and a distal end that rests along the distal end of the elongate surface member in a cradle formed by the concave surface member. The flexible band has a proximal end and a distal end, and the distal end of the flexible band is connected to the distal end of the surface member so that the flexible band forms a closed loop with the biocompatible deformable article, such as balloon, on the surface member.

In any of the devices, the sheath contains a lumen having a proximal end and a distal end. The lumen of the sheath encloses a portion of the elongate surface member and flexible band. In embodiments of the device containing a balloon, the lumen of the sheath where the lumen contains a balloon inflation line having a proximal end and a distal end that is in communication with the proximal end of the inflatable balloon to control inflation of the balloon. The balloon inflation line enclosed in the sheath rests in the surface member between the flexible band and surface member. The lumen of the sheath encloses a portion of the elongate surface member, flexible band and balloon inflation line, with the balloon inflation line resting in the cradle of the surface member between the flexible band and surface member. The surface member is longer than the sheath, thus the lumen of the sheath does not enclose the biocompatible deformable article, such as inflatable balloon, resting in the cradle at the distal end of the surface member.

In any of the devices, the sheath contains a lumen having a proximal end and a distal end. The lumen of the sheath encloses the elongate surface member and flexible band. In embodiments of the device containing a balloon, the lumen of the sheath where the lumen contains a balloon inflation line having a proximal end and a distal end that is in communication with the proximal end of the inflatable balloon to control inflation of the balloon. The balloon inflation line enclosed in the sheath rests in the surface member between the flexible band and surface member. The lumen of the sheath encloses a portion of the elongate surface member, flexible band and balloon inflation line, with the balloon inflation line resting in the cradle of the surface member between the flexible band and surface member. The surface member is longer than the sheath, thus the lumen of the sheath does not enclose the biocompatible deformable article, such as inflatable balloon, resting in the cradle at the distal end of the surface member.

In any of the devices, the sheath is configured to be linearly movable along the surface member to shorten or lengthen the portion of the surface member that is not enclosed by the lumen of the sheath. The adjustable knob is operably connected to the proximal end of the sheath and controls movement of the sheath linearly along the surface member. Axial rotation of the adjustable knob with respect to the sheath moves the sheath linearly with respect to the surface member to advance or retract the sheath into the adjustable knob, thus shortening or lengthening the portion of the surface member enclosed by the lumen of the sheath.

In any of the devices, the handle is positioned proximal to the adjustable knob and is connected to the proximal end of the surface member. The handle contains a case having an inside and an outside; a first tensioning wheel mounted in the case for access by an operator to adjustably tension the flexible band; a second tensioning wheel that is operably connected to the first tensioning wheel so that movement of the first tensioning wheel effects simultaneous movement of the second tensioning wheel in the same direction, with the second tensioning wheel configured to hold the proximal end of the flexible band around its exterior circumference; a ratchet that is configured inside the case and capable of being operably connected to the first tensioning wheel, so that movement of the ratchet engages the first tensioning wheel; and a movable switch mounted on the handle that controls the direction of movement of the first tensioning wheel. The switch is mounted to have a portion outside of the case that is accessible by an operator and a portion inside the case that is operably coupled to the ratchet located in proximity to the inner portion of the switch. Movement of the switch moves the ratchet, thus engaging the first tensioning wheel to shorten or lengthen the portion of the flexible band that forms the closed loop with the biocompatible deformable article, such as balloon, in the distal end of the elongate surface member, so that the size of the closed loop is adjustable for clamping a tissue or organ during minimally invasive surgery.

In any of the clamp devices provided herein, the flexible band is made of material that allows the closed loop to form an open area between the biocompatible deformable article, such as balloon, and the flexible band in the absence of any clamped tissue, so that tensioning or loosening the flexible band increases or decreases the space formed in the open area between the biocompatible deformable article, such as balloon, and the flexible band. In any of the examples of the device provided herein, the flexible band can be loosened to lengthen the flexible band to achieve a height of the closed loop that is greater than the thickness of the tissue or organ or portion thereof to fit the tissue or organ or portion thereof in the closed loop. For example, the flexible band can be loosened to lengthen the flexible band to achieve a height of the closed loop from 1 cm to 10 cm, 1 cm to 5 cm, 2 cm to 4 cm or 3 cm to 4 cm. In any of the examples of the device provided herein, the distal end of the flexible band is configured to be adjustably tensioned proximal to the distal end of the elongate surface member and the flexible band is longer than the elongate surface member by an amount that is greater than the thickness of the tissue or organ or portion thereof to be clamped. In any of the examples provided herein, the length of the flexible band is greater than the combined path length of the upper surface of the tissue or organ or portion thereof to be clamped, the length of the surface member and the distance required for the flexible band to engage with the second tensioning wheel. The flexible band can be made of a flexible polymer, such as a polyurethane or polyethylene. This includes, for example, a polyurethane reinforced with fiber.

In any of the examples of the device provided herein, the surface member is concave to form a cradle and the biocompatible deformable article, such as balloon, rests in the cradle and is attached to the flexible band at the distal end of the flexible band near the connection of the flexible band with the surface member. For example, the biocompatible deformable article, such as balloon, rests in the cradle of the surface member between the flexible band and surface member. In other examples, the biocompatible deformable article, such as balloon, is not attached to the flexible band, and the closed loop is formed by the connection of the flexible band to the surface member near the distal end of the biocompatible deformable article, such as balloon, resting in the surface member.

In any of the examples of the device provided herein, the elongate surface member can be flexible or rigid. In an exemplary device, the elongate surface member is rigid. In any of the examples of the device provided herein, the distal end of the surface member has a notch and the distal end of the flexible band is connected to the distal end of the surface member at the notch to form the closed loop.

In any of the examples provided herein, the device provided herein has an elongate surface member that is of a sufficient length and diameter to access a tissue or an organ or a portion thereof through an endoscopic port during minimally invasive surgery. For example, the minimally invasive surgery is laparoscopy. Among the tissue or organ or portion thereof accessed during the minimally invasive surgery are those selected from among the liver, pancreas, gallbladder, spleen, stomach, reproductive organs and portion thereof. In particular examples, the tissue or organ is the liver or portion thereof. The access portion of the liver can be the left median lobe. In such examples where the liver is the tissue or organ, the endoscopic port is located in the epigastric region of the abdomen above the portion of the liver to be clamped.

In any of the examples provided herein, the elongate surface member is of a sufficient length and diameter to access a tissue or an organ or a portion thereof through an endoscopic port during minimally invasive surgery. Hence, the device has an elongate surface member with a length from its proximal end to its distal end of from or from about 100 mm to 600 mm, 100 mm to 500 mm, 250 mm to 400 mm or 300 mm to 400 mm. Exemplary of a length is at least or about at least 300 mm or at least or about at least 400 mm.

In any of the examples provided herein, the sheath has a length and diameter that permit access to a tissue or an organ or a portion thereof during minimally invasive surgery. Hence, the sheath is from 100 mm to 500 mm or 200 mm to 400 mm in length, and up to or at least or about 3 mm, 4 mm, 5 mm, 6 mm, 7 mm, 8 mm, 9 mm, 10 mm, 11 mm, 12 mm, 13 mm, 14 mm or 15 mm in diameter. Exemplary of a length is 300 mm in length and a diameter is 10 mm in diameter.

In any examples of the device provided herein, the length of the surface member that is not enclosed by the sheath is greater than the width of the tissue or organ or a portion thereof to fit the tissue or organ or a portion thereof in the closed loop. For example, the length of the surface member that is not enclosed by the sheath is from 25 mm to 200 mm, 50 mm to 150 mm or 75 mm to 125 mm in length. In some examples, the length of surface member not enclosed by the sheath is from 75 mm to 125 mm in length. For example, the length of the surface member not enclosed by the sheath is or is about or is at least 100 mm. In any of such examples, the biocompatible deformable article, such as balloon, is substantially as long as the portion of the surface member that is longer than the sheath. For example, the length of the biocompatible deformable article, such as inflatable balloon, resting in the cradle at the distal end of the elongate member is from 25 mm to 200 mm, 50 mm to 150 mm or 75 mm to 125 mm. In particular examples, the length of the biocompatible deformable article, such as inflatable balloon, resting in the cradle at the distal end of the elongate member is or is at least 100 mm.

In any of the examples of the clamp device provided herein, the sheath contains male threads on the outside surface at the proximal end and the adjustable knob is a hollow cylinder that contains female threads on the inside surface of the distal end of the adjustable knob. Axial rotation of the adjustable knob with respect to the sheath around the sheath moves the sheath linearly with respect to the surface member to advance or retract the sheath into the adjustable knob, thus shortening or lengthening the portion of the surface member enclosed by the lumen of the sheath.

In any of the examples of the device provided herein, the second tensioning wheel contains teeth and the flexible band is made of a toothed flexible polymer, thus allowing the flexible band to engage the teeth on the second tensioning wheel. In any of the examples provided herein, the diameter of the first tensioning wheel can be greater than the diameter of the second tensioning wheel. For example, the ratio of the diameter of the first tensioning wheel to the second tensioning wheel is 2:1 to 10:1. In any of the examples of the device provided herein, a portion of the flexible band is not operably connected to the tensioning wheel and is free within the case, the free portion being movable over the tensioning wheel and accounting for the portion of the flexible band that is able to be lengthened in the closed loop.

In examples of the device provided herein, the portion of the switch outside of the case is on one side of the case and can be operated on only the one side. In other examples, the portion of the switch outside of the case is on both sides of the case and can be operated on one or both sides. In any of the examples provided herein, the ratchet can be Y-shaped, having a bottom portion and a top portion with two prongs and the inner portion of the switch is operably connected to the bottom of the Y-shaped ratchet and the top portion is operably connected to the first tensioning wheel. Movement of the switch moves the ratchet so that only one prong is engaged with the first tensioning wheel at a time, thus engaging the first tensioning wheel to shorten or lengthen the portion of the flexible band that forms the closed loop with the biocompatible deformable article, such as balloon, in the distal end of the elongate surface member, so that the size of the closed loop is adjustable for clamping a tissue or organ during minimally invasive surgery.

In any of the examples provided herein, the biocompatible deformable article is any material that has a low or medium durometer (i.e. hardness) and is capable of conforming to the target tissue without damaging the tissue. The durometer of the material is, however, sufficient enough so that a clamping pressure can be exerted by the flexible upper band on a tissue or organ or portion thereof when positioned between the flexible upper band and biocompatible deformable article. It is also a material that is biocompatible. Exemplary of such materials is an elastomeric foams, silicones (e.g. low durometer silicones), elastomers (e.g. low durometer elastomers), silicone rubbers, visco-elastic gels and hydrogels. In some examples, the diameter of the biocompatible deformable article is not greater than the diameter of the sheath component so that the clamp portion of the device can fit through an endoscopic port. For example, the diameter of the biocompatible deformable article is less than 15 mm in diameter, such as less than 14 mm, 13 mm, 12 mm, 11 mm, 10 mm, 9 mm, 8 mm, 7 mm, 6 mm, 5 mm, 4 mm, 3 mm, 2 mm or less. In some examples, the biocompatible deformable article is an inflatable balloon. Since the balloon can be inflated after insertion through an endoscopic port, in such examples the diameter of the balloon can be greater than the diameter of the sheath, but generally is not so great as to impair the fit of the tissue or portion thereof in the closed loop of the clamp formed from the flexible band and balloon. Typically, the diameter of the balloon is up to or at least or about 3 mm, 4 mm, 5 mm, 6 mm, 7 mm, 8 mm, 9 mm, 10 mm, 11 mm, 12 mm, 13 mm, 14 mm or 15 mm in diameter.

In any of the examples provided herein containing a balloon, the inflatable balloon of the device provided herein can be made of a rigid balloon material such as a medium durometer material, including a polyurethane or polyethylene material. Exemplary material for the inflatable balloon is selected from among a polyurethane with a shore hardness between 70 A and 85 A, a polyethylene terephthalate (PET) and a polyethylene terephthalate glycol-modified (PETG). The inflatable balloon is connected to the balloon inflation line. In any of the examples, the proximal end of the balloon inflation line extends from the bottom of the handle and is operably connected to an external source of fluid or gas, such as a syringe, a pump and a tank, that inflates and deflates the inflatable balloon through the balloon inflation line. In some examples, the gas is air.

In any examples of the device provided herein, the device can be used for clamping a tissue or an organ or a portion thereof, including the parenchyma of a tissue or an organ or a portion thereof. In some examples, the clamping can effect compartmentalization of the tissue or organ to stop blood flow to the tissue or organ or portion thereof from the systemic circulation.

Also provided herein are methods of clamping a tissue or an organ or a portion thereof during minimally invasive surgery that include inserting any of the above clamp devices provided herein into an endoscopic port for minimally invasive surgery, adjusting the flexible band to lengthen the flexible band in the closed loop so that a closed loop is formed between the lower biocompatible deformable article and upper flexible band of the clamp portion to fit around the tissue or organ or portion thereof, positioning the loop around the tissue or organ or portion thereof to be clamped, and tensioning the flexible band to decrease the size of the closed loop so that the flexible band fits firmly over the tissue or organ or portion thereof to exert a pressure thereon. The biocompatible deformable article is able to conform to the shape of the target tissue when the flexible upper band is in the tensioned position, thereby clamping the tissue or organ or portion thereof.

For example, provided herein are methods of clamping a tissue or an organ or a portion thereof during minimally invasive surgery that include inserting any of the above clamp devices containing a balloon as provided herein into an endoscopic port for minimally invasive surgery, adjusting the flexible band to lengthen the flexible band in the closed loop so that a closed loop is formed to fit around the tissue or organ or portion thereof, positioning the loop around the tissue or organ or portion thereof to be clamped, tensioning the flexible band to decrease the size of the closed loop so that the flexible band in the loop fits firmly over the tissue or organ or portion thereof, and inflating the balloon so that it conforms with the tissue or organ or portion thereof, thereby clamping the tissue or organ or portion thereof.

In any of such examples of the method, the endoscopic port is a laparoscopic port. In any of the examples of the method, the tissue or organ or portion thereof is selected from among the liver, pancreas, gallbladder, spleen, stomach or reproductive organs or portion thereof. In an exemplary method, the tissue or organ is the liver or portion thereof, for example, a portion of the liver is the left median lobe. The port can be located in the epigastric region of the abdomen above the portion of the liver to be clamped.

In any of the methods provided herein, the device is provided so that the flexible band is capable of laying flat over the biocompatible deformable article on the surface member when inserting the clamp device into an endoscopic port for minimally invasive surgery. In methods herein, if the biocompatible deformable article is a balloon, the device can be provided for insertion into an endoscopic port with the balloon deflated. For example, in any of the methods provided herein, the device is provided herein so that it has a deflated balloon and the flexible band that lays flat on the surface member when inserting the clamp device provided herein into an endoscopic port for minimally invasive surgery.

In any of the examples of the method herein, adjusting the flexible band to lengthen the flexible band in the closed loop so that a closed loop is formed to fit around the tissue or organ or portion thereof is done by turning the first tensioning wheel towards the distal end of the device to lengthen the flexible band in the closed loop. In any of such methods, the position of the loop around the tissue or organ or portion thereof to be clamped can be adjusted in the loop using a surgical tool to facilitate positioning the tissue or organ or portion thereof in the loop. For example, the surgical tool can be a grasper or tweezers. The loop is positioned over a portion of the tissue or organ. In any of the methods herein, after positioning the loop around the tissue or organ or portion thereof to be clamped, the adjustable knob is axially rotated with respect to the sheath, thus moving the sheath linearly with respect to the surface member to shorten the portion of surface member that is not enclosed by the sheath. In any of such methods herein, the length of surface member enclosed by the sheath is adjusted to a size that fits the anatomy of the tissue or organ or portion thereof to be clamped.

In any of the methods provided herein, tensioning the flexible band to decrease the size of the closed loop so that the flexible band in the loop fits firmly over the tissue or organ or portion thereof is accomplished by turning the first tensioning wheel towards the proximal end of the device, thus decreasing the amount of flexible band formed in the closed loop with the biocompatible deformable article, such as a balloon, and tightening the flexible band firm on the tissue or organ or portion thereof. In any of such examples, the loop is decreased to a size that fits the anatomy of the tissue or organ or portion thereof to be clamped. In any examples of the methods herein, the tension of the flexible band on the tissue is further monitored using a tension gauge. In examples of the method herein using a device containing a biocompatible deformable article that is inflatable, such as a balloon that is inflatable, the balloon is inflated to conform to the anatomy of the tissue or portion thereof, thereby applying a uniform clamping pressure to the tissue or organ or portion thereof to be clamped, thus clamping the tissue or organ or portion thereof. For example, the balloon is inflated to a pressure between 50 mmHg to 250 mmHg. For example, the balloon is inflated to a pressure greater than 120 mmHg. The pressure can be further monitored using a pressure gauge in some examples.

In any of the methods described herein, the clamping of a tissue or an organ or a portion thereof is for tissue resection or transplantation. In other methods herein, the clamping of a tissue or an organ or a portion thereof is for dissection, hysterectomy, appendectomy, cholecystectomy (to treat gallstones), bariatric surgery, gastric bypass surgery, lap band surgery, laparoscopic surgery for endometriosis, hernia repair or laparoscopic surgery to treat diseases of the gastrointestinal tract. In some examples, clamping of a tissue or an organ or a portion thereof stops blood flow to the tissue or organ from the systemic circulation resulting in compartmentalization of the tissue or organ or portion thereof from the systemic circulation.

In any of the methods herein, after firmly positioning the clamp portion over a tissue or organ or a portion thereof, thereby clamping the tissue or organ or portion thereof, a therapeutic composition is administered to the clamped tissue or organ or portion thereof. For example, after inflating the balloon so that it conforms with the tissue or organ or portion thereof, thereby clamping the tissue or organ or portion thereof, a therapeutic composition is administered to the clamped tissue or organ or portion thereof. In some examples, a nucleic acid molecule is administered directly to the parenchyma of the compartmentalized tissue or organ or portion thereof.

An exemplary method provided herein is a method of delivering a nucleic molecule to a compartmentalized tissue or organ or portion thereof of a subject where the method includes clamping a tissue or an organ or a portion thereof using the clamp device provided herein, wherein the clamping of a tissue or an organ or a portion thereof stops blood flow to the tissue or organ from the systemic circulation resulting in compartmentalization of the tissue or organ or portion thereof from the systemic circulation, and administering a nucleic acid molecule directly to the parenchyma of the compartmentalized tissue or organ or portion thereof.

In any of the examples of a method of delivering a nucleic acid to a compartmentalized tissue or organ or portion thereof, the method includes inserting the device provided herein into an endoscopic port for minimally invasive surgery, adjusting the flexible band to lengthen the flexible band in the closed loop so that a closed loop is formed to fit around the tissue or organ or portion thereof, positioning the loop around the tissue or organ or portion thereof to be clamped, tensioning the flexible band to decrease the size of the closed loop so that the flexible band in the loop fits firmly over the tissue or organ or portion thereof and the biocompatible deformable article is conformed to the anatomy of the tissue or organ or portion thereof, thereby clamping the tissue or organ or portion thereof. For example, the method includes inserting the device provided herein into an endoscopic port for minimally invasive surgery, adjusting the flexible band to lengthen the flexible band in the closed loop so that a closed loop is formed to fit around the tissue or organ or portion thereof, positioning the loop around the tissue or organ or portion thereof to be clamped, tensioning the flexible band to decrease the size of the closed loop so that the flexible band in the loop fits firmly over the tissue or organ or portion thereof, and inflating the balloon so that it conforms with the tissue or organ or portion thereof, thereby clamping the tissue or organ or portion thereof.

In any of the examples of a method of delivering a nucleic acid to a compartmentalized tissue or organ or portion thereof, the nucleic acid molecule is administered no more than 5 minutes, 4 minutes, 3 minutes, 2 minutes, 1 minute or 30 seconds after compartmentalizing the tissue or organ or portion of the tissue or organ.

In any of the examples of a method of delivering a nucleic acid to a compartmentalized tissue or organ or portion thereof, exemplary of the nucleic acid molecule are a nucleic acid molecule that encodes a polypeptide. The encoded polypeptide can be selected from among an enzyme, a hormone, a coagulation or clotting factor, a cytokine, a growth factor or active portion thereof, an antibody or antigen binding portions of antibodies, an angiogenesis modulator, an immunomodulator, a pain modulator, a receptor or active portion thereof, a transport protein, a regulatory protein, an antigen and an allergen. The encoded polypeptide is selected from among adenosine deaminase, cystic fibrosis transmembrane conductance regulator (CTFR), galsulfase, laronidase, N-acetylgalactosamine 6-sulfatase, phenylalanine ammonia lyase, acid alpha glucosidase, imiglucerase, alglucosidase alpha, thyrotropin, growth hormone, insulin, thyroid hormone, erythropoietin (EPO), interleukin-1 (IL-1), IL-2, IL-3, IL-4, IL-5, IL-7, interferon-α (IFN-α), IFN-β, IFN-γ, tumor necrosis factor (TNF), IL-12, IL-18, Fms-Related Tyrosine Kinase 3 (flt3), neuropilin-2 (NP2), bone morphogenic protein (BMPs), epidermal growth factor (EGF), erythropoietin (EPO), fibroblast growth factor (FGF), granulocyte colony stimulating factor (G-CSF), granulocyte macrophage colony stimulating factor (GM-CSF), hepatocyte growth factor (HGF), insulin-like growth factor (IGF), platelet derived growth factor (PDGF), transforming growth factor α or β, vascular endothelial growth factor (VEGF), epidermal growth factor receptor (EGFR), fibroblast growth factor receptor (FGFR), FGFR antagonist (sFGFR) transforming growth factor receptor (TGFR), vascular endothelial growth factor receptor (VEGFR), plasminogen activator, urokinase, Factor VIII, Factor IX, von Willebrand factor, growth hormone, metalloproteinase thrombospondin motifs 1 (METH-1), METH-2, tryptophanyl-tRNA synthetase (TrpRS) fragments, proliferin-related protein, prolactin fragment, pigment epithelium-derived factor (PEDF), vasostatin, angiostatin, endostatin, kininostatin, fibrinogen-E fragment, thrombospondin, tumstatin, canstatin, restin, soluble fms-like tyrosine kinase-1 (sFlt-1), soluble vascular endothelial growth factor receptors (sFlk), soluble Neuropilin 1 (sNRP1), Interferon gamma-induced protein 10 (IP-10), Platelet factor 4 (PF-4), Gro-beta, soluble Ephrin type-B receptor 4 (sEphB4), sephrinB2, IGF-1, herpes simplex virus thymidine kinase (HSV-TK), carboxypeptidase G2 (CPG2), carboxylesterase (CA), cytosine deaminase (CD), cytochrome P450 (cyt-450), deoxycytidine kinase (dCK), nitroreductase (NR), purine nucleoside phosphorylase (PNP), thymidine phosphorylase (TP), varicella zoster virus thymidine kinase (VZV-TK), xanthine-guanine phosphoribosyl transferase (XGPRT), Aspartylglucosaminidase, α-Galactosidase A, Palmitoyl Protein Thioesterase, Tripeptidyl Peptidase, Lysosomal transmembrane protein, cysteine transporter, Acid ceramidase, acid α-L-fucosidase, protective protein/cathepsin A, acid β-glucosidase or glucocerebrosidase, acid β-galactosidase, iduronate-2-sulfatase, α-L-Iduronidase, galactocerebrosidase, acid α-mannosidase, acid β-mannosidase, arylsulfatase B, arylsulfatase A, N-Acetylgalactosamine-6-sulfate sulfatase, N-Acetylglucosamine-1-phosphotransferase, Acid sphingomyelinase, Niemann-Pick disease, type C1 (NPC-1), β-Hexosaminidase B, Heparan N-sulfatase, α-N-Acetylglucosaminidase (Na-Glu), Acetyl-CoA:αglucosaminde N-acetyltransferase, N-Acetylglucosamine-6-sulfate sulfatase, β-Glucuronidase, acid lipase, neprilysin, the insulin-degrading enzyme insulysin, thimet oligopeptidase, calbindin D28, parvalbumin, hypoxia induced factor 1-alpha (HIF1-alpha), sirtuin-2 (SIRT-2), survival motor neuron protein-1 (SMN-1), SMN-2, glial cell-derived neurotrophic factor (GDNF), ciliary neurotrophic factor (CNF), low density lipoprotein receptor (LDLR), lipoprotein lipase (LPL), Alpha-1-Antitrypsin (AAT), UDP-glucuronyl-transferase (UGT), UGT1A1, glucose-6 phosphatase, phosphoenolpyruvate-carboxykinase, galactose-1 phosphate uridyl transferase, phenylalanine hydroxylase, branched chain alpha-ketoacid dehydrogenase, fumarylacetoacetate hydrolase, methylmalonyl-CoA mutase, ornithine transcarbamylase, argininosuccinic acid synthetase, adenosine deaminase, hyposanthine guanine phosphoribosyl transferase, biotinidase, beta-glucocerebrosidase, beta-glucuronidase, porphobilinogen deaminase (PBDG) and p53.

In any of the examples of a method of delivering a nucleic acid to a compartmentalized tissue or organ or portion thereof, the nucleic acid molecule is a therapeutic nucleic acid molecule that encodes a therapeutic product, thus delivery of the nucleic acid molecule effects treatment of a disease or condition. The disease or condition is selected from among an arthritis, chronic pain, HIV-related AIDS, atherosclerosis, restenosis, inherited enzyme deficiency, inherited immune deficiency, cancer, a retrovirus infection, hemophilia, diabetes, a muscular dystrophy, a cardiovascular disorder, cystic fibrosis, a neurodegenerative disorder, trauma, pain, sickle cell anemia, autoimmune disease, inflammatory disease, and hypertension, For example, in any of the above methods, the nucleic acid molecule encodes a protein selected from among a Factor VIII for the treatment of hemophilia A; a Factor IX for the treatment of hemophilia B; an insulin gene for treatment of type I diabetes mellitus; an alpha-1-antitrypsin (AAT) for the treatment of alpha-1-antitrypsin (AAT) deficiency; a hemochromatosis protein (HFE) for treatment of hemochromatosis; a copper-transporting ATPase 2 for treatment of Wilson's disease; UDP glucuronosyltransferase 1A1 (UGT1A1) for the treatment of Crigler-Najjar syndrome type I; ornithine transcarbamylase (OTC) for the treatment of ornithine transcarbamylase deficiency, type II; low density lipoprotein receptor (LDLR) for the treatment of familial hypercholesterolemia; fibrinogen alpha (FGA), beta (FGB) or gamma (FGB) for the treatment of afibrinogenemia; glucose-6-phosphate-α for the treatment of glycogen storage disease (GSD) type Ia; G6PT for the treatment of GSD type Ib; acid-α-glucosidase for the treatment of GSD type II (Pompe); α-L-iduronidase for the treatment of mucopolysaccharidosis (MPSI); sulphamidase for the treatment of MPS IIIA; α-N-acetylglucosaminidase (NaGlu) for the treatment of MPS IIIB; β-glucuronidase for the treatment of MPS VII; α-galactosidase A for the treatment of Fabry disease; glucocerebrosidase for the treatment of Gaucher's disease; acid sphingomyelinase for the treatment of Niemann-Pick syndrome; phenylalanine hydroxylase for the treatment of phenylketonuria; TIMP antagonist or anti-HSC molecules for the treatment of liver fibrosis; anti-ROS molecules for the treatment of liver ischemia reperfusion injury; amyloid-beta degrading enzyme neprilysin, the insulin-degrading enzyme insulysin, or thimet oligopeptidase for the treatment of Alzheimer's disease; insulin growth factor-1 (IGF-1), calbindin D28, parvalbumin, HIF1-alpha, SIRT-2, VEGF, SMN-1, SMN-2, GDNF or ciliary neurotrophic factor (CNF) for the treatment of Amyotrophic Lateral Sclerosis (ALS); galactose-1 phosphate uridyl transferase for the treatment of galactosemia; branched chain alpha-ketoacid dehydrogenase for the treatment of maple syrup urine disease; fumarylacetoacetate hydrolase for the treatment of tyrosinemia type 1; methylmalonyl-CoA mutase for the treatment of methylmalonic acidemia; argininosuccinic acid synthetase for the treatment of citrullinemia; hyposanthine guanine phosphoribosyl transferase for the treatment of Gout and Lesch Nyan syndrome; beta-glucuronidase for the treatment of Sly syndrome; peroxisome membrane protein 70 kDa for the treatment of Zellweger syndrome, enfuvirtide for the treatment of Human immunodeficiency virus (HIV) infection; adenosine deaminase (ADA) for the treatment of combined immunodeficiency disease (SCID); CFTR for the treatment of cystic fibrosis; porphobilinogen deaminase (PBDG) for the treatment of acute intermittent porphyria; interferon-beta for the treatment of multiple sclerosis; lipoprotein lipase for the treatment of lipoprotein lipase deficiency (LPLD), p53 for the treatment of cancer; and glutamic acid decarboxylase (GAD) for the treatment of Parkinson's Disease.

In any of the examples of a method of delivering a nucleic acid to a compartmentalized tissue or organ or portion thereof, the nucleic acid molecule encodes a polypeptide that increases muscle production in an animal, increases hair production in an animal, increases wool production in an animal, increases growth of an animal, or is involved in nutrient synthesis or utilization, and the encoded polypeptide is selected from among a polypeptide that increases muscle production in an animal that is a myostatin inhibitor, a polypeptide that increases growth in an animal that is a growth hormone, IGF-1, a growth hormone releasing factor or chicken Ski, and a polypeptide that is involved in nutrient synthesis or utilization that is a serine transacetylase and o-acetylserine sulphydrylase. For example, the myostatin inhibitor is follistatin.

In other examples of a method of delivering a nucleic acid to a compartmentalized tissue or organ or portion thereof, the nucleic agent molecule is selected from among a DNA molecule, a RNA molecule, and an aptamer, including a microRNA, a small interfering RNA, a ribozyme and an antisense nucleic acid. In any of the examples of a method of delivering a nucleic acid to a compartmentalized tissue or organ or portion thereof, the nucleic acid is delivered in a vehicle, such as a lipid vesicle, a virus or a microorganism, where the lipid vesicle is a liposome or micelle and the vehicle is a virus selected from among an adenovirus, an adeno-associated virus (AAV), a retrovirus, vaccinia virus and herpes simplex virus. For example, the retrovirus is a lentivirus, or the virus is an adenovirus, such as an adenovirus having a deletion in an E1, E2a, E2b, E3, or E4 coding region. In other examples, the serotype is adenovirus type 2 or adenovirus type 5. In some examples, the amount of virus administered is from or from about 10 to $1\times10^{12}$ particles, 10 to $1\times10^6$ particles, $1\times10^3$ to $1\times10^{12}$ particles, $1\times10^6$ to $1\times10^{10}$ particles, or $1\times10^7$ to $1\times10^9$ particles; or is from or from about 10 to $1\times10^{12}$ pfu, 10 to $1\times10^6$ pfu, $1\times10^3$ to $1\times10^{12}$ pfu, $1\times10^6$ to $1\times10^{10}$ pfu, or $1\times10^7$ to $1\times10^9$ pfu; or is less than $1\times10^{12}$ particles, $1\times10^{11}$ particles, $1\times10^{10}$ particles, $1\times10^9$ particles, $1\times10^8$ particles, $1\times10^7$ particles, $1\times10^6$ particles, $1\times10^5$ particles, $1\times10^4$ particles, $1\times10^3$ particles or less; or is less than $1\times10^{12}$ pfu, $1\times10^{11}$ pfu, $1\times10^{10}$ pfu, $1\times10^9$ pfu, $1\times10^8$ pfu, $1\times10^7$ pfu, $1\times10^6$ pfu, $1\times10^5$ pfu, $1\times10^4$ pfu, $1\times10^3$ pfu or less.

In any of the methods provided herein, the subject is selected from among a mouse, rat, cow, pig, sheep, goat, horse and human. For example, the subject is a human child under the age of 18 or is a human fetus. In other examples, the subject is a human adult.

The any of the methods provided herein, the method can further include administering the therapeutic composition using an injection device configured for minimally invasive surgery, such as a device containing a syringe and a needle. The method includes inserting the injection device into a port or cannula configured to provide access to the tissue or organ during the minimally invasive surgery and depressing the plunger to inject the fluid into the tissue. The injection device can be any as claimed in U.S. Provisional Application No. 61/863,888. For example, the injection device can be any as provided elsewhere herein.

In any of the examples of the method herein, the method further includes releasing the clamp from the clamped tissue or organ or a portion thereof. For example, the tension of the flexible band can be adjusted by turning the first tensioning wheel towards the distal end of the device, thus increasing the amount of flexible band formed in the closed loop with the biocompatible deformable article, such as a balloon, thereby loosening the flexible band so that the tissue or organ or portion thereof can be removed or released from the device. In embodiments of a method herein employing a device containing an inflatable biocompatible deformable article, such as an inflated balloon, the clamp can released by deflating the balloon and turning the first tensioning wheel towards the distal end of the device to lengthen the flexible band in the closed loop. Releasing the clamp restores communication of the tissue or organ or portion thereof with the systemic circulation. The clamp can be released a predetermined time after administering the nucleic acid molecule, such that the predetermined time is sufficient for the administered nucleic acid molecule to enter parenchymal cells, whereby upon restoration of communication no more than 20% of the delivered agent has not entered a parenchymal cell or no more than 20% of the delivered agent is exposed to the systemic circulation. For example, no more than 15%, 14%, 13%, 12%, 11%, 10%, 9%, 8%, 7%, 6%, or 5% of the delivered agent is exposed to the systemic circulation. In some examples, the predetermined time is 1 minute to 120 minutes after administering the delivered agent. In an exemplary method, the predetermined time is at least or at least about or is or is about 30 minutes after administering the delivered agent.

In any of the examples of the method provided herein, the tissue or organ or a portion of the tissue or organ is selected from among the liver, brain spinal cord, pancreas, heart, skin, kidney, lung, blood vessel, bone, muscle, uterus, cervix, prostate, urethra, and intestine. In an exemplary method, the tissue or organ or portion of the tissue or organ is the liver. Provided herein are methods where the tissue or organ or portion of the tissue or organ is the liver and the predetermined time before restoring communication with the systemic circulation is at least or at least about or is or is about 30 minutes. The method can further include removing the device(s) from the port.

Provided herein is a system for performing a minimally invasive surgery that includes the clamp device for minimally invasive surgery provided herein and an injection device configured to access an endoscopic port for the minimally invasive surgery. In examples of the systems, the injection device is as claimed in U.S. Provisional Application Ser. No. 61/863,888, filed Aug. 8, 2013, entitled "Injection Device for Minimally Invasive Procedures and Uses Thereof", and can be contained in the system provided herein with the band clamp device for minimally invasive surgery provided herein.

For example, the injection device includes a syringe barrel, that provides a fluid reservoir; a plunger configured to be controlled by the operator of the device and to move within the syringe barrel for loading and releasing fluid from the fluid reservoir in the syringe barrel; an injection needle that is operably coupled to the syringe barrel providing a fluid pathway for fluid contained in the syringe barrel to be injected into a target tissue when the plunger is depressed; an elongate sheath that includes an internal lumen that contains the injection needle and has a distal end that contains an opening for the injection needle, so that the sheath is movable around the injection needle; and a controller for positioning the sheath that includes a housing including at least a first and second stop to control exposure of the injection needle and that are provided within the housing at predetermined distance from each other, a central lumen in the housing having a connection member that is configured to be movable in the central lumen in the housing and is coupled to the sheath so that the proximal end of the sheath is coupled to the distal end of the connection member so that movement of the connection member controls movement of the sheath, and a positioner mounted within the housing configured to move forward towards the distal end of the controller and rearward towards the proximal end of the controller between the stops in the housing. The positioner is operatively connected to the connection member to guide movement of the connection member in the same direction so that movement of the positioner forward towards the distal end engages the first stop and moves the sheath to enclose the injection needle inside the lumen of the sheath and movement of the positioner rearward towards the proximal end engages the second stop and moves the sheath to expose no more than a predetermined length of the distal tip of the injection needle through the opening in the injection needle for injection into the tissue. In particular examples of the injection device, the elongate sheath is of a sufficient length and width to reach an organ through an endoscopic port.

BRIEF DESCRIPTION OF THE DRAWINGS

The drawings described herein are for illustrative purposes only of selected embodiments and not all possible implementations, and are not intended to limit the scope of the present disclosure.

FIG. 1A depicts a device containing any biocompatible deformable article. FIG. 1B depicts a device containing a biocompatible deformable article that is an inflatable balloon, where the device further contains a balloon inflation line.

FIG. 3A shows the switch in the down position and the ratchet mechanism in the loosening position which allows the tensioning wheel to rotate clockwise. FIG. 3B shows the switch in the up position and the ratchet mechanism in the tensioning position which allows the tensioning wheel to rotate counter-clockwise.

FIG. 4A shows the balloon deflated and the flexible upper band tensioned so both lay flat on the elongate surface member. FIG. 4B shows the band clamp after the flexible upper band has been payed out to the slack position. The balloon remains deflated and resting on the elongate surface member. FIG. 4C shows the flexible upper band in a tensioned position and the balloon deflated and resting on the elongate surface member. FIG. 4D shows the flexible upper band in a tensioned position and the balloon inflated. FIG. 4E is a view of FIG. 4D at a different angle, illustrating the toothed flexible upper band.

FIG. 5A shows the band in the slack position and the balloon deflated, resting on the elongate surface member. FIG. 5B shows the band in a tensioned position around the target tissue and the balloon deflated, resting on the elongate surface member. FIG. 5C shows the band in the tensioned position around the target tissue and the balloon inflated to conform to the anatomy of the target tissue and fill in void space left after tensioning the upper flexible belt.

FIG. 6A illustrates the device shown in FIG. 1B as it appears before insertion through a laparoscopic port. The balloon is deflated and the flexible upper band is tensioned so it lays flat, both resting on the elongate surface member. FIG. 6B illustrates the device of FIG. 6A after inserting the device through a laparoscopic port, positioning the band tension/loosen switch in the down position and turning the tensioning wheel clockwise to pay out the flexible upper band to the slack position. The balloon remains deflated and resting on the elongate surface member. FIG. 6C shows the device depicted in FIG. 6B, illustrating placement of the closed loop, created by the flexible upper band and elongate surface member, over the target tissue, such as a human adult liver. FIG. 6D depicts the device and target tissue, such as a human adult liver, shown in FIG. 6C, but after turning the sheath adjustment knob to advance the sheath and adjust the length of the loop to the desired size. FIG. 6E depicts the device and target tissue, such as a human adult liver, shown in FIG. 6D with the band tension/loosen switch in the up position, allowing the tensioning wheel to turn counter-clockwise and reduce the size of the loop over the target tissue by tensioning the flexible upper band to the desired position. FIG. 6F is an enlarged view of the band clamp portion of the device shown in FIG. 6E with the balloon inflated to conform to the anatomy of the target tissue.

FIG. 9A shows a perspective view of an exemplary embodiment of an injection device containing a standard syringe at the proximal end of the device. FIG. 9B illustrates connection of the syringe barrel to the needle sheath controller.

FIG. 12A is a birds-eye view showing the positioner positioned towards the distal end so that the needle sheath is in the sheathed position. FIG. 12B is a birds-eye view showing the positioner in an intermediate or middle position with the needle sheath in the transitioning position moving between the sheathed and unsheathed position. FIG. 12C is a birds-eye view showing the positioner position towards the proximal end so that the needle sheath is in the unsheathed position.

FIG. 16A shows the needle sheath in the sheathed position. FIG. 16B shows the needle sheath in the unsheathed position.

FIGS. 17A-17D show enlarged perspective views of the needle sheath in the device shown in FIGS. 9A and 9B. FIG. 17A illustrates the needle sheath in the sheathed position in a windowless needle sheath shaft. FIG. 17B illustrates the needle sheath in the unsheathed position in a windowless needle sheath shaft. FIG. 17C illustrates the needle sheath in the sheathed position in a needle shaft with a visibility window. FIG. 17D illustrates the needle sheath in the unsheathed position in a needle shaft with a visibility window.

FIG. 18A is a sectional view of the needle sheath in the sheathed position. FIG. 18B is a sectional view of the needle sheath in the unsheathed position. FIG. 18C is a perspective view of the needle sheath in the sheathed position. FIG. 18D is a perspective view of the needle sheath in the unsheathed position.

FIG. 19A is a perspective view of the distal end of the device illustrating the syringe adaptor cavity and the syringe adaptor with the dockable syringe in the undocked position. FIG. 19B is a perspective view of the distal end of the device, with the dockable syringe docked onto the syringe adaptor and the needle sheath in the sheathed position. FIG. 19C is a perspective view of the distal end of the device, with the dockable syringe docked onto the syringe adaptor and the needle sheath in the unsheathed position. FIG. 19D is a perspective view of the distal end of the device, with the dockable syringe docked onto the syringe adaptor, the needle sheath in the unsheathed position and the dockable syringe plunger in the depressed position.

Figure 1A:
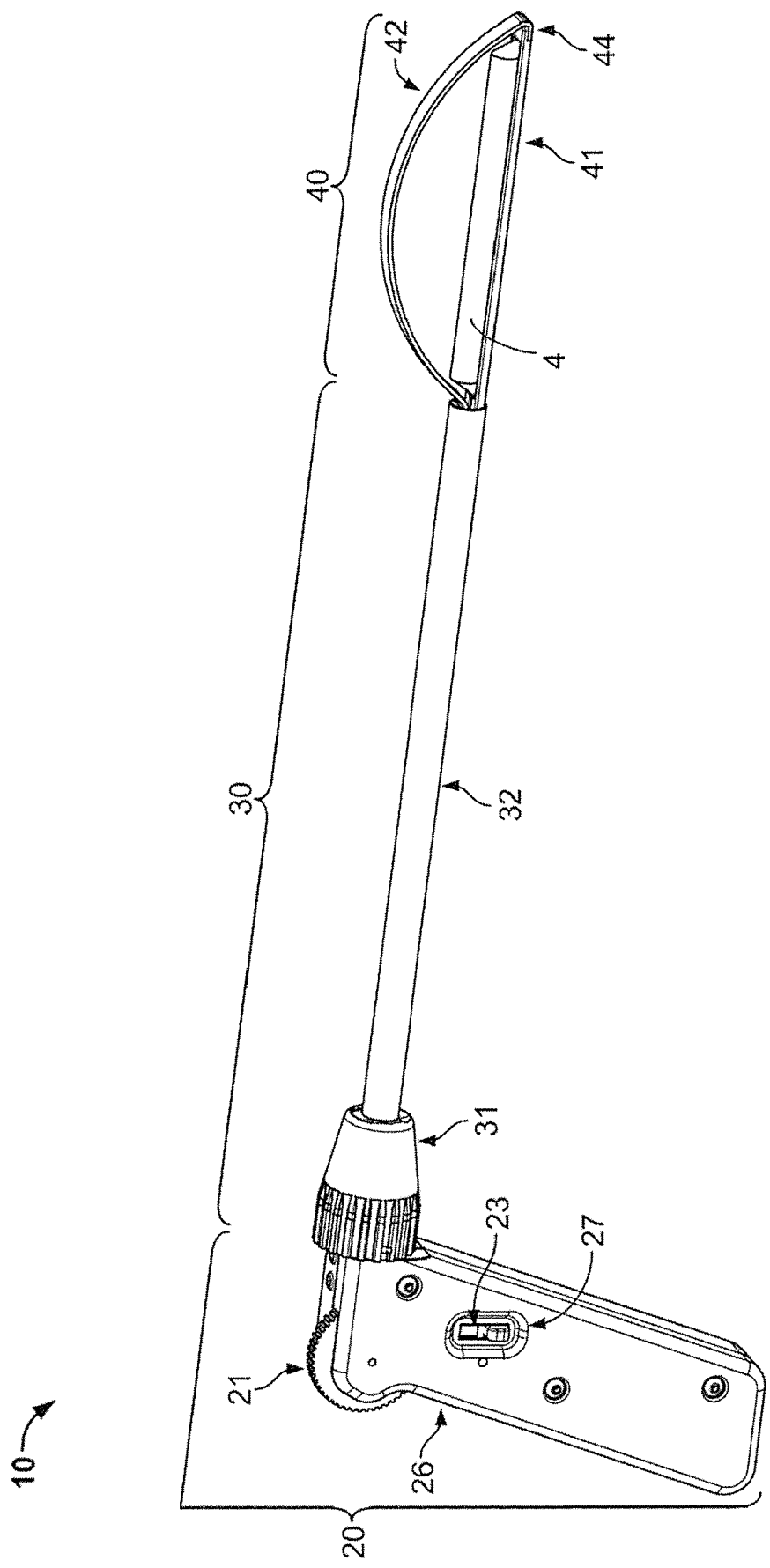
FIGS. 1A and 1B are a side elevational view of a band clamp device according to the description provided herein.

Corresponding reference numerals indicate corresponding parts throughout the several views of the drawings. For parts which are similar but not the same as parts originally specified with a given number, a prime (') of the original numbers is used. A lowercase reference numeral (e.g. a, b, etc.) refers to the same part but in different positions or states.

DETAILED DESCRIPTION

A. Definitions
B. Band Clamp Device
  1. Components of Device
    a. Pistol Grip Handle
    b. Sheath Component
    c. Clamp Portion
      i. Flexible Upper Band
      ii. Biocompatible Deformable Article Balloon
  2. Operation of the Device C. Methods and Uses of Clamp Device
1. Compartmentalized Method of Nucleic Acid Delivery
    a. Compartmentalization of a Tissue or Organ Using the Band Clamp Device
    b. Delivery of a Nucleic Acid Molecule
        i. Parenchymal Injection of Delivered Agent
        ii. Dosages and Amounts
    c. Termination/Release of Compartmentalization
2. Resection and Transplantation
3. Other Procedures
D. Delivered Agents and Compositions Thereof
1. Nucleic Acid Molecule
2. Vehicles and Constructs Containing the Nucleic Acid Molecule
    a. Virus and Viral Vectors
        i. Adenovirus
        ii. Adeno-associated virus (AAV)
        iii. Retrovirus
        iv. Lentivirus
    b. Non-Viral Vectors
3. Exemplary Gene Therapy Agents
4. Compositions
E. Injection Device
1. Standard Injection Device
2. Integrated Injection Device
3. Dockable Injection Device
F. Systems and Kits
G. Examples

A. DEFINITIONS

Unless defined otherwise, all technical and scientific terms used herein have the same meaning as is commonly understood by one of skill in the art to which the invention(s) belong. All patents, patent applications, published applications and publications, Genbank sequences, databases, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

As used herein, reference to a "minimally invasive surgery" or a "minimally invasive procedure," also sometimes referred to as endoscopy, refers to any procedure (surgical or otherwise) that is less invasive than open surgery used for the same purpose. A minimally invasive procedure is carried out through the skin or through a body cavity or anatomical opening. The procedure typically involves use of devices suitable for the procedure, such as arthroscopic devices (for joints and the spine) or laparoscopic devices (for surgeries of abdomen). Minimally invasive procedures can be carried out with indirect observation of the surgical field through an endoscope or large scale display panel, and can involve manual or remote-control manipulation of instruments. Exemplary of a minimally invasive procedure is laparoscopy. Other minimally invasive procedures include, but are not limited to, refractive surgery, percutaneous surgery, arthroscopic surgery, cryosurgery, microsurgery, keyhole surgery, thoracoscopic surgery, endovascular surgery (such as angioplasty), coronary catheterization, stereotactic surgery, image-guided surgery, and ultrasound guided percutaneous ethanol treatment.

As used herein, "laparoscopy" or "laparoscopic surgery" refers to a minimally invasive surgical procedure in which operations in the abdomen are performed through small incisions. The incisions are typically 5 millimeters (mm) to 20 mm in length. One or several incisions are made, and laparoscopic ports, typically 5 mm to 12 mm in diameter, are inserted into the incisions. Laparoscopic surgical instruments are inserted or withdrawn through the laparoscopic ports.

As used herein, "endoscope" refers to an instrument that can be introduced into the body to give a view of its internal parts. A "laparoscope" refers to an instrument that can be introduced into the abdomen to give a view of its internal parts.

As used herein, "endoscopic port" refers to a medical appliance inserted into an incision for a minimally invasive procedure that provides a pathway that allows a minimally invasive device to pass through the skin or body cavity. With reference to laparoscopy, a "laparoscopic port" is a medical appliance inserted into an incision for a laparoscopic procedure that provides a pathway that allows a laparoscopic device to pass through the skin into the abdominal cavity.

As used herein, a device for minimally invasive procedures is a device that is sufficiently long and narrow to permit access to a tissue or organ during minimally invasive procedures.

As used herein, a laparoscopic device is a device that is sufficiently long and narrow to permit access to a tissue or organ during minimally invasive procedures.

As used herein, a clamp refers to a device, such as a surgical device, used to compress a structure, such as an organ, vessel or tissue. A clamp generally has opposing sides or parts that can be mobilized or adjusted to effect pressure or force on opposite sides of a structure in order to compress the structure. A clamp can have serrated jaws, locking handles and/or inflatable balloons. Generally, the clamping force or pressure can be adjusted.

As used herein, "parenchymal clamp" refers to a clamp that can compress the parenchyma of a tissue or organ.

As used herein, a band clamp device refers to a clamp that has an adjustable flexible band and surface member containing a biocompatible deformable article, such as an inflatable balloon, that form opposing sides or parts that can be mobilized or adjusted to effect pressure or force on opposite sides of a structure, such as a tissue or an organ or a portion thereof, in order to compress the structure. The adjustable flexible band can be tensioned to effect force on the structure, while the biocompatible deformable article conforms to the tissue or organ to effect a uniform pressure on the structure. For example, the adjustable flexible band can be tensioned to effect force on the structure and the balloon can be inflated to effect a uniform pressure on the structure. The combination of the flexible band and balloon assures that the clamp is uniformly conformed and compressed around the target structure to effect a uniform clamping pressure. The band clamp device described herein is a closed loop device. The band clamp can be applied to clamp the parenchyma of tissue or organs or portions thereof. For purposes herein, the band clamp device is configured for minimally invasive procedures, such as laparoscopic procedures, and thus contain a narrow and long body that permits access to the body cavity during the procedures. The device can be manually operated outside of the port used for the minimally invasive surgery.

As used herein, clamp portion refers to the portion of a device, such as the band clamp device, that can be mobilized or adjusted to effect pressure or force on opposite sides of a structure in order to compress the structure. For example, the clamp portion of a band clamp device is made up of the flexible band and surface member containing the biocompatible deformable material, such as a balloon. For purposes herein, the clamp portion in the band clamp is a closed loop.

As used herein, closed loop with reference to the band clamp device refers to a clamp having a clamp portion that is a continuous loop without open ends. The clamp, thus, encircles the structure (e.g. a tissue or an organ or a portion thereof) that is being clamped.

As used herein, flexible band refers to a band made of a material that is flexible and can move but that contains sufficient column strength so that the band is able to retain a structure and form a loop. The band can be from materials such as silicones and flexible polymers and can be reinforced with materials to provide column strength, such as fiber. For example, the flexible band can be made of polyurethane or polyethylene, for example polyurethane reinforced with fiber.

As used herein, a biocompatible deformable article refers to an article that exhibits an ability to be deformed, and therefore is able to conform to the anatomy of a tissue or organ or portion thereof when employed in the device provided herein. Such articles typically are made from materials that have a low, low to medium or medium hardness or durometer and that are biocompatible. While exhibiting some ability to deform, the biocompatible deformable article is made of a sufficiently high durometer material so that it exhibits sufficient resistance to deformation upon application of a force and can conform to the anatomy to exert a relatively uniform clamping pressure against a tissue or organ or portion thereof using the device provided herein. For example, the durometer or shore hardness of the material as determined on a Shore A Hardness Scale can be 5 A to 95 A, and generally 10 A to 95 A or 20 A to 95 A, such as 20 A to 85 A, 20 A to 70 A, 20 A to 60 A, 20 A to 50 A, 20 A to 40 A, 30 A to 85 A, 30 A to 70 A, 30 A to 60 A, 30 A to 50 A, 30 A to 40 A, 40 A to 85 A, 40 A to 70 A, 40 A to 60 A, 40 A to 50 A, 50 A to 85 A, 50 A to 70 A, 50 A to 60 A, 60 A to 85 A, 60 A to 70 A or 70 A to 85 A, each inclusive. The material can be elastomeric or non-elastomeric. For example, the biocompatible deformable article can be manufactured from an elastomeric foam, a silicone (e.g. low durometer silicone), elastomer (e.g. low durometer elastomer), a visco-elastic gel, a hydrogel or a non-elastomeric film. Exemplary of such materials include, but are not limited to, polyurethane, polyethylene, polyethylene terephthalate (PET), polyethylene terephthalate glycol-modified (PETG), ethylene vinyl acetate (EVA) or silicone. In particular examples, the biocompatible deformable article is a balloon.

As used herein, reference to a balloon or an inflatable balloon refers to an article that is able to be filled with air or gas to increase its volume to produce an inflated balloon that is deformable so that it is able to conform to the anatomy of a tissue or organ or portion thereof when employed in the device provided herein. While deformable, the balloon, when inflated, is sufficiently resistant to deformation upon application of a force so it can conform to the anatomy and a relatively uniform clamping pressure is able to be exerted against a tissue or organ or portion thereof using the device provided herein. A balloon can be made of elastomeric or non-elastomeric material, such as, but not limited to, polyurethane, polyethylene, flexible polyvinyl chloride (PVC), polyethylene terephthalate (PET), polyethylene terephthalate glycol (PETG), nylon, ethylene vinyl acetate (EVA), ethylene methylacrylate (EMA), ethylene ethylacrylate (EEA), styrene butadiene styrene (SBS), and ethylene propylene diene rubber (EPDM). Typically an inflatable balloon is made of non-elastomeric film material, such as medium durometer (i.e., hardness) materials. A balloon or inflatable balloon can be provided in a device provided herein in inflated or deflated form as described herein.

As used herein, durometer or durometer hardness (also called shore hardness) usually refers to the resistance of materials such as rubber or plastics to deformation, typically to deformation by an indenter of specific size and shape under a known load. Durometer can be measured according to the Share A and D Scales, and Rockwell R Scales. Typically, durometer is measured according to the Shore A Hardness Scale (A), which provides a durometer value (A) on a scale of 0 to 100 with higher values indicating a harder material. As used herein, tensioning with reference to the flexible band refers to the act or process of decreasing the length of the flexible band in the closed loop of the clamp portion in order to apply a force to a tissue or an organ or a portion thereof.

As used herein, "clamp pressure" or "clamping pressure" refers to the force exerted on or against a tissue or organ or portion thereof by the clamp device provided herein. For example, it is the force exerted on the tissue or organ or portion thereof by the combination of the band tension and biocompatible deformable article of the device. The degree of the force or pressure can be controlled or adjusted, for example, by the degree of band tension. In examples of devices containing an inflatable balloon, the pressure also can be controlled by inflation of the inflated balloon, which typically is inflated to conform to the anatomy of the tissue or portion thereof. The combination of the flexible band and biocompatible deformable article, such as balloon, assures that the clamp is uniformly conformed and compressed around the target structure to effect a uniform clamping pressure. Thus, a uniform clamping pressure can be achieved across the clamped area of the tissue, i.e., thick portions are not over-clamped and thin portions are not under-clamped, during a laparoscopic procedure. A uniform clamping pressure insures that no portion of the target tissue is under-clamped or over-clamped. For example, the uniform clamping pressure can allow the blood flow to be cut off across an entire section of target tissue without thicker sections being over-clamped and thinner section being under-clamped, and without trauma to the tissue.

As used herein, a "ratchet" or "ratchet mechanism" refers to a device that allows rotary motion in only one direction while preventing motion in the opposite direction. A ratchet can be any shape or configuration that allows rotary motion of, for example, a round gear or wheel, in only one direction while preventing motion in the opposite direction. For example, the ratchet can be a Y-shape, where the top the ratchet is, for example, two prongs, that form the top of the "Y." Typically, the prongs on the top of the ratchet engage the teeth of the round gear or wheel.

As used herein, loosening with reference to the flexible band refers to the act or process of increasing the length of the flexible band in the closed loop of the clamp portion. The extent of the increase in the length of the flexible band in the loop can partially or completely remove the force applied to the tissue, organ or portion thereof or otherwise free the tissue, organ or portion thereof from force applied from the flexible band.

As used herein, an organ or tissue refers to differentiated parts of the body of a subject that performs a specific function. Tissues generally are a group of specialized cells that group together to form a specialized function. For example, muscle tissue is a specialized tissue that can contract. Organs are made up of tissues that perform a function. Examples of organs, include but are not limited to, the eyes, ears, lungs, liver, kidney, heart, or skin.

As used herein, reference to a "portion of a tissue or organ" refers to part of a tissue or organ of the body of a subject. The part can be a region, segment, lobe, section or other part of a tissue or organ. The portion is generally one that can be mobilized or isolated separate from the rest of the tissue or organ in order to permit clamping of the portion from the rest of the tissue or organ. It also can be a portion that is sufficient to effect delivery of the agent. It is within the skill of one in the art to determine the appropriate size of a portion of a tissue or organ sufficient to clamp and/or to effect delivery of the agent, and it depends upon the particular organ, the indication treated, the dosage, the size of the subject and other parameters. Typically, a portion of a tissue or organ has a volume of at least about 5 mm$^3$, 10 mm$^3$ or more. For example, the portion can be any area of a tissue or organ that has a length ranging from 0.5 cm to 25 cm, a height (or thickness) of 0.5 cm to 20 cm and/or a depth from 0.5 cm to 15 cm. As an example, a portion of a liver lobe or segment is one that has a length of 5 cm to 10 cm, a height of 1 cm to 3 cm and a depth (from the tip) of 1.5 cm to 3 cm. Smaller regions or portions are also contemplated so long as the portion is able to be clamped.

As used herein, "proximal" with reference to a component of the device or the device refers to the end of the component or the device that is closest to the medical professional operating the device during use of the device. It is understood that the proximal portion need not be the end of the component, but includes the entire portion of the component that is closest to the medical professional operating the device during use of the device. For example, with reference to the flexible band, the proximal portion includes the portion that is engaged with the tensioning wheel or can be engaged with the tensioning wheel by virtue of the fact that it hangs freely down from the tensioning wheel.

As used herein, "distal" with reference to a component of the device or the device refers to the end of the device furthest from the medical professional during use of the device.

As used herein, "operably" or "operatively" when referring to two components means that the segments are arranged so that they function in concert for their intended purposes, e.g., movement of one component by another component.

As used herein, "engaged" refers to the condition in which two members that are designed to be contacted or connected are physically contacted to connected to each other in a manner in which they are designed to be contacted or connected. For example, a female and male thread can be engaged when they are physically connected to each other in a manner in which they are designed to be connected.

As used herein, "male" with reference to a thread refers to a member that includes a thread on its outer surface.

As used herein, "female" with reference to a thread refers to a connecting member that includes a thread on its inner surface.

As used herein, elongate with reference to the surface member means that the surface member is long in relation to width or diameter. The elongate structure permits use of the device through ports to access the body cavity in minimally invasive procedures, such as laparoscopic procedures or surgeries.

As used herein, "axial rotation" or "axially" in reference to rotation refer to rotary motion of an object around its own axis.

As used herein, linearly or linear movement refers to motion along a straight line. The movement can be along a line in a horizontal plane or a vertical plane. For example, with reference to the movement of the sheath, the sheath can move in one direction along its horizontal plane either forward towards the distal end of the device or rearward/backward towards the proximal end of the device.

As used herein, mounted with reference to a component or part refers to setting in or attaching to a base, backing or setting. Hence, the component or part projects from the base, backing or setting. The component or part can be completely set upon the base, backing or setting or can be set within the base, backing or setting, so long as a part projects outward from the base, backing or setting and can be accessed.

As used herein, "compartmentalized nucleic acid delivery" refers to delivery of nucleic acid to a compartmentalized tissue or organ or portion thereof.

As used herein, "compartmentalization," "compartmentalized" or grammatical variations thereof, (also referred to herein as circulatory isolation or vasculature isolation) with reference to a tissue or an organ or a portion thereof refers to isolation of a tissue or an organ or a portion thereof from the systemic circulation. The isolation can be achieved by blocking or occluding one or more, and generally all, arteries, veins, ducts or vessels that traverse a tissue or an organ or a portion thereof, and that empty into, access or otherwise communicate with the systemic circulation. Compartmentalization of a tissue or organ is characterized by a stop or arrest of blood flow to the tissue or organ, or a portion or region of the tissue or organ. The compartmentalization disrupts communication or access between and among the tissue and organ, or a portion or region of the tissue or organ, and the rest of the body through the systemic circulation. Compartmentalization can be achieved by any method that blocks or occludes one or more arteries, veins, ducts or vessels, such as by using the band clamp device described herein.

As used herein, recitation that "blood flow to a tissue or an organ or a portion thereof is reduced or eliminated," or similar such language, means that there is an interference or block in blood supply or flow from the arteries, veins, ducts and/or vessels servicing or traversing the tissue or organ or portion thereof, thereby depriving the tissue or a portion of the tissue access to substances carried in the blood. Such block can result in anoxia or ischemia to the tissue or organ or portion of the tissue or organ. It is within the level of a skilled artisan to monitor the reduction or elimination of blood flow to a tissue or organ. For example, reduction or elimination of blood flow can be monitored based on the color of tissue; electron paramagnetic resonance (EPR) oximetry using India ink or other reportable dye; using a Tissue Spectroscope (TiSpec); perfusion magnetic resonance imaging, positron emission tomography, near-infrared (NIR) spectroscopy, optical Doppler tomography, ultrasound and other methods known to a skilled artisan. For purposes of compartmentalized nucleic acid delivery, blood flow to a tissue or organ or a portion of a tissue or organ should be decreased more than 75%, 80%, 85%, 90%, 95% and up to about or 100% during compartmentalization of the tissue or organ or portion thereof.

As used herein, "systemic circulation" or "general circulation" refers to the general circulation that carries oxygenated blood from the left ventricle to the body tissues, and returning venous blood to the right atrium.

As used herein, restoring communication with reference to compartmentalization refers to the process by which compartmentalization of a tissue or an organ or a portion of a tissue or organ is terminated so as to restore or resume access of the systemic circulation with the tissue or organ. This can be achieved by removal or release of the device, apparatus or process used to block or occlude one or more, and generally all, arteries, veins, ducts or vessels that traverse a tissue or an organ or a portion thereof.

As used herein, predetermined time with reference to termination of compartmentalization before restoration of communication with the systemic circulation means a limited time that is known before and can be controlled. Typically, the predetermined time is a time subsequent to administration or delivery of a delivered agent in which at least or about at least 80%, 85%, 90%, 95% or more of the delivered agent is intracellular in cells of the parenchyma of a tissue or organ (e.g. hepatocytes of the liver). Generally, such time is a time in which less than 10%, 5% or less of the delivered agent is present in the systemic circulation upon restoration of communication by termination of the compartmentalization. Such time can be empirically determined by one of skill in the art, and is a function, for example, of the particular target organ and delivered agent. In particular examples, the predetermined time is at least about or 15 minutes, 20 minutes, 25 minutes, 30 minutes, 35 minutes, 40 minutes, 45 minutes, 50 minutes or 60 minutes subsequent to initiation of compartmentalization and/or administration of the delivered agent. The predetermined time can be controlled by methods, mechanism or techniques that increase uptake of a delivered agent by cells. Such methods are known to one of skill in the art and are described herein. Thus, in some examples, the predetermined time can be less than 15 minutes, such as 5 minutes to 15 minutes.

As used herein, "sustained' expression with reference to a delivered nucleic acid molecule refers to the period of time after introduction of the nucleic acid into the organ during which at least 70%, 80%, 85%, 90%, 91%, 92%, 93%, 94%, 95%, 96%, 97%, 98%, 99% or more of the peak expression is observed. Typically, expression is sustained if the encoded protein is expressed over a length of time of greater than 6 months, 7 months, 8 months, 9 months, 10 months, 11 months, 12 months, 16 months, 24 months or more.

As used herein, subject can be a vertebrate, more specifically a mammal (e.g., a human, horse, cat, dog, cow, pig, sheep, goat, mouse, rabbit, rat, and guinea pig), birds, reptiles, amphibians, fish, and any other animal. The term does not denote a particular age or sex. Thus, adult and newborn subjects, whether male or female, are intended to be covered. As used herein, patient or subject may be used interchangeably and can refer to a subject in need of a therapeutic agent. The term patient or subject includes human and veterinary subjects. Both therapeutic, industrial, veterinary and agricultural (e.g., meat production) uses are disclosed herein.

As used herein, a patient refers to a human subject.

As used herein, parenchyma refers to the portions of the tissue and associated cells of an organ that conducts the specific function of the organ and that makes up the bulk of the organ. Hence, the parenchyma is the main underlying functional tissue of an organ. These can include the epithelial tissue, muscle tissue, nervous tissue and associated cells thereof. Parenchyma is distinct from the stroma, which is the connective tissue, blood vessels, nerves and ducts. Hence, parenchyma does not include connective tissue, blood vessels, nerves and ducts. For example, the parenchyma of the liver includes hepatocytes, the parenchyma of the heart includes cardiac muscle cells such as myocytes, the parenchyma of the kidney includes nephrons. The parenchyma of the skin is the epidermis.

As used herein, "parenchymal cells" refers to the cells that are contained in or that make up the parenchyma of a tissue or organ. For example, hepatocytes are cells of the main tissue of the liver, which make up 70-80% of the liver's mass. In the lung, 75% of all lung cells are contained in the parenchyma. These include, for example, fibroblasts of the interstitium and epithelial cells that line that alveoli, such as type 1 and type 2 cells (pneumocytes) and brush cells. In the skin, cells found in the parenchyma include epidermal cells such as keratinocytes. One of skill in the art is familiar with the parenchyma of various tissue and organs and cells therein.

As used herein, parenchymal administration refers to administration to the parenchyma of a tissue or organ. Administration to the parenchyma is typically by injection or capillary diffusion.

As used herein, a composition refers to any mixture. It can be a solution, suspension, liquid, powder, paste, aqueous, non-aqueous or any combination thereof.

As used herein, fluid refers to any composition that can flow. Fluids thus encompass compositions that are in the form of semi-solids, pastes, solutions, aqueous mixtures, gels, lotions, creams and other such compositions. For purposes herein, a fluid generally is injectable.

As used herein, a therapeutic refers to an agent, a product, a compound or a composition that is capable of producing a therapeutic effect. The agent, product, compound or composition can comprise small molecule drugs, prodrugs, proteins, peptides, DNA, RNA, viruses, antibodies, organic molecules, saccharides, polysaccharides, lipids and combinations or conjugates thereof. The agent, product, compound or composition can include other pharmaceutically effective agents known in the general art to be of value in treating one or more of the diseases or medical conditions. Exemplary therapeutics are described herein.

As used herein, therapeutic effect means an effect resulting from treatment of a subject that alters, typically improves or ameliorates the symptoms of a disease or condition or that cures a disease or condition. A therapeutically effective amount refers to the amount of a composition, molecule or compound which results in a therapeutic effect following administration to a subject.

As used herein, "genetic therapy" or "gene therapy" involves the transfer of a nucleic acid molecule, such as heterologous DNA to certain cells, target cells, of a mammal, particularly a human, with a disorder or condition for which such therapy is sought. The DNA is introduced into the selected target cells in a manner such that the heterologous DNA is expressed and a therapeutic product encoded thereby is produced. Alternatively, the heterologous DNA can in some manner mediate expression of DNA that encodes the therapeutic product, it can encode a product, such as a peptide or RNA that in some manner mediates, directly or indirectly, expression of a therapeutic product. Genetic therapy also can be used to deliver nucleic acid encoding a gene product to replace a defective gene or supplement a gene product produced by the mammal or the cell in which it is introduced. The introduced nucleic acid can encode a therapeutic compound (e.g. a growth factor inhibitor thereof, or a tumor necrosis factor or inhibitor thereof, such as a receptor therefore), that is not normally produced in the mammalian host or that is not produced in therapeutically effective amounts or at a therapeutically useful time. The heterologous DNA encoding the therapeutic product can be modified prior to introduction into the cells of the afflicted host in order to enhance or otherwise alter the product or expression thereof.

As used herein, nucleic acid molecule refers to single-stranded and/or double-stranded polynucleotides, such as deoxyribonucleic acid (DNA) and ribonucleic acid (RNA), as well as analogs or derivatives of either RNA or DNA. Also included in the term "nucleic acid" are analogs of nucleic acids such as peptide nucleic acid (PNA), phosphorothioate DNA, and other such analogs and derivatives. Nucleic acids can encode gene products, such as, for example, polypeptides, regulatory RNAs, microRNAs, small inhibitory RNAs (siRNAs) and functional RNAs. Hence, nucleic acid molecule is meant to include all types and sizes of DNA molecules including siRNA, aptamers, ribozymes, complementary DNA (cDNA), plasmids and DNA including modified nucleotides and nucleotide analogs.

As used herein, a therapeutic nucleic acid is a nucleic acid molecule that encodes a therapeutic product or is capable of producing a therapeutic effect. The product can be nucleic acid, such as a regulatory sequence or gene, or can encode a protein that has a therapeutic activity or effect. For example, therapeutic nucleic acid can be a ribozyme, antisense, double-stranded RNA, a nucleic acid encoding a protein and others.

As used herein, "vehicle" refers to the agent or conduit, such as vector or construct, that contains a nucleic acid molecule for gene therapy and that facilitates entry of the nucleic acid molecule into cells and/or expression thereof. Hence, the vehicle containing the nucleic acid is the delivered agent that is administered to a subject and that contains the nucleic acid molecule packaged therein or associated therewith. Examples of vehicles include, but are not limited to, a virus, virus-like particles, mini-circles, a plasmid or vector, a liposome and/or nanoparticle. For example, a vehicle can include a lipid-based or other polymer-based composition, such as liposome, micelle or reverse micelle, that is associated with a nucleic acid molecule or other agent, such as a non-viral vector or virus provided herein, for delivery into a host subject. The uptake of vehicles can be further increased or facilitated using various mechanical techniques such as electroporation, sonoporation or "gene gun."

As used herein, a heterologous nucleic acid (also referred to as exogenous nucleic acid or foreign nucleic acid) with reference to nucleic acid contained in the genome of a virus refers to a nucleic acid that is not normally produced in vivo by an organism or virus from which it is expressed or that is produced by an organism or a virus but is at a different locus, or that mediates or encodes mediators that alter expression of endogenous nucleic acid, such as DNA, by affecting transcription, translation, or other regulatable biochemical processes. Hence, heterologous nucleic acid is often not normally endogenous to an organism or a virus into which it is introduced. Heterologous nucleic acid can refer to a nucleic acid molecule from another virus in the same organism or another organism, including the same species or another species. Heterologous nucleic acid, however, can be endogenous, but is nucleic acid that is expressed from a different locus or altered in its expression or sequence (e.g., a plasmid). Thus, heterologous nucleic acid includes a nucleic acid molecule not present in the exact orientation or position as the counterpart nucleic acid molecule, such as DNA, is found in a genome. Generally, although not necessarily, such nucleic acid encodes RNA and proteins that are not normally produced by the organism or virus or in the same way in the virus in which it is expressed. Any nucleic acid, such as DNA, that one of skill in the art recognizes or considers as heterologous, exogenous or foreign to the virus in which the nucleic acid is expressed is herein encompassed by heterologous nucleic acid. Examples of heterologous nucleic acid include, but are not limited to, nucleic acid that encodes exogenous peptides/proteins, including diagnostic and/or therapeutic agents. Proteins that are encoded by heterologous nucleic acid can be expressed within the virus, secreted, or expressed on the surface of the virus in which the heterologous nucleic acid has been introduced.

As used herein, a DNA construct is a single or double stranded, linear or circular DNA molecule that contains segments of DNA combined and juxtaposed in a manner not found in nature. DNA constructs exist as a result of human manipulation, and include clones and other copies of manipulated molecules.

As used herein, vector (or plasmid) refers to discrete elements that are used to introduce a heterologous nucleic acid into cells for either expression or replication thereof. The vectors typically remain episomal, but can be designed to effect integration of a gene or portion thereof into a chromosome of the genome. Vectors include non-viral vectors, such as non-viral expression vectors. Also contemplated are vectors that are artificial chromosomes, such as yeast artificial chromosomes and mammalian artificial chromosomes. Vectors also include "virus vectors" or "viral vectors." Selection and use of such vehicles are well known to those of skill in the art.

As used herein, an expression vector includes vectors capable of expressing DNA that is operatively linked with regulatory sequences, such as promoter regions, that are capable of effecting expression of such DNA fragments. Such additional segments can include promoter and terminator sequences, and optionally can include one or more origins of replication, one or more selectable markers, an enhancer, a polyadenylation signal, and the like. Expression vectors are generally derived from plasmid or viral DNA, or can contain elements of both. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

As used herein, "virus," refers to any of a large group of infectious entities that cannot grow or replicate without a host cell. Viruses typically contain a protein coat surrounding an RNA or DNA core of genetic material, but no semipermeable membrane, and are capable of growth and multiplication only in living cells. Viruses include those that are formed when, such as when a vector containing all or a part of a viral genome, is transduced into an appropriate cell or cell line for the generation of such particles. The resulting viral particles have a variety of uses, including, but not limited to, transferring nucleic acids into cells either in vitro or in vivo. Thus, a virus is a packaged viral genome. A virus can refer to a single particle, a stock of particles or a viral genome.

As used herein, viral vector refers to a nucleic acid vector construct that includes at least one element of viral origin and can be packaged into a viral vector particle or virus. Reference to viral vector herein is used interchangeably with virus when it is packaged inside a protein coat. The viral vector particles or virus can be used for the purpose of transferring DNA, RNA or other nucleic acids into cells either in vitro or in vivo. Viral vectors include, but are not limited to, retroviral vectors, vaccinia vectors, lentiviral vectors, herpes virus vectors (e.g., HSV), baculoviral vectors, cytomegalovirus (CMV) vectors, papillomavirus vectors, simian virus (SV40) vectors, Sindbis vectors, Semliki Forest virus vectors, phage vectors, adenoviral vectors, and adeno-associated viral (AAV) vectors. Suitable viral vectors are described, for example, in U.S. Pat. Nos. 6,057,155, 5,543,328 and 5,756,086. Viral vectors typically include engineered viruses that are operatively linked to exogenous genes to transfer (as vehicles or shuttles) the exogenous genes into cells.

As used herein, "adenovirus vector" and "adenoviral vector" are used interchangeably and are well understood in the art to mean a polynucleotide containing all or a portion of an adenovirus genome. An adenoviral vector, refers to nucleic acid encoding a complete genome or a modified genome or one that can be used to introduce heterologous nucleic acid when transferred into a cell, particularly when packaged as a particle. An adenoviral vector can be in any of several forms, including, but not limited to, naked DNA, DNA encapsulated in an adenovirus capsid, DNA packaged in another viral or viral-like form (such as herpes simplex, and AAV), DNA encapsulated in liposomes, DNA complexed with polylysine, complexed with synthetic polycationic molecules, conjugated with transferrin, complexed with compounds such as PEG to immunologically "mask" the molecule and/or increase half-life, or conjugated to a non-viral protein.

As used herein, the term "adenovirus" or "adenoviral particle" is used to include any and all viruses that can be categorized as an adenovirus, including any adenovirus that infects a human or an animal, including all groups, subgroups, and serotypes. Depending upon the context reference to "adenovirus" can include adenoviral vectors. There are at least 51 serotypes of adenovirus that are classified into several subgroups. For example, subgroup A includes adenovirus serotypes 12, 18, and 31. Subgroup B includes adenovirus serotypes 3, 7, 11a, 11p, 14, 16, 21, 34, 35 and 50. Subgroup C includes adenovirus serotypes 1, 2, 5, and 6. Subgroup D includes adenovirus serotypes 8, 9, 10, 13, 15, 17, 19, 19p, 20, 22-30, 32, 33, 36-39, 42-49 and 51. Subgroup E includes adenovirus serotype 4. Subgroup F includes adenovirus serotypes 40 and 41. Thus, as used herein an adenovirus or adenovirus particle is a packaged vector or genome. For purposes herein, the viruses typically are recombinant adenoviruses containing a heterologous nucleic acid molecule in its genome and formed when an adenovirus vector is encapsulated in an adenovirus capsid.

Included among adenoviruses are any and all viruses that can be categorized as an adenovirus, including any adenovirus that infects a human or an animal, including all groups, subgroups, and serotypes. Thus, as used herein, "adenovirus" and "adenovirus particle" refer to the virus itself and derivatives thereof and cover all serotypes and subgroups and naturally occurring and recombinant forms, except where indicated otherwise. Included are adenoviruses that infect human cells. Adenoviruses can be wildtype or can be modified in various ways known in the art or as disclosed herein. Such modifications include, but are not limited to, modifications to the adenovirus genome that is packaged in the particle in order to make an infectious virus. Exemplary modifications include deletions known in the art, such as deletions in one or more of the E1a, E1b, E2a, E2b, E3, or E4 coding regions. Other exemplary modifications include deletions of all of the coding regions of the adenoviral genome. Such adenoviruses are known as "gutless" adenoviruses. The terms also include replication conditional adenoviruses, which are viruses that preferentially replicate in certain types of cells or tissues but to a lesser degree or not at all in other types.

As used herein, transduction refers to the transfer of genetic material into cells by a virus.

As used herein, injection device refers to a device that can be used to deliver fluids into the body or its cavities, such as a tissue or an organ or a portion thereof. The device generally contains a hollow barrel or syringe fitted with a plunger and a needle, such as a hollow needle, for penetrating the target. For purposes herein, an injection device is one that can be used for minimally invasive procedures, such as laparoscopic surgeries or procedures.

As used herein, direct injection refers to injections given straight into the target, for example, straight into the tissue or organ or portion thereof.

As used herein, extended with reference to the plunger of an injection device means that the proximal end of the plunger is not in proximity to the syringe barrel, such that the plunger is expanded or increased in length to cover a larger area so that it is able to operably connect with the syringe barrel.

As used herein, "substantially the same" with reference to the length of the exposed needle compared to the distance between sheath stops means that the length and distance are for the most part the same or essentially the same, but can differ slightly in a manner that is not significant. For example, the length of the exposed needle and the distance between sheath stops is substantially the same if the length of the exposed needle is longer or shorter than the distance between the sheath stops by no more than 1 mm, and generally less than 1 mm, 0.8 mm, 0.6 mm, 0.5 mm, 0.4 mm or less.

As used herein, sheath stop with reference to the needle sheath controller refers to an opening or groove formed in the controller to cease or halt or prevent the movement of the sheath. The engagement of the sheath with the stops need not be direct, but can be indirect. For example, the sheath can be operably coupled to a component that itself engages with stop. In examples of the injection device herein, the sheath is connected to a connection member that is connected to a positioner that engages directly with the stop to cease, halt or prevent the movement of the sheath. Hence, the stops lock the sheath from moving. The stops can be positioned at different lengths from each other so that the sheath can be movably locked into more than one position (e.g. the sheathed and unsheathed position).

As used herein, "sheathed" or "the sheathed position" with reference to the injection needle means that the sheath is enclosed over the needle so that the sheath is not extended or exposed outside of the blunt end of the sheath.

As used herein, "unsheathed" or "the unsheathed position" with reference to the injection needle means that the distal tip of the needle is extended or exposed outside of the sheath, and the sheath does not enclose the distal tip of the needle. The extent by which the distal tip of the needle is unsheathed is dependent on the particular device (e.g. sheath stops).

As used herein, axial force refers to force that directly acts on the center axis of an object. The axial force used herein is applied along the longitudinal axis. For example, axial force must be applied to depress or pull back the plunger. Axial force is typically compression force, e.g. depression of a plunger, or a stretching force, e.g. pulling back of a plunger.

As used herein, lumen refers to the inside space of a tubular structure. The tubular structure can have a regular tubular or cylindrical shape, or irregular tubular or cylindrical shape.

As used herein, cavity refers to an empty or hallow space or an opening leading to an empty space within an object.

As used herein, recess refers to an empty or hallow space created by part of an object which is constructed further back from the rest. It can be a hallow space created by walls surrounding the space. For example, a recess can be a groove with openings at one or both ends so that an item can pass through.

As used herein, predetermined length refers to a length that is set by the configuration of the device. Once the device has been constructed and configured, the predetermined length cannot be changed.

As used herein, loading a syringe refers to filling the syringe barrel, the fluid reservoir, with fluid. The syringe barrel is typically loaded or filled by pulling the plunger backward, toward the proximal end of the device.

As used herein, releasing, dispelling, expelling or ejecting a fluid from the syringe refers to emptying the fluid content of the syringe through the distal end of the syringe by depressing the plunger.

As used herein, lining refers to a separate layer of material positioned on the inside surface of an object. For example, if a hallow tubular structure has another hallow tubular structure with a slightly smaller diameter fitted on the inside surface, the inner tubular structure is a lining for the outer tubular structure.

As used herein, integrated describes a part which is physically enclosed or encased with another part. Integrated parts cannot be separated from the part that encases or encloses the integrated part. With reference to the integrated injection device, the syringe barrel is enclosed or encased by the sheath and cannot be separated from the sheath.

As used herein, dockable or detachable describes a part which can be attached, docked, snap-fitted or placed into an adaptor of another part. Dockable parts can be attached docked, snap-fitted or placed into an adaptor in a reversible manner. For example, the part can be undocked or removed, i.e. separated from the part. Hence, the part is not physically bonded to the other part which contains the dock or the adaptor. With reference to the dockable syringe injection device, the syringe can be removed or undocked from the sheath. Likewise, with reference to the standard injection device, the syringe can be detached from the device.

As used herein, dead volume refers to the volume of fluid that is loaded into the syringe barrel but cannot be expelled from the device and remains in the syringe barrel or needle. Factors that influence the amount of dead volume include the length of the needle, the diameter of the needle, and the diameter of the syringe barrel.

As used herein, injection pressure refers to the pressure required to inject the fluid out of the fluid reservoir into the target. Required injection pressure may differ depending on the properties of the composition of the fluid (e.g. viscosity), the length of the needle and the target site (e.g. hardness).

As used herein, pressure drop refers to the decrease in pressure as fluid flows through the fluid path, due to factors such as drag and frictional effect. Factors that can influence pressure drop include length of the needle, the diameter of the needle, and the viscosity of the fluid. If significant pressure drop occurs, the axial force applied to the plunger does not result in sufficient injection pressure at the needle.

As used herein, a combination refers to any association between or among two or more items. The combination can be two or more separate items, such as two compositions or two collections, can be a mixture thereof, such as a single mixture of the two or more items, or any variation thereof. The elements of a combination are generally functionally associated or related.

As used herein, a system is a combination containing two or more items or components that are purposed to be employed together for a common end. For example, the components can be used together in the implementation of a procedure, such as a surgery, for example a minimally invasive procedure or surgery. The components can be manufactured for use together.

As used herein, a kit is a packaged combination or system that optionally includes other elements, such as additional reagents and instructions for use of the combination or elements thereof. Kits optionally include instructions for use.

As used herein, the singular forms "a," "an" and "the" include plural referents unless the context clearly dictates otherwise.

As used herein, the term "or" is used to mean "and/or" unless explicitly indicated to refer to alternatives only or the alternatives are mutually exclusive.

As used herein, ranges and amounts can be expressed as "about" a particular value or range. About also includes the exact amount. Hence "about 5 grams" means "about 5 grams" and also "5 grams." It also is understood that ranges expressed herein include whole numbers within the ranges and fractions thereof. For example, a range of between 5 grams and 20 grams includes whole number values such as 5, 6, 7, 8, 9, 10, 11, 12, 13, 14, 15, 16, 17, 18, 19 and 20 grams, and fractions within the range including, but not limited to, 5.25, 6.72, 8.5 and 11.95 grams.

As used herein, "optional" or "optionally" means that the subsequently described event or circumstance does or does not occur and that the description includes instances where said event or circumstance occurs and instances where it does not.

For clarity of disclosure, and not by way of limitation, the detailed description is divided into the subsections that follow.

B. BAND CLAMP DEVICE

The device described herein is a band clamp device that can be used in minimally invasive procedures, such as laparoscopic procedures, to clamp a tissue or an organ or a portion thereof. The device can be inserted through endoscopic ports, such as laparoscopic ports, and manipulated during minimally invasive procedures (e.g., laparoscopic procedures), and thus can be used during minimally invasive surgeries to cut off the blood flow to a portion of a tissue. The device can be used in any surgery or technique in which clamping of a tissue or an organ or a portion thereof is desired. For example, the device can clamp the tissue or organ or portion thereof to effect compartmentalization of the tissue or organ or a portion of a tissue from the systemic circulation for gene therapy methods involving nucleic acid delivery to a compartmentalized target tissue or portion thereof. The device described herein also can be used in other tissue surgeries, such as transplantation and resection. The device can be used in conjunction with other minimally invasive (e.g., laparoscopic) surgical devices during single-port or multi-port procedures.

The band clamp device is useful for clamping a portion of any tissue or organ. In some cases, the clamping can compartmentalize a portion of the tissue or organ from systemic circulation, depending on the particular tension and pressure applied to the portion of the tissue or organ. The extent of such pressure or force applied is dependent on the particular application. Such tissues or organs include, but are not limited to liver, brain spinal cord, pancreas, heart, skin, kidney, lung, blood vessel, bone, muscle, uterus, cervix, prostate, urethra, or intestine. This list is not intended to be exhaustive, as one of skill in the art will recognize additional target organs and portions thereof. In particular examples, the tissue or organ or portion thereof for use with the band clamp device described herein is the liver or a portion thereof.

As described in further detail below with reference to the accompanying Figures, the band clamp device provided herein contains a handle grip for operation of the device outside of the endoscopic port (e.g., laparoscopic port), a long and extended movable sheath that has a sufficiently small diameter to fit through an endoscopic port (e.g., laparoscopic port) and that terminates in a clamp portion at the distal end of the device. The clamp portion includes a flexible upper band that originates in the handle grip and that traverses through the sheath and is attached at the distal end of the device to the distal end of the elongate surface member that extends the length of the device from the handle. The elongate surface member contains a biocompatible deformable article, such as a balloon, resting on its distal surface so that the connection of the flexible band to the distal end of the elongate surface forms a closed loop with the elongate surface member, and hence the biocompatible deformable article, such as balloon.

The closed loop formed by the elongate surface member, biocompatible deformable article, such as balloon, and flexible upper band form the clamp portion of the device. The clamp portion is adjustable and can fit around a portion of a tissue or organ. In embodiments of the device containing a balloon as described herein, the lower balloon is capable of being inflated and deflated. The opposing flexible upper band and lower biocompatible deformable article, such as balloon, of the clamp portion can be mobilized or adjusted to effect force or pressure on opposite sides of a portion of a tissue or organ. Under a clamping force, the biocompatible deformable article, such as the inflated balloon, can conform to the anatomy to assure even distribution of clamping force to uniformly compress the portion of the tissue or organ that is being clamped. This means that the band-clamp avoids problems of over-clamping and under-clamping of a clamped tissue that occurs with other clamping devices. In addition, embodiments of a device containing a balloon allows the user to precisely control and monitor the clamping force. In other examples, the clamping force can be controlled by the band tension.

For example, the flexible upper band is adjustable to increase (i.e., loosen) or decrease (i.e., tension) the size of the closed loop, thereby permitting a snug fit with any desired portion of a tissue or organ. The movable sheath can be further adjusted linearly, by axial rotation, to alter or adjust the size of the clamp portion so that it fits the portion of the tissue or organ. Because the flexible band and the biocompatible deformable article, such as balloon, resting in the elongate surface member in proximity to the flexible band form a closed-loop, the clamp portion of the band clamp device provided herein can conform to the anatomy of any desired portion of a tissue or organ with tension. The tension can be adjusted by the operator to ensure a snug fit on the tissue or organ without exerting a clamping force that is damaging to the tissue or organ. The adjustability of the flexible upper band and the movable sheath also can accommodate any of a large variety of thickness of tissues.

Moreover, most tissues are not uniform in size (e.g., not uniformly thick throughout the tissue). In particular, the liver, such as an adult human liver, is not uniform in composition throughout, i.e., the thickness of the liver can vary throughout the tissue, thus clamping during a laparoscopic procedure can be difficult. The ability of the biocompatible deformable article to conform to the anatomy of the tissue, such as when band tension is applied, fills in any voids where the tissue otherwise would not be contacted with the clamp portion. For example, in embodiments of the device containing a balloon, the ability to inflate the balloon further conforms the clamp portion to the anatomy of the tissue and fills in any voids in the clamp portion where the flexible band does not perfectly conform. This means that a uniform pressure to the entire portion of the tissue being clamped is achieved. This ensures that the clamp portion is uniformly engaged around the entire portion being clamped and avoids under-clamping or over-clamping of select regions. Thus, the band clamp device described herein can achieve a uniform clamping pressure across the clamped area of the tissue and compartmentalization of the entire portion being clamped, i.e., thick portions are not over-clamped and thin portions are not under-clamped, during a laparoscopic procedure.

The band clamp device described herein can be inserted through an endoscopic port, such as a laparoscopic port, during a minimally invasive procedures. Typically, ports range in size from 3 mm to 15 mm, for example, ports can be up to or about up to 3 mm, 4 mm, 5 mm, 6 mm, 7 mm, 8 mm, 9 mm, 10 mm, 11 mm, 12 mm, 13 mm, 14 mm, or 15 mm in size, i.e., diameter, but can be smaller, e.g., less than 3 mm, or larger, e.g., greater than 15 mm, in some examples. The device described herein is designed to fit within a typical port used for minimally invasive procedures, such as a typical laparoscopic port, for example, a port that is between or between about 3 mm and 15 mm in diameter, typically at least or about at least 5 mm, 10 mm or 12 mm, and generally at least or about at least 10 mm in diameter. For example, the diameter of the portion of the device to be inserted through a port, i.e., the sheath component and clamp portion of the device described herein, can be the same size as the port. For example, the diameter of the portion of the device to be inserted through a port, i.e., the sheath component and clamp portion of the device described herein, can be between or between about 3 mm to 15 mm, for example, the diameter can be up to or up to about 3 mm, 4 mm, 5 mm, 6 mm, 7 mm, 8 mm, 9 mm, 10 mm, 11 mm, 12 mm, 13 mm, 14 mm, or 15 mm, but can be smaller, e.g., less than 3 mm, or larger, e.g., greater than 15 mm, in some examples. Typically, the diameter is at least or about at least 5 mm, 10 mm or 12 mm, and generally at least or about at least 10 mm. In one example, the diameter of the portion of the device to be inserted through a port, i.e., the sheath component and clamp portion of the device described herein, is or is about 10 mm.

The size and dimensions of the individual components of the band clamp device, including the pistol grip handle portion, the sheath component and the clamp portion, can be adjusted to the desired size. For example, the size and dimensions of the band clamp device can be determined based upon one or more considerations, including, but not limited to, the procedure to be performed, the user of the device, and the identity and physical characteristics of the target tissue, and other factors within the level of a skilled artisan. As an example, the size and dimensions of the band clamp device provided herein are generally described with reference to the liver, for example, an adult human liver, but can be adjusted and altered for a band clamp device capable of clamping any tissue or organ.

The band clamp device, including exemplary embodiments of the device, will be described with reference to the accompanying drawings. The band clamp device generally has two ends, the handle end and the clamp end. Unless otherwise noted, the exemplary embodiments of the device described herein are depicted from the "front side," with the clamp end generally toward the right side in the drawings, and the handle end generally toward the left side of the drawing. The clamp end will generally be described as the "distal end" and the handle end will generally be described as the "proximal end." The term "distal end" is intended to refer to the end of the band clamp device furthest from the person holding the device, and the term "proximal end" is intended to refer to the end of the band clamp device closest to the holder of the device. If a component is described to be more "proximal" to another component, the component is closer to the proximal (handle) end. If a component is described to be more "distal" to another component, the component is closer to the distal (clamp) end.

Some components of the band clamp device can rotate or turn clockwise and counter-clockwise. The terms "clockwise" and "counter-clockwise" will be used to describe the direction of the rotation when viewed from the front side of the device. Some components can turn or rotate around an axis. The rotation will be described as "axial rotation" or "axially" with respect to the axis the component is turning or rotating around. The axial movement can be rotation toward the front side of the device and toward the back side of the device. The term "forward rotation" will be used to describe the direction of rotation toward the front side of the device. The term "backward rotation" will be used to describe the direction of rotation toward the back side of the device. Generally, the direction of rotation will be indicated by arrows in the accompanying drawings. Some components can move, advance or retract, linearly. The movement will be described as "linear movement" or "linearly" with respect to the other component the movement is in relation to. The linear movement can be towards the distal end of the device or towards the proximal end of the device. For example, as described below, the linear movement of the sheath can be induced by forward or backward axial rotation, so that the sheath advances or retracts linearly.

1. Components of Device

Figure 1B:
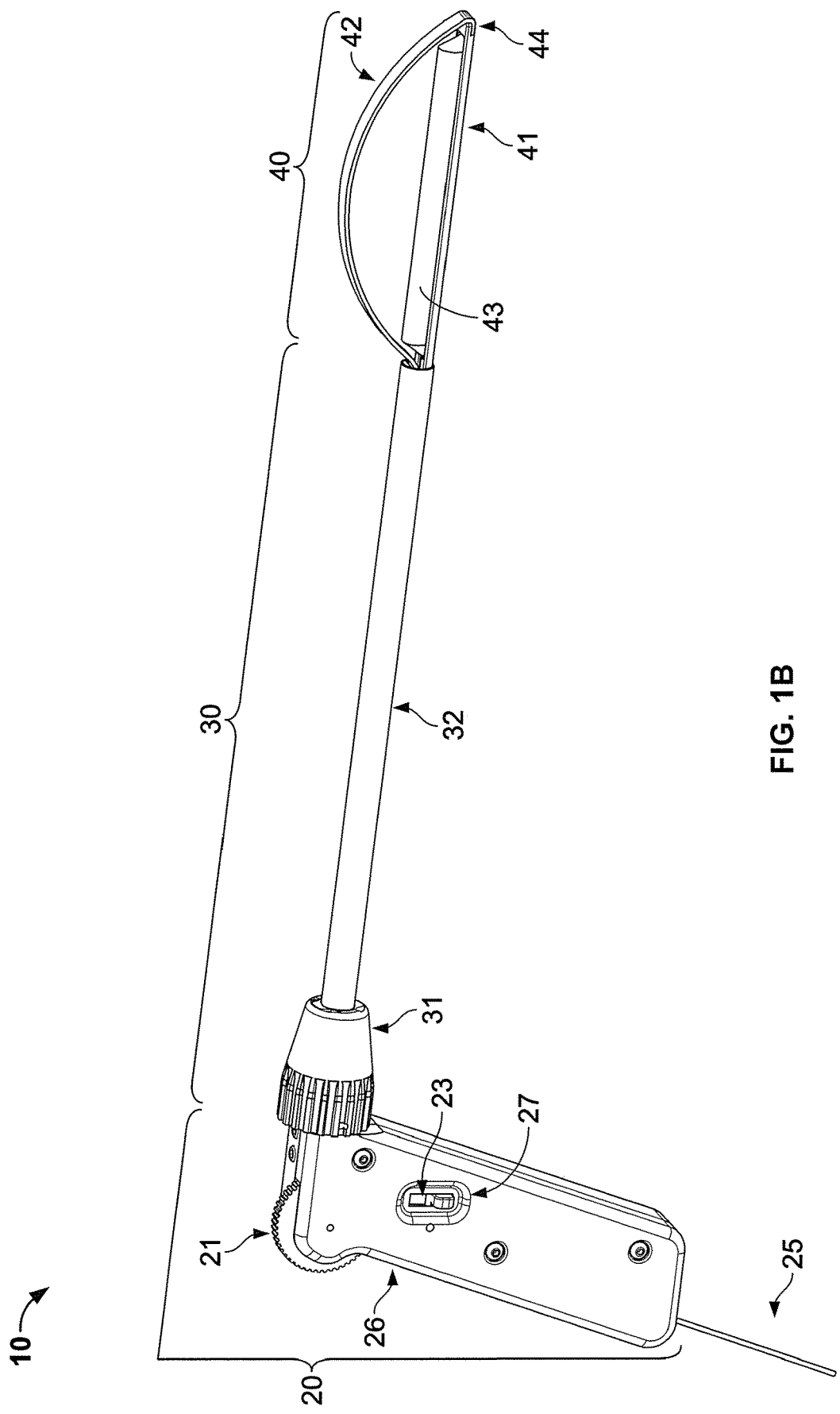

FIGS. 1A and 1B illustrate embodiments of the band clamp device described herein. The band clamp device 10 described herein generally contains a pistol grip handle portion 20, a sheath component 30 and a clamp portion 40. An elongate surface member 41 is connected to the pistol grip handle 20, where it is fixed within the upper portion of case 26 of the pistol grip handle portion 20 (shown in detail in FIGS. 3A and 3B). The elongate surface member 41 can be fixed to the pistol grip handle 20 by any means capable of joining and holding the two components together, for example, the elongate surface member 41 can be fixed to the pistol grip handle 20 with screws, pins, slots, grooves, or mechanical methods, including welding or using an adhesive. In one example, the elongated surface member 41 is affixed to the pistol grip handle 20 with screws.

As shown in FIGS. 1A and 1B, the elongate surface member 41 extends horizontally from the pistol grip handle 20 to the distal end of the device, and serves as the base that connects the sheath component 30 and clamp portion 40 to the pistol grip handle 20. The lumen of the hollow sheath 32 of the sheath component 30 is cylindrical around the elongate surface member 41 and can move linearly with respect to the fixed elongate surface member 41, as is described in detail below in reference to FIG. 6D. The elongate surface member 41 exits out of the distal end of the hollow sheath 32 and extends the length of clamp portion 40 where it forms the base on the clamp portion 40.

Thus, the elongate surface member 41 extends the entire length of the sheath component 30 and clamp portion 40 of band clamp device 10, which is the portion that is inserted into an endoscopic port (e.g., laparoscopic port). The total length of the sheath component 30 and clamp portion 40 is of a sufficient length to permit access to the inside of the body during minimally invasive procedures (e.g., laparoscopic procedures) and access to the target of interest, such as generally a length of 100 mm to 600 mm, such as between or between about 100 mm and 500 mm, generally between or between about 250 mm and 400 mm or 300 mm and 400 mm. For example, the choice of the combined length of the sheath component 30 and clamp portion 40, and hence the elongate surface member 41, is dependent on factors such as the type of procedure to be performed, the tissue or organ to be clamped, or the type of patient, e.g., an adult patient or a child patient, and other factors. A more detailed description of each of the individual components and configurations will be discussed below in reference to particular drawings.

a. Pistol Grip Handle

As illustrated in FIGS. 1A and 1B, the pistol grip handle portion 20 serves as a grip or handle for a user of the band clamp device 10. The dimensions, i.e., length, width and height, of the pistol grip handle 20 can be any dimensions that are sufficient to provide the user with a grip of the band clamp device 10 while also enclosing the internal components that control operation of the band clamp device 10. Typically, the length, i.e., proximal end to distal end, of pistol grip handle 20 is between or between about 15 mm and 50 mm, and generally between or between about 20 mm and 40 mm, for example, about 30 mm. The width, i.e., front side to back side, of the pistol grip handle 20 can be between or between about 10 mm and 40 mm, typically between or between about 15 mm and 30 mm, for example, 20 mm. The height, i.e., top to bottom, can be between or between about 75 mm and 200 mm, typically between or between about 100 mm and 150 mm, for example, 125 mm.

The pistol grip handle 20 includes a case 26 that encloses the internal components that control operation of the band clamp device 10, as depicted in FIGS. 1A and 1B. The case 26 includes an opening 27 that exposes the band tension/loosen switch 23. The band tension/loosen switch 23 can be exposed on both sides of the case 26, i.e., there can be two openings, one on each side of case 26, or the band tension/loosen switch 23 can be exposed only on one side of case 26, i.e., there is one opening in case 26. The opening 27 can be on either or both sides of case 26. For example, the switch 23 can be exposed on both sides of case 26 to allow the operator of the device 10 flexibility in controlling and operating the device, e.g., the operator can use either the left hand or the right hand to access the switch 23. The band tension/loosen switch 23 is movable and is capable of moving up and down, i.e., to an up position and a down position (see FIGS. 3A and 3B).

The case 26, as shown in FIGS. 1A and 1B, encloses the internal components of the band clamp device 10. The case 26 can be made of a hard plastic material, such as an injection molded plastic. For example, the plastic can be any type that can be injection molded, for example, any thermoplastic or thermosetting polymer, including, but not limited to acrylics (i.e., poly(methyl methacrylate) (PMMA)), polyethylenes, polypropylenes, polystyrenes, acrylonitrile butadiene styrene (ABS) and polycarbonates. The case 26 can be made of a metal. The case 26 includes a front side and a back side. The front side and back side of case 26 can be made up of one continuous component, i.e., piece. The front side and back side of case 26 can be made up of two separate components, i.e., pieces. In one example, the front side and back side of case 26 are made up of two separate components, for example, two pieces of a plastic material. The two components, i.e., pieces, can be closed and affixed to one another to enclose the internal components located in the pistol grip handle portion 20. The two components can be affixed to one another by any means capable of joining and holding the two components together, for example, the two components, i.e., pieces, can be screwed together, glued together, heat-sealed, welded together, or molded together along a seam to form the case 26.

Figure 2:
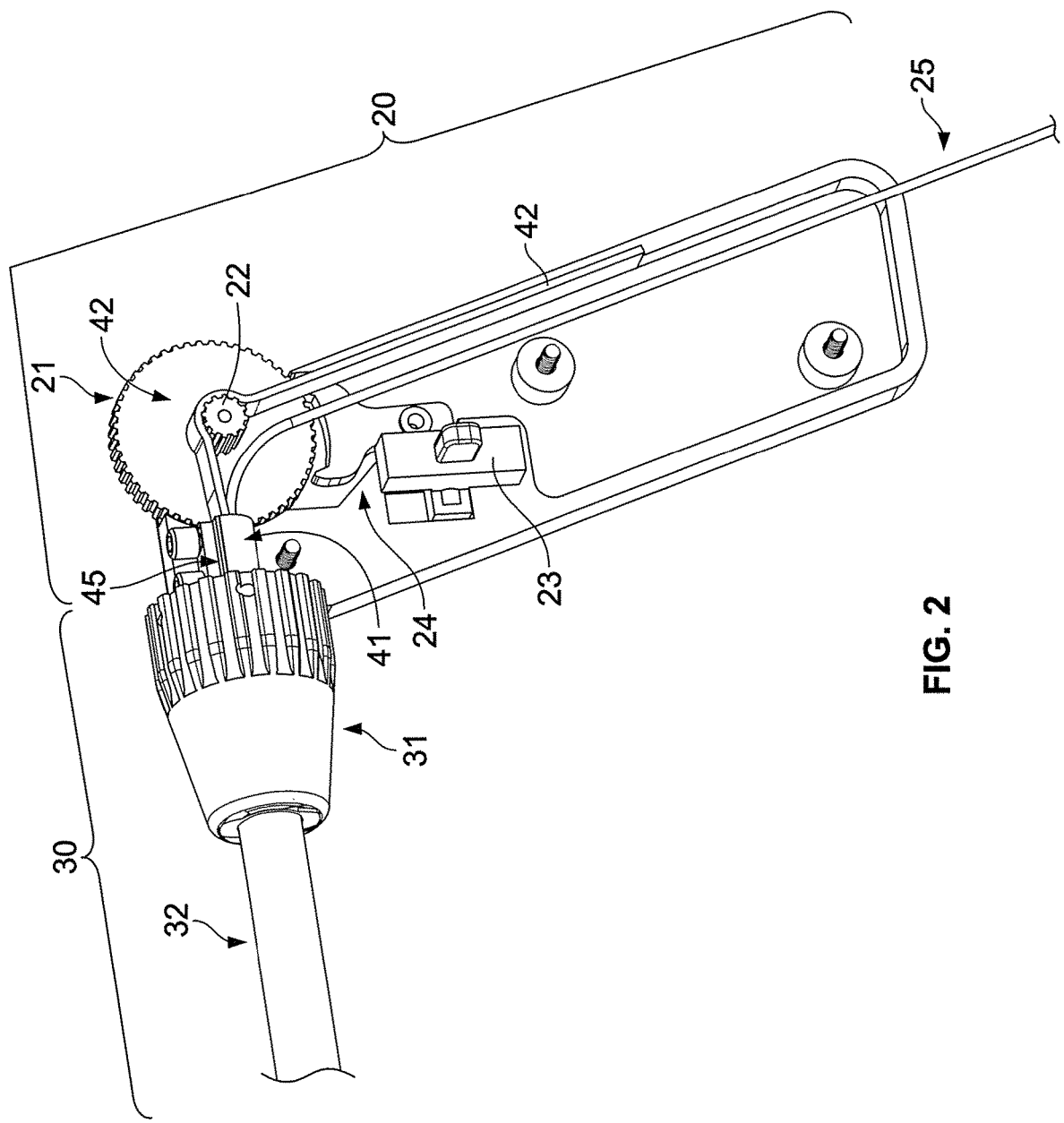
FIG. 2 is an enlarged cutaway view of the pistol grip handle and sheath component shown in FIGS. 1A and 1B, illustrating the internal components of the device that are housed under the case.

FIG. 2 shows an enlarged cutaway view of the pistol grip handle 20 and the coupling with the sheath adjustment knob 31 and sheath 32 of sheath component 30, as shown in FIGS. 1A and 1B. The cutaway view of FIG. 2 illustrates the internal components of the pistol grip handle portion 20 of the band clamp device 10 as they appear under the case 26.

As shown in FIG. 2, the proximal end of the flexible upper band 42 is enclosed within the inside of the pistol grip handle portion 20 of band clamp device 10. A portion of the flexible upper band 42 curves around and is engaged with a second band tensioning wheel 22, while the proximal end of the flexible upper band 42 hangs freely in the inside of the pistol grip handle portion 20. For example, the proximal end of the flexible upper band 42 is not attached inside the pistol grip handle portion 20 to allow movement, i.e., tensioning or loosening, of the flexible upper band 42. The distal portion of the flexible upper band 42 rides in and is guided by cradle 45 of the elongate surface member 41 as the flexible upper band 42 and the elongate surface member 41 extend horizontally into the proximal end of the hollow sheath adjustment knob 31. The flexible upper band 42 continues through the sheath adjustment knob 31 and extends the length of the hollow sheath 32, extending out into the clamp portion 40 (as shown in FIGS. 1A and 1B).

With reference to description of the flexible band below, the total length of flexible upper band 42, i.e., the length of flexible upper band 42 that is enclosed within the pistol grip handle portion 20, extends through the sheath 32 and extends into the clamp portion 40, is at least as long as the amount of flexible upper band 42 needed to engage the second band tensioning wheel 22, plus the length of the sheath component 30 and clamp portion 40 plus the length of flexible upper band 42 that can be loosened or payed out of the hollow sheath 32 to form a loop large enough to place over the target tissue (described in more detail below in reference to FIG. 6B). Generally, the total length of flexible upper band 42 is between or between about 200 mm and 1000 mm, and typically between 300 mm and 800 mm, for example, between 400 mm and 600 mm, but can be longer or shorter depending on the size of the device and size of the tissue to be clamped. In one example, the total length of flexible upper band 42 is at least 450 mm long when the target tissue requires a loop that is 3 cm to 4 cm large and the length of the sheath component 30 and clamp portion 40 are or are about 400 mm long.

As FIG. 2 illustrates, a first band tensioning wheel 21 and second band tensioning wheel 22 are positioned at the top of the inside of the pistol grip handle 20. The first band tensioning wheel 21 is partially enclosed within the inside of the pistol grip handle 20 and the second band tensioning wheel 22 is completely enclosed within the inside of the pistol grip handle 20, i.e., no portion of the second band tensioning wheel 22 is external to the pistol grip handle 20. The remaining portion of the first band tensioning wheel 21 projects out of the pistol grip handle 20 and is not enclosed within the pistol grip handle 20.

The first band tensioning wheel 21 is coupled to the second band tensioning wheel 22. The first band tensioning wheel 21 and the second band tensioning wheel 22 are coupled together at or near the center of the first band tensioning wheel 21. The first band tensioning wheel 21 and second band tensioning wheel 22 can be coupled together by any means capable of fixing the two wheels together, for example the wheels can be fused together, screwed together, glued together, heat-sealed, welded together, or molded together. The first and second band tensioning wheels, 21 and 22, respectively, are movable and move in relation to each other, i.e., the first band tensioning wheel 21 and second band tensioning wheel 22 do not move independently of each other. The first and second band tensioning wheels, 21 and 22, respectively, can be turned, or rotated, clockwise and counter-clockwise. Rotation of the first band tensioning wheel 21 simultaneously rotates the second band tensioning wheel 22 and engages the flexible upper band 42 that rests on the second tensioning wheel 22.

As illustrated in FIG. 2, the outer edges of both the first band tensioning wheel 21 and the second band tensioning wheel 22 can be toothed. The outer edge of the first band tensioning wheel 21 can be toothed, for example, to provide traction for the user when rotating the first band tensioning wheel 21, such as when rotating the first band tensioning wheel 21 clockwise or counter-clockwise. The outer edge of the second band tensioning wheel 22 can be toothed, for example, to engage and move the flexible upper band 42 that rests on the second band tensioning wheel 22, such as when the first and second band tensioning wheels, 21 and 22, respectively, are simultaneously rotated, e.g., clockwise or counter-clockwise. For example, as discussed earlier, the flexible upper band 42 can be toothed, such as having teeth that are set width-wise or length-wise across the flexible upper band 42. The distance between each individual tooth, i.e., the tooth gap, of the flexible upper band 42 can be a complementary distance, e.g., the same tooth gap, as the teeth of the second band tensioning wheel 22. For example, when the teeth of the flexible upper band 42 are set width-wise and the tooth gap of the flexible upper band 42 is complementary, e.g., the same, as the tooth gap of the second band tensioning wheel 22, the teeth of the second band tensioning wheel 22 can engage the teeth of the flexible upper band 42, thus holding the flexible upper band 42 in place over the second band tensioning wheel 22 as the band 42 curves around second band tensioning wheel 22, and causing the flexible upper band 42 to move when the first and second band tensioning wheels, 21 and 22, respectively, are simultaneously rotated.

Generally, as depicted in FIG. 2, the first band tensioning wheel 21 is larger in diameter than the second band tensioning wheel 22. The first band tensioning wheel 21 can have a diameter of between or between about 20 mm and 50 mm, such as between or between about 25 mm and 45 mm, or 30 mm and 40 mm, but can be larger or smaller if desired. The second band tensioning wheel 22 can have a diameter of between or between about 5 mm and 30 mm, such as between or between about 5 mm and 25 mm, or 10 mm and 20 mm, but can be larger or smaller if desired. In some embodiments, the ratio of size of the first band tensioning wheel 21 to the second band tensioning wheel 22 is or is about 10:1, 9:1, 8:1, 7:1, 6:1, 5:1, 4:1, 3.3:1, 3:1, 2:1, 1.5:1 or 1:1 or less. Generally, the ratio and diameters of the first band tensioning wheel 21 and second band tensioning wheel 22 are determined to provide the operator of the device 10 with a mechanical advantage between the force applied by the operator's thumb and the band tension (of the flexible upper band 42). For example, the size of the larger first band tensioning wheel 21 can be determined by ergonomics and the ratio between the first band tensioning wheel 21 and second band tensioning wheel 22 can be determined by the desired amount of tensioning of the flexible upper band 42 per ratchet click, as described below in reference to FIGS. 3A and 3B below. In one example, the ratio between the diameters of the first band tensioning wheel 21 and second band tensioning wheel 22 is 3.3:1. In another example, the first band tensioning wheel 21 has a diameter of 33 mm and the second band tensioning wheel 22 has a diameter of 10 mm.

FIG. 2 illustrates the location of the band tension/loosen switch 23 and ratchet mechanism 24. The band tension loosen switch 23 and ratchet mechanism 24 work together to control the direction the first band tensioning wheel 21 is able to rotate, e.g., clockwise or counter-clockwise. The clockwise and counter-clockwise rotation of the first band tensioning wheel 21 in turn controls the flexible upper band 42 as it is payed out, i.e., loosened, and taken in, i.e., tensioned, respectively, as described in detail in reference to FIGS. 6B and 6E.

As depicted in FIG. 2, the band tension/loosen switch 23 is positioned beneath the first band tensioning wheel 21 at or near the center of the pistol grip handle 20. Switch 23 protrudes out through an opening on each side of the case 26, or on only one side, and can be accessible on either side or both sides of case 26, as described above in reference to FIGS. 1A and 1B. The band tension/loosen switch 23 can be moved up or down, such as manually moved up or down, for example, by the user of band clamp device 10.

Ratchet mechanism 24 is located directly beneath the first band tensioning wheel 21, as seen in FIG. 2. As will be described in more detail below in reference to FIGS. 3A and 3B, moving the band tension/loosen switch 23 into the up or down position simultaneously moves the ratchet mechanism 24 into the tensioning and loosening positions, respectively. The ratchet mechanism 24 can be a Y-shape or any shape that can contact, i.e., touch, both the first band tensioning wheel 21 and the band tension/loosen switch 23 when the band tension/loosen switch 23 is moved into the up or down position. For example, the bottom of the ratchet mechanism 24 can contact, i.e., touch, the band tension/loosen switch 23, while the top of the ratchet mechanism 24 can contact, i.e., touch, the bottom of the first band tensioning wheel 21. The bottom of the Y-shaped ratchet mechanism 24 rests against the side of switch 23 and can be moved, i.e., shifted, by moving switch 23 up or down, as described in detail in reference to FIGS. 3A and 3B, below. The top of the Y-shaped ratchet mechanism 24 ends in two prongs. The top of each prong can contact, i.e., touch, the bottom of the first band tensioning wheel 21, depending on the position of the band tension/loosen switch 23. The prongs can be any size that can be positioned, i.e., lodged, between the teeth of the first band tensioning wheel 21 when the ratchet mechanism 24 is in the tensioning or loosening position, as described below in reference to FIGS. 3A and 3B. The proximal side (with respect to the switch 23) of the lower portion of the Y-shaped ratchet mechanism 24 can have one or more grooves or notches that the band tension/loosen switch 23 can fit into when switch 23 is moved into the up or down positions, as can be seen in detail in FIGS. 3A and 3B.

Figure 3A:
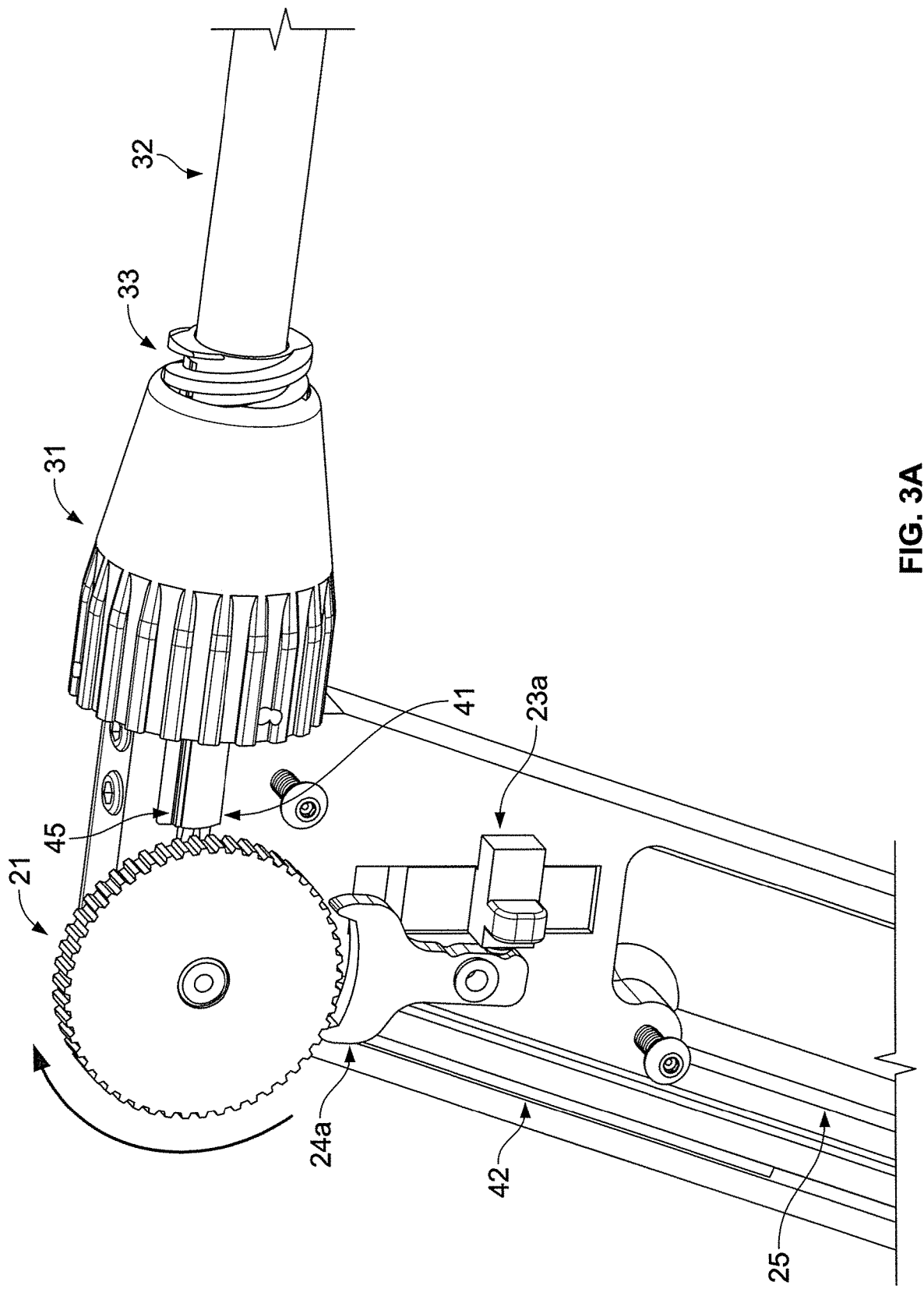
FIGS. 3A and 3B are enlarged views of the switch, ratchet mechanism and large tensioning wheel shown in FIG. 2.
Figure 3B:
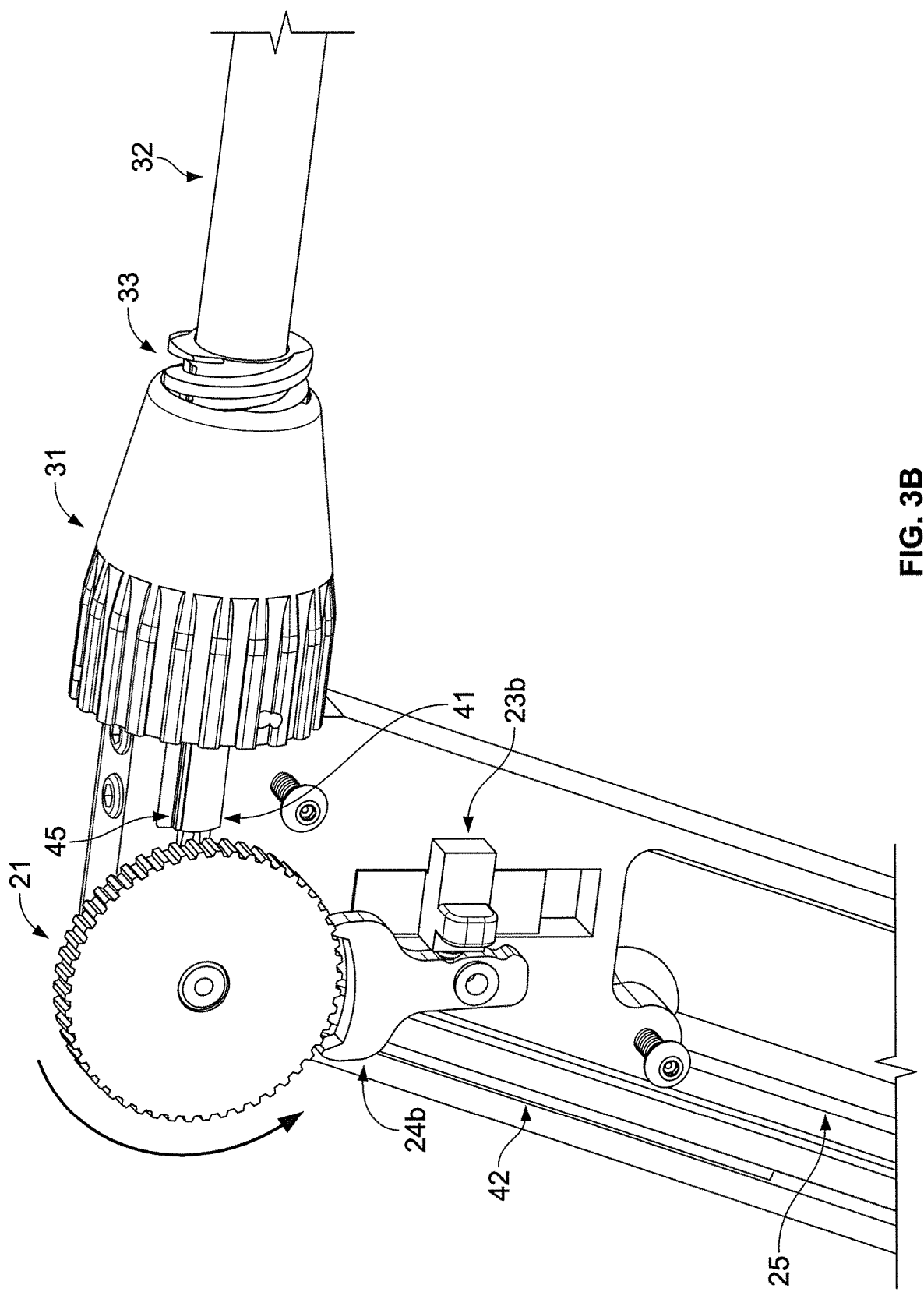

FIGS. 3A and 3B are enlarged cutaway views of the pistol grip handle portion 20 shown in FIGS. 1A and 1B and FIG. 2, illustrating the relationship between the first band tensioning wheel 21, the ratchet mechanism 24 (24a and 24b) and the band tension/loosen switch 23 (23a and 23b). The positions of the band tension/loosen switch 23 (23a and 23b) and ratchet mechanism 24 (24a and 24b) control the direction (i.e., clockwise or counter-clockwise) the first band tensioning wheel 21 is able to rotate, thus controlling the movement of the flexible upper band 42 (i.e., loosening or tensioning). The extent the flexible upper band 42 can be tensioned or loosened by rotating the first band tensioning wheel 21 can be determined by the amount of flexible upper band 42 that is payed out or taken in per click of the ratchet mechanism, where a click describes the movement of a tooth of the first band tensioning wheel 21 over a prong of the Y-shaped ratchet mechanism 24. For example, the amount of flexible upper band 42 that can be payed out or taken in per ratchet click can be between or between about 0.1 mm and 1 mm, generally between 0.25 mm and 0.75 mm, typically about 0.5 mm, but can be more or less, if desired.

The band tension/loosen switch 23 (23a and 23b) can be moved up or down to simultaneously move the Y-shaped ratchet mechanism 24 (24a and 24b) into the tensioning or loosening positions, respectively. For example, the top of one prong of the Y-shaped ratchet mechanism 24a, e.g., the prong that is farther from the switch 23, can contact, i.e., touch, the bottom of the first band tensioning wheel 21 when the switch 23a is in the down position and the top of the other prong of the Y-shaped ratchet mechanism 24b, e.g., the prong that is closer to the switch 23, can contact, i.e., touch, the bottom of the first band tensioning wheel 21 when the switch 23b is in the up position, as is described below).

FIG. 3A shows the positions of the first band tensioning wheel 21, the ratchet mechanism 24a and the band tension/loosen switch 23a in relation to each other when switch 23a is in the down position. Switch 23a in the down position contacts the bottom portion of ratchet mechanism 24a, placing, or moving, ratchet mechanism 24a into the loosening position. When ratchet mechanism 24a is in the loosening position, the ratchet mechanism 24a is positioned such that the bottom portion of ratchet 24a is pushed away from switch 23a (i.e., toward the proximal (handle) end of band clamp device 10) and the upper portion of the Y-shaped ratchet 24a is pushed toward switch 23a (i.e., toward the distal (clamp) end of band clamp device 10). In the loosening position, the top of the prong that is farther from the switch 23 contacts, i.e., touches, the bottom of the first tensioning wheel 21. This allows the first tensioning wheel 21 to be rotated clockwise and prevents counter-clockwise rotation. The prong will lift off the teeth of the first band tensioning wheel 21 as it is moving clockwise, but bind against the teeth of the wheel 21 in the reverse (i.e., counter-clockwise) direction. For example, the top of the prong that is farther from the switch of the Y-shaped ratchet mechanism 24a can be positioned, i.e., lodged, between two teeth on the bottom of the first band tensioning wheel 21, thus preventing counter-clockwise rotation. Rotation of the first band tensioning wheel 21 clockwise similarly rotates the coupled second tensioning wheel 22 clockwise (shown and described above in reference to FIG. 2). The clockwise rotation of the first and second band tensioning wheels 21 and 22, respectively, pays out, or loosens the flexible upper band 42 that is engaged with the second band tensioning wheel 22. For example, the clockwise rotation of the first and second band tensioning wheels, 21 and 22, respectively, pays out the flexible upper band 42 through hollow sheath 32 and into the clamp portion 40 (as shown and described below in reference to FIG. 4B).

FIG. 3B shows the positions of the first band tensioning wheel 21, the ratchet mechanism 24b and the band tension/loosen switch 23b in relation to each other when switch 23b is in the up position. Switch 23b in the up position contacts the middle portion of the ratchet mechanism 24b, placing, or moving, ratchet mechanism 24b into the tensioning position. When ratchet mechanism 24b is in the tensioning position, the ratchet mechanism 24b is positioned such that the bottom portion of ratchet 24b is pushed toward switch 23b (i.e., toward the distal (clamp) end of band clamp device 10) and the upper portion of the Y-shaped ratchet 24b is pushed away from switch 23b (i.e., toward the proximal (handle) end of band clamp device 10). In the tensioning position 24b, the top of the prong that is closer to the switch 23 contacts, i.e., touches, the bottom of the first tensioning wheel 21. This allows the first tensioning wheel 21 to be rotated counter-clockwise and prevents clockwise rotation. The prong will lift off the teeth of the first band tensioning wheel 21 as it is moving counter-clockwise, but bind against the teeth of the wheel 21 in the reverse (i.e., clockwise) direction. For example, the top of the prong that is closer to the switch of the Y-shaped ratchet mechanism 24b can be positioned, i.e., lodged, between two teeth on the bottom of the first band tensioning wheel 21, thus preventing clockwise rotation. Rotation of the first tensioning wheel 21 counter-clockwise similarly rotates the coupled second band tensioning wheel 22 counter-clockwise (shown and described above in reference to FIG. 2). The counter-clockwise rotation of the first and second band tensioning wheels 21 and 22, respectively, takes in, or tensions the flexible upper band 42 that is engaged with the second band tensioning wheel 22 (as described above in reference to FIG. 2). For example, the counter-clockwise rotation of the first and second band tensioning wheels, 21 and 22, respectively, takes in, i.e., tensions, the flexible upper band 42 through hollow sheath 32 from the clamp portion 40 (as shown and described below in reference to FIG. 4C).

b. Sheath Component

As mentioned above, the pistol grip handle 20 is coupled to the sheath component 30 by elongate surface member 41 that is fixed to the upper distal portion of the pistol grip handle 20 (as shown in FIGS. 1A and 1B) and extends the entire length of the sheath component 30 and clamp portion 40. The elongate surface member can be flexible or rigid. Generally, the elongate surface member 41 is rigid so that it is stiff and inflexible and can be made of any material that will not bend, such as a metal or rigid plastic. For example, the elongate surface member 41 can be made of a metal, such as brass, stainless steel, titanium or aluminum, or can be made of a rigid plastic, such as glass filled nylon. In one example, the elongate surface member 41 is made of brass. In another example, the elongate surface member 41 is made of stainless steel.

The elongate surface member 41 can be flat or grooved. For example, with reference to FIGS. 2, 3A, 3B, 4B and 4C, the elongate surface member 41 can be concave and having a cradle 45 running down the middle of the elongate surface member 41. In one example, the elongate surface member 41 has a cradle 45 running down the center for the entire length of the elongate surface member 41, i.e., the length of elongate surface member 41 that extends through the sheath component 30 and clamp portion 40 (as shown in detail in FIGS. 2, 3A, 3B, 4B and 4C). The cradle 45 of the elongate surface member 41 can be used, for example, to stabilize, i.e., keep in place, the flexible upper band 42 resting on the elongate surface member 41 in the sheath component 30 and clamp portion 40 of device 10 and. In embodiments of the device containing a biocompatible deformable article that can be inflated, such as an inflatable balloon, the cradle 45 of the elongate surface member 41 also can keep in place the balloon inflation line 25 and balloon 43 resting on the elongate surface member 41 in the sheath component 30 and clamp portion 40, respectively.

As shown in FIGS. 1A and 1B, the elongate surface member 41 extends from the distal end of sheath 32 to form the lower segment of the clamp portion 40 of device 10. A segment of elongate surface member 41, i.e., the segment of elongate surface member connected to the pistol grip handle 20 and that extends distally from the pistol grip handle 20, is enclosed by sheath 32, a hollow, cylindrical shaft that extends the length of the sheath component 30. Sheath 32 extends distally from the sheath adjustment knob 31 (discussed further below), terminating at the proximal end of the clamp portion 40.

Sheath 32 is coupled to the pistol grip handle 20 through the sheath adjustment knob 31. The sheath adjustment knob 31 is an adjustable knob that is a hollow cylinder and has openings at both ends, i.e., the proximal end and the distal end, to accommodate the pistol grip handle 20 and hollow sheath 32, respectively. The proximal opening of sheath adjustment knob 31 is coupled to the pistol grip handle 20. The sheath adjustment knob 31 can be coupled to the pistol grip handle 20 by any means that also allows the sheath adjustment knob 31 to rotate axially and freely around the sheath 32 when turned or rotated, e.g., rotated forwards or rotated backwards. For example, a pin or screw can be inserted into the sheath adjustment knob 31 that can ride in a corresponding groove in the pistol grip handle 20. In another example, the inner surface of the sheath adjustment knob 31 can be fitted with a ring that can engage a corresponding groove in the pistol grip handle 20. The distal opening of sheath adjustment knob 31 is coupled to the proximal end of sheath 32. The proximal end of sheath 32 can be screwed into the distal opening of sheath adjustment knob 31 via the screw mechanism 33 of the sheath (as shown in FIGS. 3A and 3B). For example, the inner surface of sheath adjustment knob can be threaded, for example, with female threads, and the outer surface of the proximal end of sheath 32 can be threaded with complimentary threads, for example, with male threads of the screw mechanism 33.

The openings on either end of the sheath adjustment knob 31 can be any size, i.e., diameter, that is large enough to accommodate the pistol grip handle 20 on the proximal end and the sheath 32 on the distal end. For example, when sheath 32 has a diameter of 10 mm, the distal opening of sheath adjustment knob 31 is slightly larger than 10 mm. The sheath adjustment knob 31 can be axially rotated and can be turned, or rotated, to control movement of sheath 32, as described below in reference to FIG. 6D.

The sheath adjustment knob 31 typically is made of a hard plastic material, such as an injection molded plastic. For example, the plastic can be any type that can be injection molded, for example, any thermoplastic or thermosetting polymer, including, but not limited to acrylics (i.e., poly (methyl methacrylate) (PMMA)), polyethylenes, polypropylenes, polystyrenes, acrylonitrile butadiene styrene (ABS) and polycarbonates. The proximal outer surface of sheath adjustment knob 31 can be notched, or ridged, to form a grip portion on knob 31 for the user.

Figure 6A:
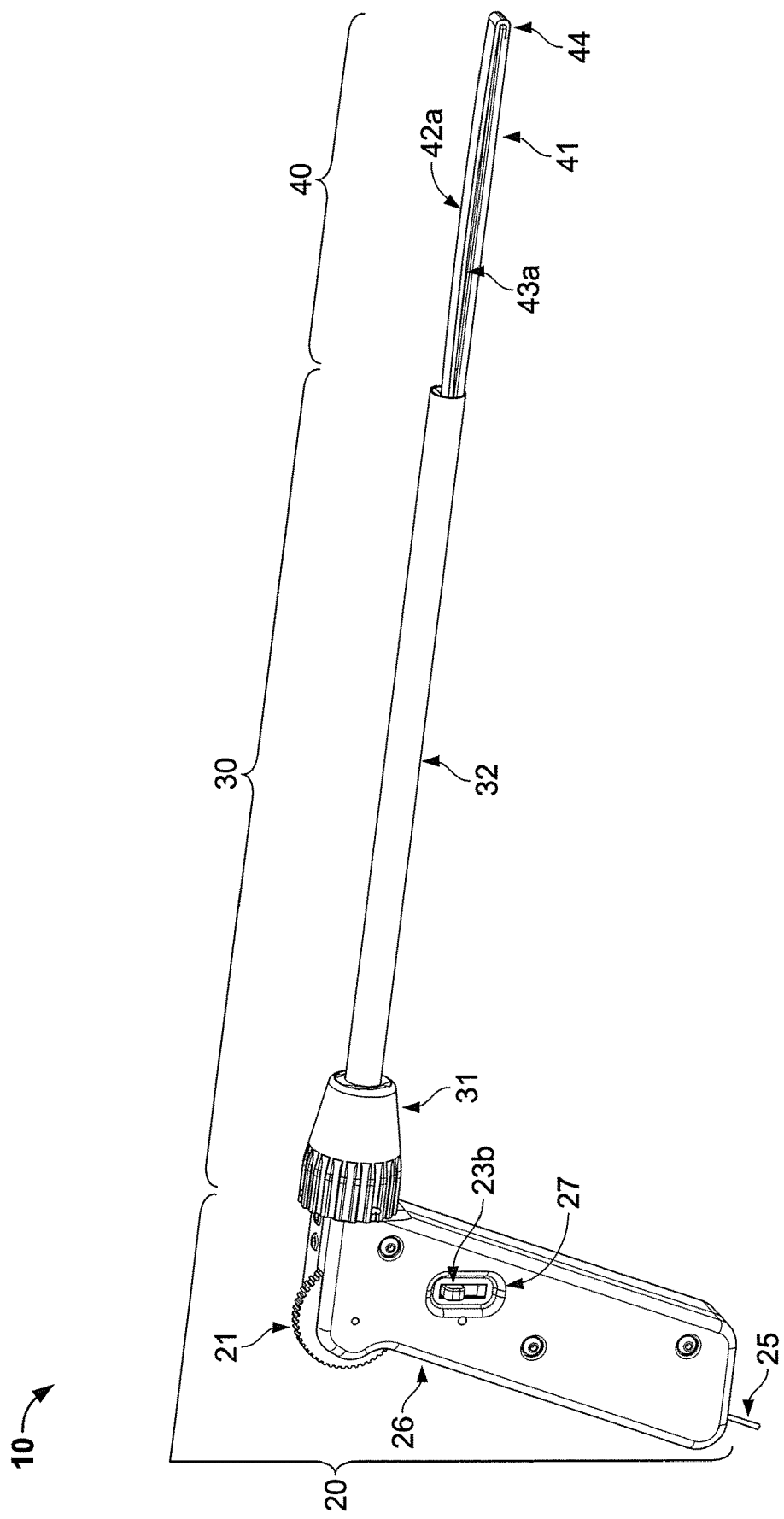
FIGS. 6A-6F illustrate a method of using the device shown in FIG. 1B with a target tissue, such as a human adult liver, for a laparoscopic procedure.

Sheath 32, shown in FIGS. 1A and AB, is movable linearly with respect to the elongate surface member 41. For example, sheath 32 can be advanced along the length of the elongate surface member 41 distally, i.e., toward the clamp end or the distal end of the device 10, and can be retracted along the length of the elongate surface member 41 proximally, i.e., toward the handle end or the proximal end of the device 10. Advancing the sheath 32 reduces the amount of the clamp portion 40 that extends out of the distal end of the hollow sheath 32 and retracting the sheath 32 increases the amount of the clamp portion 40 that extends out of the distal end of the hollow sheath 32. For example, the sheath 32 can be adjusted to enclose more or less of the elongate surface member 41 by advancing or retracting the sheath 32, respectively. The position and linear movement of sheath 32 is controlled by the sheath adjustment knob 31 via the screw mechanism 33 (shown in detail in FIG. 6D). With reference to FIGS. 3A and 3B and FIG. 6D, the distal portion of the inner surface of the sheath adjustment knob 31 is threaded, for example, with female threads, and engages the male-threaded screw mechanism 33 to advance and retract sheath 32 linearly with respect to the elongate surface member 41 when sheath adjustment knob 31 is turned or rotated, as described below in reference to FIG. 6D.

The length of sheath 32 typically is between or between about 100 mm and 500 mm, and generally between or between about 200 mm and 400 mm, for example 300 mm, but can be longer, i.e., more than 500 mm, or shorter, i.e., less than 100 mm, in length, if desired. In one example, the length of sheath 32 is or is about 300 mm.

Typically, the hollow sheath 32, as shown in FIG. 1, has a diameter of between or between about 3 mm to 15 mm, for example, the diameter is up to or up to about or about 3 mm, 4 mm, 5 mm, 6 mm, 7 mm, 8 mm, 9 mm, 10 mm, 11 mm, 12 mm, 13 mm, 14 mm, or 15 mm, but can be smaller, e.g., less than 3 mm, or larger, e.g., greater than 15 mm, in some examples. Typically, the diameter of sheath 32 is at least or about at least 5 mm, 10 mm or 12 mm, and generally at least or about at least 10 mm. In one example, the diameter of sheath 32 is or is about 10 mm.

The sheath 32 can be made of any durable material, such as those commonly used for laparoscopic surgical instruments, for example, stainless steel or a durable plastic.

c. Clamp Portion

As depicted in FIGS. 1A and 1B, the elongate surface member 41 extends out of the distal end of hollow sheath 32 and forms the bottom portion of the clamp portion 40. The length of the clamp portion 40, e.g., length, of the elongate surface member 41 that extends out of the hollow sheath 32, as shown in FIGS. 1A and 1B, can be any length to accommodate a desired region or portion of a tissue that is desired to be clamped. The particular dimensions can be determined based on the size and physical characteristics of the tissue to be clamped, and the particular amount of the tissue to be clamped. For example, the amount of tissue to clamp can be based, for example, on the nature of the procedure to be performed or on the particular tissue to be clamped. The size of the tissue, and thus the size of the clamp, can vary depending on the location of the clamp on the tissue. For example, when the tissue is the liver, such as a human liver, the tissue will be thinner at the edges of the tissue and increase in size, e.g., thickness, towards the center of the tissue. The size of the tissue to be clamped can vary, for example, depending on the subject. In one example, the tissue can be larger, for example, a human adult liver. In another example, the tissue can be smaller, for example, a human child liver. A larger tissue can require a longer clamp portion 40, while a smaller tissue can require a shorter clamp portion 40. In one example, the tissue to be clamped is the liver, such as an adult human liver, and the amount of tissue to be clamped with the band clamp device described herein is typically between or between about 1 g and 100 g, such as between or between about 5 g and 50 g of liver.

In particular examples, modeling studies, for example, 3-D modeling studies, such as MRI modeling studies, can be performed with respect to the tissue to be clamped, i.e., target tissue, to determine the anatomy and other physical characteristics of the tissue, and the size of clamp required to accommodate a given region or portion. In some examples, results from a modeling study are used to determine the size and dimensions of the components of the band clamp device 10. In one example, results from 3-D MRI modeling studies of the liver, for example, an adult human liver, are used to determine the size and dimensions of the components of the band clamp device 10. The results of modeling studies, for example, 3-D modeling studies, e.g., 3-D MRI modeling studies, can be used to determine the amount of tissue to be clamped or compartmentalized during a procedure, such as a laparoscopic procedure. For example, a 3-D model of a tissue, such as a human liver, can be progressively sectioned to determine the volume of tissue which can be isolated. The volume can be of the tissue to be isolated can then be used to determine the appropriate dimensions, i.e., width and height, of the clamp 40.

Typically, the length of elongate surface member 41 that extends out of hollow sheath 32 to form the base of the clamp portion 40 is between or between about 50 mm and 500 mm, and generally between or between about 75 mm and 200 mm, for example up to or at least or about 100 mm, but can be longer, i.e., more than 500 mm, or shorter, i.e., less than 50 mm, in length, if desired. In one example, the tissue to be clamped is the liver, such as an adult human liver, and the length of the clamp portion 40, e.g., the length of the elongate surface member 41 that extends out of the hollow sheath 32, is or is about 100 mm.

i. Flexible Upper Band

The elongate surface member 41 terminates at the distal end of the clamp portion 40. The distal end of elongate surface member 41 contains a notch 44, as shown in FIGS. 1A and 1B. The elongate surface member 41 is connected to a flexible upper band 42 at notch 44. The end of the flexible upper band 42 can be inserted into the notch 44 to form a closed loop between the elongate surface member 41 and flexible upper band 42. The notch 44 can be any size, i.e., depth, that is capable of accepting the end of the flexible upper band 42. For example, notch 44 can be or be about as deep as the thickness of the flexible upper band 42. The closed loop formed between the elongate surface member 41 and flexible upper band 42 at notch 44 can be fixed, i.e., the elongate surface member 41 and the flexible upper band 42 can be sealed together at notch 44 to form a sealed closed loop. For example, the flexible upper band 42 and elongate surface member 41 can be glued together, heat-sealed, welded together, or molded together. Alternatively, the closed loop formed between the elongate surface member 41 and flexible upper band 42 at notch 44 can be detachable or fastenable, i.e., the flexible upper band 42 can be inserted into notch 44 to form a closed loop with the elongate surface member 41 and can be removed from notch 44 to open the loop, e.g., with a hook. For example, the flexible upper band 42 can be removed from notch 44 in the elongate surface member 41 and reinserted in notch 44 in the elongate surface member 41 when desired.

The flexible upper band 42 shown in FIGS. 1A and 1B originates within the pistol grip handle portion 20 and extends through the hollow sheath 32 as will be discussed in more detail below with reference to FIG. 2. The flexible upper band 42 extends out of the distal end of hollow sheath 32 and terminates at notch 44 of the elongate surface member 41 of the clamp portion 40. The length of flexible upper band 42 that extends out of the sheath 32 can be adjusted and can depend upon the position of the flexible upper band 42. For example, the band 42 can be in a slack position (as shown in FIGS. 1A and 1B), a flat position or a tensioned position, as will be discussed in more detail below in reference to FIGS. 4A-4D. Generally, the length of the flexible upper band 42 that extends out of the hollow sheath 32 is at least as long the length of the elongate surface member 41 that extends out of the hollow sheath 32, for example, at least or at least about 50 mm, 75 mm, 100 mm, 150 mm, 200 mm, 250 mm, 300 mm, 350 mm, 400 mm, 450 mm, or 500 mm, or more. In one example, the length of the flexible upper band 42 that extends out of the hollow sheath 32 is at least 100 mm in length.

The flexible upper band 42, as shown in FIGS. 1A and 1B, can be made of any material that is capable of forming a loop with the elongate surface member 41 that will not lay flat on the elongate surface member 41 as the band is loosened or payed out of sheath 32. For example, the material can be any material that has adequate stiffness and/or shape memory to allow formation of a loop with the elongate surface member 41 as the flexible upper band 42 is loosened or payed out of sheath 32. Exemplary of materials that can be used for the flexible upper band 42 include any material that possesses a combination of column strength and flexibility that allows the flexible upper band 42 to form a loop with the elongate surface member 41 rather than lying flat on the elongate surface member 41 after the flexible upper band 42 has been payed out, and is soft enough to conform to the anatomy of the target tissue when tensioned. Exemplary materials include materials commonly used to make belts, for example, timing belts, such as, but not limited to, silicones and flexible polymers, such as polyurethane or polyethylene, for example, a flexible, reinforced polyurethane, e.g., a polyurethane reinforced with fiber. In some examples, the fiber reinforcement is completely encapsulated by the polymer and/or is biocompatible.

Figure 4A:
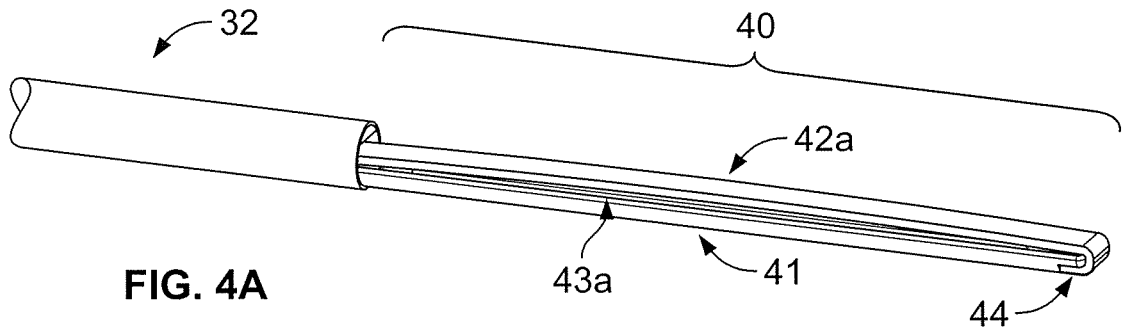
FIGS. 4A-4E are enlarged views of the band clamp portion of the device shown in FIG. 1B with the components of the clamp portion in exemplary positions.
Figure 4B:
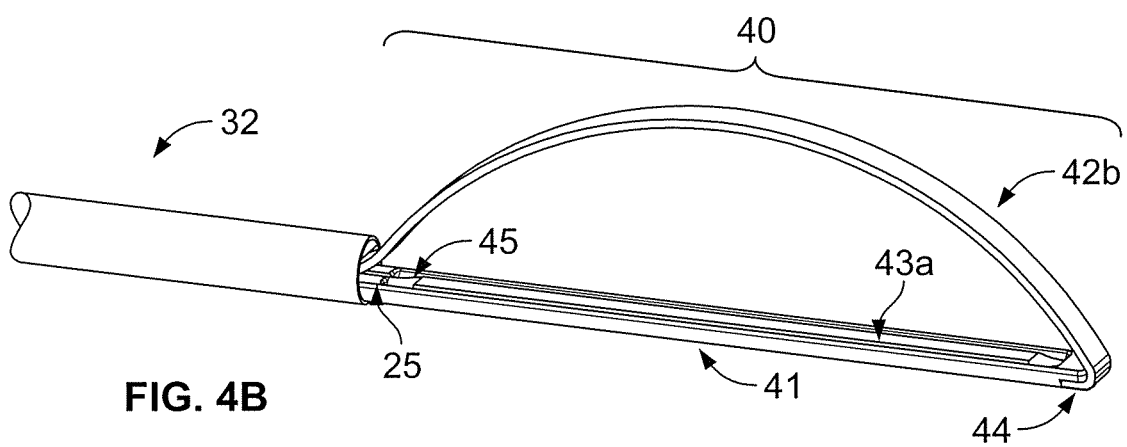
Figure 4C:
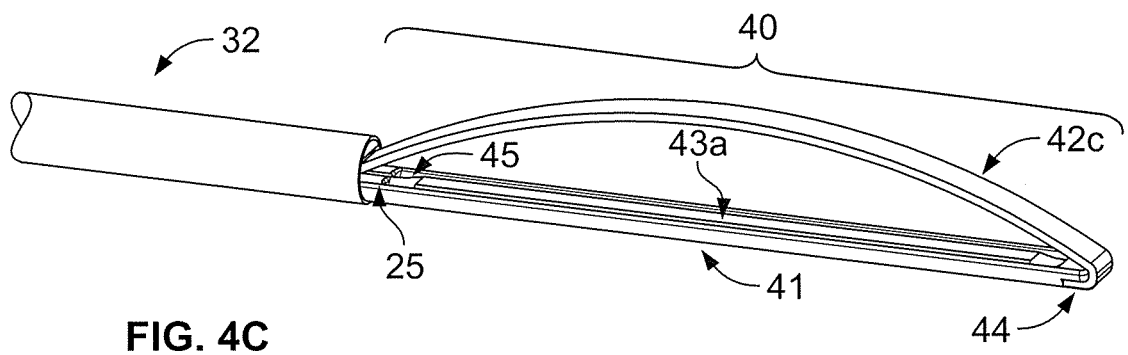
Figure 4D:
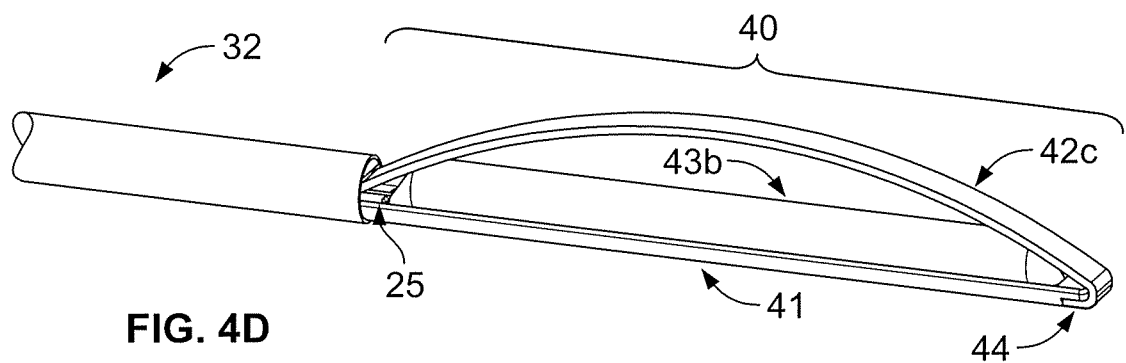
Figure 4E:
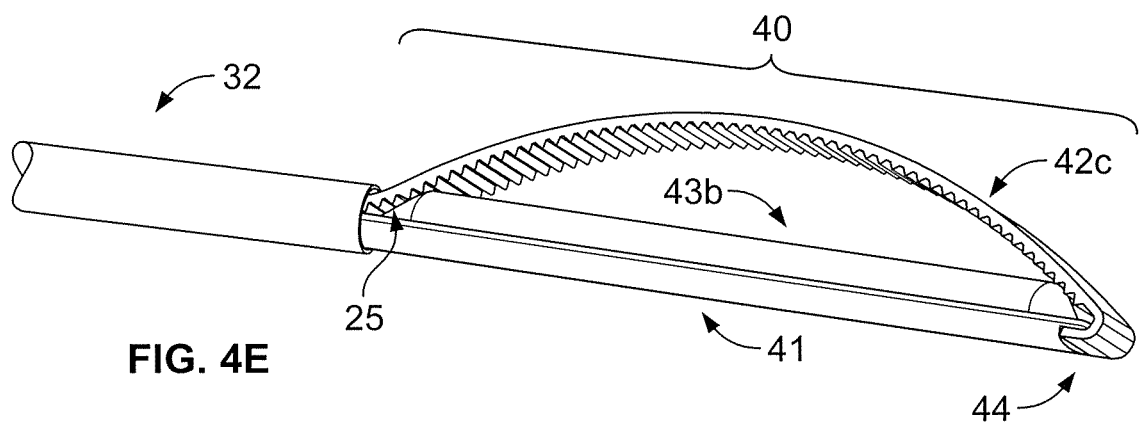

The flexible upper band 42 can be toothed (see, e.g., FIG. 4E). The teeth on the flexible upper band can be set length-wise or width-wise across flexible upper band 42. For example, the teeth can be set length-wise or width-wise across flexible upper band 42 for the entire length of the flexible upper band 42, i.e., the entire length of flexible upper band 42 that extends from the pistol grip handle portion 20 through the sheath component 30 and clamp portion 40. In one example, the teeth at one end, e.g., the handle end, of the device 10 can be set width-wise across a portion of the flexible upper band 42, and the teeth at the other end, e.g., the clamp end, of device 10 can be set length-wise across the flexible upper band 42. In one example, the flexible upper band 42 is made of a flexible, toothed polyurethane reinforced with fiberglass. In another example, the flexible upper band 42 is made of a molded, flexible polyurethane material without fiberglass reinforcement. The space between each individual tooth, i.e., tooth gap, of the flexible upper band 42 can be chosen to be the same space, i.e., tooth gap, as on the second band tensioning wheel 22 (shown and described in more detail below in reference to FIG. 2). The tooth gap of flexible upper band 42 can be chosen based on one or more factors, including, but not limited to, the size, or width, of the flexible upper band 42, the tooth gap on the second band tensioning wheel 22, or the characteristics of the target tissue. Typically, a smaller tooth gap is desired as it gives smaller spacing between the teeth and can result in finer control and smoother operation of the flexible upper band 42. Generally, the tooth gap on the flexible upper band 42 is the same as the tooth gap on the second band tensioning wheel 22.

ii. Biocompatible Deformable Article

Biocompatible deformable article 4 rests on the elongate surface member 41 of the clamp portion 40, as shown in FIG. 1A. Since the biocompatible deformable article 4 rests in the distal end of the elongate surface member 41 and the flexible band is connected to the distal end of the elongate surface member 41, a closed loop also is formed with the flexible band 42 and biocompatible deformable article 4. In the closed loop, the biocompatible deformable article 4 is between the elongate surface member 41 and flexible upper band 42. The closed loop that is formed is sufficient to be able to fit a tissue or an organ or a portion thereof during minimally invasive surgery. Thus, the biocompatible deformable article 4 forms part of the opposing side of the clamp portion of the device to effect pressure or force on a tissue or organ or a portion thereof in order to compress the structure.

For purposes of the device herein, the biocompatible deformable article is any article that is capable of conforming to the anatomy of a tissue or organ or portion thereof to assure even distribution of clamping forces, and hence uniform pressure, using the device herein. The biocompatible deformable article 4 can be made of any material that can conform to the target tissue and apply pressure to the target tissue without damaging the tissue, when the target tissue is placed in the closed loop and clamping pressure or force is applied from the band tension. The biocompatible deformable article 4 can be made from any deformable polymeric material. Exemplary of materials that can be used for the biocompatible deformable article 4 are low, low to medium or medium durometer (i.e., hardness) materials. For example, the durometer or shore hardness of the material as determined on a Shore A Hardness Scale can be 5 A to 95 A, and generally 10 A to 95 A or 20 A to 95 A, such as 20 A to 85 A, 20 A to 70 A, 20 A to 60 A, 20 A to 50 A, 20 A to 40 A, 30 A to 85 A, 30 A to 70 A, 30 A to 60 A, 30 A to 50 A, 30 A to 40 A, 40 A to 85 A, 40 A to 70 A, 40 A to 60 A, 40 A to 50 A, 50 A to 85 A, 50 A to 70 A, 50 A to 60 A, 60 A to 85 A, 60 A to 70 A or 70 A to 85 A, each inclusive. In some cases, a material in the Shore 00 scale can be used. It is within the level of a skilled artisan to choose an appropriate material depending on the particular target tissue, application, clamping pressure to be applied, and other factors. The biocompatible deformable article 4 can be manufactured from elastomeric foam, a silicone (e.g. low durometer silicone), an elastomer (e.g. low durometer elastomer), silicone rubber, visco-elastic gel, a hydrogel or a non-elastomeric film material. Exemplary of such materials include, but are not limited to, polyurethane, polyethylene, polyethylene terephthalate (PET), polyethylene terephthalate glycol-modified (PETG), ethylene vinyl acetate (EVA) or silicone. In particular examples, a biocompatible deformable article can be any that is able to be inflated, such as a balloon 43, which is exemplified in FIG. 1B.

Elongate surface member 41 can contain a cradle 45 (as described above and shown in detail in FIGS. 2, 3A, 3B, 4B and 4C) that can stabilize, i.e., keep in place, biocompatible deformable article 4 and prevent the biocompatible deformable article 4 from moving away from the elongate surface member 41 in the clamp portion 40. As indicated above, the biocompatible deformable article 4 is of a size to fit a tissue or organ or portion thereof that is desired to be clamped into the closed loop of the clamped portion and to permit application of a uniform pressure across the tissue or organ or portion thereof to clamp. It is within the level of a skilled artisan to adjust or choose the size of article depending on the particular article, the tissue or organ or portion thereof being clamped, the particular application of the clamp, the pressure to be applied and other factors. Typically, the biocompatible deformable article is substantially as long as the portion of the surface member that is longer than the sheath. For example, the length of the biocompatible deformable article resting in the cradle at the distal end of the elongate member is from 25 mm to 200 mm, 50 mm to 150 mm or 75 mm to 125 mm. In particular examples, the length of the biocompatible deformable article resting in the cradle at the distal end of the elongate member is or is at least 100 mm.

Generally, the diameter of the biocompatible deformable article is not greater than the diameter of the sheath component 32 so that the clamp portion of the device can fit through an endoscopic port. For example, the diameter of the biocompatible deformable article is less than 15 mm in diameter, such as less than 14 mm, 13 mm, 12 mm, 11 mm, 10 mm, 9 mm, 8 mm, 7 mm, 6 mm, 5 mm, 4 mm, 3 mm, 2 mm or less. In some examples, the biocompatible deformable article is an inflatable balloon as exemplified in the device shown in FIG. 1B. Since the balloon can be inflated after insertion through an endoscopic port, in such examples the diameter of the balloon can be greater than the diameter of the sheath, but generally is not so great as to impair the fit of the tissue or portion thereof in the closed loop of the clamp formed from the flexible band and balloon. Typically, the diameter of the balloon is up to or at least or about 3 mm, 4 mm, 5 mm, 6 mm, 7 mm, 8 mm, 9 mm, 10 mm, 11 mm, 12 mm, 13 mm, 14 mm or 15 mm in diameter.

Balloon

In an embodiment of the device provided herein, the biocompatible deformable article 4 is a balloon 43, which is exemplified in FIG. 1B. The balloon, when inflated, is able to conform to the anatomy and assure even distribution of clamping force. An additional advantageous design attribute of the balloon, or other inflatable article, is the ability of the user to precisely control and monitor the clamping force by monitoring the pressure of the balloon. For example, as described further below, the balloon pressure can be monitored to determine when the desired amount of pressure has been achieved or to determine if there has been a change, e.g., loss, in pressure. In some cases, monitoring of the clamping force or pressure is not required because the clamping force can be adequately controlled with the band tension.

Balloon 43 rests on the elongate surface member 41 of the clamp portion 40, as shown in FIG. 1B. Elongate surface member 41 can contain a cradle 45 (as described above and shown in detail in FIGS. 2, 3A, 3B, 4B and 4C) that can stabilize, i.e., keep in place, balloon 43 and prevent the balloon 43 from moving away from the elongate surface member 41 in the clamp portion 40, for example, when balloon 43 is deflated 43a. Since the balloon 43 rests in the distal end of the elongate surface member 41 and the flexible band is connected to the distal end of the elongate surface member 41, a closed loop also is formed with the flexible band 42 and balloon 43. In the closed loop, the balloon 43 is between the elongate surface member 41 and flexible upper band 42. Balloon 43, shown in FIG. 1B, can be made of any material that can conform to the target tissue and apply pressure to the target tissue when inflated, while not over-expanding and damaging the tissue. These can include elastomeric or non-elastomeric materials, for example, a non-elastomeric film material. Typically, the balloon is made of materials with a hardness falling in the A scale of the Shore harness test, such as from 20 A to 95 A, for example 40A to 90 A, such as 50 A to 70 A or 70 A to 85 A. Exemplary of materials that can be used for the balloon 43 are medium durometer (i.e., hardness) materials, such as rigid balloon materials known to those of skill in the art, for example, materials used for angioplasty balloons. For example, the medium durometer material can be a polyurethane, such as a polyurethane that has a shore hardness of between or between about 70 A and 85 A. The medium durometer material can be a polyethylene material, for example, a polyethylene terephthalate (PET) or polyethylene terephthalate glycol-modified (PETG). Typically, the material for balloon 43 will not be so elastic that the balloon 43 bulges without applying pressure to the target tissue when the balloon 43 is inflated, e.g., typically, the balloon 43 will not be made of a material such as latex.

The balloon 43 is connected to the distal end of a balloon inflation line 25 at the end of the balloon 43 proximal to the hollow sheath 32. As illustrated in FIG. 1B, the balloon inflation line 25 enters the case 26 through an opening at the bottom of case 26, continues through the pistol grip handle portion 20 and the hollow sheath 32 of sheath component 30, extending out through the distal end of the hollow sheath 32 and connecting to the proximal end of balloon 43 in clamp portion 40. The balloon inflation line 25 can be used to inflate and deflate the balloon 43, and will be discussed in more detail below in reference to FIG. 6F. The external portion (i.e., proximal end) of the balloon inflation line 25, i.e., the portion of balloon inflation line 25 that extends out of the bottom of case 26, can be connected to an external source of fluid or gas, e.g., air, that can be used to inflate and deflate the balloon 43.

The balloon inflation line 25 can be made of a wide range of materials, including, but not limited to urethane, polyvinyl chloride (PVC), polypropylene and polyurethane. In one example, the balloon inflation line 25 is made of PVC. In other examples, the balloon inflation line 25 is made of the same material as the balloon 43, for example, the balloon inflation line 25 and the balloon 43 are both made of urethane. The balloon inflation line 25 can vary in size depending upon one or more factors, such as the size of the balloon, the size of the hollow sheath 32, the source and nature of the fluid or gas used to inflate the balloon 43 and the type of procedure to be performed. Generally, the inner diameter of the balloon inflation line 25 can be between or between about 0.01 inches and 0.05 inches, typically between or between about 0.02 inches and 0.04 inches, such as 0.02 inches or 0.03 inches. The outer diameter of the balloon inflation line 25 can be between or between about 0.04 inches and 0.08 inches, typically between or between about 0.05 inches and 0.07 inches, such as 0.06 inches. In one example, the balloon inflation line 25 is made of PVC and has an inner diameter of 0.02 or 0.03 inches and an outer diameter of 0.06 inches.

2. Operation of the Device

The device provided herein can be used in any surgery or technique in which clamping of a tissue or an organ or a portion thereof is desired. For example, the device can clamp the tissue or organ or portion thereof to effect compartmentalization of the tissue or organ or a portion of a tissue from the systemic circulation for gene therapy methods involving nucleic acid delivery to a compartmentalized target tissue or portion thereof. The device described herein also can be used in other tissue surgeries, such as transplantation and resection. The device can be used in minimally invasive procedures, such as laparoscopic procedures, to clamp a tissue or an organ or a portion thereof. The device can be inserted through endoscopic ports, such as laparoscopic ports, and manipulated during minimally invasive procedures (e.g., laparoscopic procedures), and thus can be used during minimally invasive surgeries to cut off the blood flow to a portion of a tissue. The device can be used in conjunction with other minimally invasive (e.g., laparoscopic) surgical devices during single-port or multi-port procedures.

The operation or use of the device in such procedures are described below. The description below is exemplified by a device that contains a biocompatible deformable article that is a balloon, which can be inflated or deflated by a balloon inflation line. As described above, such a device offers advantages over other biocompatible deformable articles provided herein, since it allows the user to precisely control and monitor the clamping force. It is understood, however, that any biocompatible deformable article as described herein that can conform to the anatomy can be employed. In particular, such other articles can be used when such precise control and monitoring of the clamping force is not required or if another means of controlling the clamping force, such as band tension, is adequate. It is within the level of a skilled artisan to substitute another biocompatible deformable article and to otherwise use the device substantially as described, but without the requirement to inflate or deflate the article.

As described in more detail with reference to FIGS. 6A-F, generally, the components of the clamp portion 40 and positions thereof are controlled by other components of the band clamp device 10 that are located in the pistol grip handle portion 20 and sheath component 30, as illustrated and described above in reference to FIGS. 1A-1B, 2 and 3A-3B. For example, movement, e.g., paying out or tensioning, of the flexible upper band 42 (42a, 42b and 42c) in the clamp portion 40 is controlled by rotating the first band tensioning wheel 21 of the pistol grip handle 20 clockwise or counter-clockwise, respectively (as described above in reference to FIGS. 2 and 3A-3B). The balloon 43 (43a and 43b) can be inflated or deflated through the balloon inflation line 25. Balloon inflation line 25 is connected to the distal end of the balloon 43 (43a and 43b), extends through the sheath component 30 and pistol grip handle portion 20 and is connected externally to a source of fluid or gas, e.g., air, as described above in reference to FIG. 1B.

FIGS. 4A-4E illustrate enlarged views of the clamp portion 40 of band clamp device 10 shown in FIGS. 1A and 1B. The clamp portion 40 extends out from the distal end of the hollow sheath 32. The clamp portion 40 is made up of the elongate surface member 41, the flexible upper band 42 (42a, 42b and 42c) and balloon 43 (43a and 43b), as described above in reference to FIGS. 1A and 1B. Flexible upper band 42 (42a, 42b and 42c) and elongate surface member 41 connect at notch 44 to form a closed loop, as described above.

FIG. 4A shows an exemplary position of the components of clamp portion 40 where the balloon 43a is deflated and the flexible upper band 42a is in the flat position. The clamp portion 40 can be in this position, for example, before insertion of the band clamp device 10 through an endoscopic port (e.g., laparoscopic port). The clamp portion 40 can be in this position, for example, while the band clamp device 10 is inserted through a laparoscopic port. Balloon 43a is in the deflated position and rests in the cradle 45 (not visible in FIG. 4A) of the elongate surface member 41, as discussed above in reference to FIG. 1B. The flexible upper band 42a is in the flat position and rests on top of the deflated balloon 43a and elongate surface member 41. Generally, when flexible upper band 42a is in the flat position, there is no slack, i.e., the flexible upper band 42a lies flat on the elongate surface member 41 and there is no open space between the flexible upper band 42a and elongate surface member 41. For example, when flexible upper band 42a is in the flat position, the flexible upper band 42a is tensioned, i.e., there is no slack. When flexible upper band 42a is in the flat position, the length of flexible upper band 42a that extends from the end of hollow sheath 32 can be equal to or about equal to the length of the elongate surface member 41 that extends out of the hollow sheath 32. In one example, the length of the elongate surface member that extends out of the hollow sheath 32 is or is about 100 mm and the length of flexible upper band 42a that extends out of the hollow sheath 32 is or is about 100 mm.

FIG. 4B illustrates an exemplary position of the clamp portion 40 of band clamp device 10. Balloon 43a is deflated and rests in the cradle 45 of the elongate surface member 41. Cradle 45 acts to stabilize the position, i.e., keep in place, of balloon 43a on the elongate surface member 41 and prevent balloon 43a from dislodging while in the deflated position. Flexible upper band 42b is in the slack position. Generally, when flexible upper band 42b is in the slack position, the flexible upper band 42b has been payed out through the hollow sheath 32. Paying out the flexible upper band 42b increases the amount (i.e., length) of flexible upper band 42b that extends out of the hollow sheath 32 as compared to the amount (i.e., length) of flexible upper band that extends out of the hollow sheath 32 when the flexible upper band 42a is in the flat position. Paying out the flexible upper band 42b widens, i.e., increases the size of, the closed loop formed by the flexible upper band 42 and elongate surface member 41.

The amount of flexible upper band 42b, as shown in FIG. 4B, that is payed out when flexible upper band 42b is in the slack position can be any amount sufficient to form a loop large, i.e., wide, enough to fit around the target tissue. For example, the amount of flexible upper band 42b payed out of the hollow sheath 32 can be any amount that can form a widened loop between the elongate surface member 41 and flexible upper band 42b in the slack position that is between or between about 1 cm and 10 cm, and generally between or between about 2 cm and 5 cm, for example between or between about 3 cm and 4 cm, but can be larger, i.e., more than 10 cm, or smaller, i.e., less than 1 cm, in width, if desired. In one example, the size of the widened loop formed between the elongate surface member 41 and flexible upper band 42b in the slack position is about 30 mm to 40 mm. The clamp portion 40 can be in this position, i.e., the flexible upper band 42b is in the slack position and forms a widened loop with the elongate surface member 41, for example, after the band clamp device 10 has been inserted through a laparoscopic port. The clamp portion 40 can be in this position, i.e., the flexible upper band 42b is in the slack position and forms a widened loop with the elongate surface member 41, for example, before the widened loop formed by flexible upper band 42b and the elongate surface member 41 is placed around a target tissue, such as a liver.

An exemplary position of the clamp portion 40 of band clamp device 10 is illustrated in FIG. 4C. Balloon 43a is deflated and rests in cradle 45 of the elongate surface member 41. Flexible upper band 42c is in the tensioned position. Generally, when flexible upper band 42c is in the tensioned position, the flexible upper band 42c has been taken back in through the hollow sheath 32, i.e., tensioned, and the loop has been tightened (i.e., tensioned). Tensioning the flexible upper band 42c decreases the amount (i.e., length) of flexible upper band 42c that extends out of the hollow sheath 32 as compared to the amount (i.e., length) of flexible upper band that extends out of the hollow sheath 32 when the flexible upper band 42b is in the slack position. For example, when the flexible upper band 42c is in the tensioned position, the amount of flexible upper band 42c that extends out of the hollow sheath 32 can be less than the amount of flexible upper band 42 that extends out of the sheath 32 when the flexible upper band 42 is in the slack position 42b, but more than when the flexible upper band is in the flat position 42a. Taking in, i.e., tensioning, the flexible upper band 42c narrows, i.e., collapses, the closed loop formed by the flexible upper band 42 and elongate surface member 41. The clamp portion 40 can be in this position, for example, after the band clamp device 10 has been inserted through an endoscopic port (e.g, laparoscopic port). The clamp portion 40 can be in this position, for example, after the closed loop formed by the flexible upper band 42 and the elongate surface member 41 has been placed around a target tissue, such as a liver, and the flexible upper band 42c has been taken in, i.e., tensioned, as described below in reference to FIG. 5B.

The amount of flexible upper band 42c, as shown in FIG. 4C, that is taken in when flexible upper band 42c is in the tensioned position can be any amount sufficient to tighten the closed loop formed between the flexible upper band 42c and elongate surface member 41 enough to fit snugly around the target tissue and conform to the anatomy of the target tissue, as shown and described in more detail in reference to FIG. 5B below. For example, when tensioned, flexible upper band 42c is snug against the target tissue, but not applying significant clamping force. Typically, the length of the tensioned loop can be or be about the length of the upper surface of the tissue being clamped and the height of the tensioned loop can be at or about the thickness of the tissue or organ or portion thereof being clamped. In some examples, the tension the flexible upper band 42c exerts around the target tissue can be measured, as is described in detail below in reference to FIG. 5B. The clamp portion 40 can be in this position, i.e., the flexible upper band 42c is in the tensioned position and forms a tightened loop with the elongate surface member 41 around the target tissue, for example, after the band clamp device 10 has been inserted through an endoscopic port (e.g., laparoscopic port), placed around a target tissue, such as a liver, and the flexible upper band 42c has been taken in, i.e., tensioned.

FIG. 4D shows an exemplary position of the clamp portion 40 of band clamp device 10 where balloon 43b is in the inflated position and flexible upper band 42c is in the tensioned position. As will be described in more detail below in reference to FIG. 6F, balloon 43b can be inflated with a fluid or a gas, e.g., air, through the balloon inflation line 25, which can be connected to an external source of a fluid or gas, e.g., air. Generally, when balloon 43b is in the inflated position, balloon 43b is expanded as compared to the balloon 43a in the deflated position. For example, the balloon 43 can be inflated to a diameter of between or between about 5 mm and 15 mm, e.g., at least or about at least 5 mm, 6 mm, 7 mm, 8 mm, 9 mm, 10 mm, 11 mm, 12 mm, 13 mm, 14 mm, 15 mm, or more. The diameter of the inflated balloon 43b can depend on any one or more factors, including the procedure to be performed and the size and dimensions of the device 10. In one example, the inflated diameter of balloon 43b is or is about 8 mm. In some examples, the pressure the inflated balloon 43b exerts on the target tissue can be measured, as is described in detail below in reference to FIG. 5C. The clamp portion 40 can be in this position, for example, after the closed loop formed by the flexible upper band 42c and the elongate surface member 41 has been placed around a target tissue, such as a liver, the flexible upper band 42c has been taken in, i.e., tensioned, to form a tightened loop, and the balloon 43b has been inflated.

FIG. 4E represents an alternate view of FIG. 4D, where the clamp portion 40 is tilted backwards to expose the bottom side of the flexible upper band 42c. In an exemplary embodiment of the band clamp device described here, the flexible upper band 42c can be toothed. Typically, the teeth of the flexible upper band 42c can run across the width of the band. In some embodiments the teeth of the flexible upper band 42c can run the length of the band. In other embodiments the teeth on one end of the band 42c, e.g., the handle end, can be set length-wise and the teeth on the other end of the band 42c, e.g., the clamp end, can be set width-wise. The space between each individual tooth, i.e., the tooth gap, of the flexible upper band 42c can depend upon one or more factors, including, but not limited to, the size, or width, of the flexible upper band 42c, the characteristics of the target tissue, or the tooth gap on the second band tensioning wheel 22 (as discussed above in reference to FIGS. 1A and 1B and 2). In one example, the tooth gap on the flexible upper band 42c is the same as the tooth gap on the second band tensioning wheel 22.

Figure 5A:
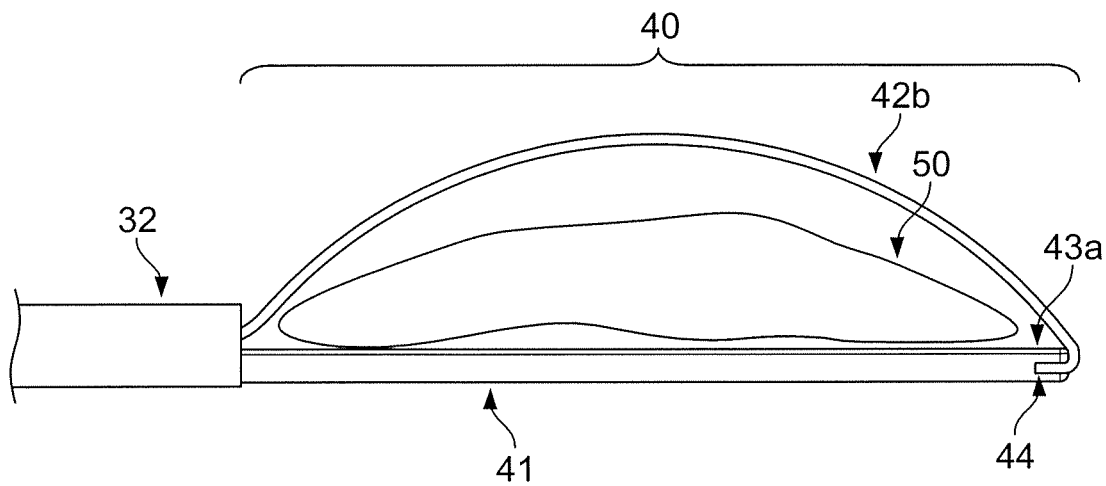
FIGS. 5A-5C illustrate the various positions of the band clamp portion of the device shown in FIG. 1B as applied to a target tissue.
Figure 5B:
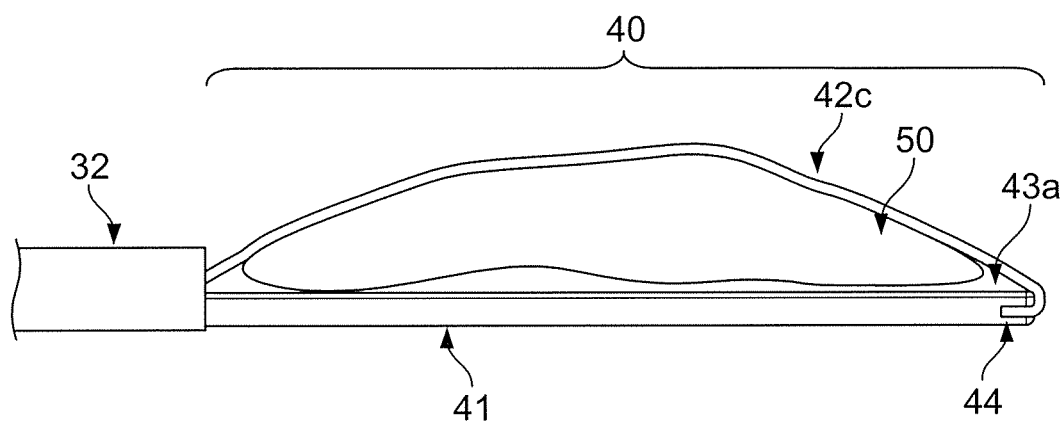
Figure 5C:
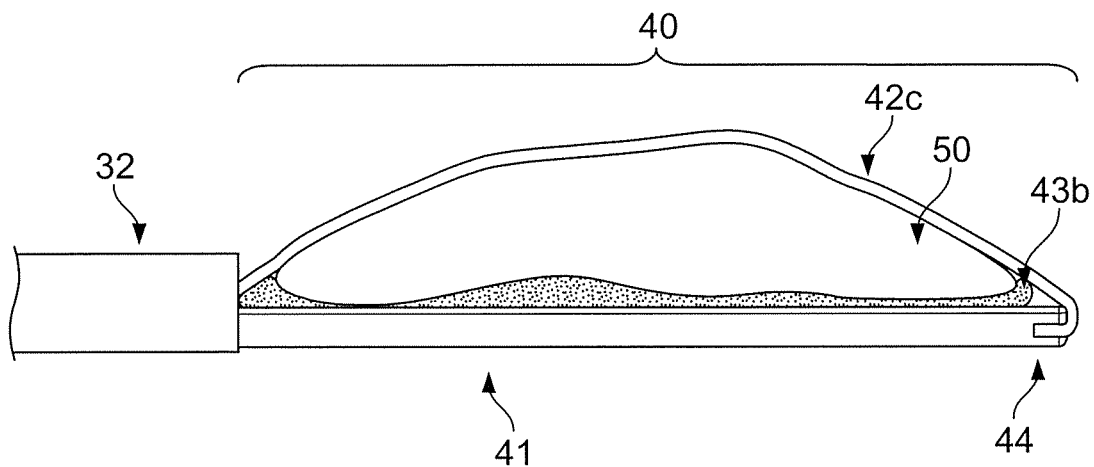

FIGS. 5A-5C represent enlarged images of the clamp portion 40 of band clamp device 10 applied to a target tissue 50. The target tissue can be any tissue or organ or portion thereof. Non-limiting examples of target tissues to which the clamp can be applied are liver, brain spinal cord, pancreas, heart, skin, kidney, lung, blood vessel, bone, muscle, uterus, cervix, prostate, urethra, or intestine or portions thereof. FIG. 5A shows the clamp portion 40 with the flexible upper band 42b in the slack position and the balloon in the deflated position 43a. The flexible upper band 42b extends out of the hollow sheath 32 and forms a loop with the elongate surface member 41 by connecting to the elongate surface member 41 at notch 44. The connection at notch 44 can be fixed, i.e., sealed, or can be fastenable, e.g., with a hook. The portion of the target tissue 50 to be clamped is situated inside of the loop, with the bottom portion of target tissue 50 resting on the deflated balloon 43a and elongate surface member 41. When the flexible upper band 42b is in the slack position, there is empty space or an open area between the top portion of target tissue 50 and flexible upper band 42b, i.e., the flexible upper band 42b is not tightened, or tensioned, around the target tissue 50.

FIG. 5B depicts the clamp portion 40 with the flexible upper band 42c tensioned around the portion of the target tissue 50 to be clamped. The target tissue 50 rests on deflated balloon 43a and elongate surface member 41. The flexible upper band 42c is tensioned so that it fits snugly around the portion of the target tissue 50 to be clamped, i.e., the band is tightened around the target tissue 50 to conform to the anatomy of the target tissue 50. When tensioned, flexible upper band 42c is snug against the target tissue 50, but not applying significant clamping force. For example, the flexible upper band 42c can be tensioned at least until all slack is removed. Flexible upper band 42c can be further tensioned if desired, for example, until the flexible upper band 42c begins to compress the tissue 50 and displace the tissue 50 to either side of the flexible upper band 42c. The desired amount of tensioning of the flexible upper band 42c can be determined, or measured, visually, for example, by visually observing the tension of the flexible upper band 42c around the target tissue 50 as the flexible upper band 42c is tightened. The desired amount of tensioning of the flexible upper band 42c can be determined, or measured, using procedures known in the art, such as by a gauge, such as an external gauge, for example a tension or force gauge, e.g., a spring gauge, a digital strain gauge, an analog gauge; visually, for example, by visually observing the tension of the flexible upper band 42c around the target tissue 50 as the flexible upper band 42c is tightened; or by a compression load cell transducer, for example a 2.2. button style compression load transducer (Interface Advanced Force Measurement; Scottsdale, Ariz.). In one example, the tension can be measured directly by a gauge connected to the flexible upper band 42c. For example, a gauge can be spliced into a segment of the flexible upper band 42c. The gauge can be used to measure the tension applied to the target tissue 50 by the flexible upper band 42c and determine when the desired amount of tensioning has been achieved. In another example, the tension can be measured indirectly by routing the flexible upper band 42c over a movable bearing, where the deflection of the bearing can indicate the tension in the band 42c.

FIG. 5C illustrates the clamping of a portion of the target tissue 50. The flexible upper band 42c is in the tensioned position and snug around target tissue 50, as described above in reference to FIG. 5B. Balloon 43b, which rests upon elongate surface member 41, is inflated and conforms to the anatomy of the target tissue 50. The balloon 43b can be inflated to a pressure of 50 mmHg to 250 mmHg, and generally to a pressure that is greater than 120 mmHg (systolic pressure). The inflated balloon 43b applies uniform clamping pressure to target tissue 50. For example, the inflated balloon 43b applies a uniform pressure to the target tissue 50 regardless of the physical dimensions, e.g., thickness or thinness, of the portion of target tissue 50 that is clamped. The uniform clamping pressure applied to the target tissue 50 is achieved due to the flexible and conforming clamping elements, i.e., the flexible upper band and the balloon, of band clamp device 10. A uniform clamping pressure insures that no portion of the target tissue 50 is under-clamped or over-clamped. For example, the uniform clamping pressure allows the blood flow to be cut off across an entire section of target tissue 50 without thicker sections being over-clamped and thinner section being under-clamped, and without trauma to the tissue.

If desired, the balloon pressure can be measured and/or monitored during and after inflation and deflation of the balloon 43b (shown in FIG. 5C). For example, the balloon pressure can be monitored to determine when the desired amount of pressure has been achieved or to determine if there has been a change, e.g., loss, in pressure. For example, a loss in pressure can indicate that the clamp portion 40 has shifted position around the target tissue 50 and there is a loss of clamping. The balloon pressure can be determined using procedures known in the art, for example, ex vivo or in vivo using a pressure gauge, such as a digital gauge or an analog gauge, such as a Cole Parmer digital pressure measuring device (e.g., Cole-Parmer®; Vernon Hills, Ill.); by intraoperative ultrasound; electronically, through a user interface that can include a pressure display, indicator LEDs and alarms, for example, to indicate a change in pressure, such as a drop in pressure, that indicates clamping has failed; or visually, for example, the balloon 43b can be observed visually during inflation and deflation and adjusted to the desired pressure by inflating or deflating the balloon 43b more or less. In one example, the pressure is monitored by a pressure gauge connected to balloon fill line 25, for example, at a point in the balloon fill line 25 that is external to the band clamp device 10 (as described below in reference to FIG. 6F).

In some examples, pressure can be assessed by measuring the level of clamping, and hence compartmentalization of the area clamp, by various other procedures known in the art. For example, a dye, such as methylene blue or bromophenol blue or other similar dye, can be injected into the target region or segment that is clamped or compartmentalized and assessing its localization to that region. For example, after removal of the clamp, the tissue on both sides where the clamp had been placed can be dissected and analyzed for the presence of the dye. Clamping, such as compartmentalization achieved by clamping, is complete when the dye does not penetrate a portion or region of the isolated tissue. It is understood that some leakage of the dye (indicative of blood flow) can occur at the peripheral regions around the boundary of the clamp, so long as there is a region or portion of the tissue that is isolated from the vasculature for the entire period of parenchymal compression. For clamping procedures requiring compartmentalization, ideally, compartmentalization is achieved so that the dye does not penetrate the adjacent tissue beyond the boundary of the clamp. Monitoring or measuring the clamp pressure can be done during any stage of the procedure, such as a laparoscopic procedure, and can be adjusted and controlled during any stage of the procedure, such as a laparoscopic procedure, to achieve the desired clamp pressure.

In an exemplary embodiment, the pressure that is applied to the target tissue 50 is enough to stop blood flood in order to compartmentalize the tissue or organ or portion thereof that is clamped, but is not so much as to cause serious damage to the surrounding tissue. For example, the pressure that is applied to the target tissue 50 can result in compartmentalization of a portion of the target tissue 50. Generally, the pressure is uniform across the entire clamp portion 40 of the device 10. The clamp, and pressure applied, should be capable of compartmentalizing a region or segment of a tissue or organ from adjacent tissue areas and from the surrounding vasculature. It is within the level of one of skill in the art, such as a skilled surgeon, to determine the ideal pressure to achieve optimal clamping and/or compartmentalization of an organ or portion thereof while minimizing tissue damage or trauma.

FIGS. 6A-6F illustrate an exemplary method of using the band clamp device 10 described herein. The band clamp device 10 described herein can be used to clamp a portion of a target tissue for any medical procedure or surgery that requires a stop of blood flow to the tissue or portion during the course of the procedure. Exemplary of such methods in which the band-clamp device can be used are described elsewhere herein in Section C. The band clamp device 10 described herein, and illustrated in FIGS. 6A-6F, can be used in any minimally invasive procedures (e.g., laparoscopic procedures), particularly in procedures where clamping of part or a portion of a tissue is desired. In an exemplary embodiment described herein, and illustrated in FIGS. 6A-6F, the target tissue is a liver 501, for example, a human adult liver.

Band clamp device 10 is first inserted through an endoscopic port (e.g., laparoscopic port). FIG. 6A depicts the band clamp device 10 as it appears before and during insertion through a port. The band tension/loosen switch 23b is in the up position. As described above, the first tensioning wheel 21 is prevented from moving clockwise and paying out or loosening the flexible upper band 42a when the band tension/loosen switch 23b is in the up position. The flexible upper band 42a lies in the flat position over the deflated balloon 43a and the elongate surface member 41. The band clamp device 10 is inserted through the port at the clamp end of the device. The clamp portion 40 and the sheath portion 30 can be inserted partially through or entirely through the port. The amount of the clamp portion 40 and sheath portion 30 that are inserted into the laparoscopic port can depend upon one or more factors, including, but not limited to, the type of procedure, the nature and location of the tissue to be clamped, the patient, e.g., the age, height and/or weight of the patient, and the level of insufflation in the body cavity. Once inserted through the laparoscopic port, the amount of clamp portion 40 and sheath component 30 can be adjusted until the desired position of band clamp device 10 within the patient is achieved.

Figure 6B:
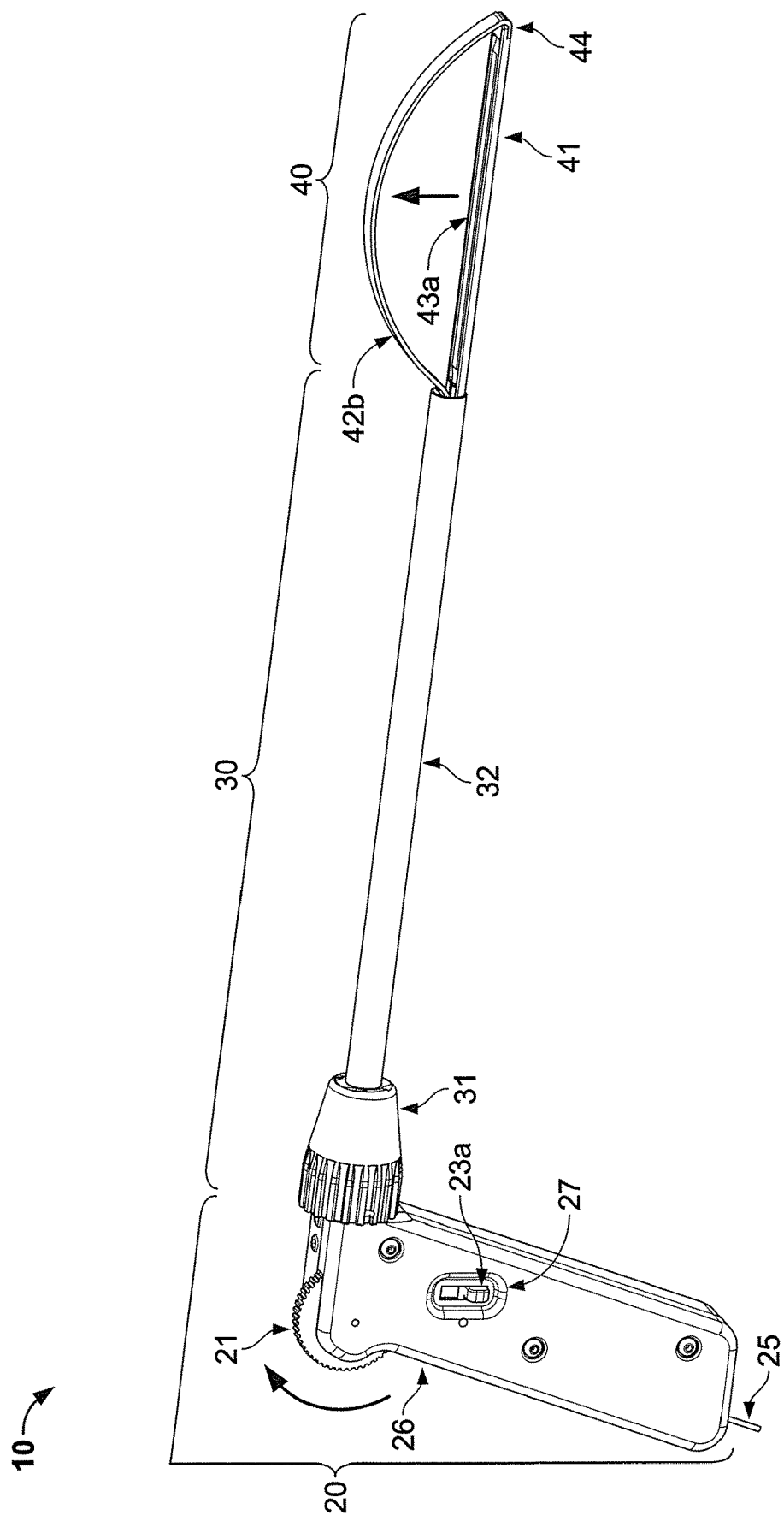

Once band clamp device 10 has been inserted through the laparoscopic port, the flexible upper band 42b can be payed out through sheath 32, as illustrated in FIG. 6B. The band tension/loosen switch 23a is moved to the down position, allowing the first tensioning wheel 21 to be moved, or rotated, clockwise. The clockwise movement of the first tensioning wheel 21 engages the flexible upper band 42b, advancing the band forward through sheath 32, creating a slack loop 42b with the elongate surface member 41 in the clamp portion 40 of device 10. As described above, the flexible upper band 42b can be made of a material that has adequate stiffness and/or shape memory to allow formation of a widened loop with the elongate surface member 41 as the flexible upper band 42b is payed out. For example, the material is such that the flexible upper band 42b will not lay flat on the elongate surface member as the band is payed out. Exemplary of a material that can be used for the flexible upper band 42b includes any material that possesses a combination of column strength and flexibility that allows the flexible upper band 42b to form a widened loop with the elongate surface member 41 rather than lying flat on the elongate surface member 41 after the flexible upper band 42b has been payed out and is soft enough to conform to the anatomy of the target tissue when tensioned. Exemplary materials include materials commonly used to make belts, for example, timing belts, such as, but not limited to, flexible polymers, such as polyurethane or polyethylene, for example, a flexible, reinforced polyurethane belt, such as a flexible polyurethane reinforced with fiberglass. In some examples, the flexible upper band 42b is toothed.

The size, or height, of the widened loop that is formed can depend upon, for example, the size of the portion of target tissue that is to be clamped. For example, the flexible upper band 42b can be loosened or payed out to form a widened loop that can be, for example, from or from about 1 cm to 10 cm, such as 1 cm to 9 cm, 1 cm to 8 cm, 1 cm to 7 cm, 1 cm to 6 cm, 1 cm to 5 cm, 1 cm to 4 cm, 1 cm to 3 cm, 1 cm to 2 cm, 2 cm to 10 cm, 2 cm to 9 cm, 2 cm to 8 cm, 2 cm to 7 cm, 2 cm to 6 cm, 2 cm to 5 cm, 2 cm to 4 cm, 2 cm to 3 cm, 3 cm to 10 cm, 3 cm to 9 cm, 3 cm to 8 cm, 3 cm to 7 cm, 3 cm to 6 cm, 3 cm to 5 cm, 3 cm to 4 cm, 4 cm to 10 cm, 4 cm to 9 cm, 4 cm to 8 cm, 4 cm to 7 cm, 4 cm to 6 cm, 4 cm to 5 cm, 5 cm to 10 cm, 5 cm to 9 cm, 5 cm to 8 cm, 5 cm to 7 cm, 5 cm to 6 cm, 6 cm to 10 cm, 6 cm to 9 cm, 6 cm to 8 cm, 6 cm to 7 cm, 7 cm to 10 cm, 7 cm to 9 cm, 7 cm to 8 cm, 8 cm to 10 cm, 8 cm to 9 cm, and 9 cm to 10 cm in width. Generally, the height of the widened loop that is formed between the flexible upper band 42b and the elongate surface member 41 is less than 10 cm, for example, less than 5 cm. For example, the widened loop that is formed between the flexible upper band 42b and the elongate surface member 41 can be at least or about at least 1 cm, 2 cm, 3 cm, 4 cm, 5 cm, 6 cm, 7 cm, 8 cm, 9 cm, but less than 10 cm in height. In one example, the target tissue is the liver, for example, an adult liver, and the widened loop that is formed with the flexible upper band 42b and elongate surface member 41 is between or is between about 2 cm and 5 cm, such as between 3 cm and 4 cm in height.

Figure 6C:
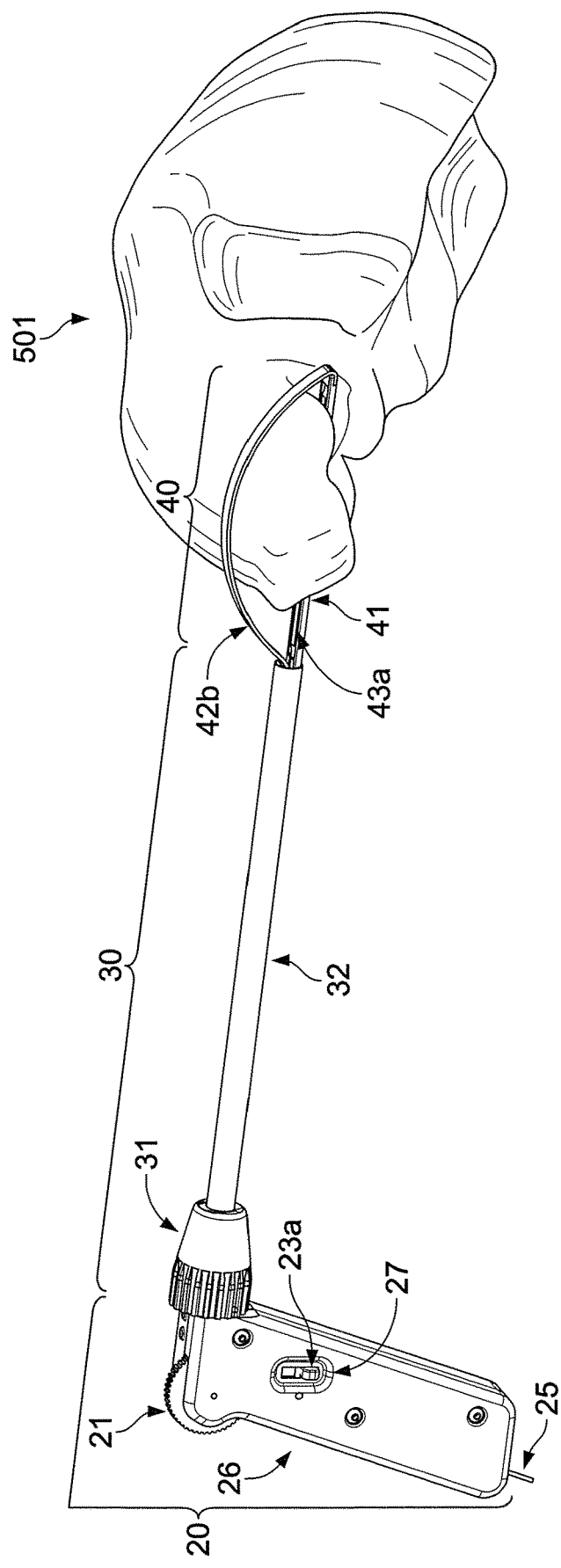
Figure 6D:
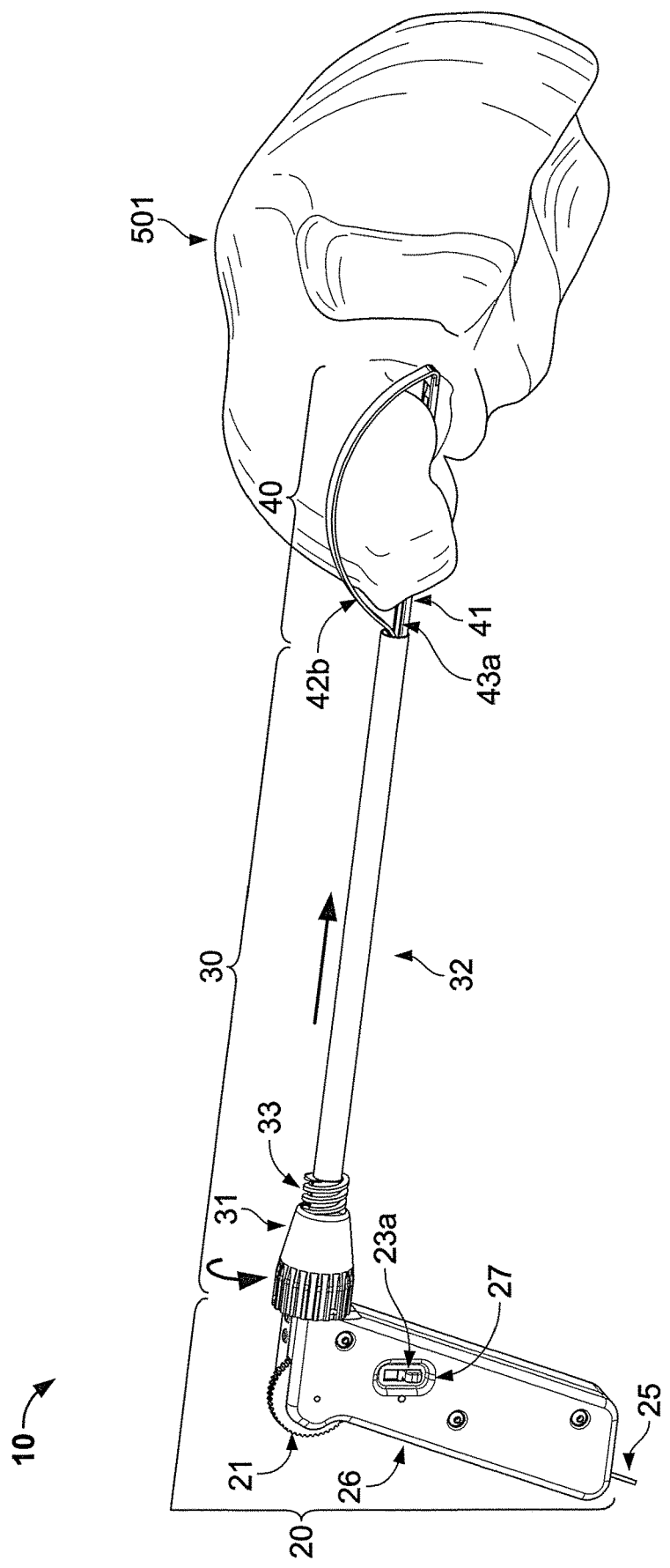

After the flexible upper band 42b is payed out and has formed a loop of the desired size, i.e., width, with the elongate surface member 41, the loop can be placed over the portion of the target tissue to be clamped, such as the liver 501 as exemplified in FIG. 6C. It is understood that the procedure can be performed on other tissues or organs or portions thereof as described elsewhere herein. The amount of tissue to be clamped can be between or between about, for example, 1 g (i.e., 1 cc) and 100 g (i.e., 100 cc), generally between or between about 2 g and 75 g, typically, between or between about 5 g and 50 g. Generally, the amount of tissue to be clamped depends upon the nature and identity of the target tissue. For example, when the target tissue is liver, such as a human adult liver 501, the amount of tissue to be clamped can be between or between about 1 g to 100 g (i.e., between or between about 1 cc to 100 cc), such as between or between about 1 g to 50 g, for example, between or between about 5 g and 50 g. The amount of target tissue to clamp can be determined by performing modeling studies, for example, 3-D modeling studies, such as MRI modeling studies.

In one example, between or between about 5 g and 50 g of target tissue, e.g., liver 501, is clamped. To clamp between or between about 5 g and 50 g of target tissue, e.g., liver 501, for example, a human adult liver, the widened loop of clamp portion 40 can be placed at or about at 1 cm to 5 cm from the tip of the target tissue, e.g., liver 501, typically at or about at 1 cm to 3 cm, generally at or about at 2 cm from the tip of the target tissue, e.g., liver 501. Typically, a liver, for example, a human adult liver, is or is about 5 cm to 10 cm wide, generally, 7 cm wide, and 1 cm to 2 cm thick, generally, 1.5 cm thick, when the widened loop of clamp portion 40 is placed at or about 1 to 5 cm, typically, 2 cm, from the tip of the liver 501. The thickness of the liver increases the further away from the edge, i.e., the liver thickness increases towards the center of the liver. Typically, when the liver is or is about 10 cm wide, the liver is or is about 3 cm thick.

If the initial loop size, i.e., width, is not large enough to encompass the portion of the target tissue, such as the liver 501, to be clamped, the size, i.e., width, of the loop can be further increased by rotating, or turning, the first band tensioning wheel 21 in the clockwise position to pay out additional flexible upper band 42b and increase the size, i.e., width, of the loop until the loop is able to fit over the desired amount of target tissue, e.g., liver 501. The band tension/loosen switch 23a remains in the down position, which allows the clockwise rotation of the first band tensioning wheel 21, and prevents the first band tensioning wheel 21 from rotating, or turning, counter-clockwise to tension the flexible upper band 42b. The balloon 43a remains in the deflated position, and rests on the elongate surface member 41 in the cradle 45, as discussed above in reference to FIGS. 4B and 4C (cradle 45 not visible in FIG. 6C).

The amount of target tissue, such as the liver 501, encompassed by the loop, as depicted in FIG. 6C, can be manipulated and adjusted, for example, by placing the loop over the desired amount of target tissue, e.g., liver 501, and moving the loop into the desired position, for example, so that the target tissue, e.g., liver 501, lays flat on the elongate surface member 41. The amount of target tissue, e.g., liver 501, encompassed by the loop can be manipulated or adjusted grabbing and pulling the portion of the target tissue, e.g., liver 501, through the loop to the desired position, for example, by using a device that can grab and pull the target tissue, e.g., liver 501, through the loop, such as a grasper or tweezers. In one example, the target tissue, e.g., liver 501, can be grabbed and pulled through the loop formed by the flexible upper band 42*b* and the elongate surface member 41 to the desired position, for example, with a grasper. In some examples, ligaments connected to the target tissue, e.g., liver 501, can be cut before placing the loop over the target tissue, e.g., liver 501. The ligaments connected to the target tissue, e.g., liver 501, can be cut using any device or method used to surgically cut ligaments known to those of skill in the art, such as, for example, with a laparoscopic scalpel, e.g., a laparoscopic harmonic scalpel, or laparoscopic scissors. In one example, the target tissue is the liver 501, and the portion of the liver 501 to be clamped is the left lobe, for example, the left median lobe.

As illustrated in FIG. 6D, the sheath 32 position can be adjusted after the loop formed by the flexible upper band 42*b* and elongate surface member 41 of clamp portion 40 is in place over the desired portion of the target tissue to be clamped, e.g., liver 501, in order to fit the anatomy of the target tissue, e.g., liver 501. Sheath 32 is linearly movable with respect to elongate surface member 41 and can be advanced or retracted along the length of the elongate surface member 41 to adjust the size of the clamp portion 40 that extends out of the distal end of sheath 32. The position of the sheath 32 is controlled by the sheath adjustment knob 31 via the screw mechanism 33. The distal portion of the inner surface of the sheath adjustment knob 31 is threaded with female threads and engages the male-threaded screw mechanism 33 to advance and retract the sheath 32 when sheath adjustment knob 31 is turned or rotated.

The sheath adjustment knob 31 can be axially rotated and can be turned, or rotated, forwards, i.e., towards the front side of the band clamp device 10, or can be turned, or rotated, backwards, i.e., towards the back side of the band clamp device 10. Turning, or rotating, the sheath adjustment knob 31 forward, as depicted in FIG. 6D, advances the sheath 32 linearly with respect to elongate surface member 41 toward the clamp end of band clamp device 10. Advancing the sheath 32 reduces the amount of the clamp portion 40 that extends out of the end of the hollow sheath 32. For example, the sheath 32 can be adjusted to enclose more or less of the elongate surface member 41. For example, turning sheath adjustment knob 31 forward can reduce the length of clamp portion 40 that extends out of the hollow sheath 32 to the size of the portion of the target tissue, such as the liver 501, that is to be clamped, i.e., clamp portion 40 can be reduced to a size that fits the anatomy and size of the portion of the liver 501 to be clamped. The sheath 32 can be advanced as far as required to enclose the desired amount of clamp portion 40. For example, the sheath 32 can be advanced until all or almost all of the clamp portion 40 is enclosed by the sheath 32.

The sheath adjustment knob 31 can be turned, or rotated, backwards, i.e., towards the back side of the band clamp device 10 (not depicted in FIG. 6D). Turning, or rotating, the sheath adjustment knob 31 backward retracts the sheath 32 linearly with respect to elongate surface member 41 away from the clamp end and toward the handle end of band clamp device 10. Retracting the sheath 32 increases the amount of the clamp portion 40 that extends out of the end of the hollow sheath 32. For example, turning sheath adjustment knob 31 backward can increase the length of clamp portion 40 that extends out of the hollow sheath 32 to accommodate the size of the portion of the target tissue, such as the liver 501, that is to be clamped, i.e., clamp portion 40 can be increased to a size that fits the anatomy and size of the portion of the target tissue, e.g., liver 501, to be clamped.

Figure 6E:
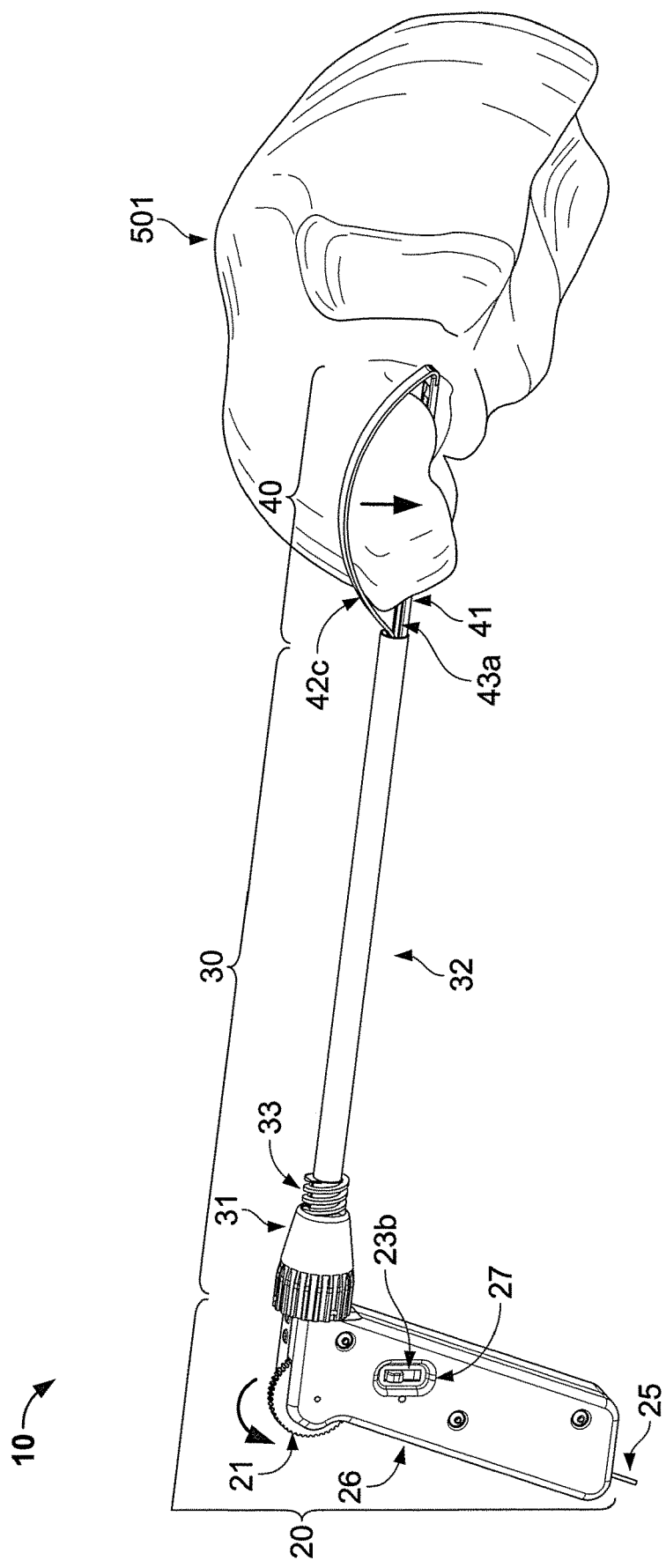

FIG. 6E illustrates tensioning of the flexible upper band 42*c* to fit around the target tissue, such as the liver 501. The band tension/loosen switch 23*b* is moved to the up position, which allows the first band tensioning wheel 21 to be turned, or rotated, in the counter-clockwise direction. Rotation of the first band tensioning wheel 21 in the counter-clockwise direction engages the flexible upper band 42*c* and tensions, or takes in, the band through sheath 32. Tensioning of the flexible upper band 42*c* tensions the loop formed between flexible upper band 42*c* and the elongate surface member 41 in the clamp portion 40 of device 10. The flexible upper band 42*c* can be taken in, or tensioned, until the size, i.e., width, of the loop is reduced to the desired size. For example, the first band tensioning wheel 21 can be turned counter-clockwise, tensioning flexible upper band 42*c* until the band is snug against the target tissue, e.g., liver 501, but not applying significant clamping force. The flexible upper band 42*c* can be tensioned, for example, to take up any excess space surrounding the target tissue, e.g., liver 501, i.e., conform to the anatomy of the target tissue, e.g., liver 501. As described above in reference to FIG. 5B, the tension of the flexible upper band 42*c* can be measured by any method known to those of skill in the art, for example, by a gauge, such as an external gauge, for example a tension or force gauge, e.g., a spring gauge, a digital strain gauge, an analog gauge or a digital pressure gauge, such as a Cole Parmer digital pressure measuring device (e.g., Cole-Parmer®; Vernon Hills, Ill.); visually, for example, by visually observing the tension of the flexible upper band 42*c* around the target tissue 50 as the flexible upper band 42*c* is tightened; or by a compression load cell transducer, for example a 2.2. button style compression load transducer (Interface Advanced Force Measurement; Scottsdale, Ariz.).

As described above, the flexible upper band 42 can be made of any material that is flexible and able to conform to the anatomy and size of the target tissue, e.g., liver 501, as the band 42 is tensioned, such as, for example, a polyurethane. In some examples, the flexible upper band 42 can be toothed. The flexible upper band 42 can be toothed to provide a grip on the liver 501. For example, the teeth on the flexible upper band 42 can be used to prevent the portion of the target tissue, e.g., liver 501, to be clamped from slipping out of the clamp portion 40, i.e., the teeth can keep the clamp portion 40 in the desired position around the portion of the target tissue, e.g., liver 501, to be clamped.

Figure 6F:
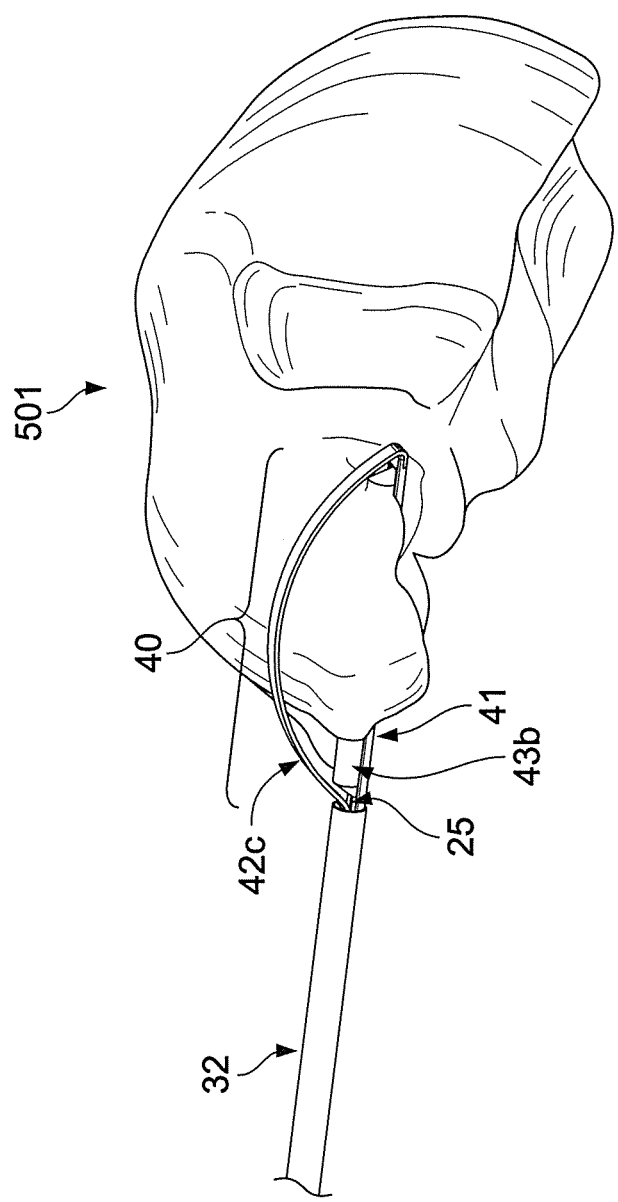

After the flexible upper band 42*c* has been tensioned and has conformed to the size and anatomy of the target tissue, for example, the liver 501, the balloon 43*b* can be inflated, as depicted in FIG. 6F. Balloon 43*b* is inflated through balloon fill line 25. As described above and illustrated in FIG. 1, balloon fill line 25 is connected to the proximal end of balloon 43*b* and extends through the sheath component 30 and pistol grip handle 20 with the other end exiting the bottom of the pistol grip handle 20 and connecting to an external source of fluid or gas, e.g., air. Balloon 43*b* can be inflated with any fluid or gas, for example, air, that is capable of filling the balloon to the desired size and/or balloon inflation pressure. The external source of fluid or gas, e.g., air, can be a syringe, e.g., a plastic syringe or glass syringe, a reusable or single-use syringe; a pump, e.g., a blood pressure pump or cuff; or a tank or a cylinder, e.g., a gas tank or cylinder, for example, a pressurized gas tank or cylinder. For example, the external source of fluid or gas, e.g., air, can be a syringe, such as a glass syringe or plastic syringe, of any size, for example, 500 mL, 250 mL, 100 mL, 75 mL, 50 mL, 30 mL, 25 mL, 20 mL, 15 mL, 10 mL, 5 mL, 1 mL, or smaller. In one example, the external source of fluid or gas is a syringe, for example, a 20 mL standard syringe, filled with air.

Balloon 43 can be inflated and deflated manually, for example, with a syringe or other manual pump, or can be inflated and deflated electronically, for example, controlled through a user interface. The inflated balloon 43b, as illustrated in FIG. 6F, will conform to the anatomy of the target tissue, e.g., liver 501, and apply uniform pressure evenly over the clamped area of target tissue, e.g., liver 501. The amount of fluid or gas, e.g., air, used to inflate balloon 43b can be determined by the amount of pressure the inflated balloon 43b exerts, for example, on the target tissue, such as liver 501. The inflated balloon 43b can be inflated to a pressure of 50 mmHg to 250 mmHg, and typically a pressure that is greater than 120 mmHg (e.g systolic pressure). The inflated balloon 43b can apply a uniform pressure to the target tissue, e.g., liver 501, regardless of the physical dimensions, e.g., thickness or thinness, of the portion of target tissue, e.g., liver 501, that is clamped, i.e., uniform pressure is applied evenly over thick portions of tissue as well as thin portions of tissue. Inflation of balloon 43b allows the desired clamping pressure to be achieved. For example, balloon 43b can be inflated to a size that allows balloon 43b to conform to the anatomy of the target tissue, e.g., liver 501, and fill in any empty space around the target tissue, e.g., liver 501, in the loop created by the flexible upper band 42c and the elongate surface member 41. The uniform pressure applied to the target tissue, e.g., liver 501, is safely below pressure that may damage tissue.

In an exemplary embodiment, the clamping and balloon inflation can compartmentalize the clamped portion of the tissue or organ from the systemic circulation depending on the particular tension and pressure applied to the portion of tissue or organ. For example, the uniform pressure applied by inflated balloon 43b on the liver minimizes trauma to the tissue and assures complete compartmentalization of the clamped portion of the target tissue, e.g., liver 501. For example, the balloon inflation pressure range can be between or between about 50 mmHg and 300 mmHg, typically between or between about 100 mmHg and 300 mmHg, such as 200 mmHg and 300 mmHg. In one example, to achieve complete compartmentalization, the uniform pressure applied by inflated balloon 43b on the target tissue, e.g., liver 501, can be greater than systolic pressure, i.e., 120 mmHg, but less than a pressure that may damage tissue.

During inflation and deflation of balloon 43, shown in FIG. 6F, the balloon pressure can be monitored or measured, as described above in reference to FIG. 5C. For example, the balloon pressure can be monitored to determine when the desired amount of pressure has been achieved or to determine if there has been a change, e.g., loss, in pressure. The balloon pressure can be monitored, for example, with a pressure gauge, such as a digital gauge or an analog gauge. The pressure gauge can be connected to balloon fill line 25, for example, at a point in the balloon fill line 25 that is external to the band clamp device 10. The pressure can be monitored electronically, through a user interface that can include a pressure display, indicator LEDs and alarms, for example, to indicate a change in pressure, such as a drop in pressure, that indicates compartmentalization has failed. The balloon inflation pressure can be monitored, for example, visually. For example, the balloon 43 can be observed visually during inflation and deflation and adjusted to the desired pressure by inflating or deflating the balloon 43 more or less. Monitoring or measuring the balloon pressure can be done during any stage of the procedure, such as a laparoscopic procedure, and can be adjusted and controlled during any stage of the procedure, such as a laparoscopic procedure, to achieve the desired balloon pressure.

C. METHODS AND USES OF CLAMP DEVICE

The band clamp device provided herein can be used during any type of minimally invasive surgical procedure, for example, laparoscopic procedures. The clamp device provided herein can be used in any minimally invasive surgical procedure in which clamping of a tissue or an organ or a portion thereof is desired. The band clamp device can be used in single port or multiple-port minimally invasive surgical procedures. The precise location of the port by which the band clamp is introduced is dependent on the particular target or organ that is to be clamped and the particular purpose of the clamping procedure (e.g., compartmentalized gene delivery, transplant or resection). For example, laparoscopic procedures can be employed for clamping tissue or organs in the abdomen, including for example, the liver, pancreas, gallbladder, spleen, stomach or reproductive organs.

Figure 8B:
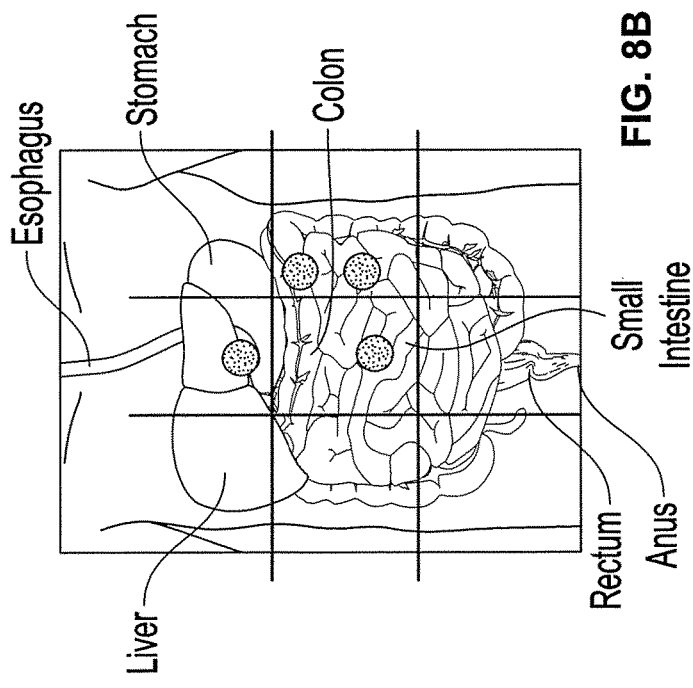
FIGS. 8A-8C depict exemplary positions of laparoscopic ports, in reference to anatomical regions of the human body, that can be used with the device shown in FIG. 1A or 1B and other surgical tools during a laparoscopic procedure.
Figure 8A:
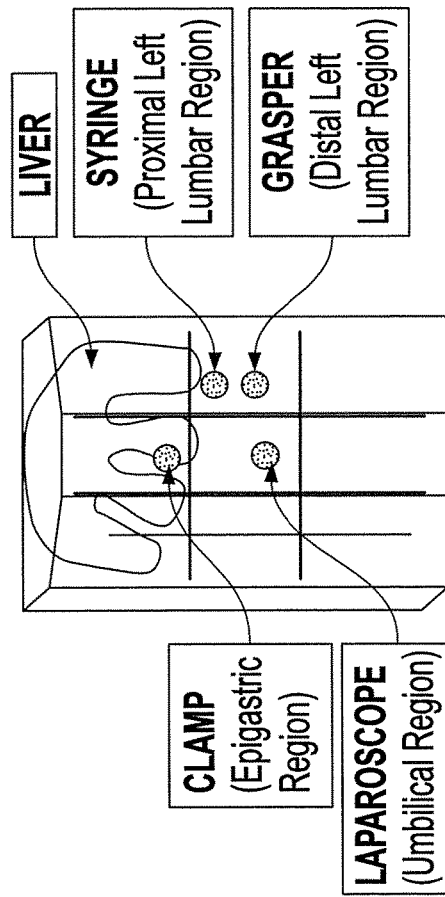
Figure 8C:
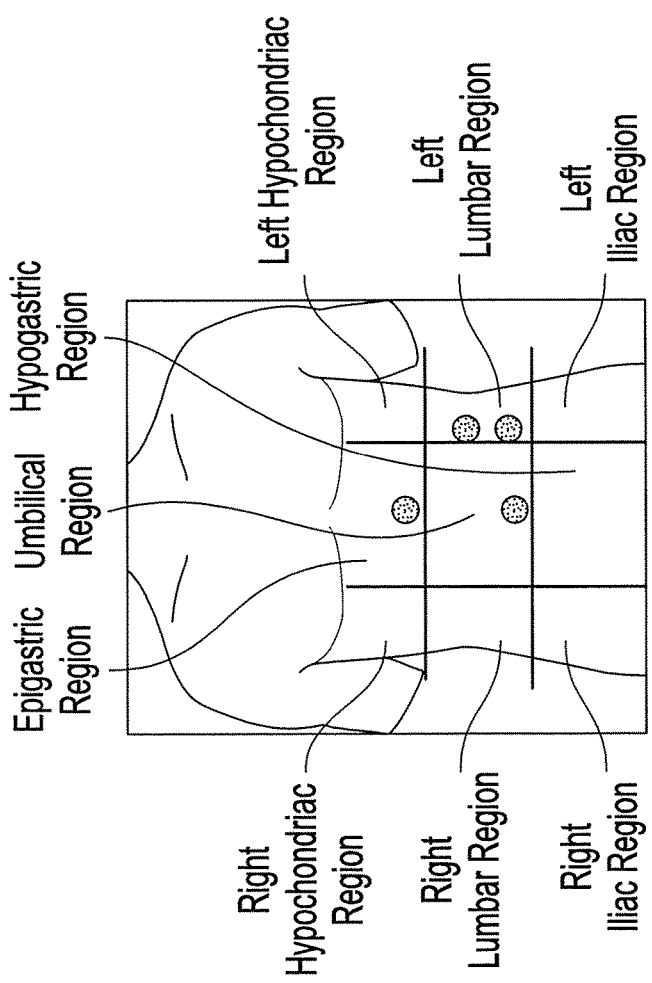

Generally, a laparoscopic procedure will use between one and six ports, typically between two and five ports, such as three or four ports, depending on the scope and nature of the laparoscopic procedure and the amount of laparoscopic instruments to be used. The exact size and location of each of the ports can vary depending on, for example, the nature of the procedure, the target tissue, the size of the laparoscopic instruments, and the number of laparoscopic instruments being employed. As an example, FIGS. 8A-8C depict an exemplary laparoscopic surgical scheme for clamping the liver or portion thereof. As shown in FIG. 8A-8C, a port located in the epigastric region can be positioned above the portion of the liver to be clamped. As shown in FIG. 8A-8C, other ports can be positioned in the abdominal area to provide access of other minimally invasive instruments used during the surgery, for example, as discussed further below. These include ports located in the proximal left lumbar region, the umbilical region or the left lumbar region. For example, the port located in the umbilical region, directly below the epigastric region, can be used for the laparoscope.

1. Compartmentalized Method of Nucleic Acid Delivery

The device provided herein can be used for delivery of a nucleic acid molecule to a compartmentalized tissue or organ or portion thereof by temporarily clamping a tissue, organ or portion thereof so that it is isolated from the systemic circulation. In this compartmentalized method of nucleic acid delivery, the method is characterized by 1) clamping a tissue or an organ or a portion thereof using the band clamp device provided herein to block blood flow to and from an organ or portion thereof to prevent or substantially prevent communication with the systemic circulation; 2) directly administrating a delivered agent containing a nucleic acid molecule to tissue parenchymal cells of the tissue or portion thereof; and 3) maintaining vascular isolation for a time period sufficient to permit cellular uptake of the selected agent. The effect of these aspects means that the delivered agent, such as viral vector, is not exposed to the general circulation, such that systemic immune responses are not initiated, systemic toxicity is avoided and there is no contamination of other non-targeted organs or tissues.

Further, by directly administering the delivered agent to parenchymal cells of the compartmentalized tissue or organ, cellular uptake is maximized. Maximizing cellular uptake of the agent means that, upon release of the tissue or organ compartmentalization, virtually all of the delivered nucleic acid molecule is available for transgene expression in the cell, and the amount of delivered agent that could escape into the systemic circulation is reduced or eliminated. Thus, the methods provided herein permit targeting of only the desired cells within the target organ and expression of a transgene produce for a sustained length of time.

Figure 7:
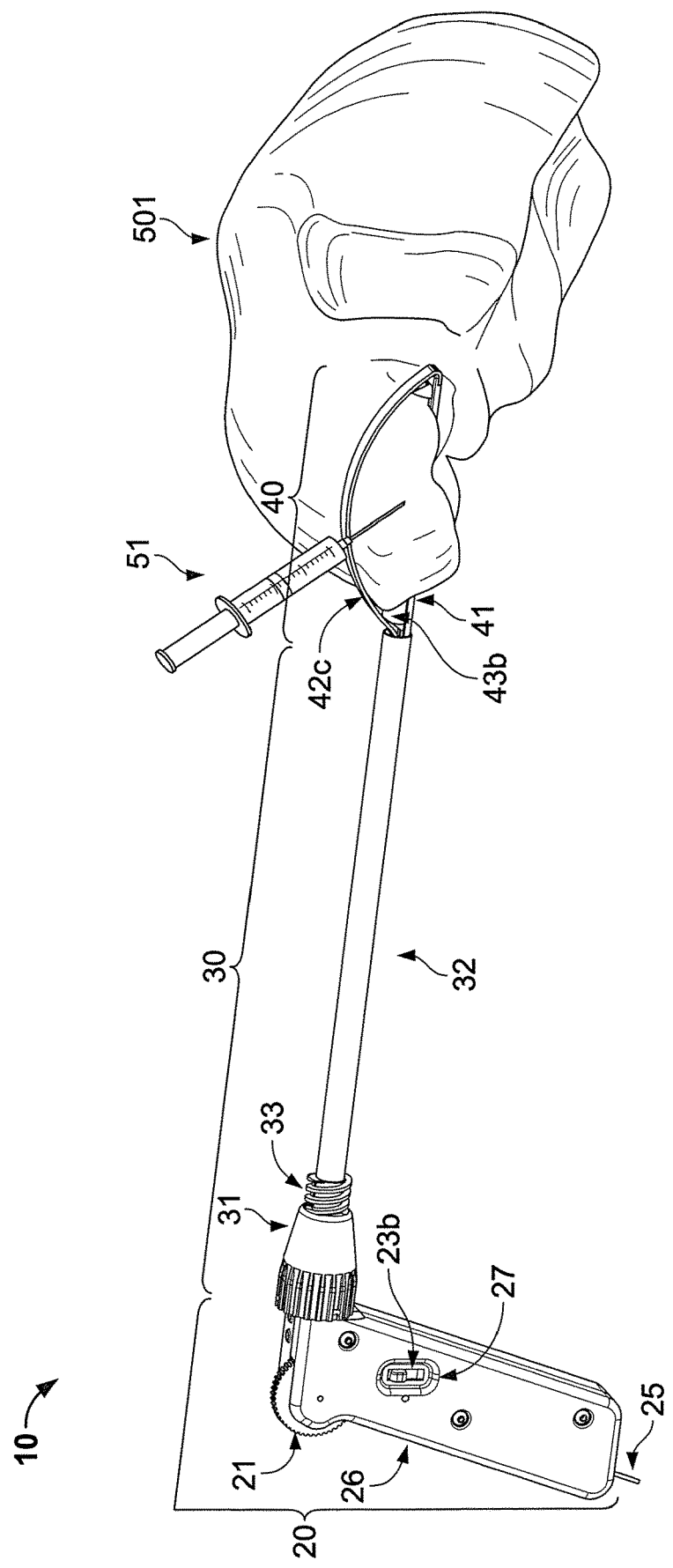
FIG. 7 illustrates the use of the band clamp device for compartmentalizing a target tissue for delivering a therapeutic agent or drug.

As described further below, the band clamp device is used to clamp a tissue or an organ or a portion thereof in order to stop or arrest of blood flow to the tissue or organ, or a portion or region of the tissue or organ, thereby compartmentalizing the tissue or organ or portion thereof from the systemic circulation. This is achieved by adjusting the flexible band so that it is tensioned to be snug and tight on the tissue, and to inflate the balloon so that the balloon applies a uniform pressure to the area being clamped. As described below, the tension and pressure that is applied to the parenchymal tissue by the band clamp is enough to stop blood flood, but is not so much as to cause serious damage to the surrounding tissue. Thus, as shown in FIG. 7, compartmentalization of a tissue or an organ or a portion thereof, such as the liver 501, can be effected when the portion of the target tissue, such as the liver 501, is positioned in the band clamp device 10 between the elongate surface member 41 and flexible upper band in its tensioned position 42c with the loop snugly fit around the top or target tissue 501. The balloon also is in the inflated position 43b to conform to the anatomy of the tissue, such as liver 501 or other target tissue, thereby applying a uniform clamping pressure over the clamped area. As discussed further below, the extent of clamping can be measured, monitored or adjusted during the course of the procedure. The clamp portion (i.e., including tensioning band and biocompaticle deformable article, e.g. balloon) can be appropriately adjusted so that the device can be used to block or occlude one or more, and generally all, arteries, veins, ducts or vessels that traverse a tissue or an organ or a portion thereof, and that empty into, access or otherwise communicate with the systemic circulation.

In the method, compartmentalization of the tissue or organ or portion thereof is maintained for a time period subsequent to the administration of the nucleic agent sufficient so that less than 10% of the delivered agent is exposed to the systemic circulation and/or to allow cellular uptake of greater than 80% of the selected delivered agent by cells of the organ or portion thereof. The method provided herein permits sustained expression of a transgene product in the tissue or organ or portion thereof for more than 60 days, more than 90 days, more than 6 months, more than 9 months, or more than one year.

The compartmentalized method of nucleic acid delivery permits sustained and long-term high level expression of a transgene product. Accordingly, the method can be used in diverse applications, including, but not limited to, medical applications, including applications to replace a defective gene product or in applications to exogenously administer a therapeutic agent; production of organs for transplant; production of therapeutic proteins in transgenic animals (e.g., bioreactors); and in agricultural, veterinary and industrial applications. For example, the methods can be used for cellular expression in vivo of a selected polypeptide. In some examples, the polypeptide agent can be useful in therapeutic settings where the polypeptide treats or ameliorates a disorder or condition in a subject or otherwise improves the quality of life in a subject. In other examples, the polypeptide agent can be useful in agriculture setting, for example, applications that improve the quality or quantity of meat production. The particular application of the method depends on the particular nucleic acid molecule that is being administered. It is within the level of skill in the art to choose a nucleic acid molecule of interest based on any desired application.

In particular examples, the nucleic acid is chosen so that expression thereof following delivery in the compartmentalized nucleic acid method effects treatment of a disease or conditions. Exemplary of such nucleic acids, and associated disease and conditions, are provided in Section D below. For example, exemplary diseases or disorders that can be treated by delivery of a nucleic acid molecule by the compartmentalized nucleic acid delivery method include, but are not limited to, an inherited enzyme deficiency (e.g., mucopolysaccharidosis, glycogen storage disease, and lysosomal storage disease), cancer, hemophilia, diabetes, muscular dystrophy, cardiovascular disorder, cystic fibrosis, neurodegenerative disorder, trauma, pain, sickle cell anemia, autoimmune disease, inflammatory disease, inherited immune deficiency, hypertension and Parkinson's Disease. For example, the disease or condition is selected from among hemophilia A and B, type I diabetes mellitus, alpha-1-antitrypsin (AAT) deficiency, hemochromatosis, Wilson's disease, Crigler-Najjar syndrome type I, ornithine transcarbamylase deficiency, type II, familial hypercholesterolemia, afibrinogenemia, glycogen storage disease (GSD) type Ia, GSD type Ib, GSD type II (Pompe), mucopolysaccharidosis (MPS1), MPS IIIA, MPS IIIB, MPS VII, Fabry disease, Gaucher's disease, Niemann-Pick syndrome, ornithine transcarbamylase deficiency (OTC) deficiency, phenylketonuria, liver fibrosis, liver ischemia reperfusion injury, Alzheimer's disease, Amyotrophic Lateral Sclerosis (ALS), galactosemia, phenylketonuria, maple syrup urine disease, tyrosinemia type 1, methylmalonic acidemia, citrullinemia, Gout and Lesch Nyan syndrome, Sly syndrome, Zellweger syndrome, severe combined immunodeficiency disease (SCID), cystic fibrosis, acute intermittent porphyria, lipoprotein lipase deficiency (LPLD), or multiple sclerosis. With exemplification to the liver, the methods herein can be used in the delivery of a delivered agent containing any nucleic acid, such as any described in Section D, to a compartmentalized liver or portion of the liver to treat any disease in which gene therapy has been used in the art. For example, the liver (or other tissue or organ) can be compartmentalized using the band clamp device for delivery of and treatment of diseases and conditions including, but not limited to: delivery of Factor VIII for treatment of hemophilia A; delivery of Factor IX for treatment of hemophilia B; delivery of a(alpha) 1-antitrypsin for treatment of a(alpha) 1-antitrypsin deficiency; delivery of glucose-6-phosphate-α for the treatment of glycogen storage disease (GSD) type Ia; delivery of G6PT for treatment of GSD type Ib; delivery of acid-α-glucosidase for treatment of GSD type II (Pompe); delivery of α-L-iduronidase for treatment of mucopolysaccharidosis (MPS1); delivery of sulphamidase for treatment of MPS IIIA; delivery of α-N-acetylglucosaminidase (NaGlu) for treatment of MPS IIIB; delivery of β-glucuronidase for treatment of MPS VII; delivery of α-galactosidase A for treatment of Fabry disease; delivery of glucocerebrosidase for treatment of Gaucher's disease; delivery of acid sphingomyelinase for treatment of Niemann-Pick syndrome; delivery of ornithine transcarbamylase deficiency (OTC) for treatment of OTC deficiency; UDP glucuronosyltransferase 1A1 (UGT1A1) for treatment of Crigler-Najjar syndrome; LDL receptor for treatment of familial hypercholesterolemia; phenylalanine hydroxylase for treatment of phenylketonuria; metalloprotease (MMP1 or MMP8); u-PA, TIMP antagonist or anti-HSC molecules for treatment of liver fibrosis; anti-ROS molecules for treatment of liver ischemia reperfusion injury; proinsulin precursor or transcription factors for β cell transdifferentiation for treatment of diabetes mellitus; RNAi against viral RNA for treatment of Hepatitis B; RNAi against viral RNA for treatment of hepatitis C; p53 for treatment of liver cancers; IFN-β or other anti-inflammatory cytokine for the treatment of multiple sclerosis; interferon-α for the treatment of induced hepatitis; lipoprotein lipase for the treatment of lipoprotein lipase deficiency (LPLD); or an anti-angiogenic agent, such as endostatin or angiostatin, for the treatment of a cancer.

The method of delivering a nucleic acid using the band clamp device provided herein can be performed on any mammalian subject. The size of the device, including the laparoscopic access length and/or clamp portion, can be adjusted to accommodate the particular subject. Typically, the device is configured to be adjustable, and can accommodate diverse subjects. Exemplary of such subjects include, but are not limited to, mice, rats, dogs, cows, pigs, sheep, goats, horses and humans. In particular, the methods provided herein are performed in human subjects. In particular, the method can be performed on human subjects that are children under the age of 18, such as infants, toddlers and younger children. In some examples, the method can be performed in utero on a fetus. Since the method permits sustained and long-term high level expression of a transgene product, the method can be used in diverse applications, including, but not limited to, medical applications, including applications to replace a defective gene product or in applications to exogenously administer a therapeutic agent; production of organs for transplant; production of therapeutic proteins in transgenic animals (e.g., bioreactors); and in agricultural or veterinary applications as well as industrial applications.

The method using the band clamp device to compartmentalize a tissue or an organ or a portion thereof for delivery of nucleic acid molecule can be performed one time on the subject, or can be performed a plurality of times. For example, the band clamp device can be repositioned during the course of treatment to effect delivery at multiple target loci, particularly where high levels of transduction or expression is sought throughout the tissue or organ. Alternatively, instead of repositioning the band clamp device, the method can be performed with an injection device that can be movable during the laparoscopic surgery and/or otherwise is capable of effecting delivery to multiple loci within the clamped or compartmentalized region of the tissue or portion thereof. In such examples, the method is generally repeated within minutes, hours or days of the first application of the method. In other examples, the method can be repeated weeks, months or years after the first application.

Description of steps of the method, and various exemplary non-limiting embodiments thereof, is provided in the following subsections.

a. Compartmentalization of a Tissue or Organ Using the Band Clamp Device

In the methods provided herein, the band clamp device provided herein is used to clamp a tissue, organ or portion thereof in a minimally invasive surgery to effect compartmentalization of the tissue, organ or portion thereof by isolating it from the vasculature system. In some examples, depending on the particular tissue or organ or portion thereof, compartmentalization is also additionally achieved by isolation from the ductal system and/or lymph system. Initiation of the compartmentalization precedes administration of the selected agent and the clamp is not released or ended to restore vascular circulation to the organ or portion thereof until after a period of time sufficient to allow cellular uptake of the selected agent.

Any tissue or organ or portion thereof can be clamped by the band clamp for delivery of nucleic acids to a compartmentalized area, so long as it can be accessed by a skilled physician or surgeon in minimally invasive surgical methods and the band clamp is able to be configured over the tissue or organ or portion thereof to effect tensioning of the flexible band and inflation of the balloon. Such tissues or organs include, but are not limited to, liver, lung, CNS (brain or spinal cord), peripheral nervous system (e.g., nerve), pancreas, gall bladder, endocrine glands (pituitary, adrenal, thyroid, etc.), cardiovascular organs (e.g., heart and blood vessels), skin, urogenital organs (kidney, uterus, cervix, prostate, urethra), organs of the respiratory system (e.g., lung or airways), bone, muscle, and intestine. This list is not intended to be exhaustive, as one of skill in the art will recognize additional target organs and portions thereof. In particular examples, the band clamp is used to compartmentalize the liver or portion thereof for delivery of nucleic acids.

Generally, the tissue or organ or portion thereof that is clamped and compartmentalized in the method herein is one that is amenable to vascular isolation for a time period sufficient to permit virtually all of the delivered agent to be taken up by parenchymal cells. In particular examples herein, the band clamp provided herein is maintained on the tissue or organ or portion thereof to maintain compartmentalization of an organ or portion thereof for at least 10 minutes, 15 minutes, 20 minutes, 25 minutes, 30 minutes, 35 minutes, 40 minutes, 45 minutes, 50 minutes, 55 minutes or 60 minutes, or more. Generally, clamping and compartmentalization is for at least 20 minutes but not longer than 60 minutes. For example, the band clamp is maintained to compartmentalize an organ or portion thereof, such as the liver or portion thereof, for at least 30 minutes and generally for not longer than 60 minutes. Thus, depending on the particular delivered agent, the compartmentalization is maintained under conditions that can result in ischemia to the organ tissue or portion thereof for a brief time period. Hence, the organ or portion thereof used in the methods herein is one that is amenable to periods of brief ischemia.

The method can be performed using minimally invasive surgical procedures, such as laparoscopy. The band clamp device is used to clamp the parenchyma of a tissue or an organ or a portion thereof to compress blood vessels, arteries, ducts or lymph vessels and block blood flow to a region, lobe, section or segment of a tissue or organ. For use in minimally invasive surgeries, the band clamp can be applied to a tissue or an organ or a portion thereof as described herein with reference to FIGS. 6A-6F. As discussed above with reference to FIG. 6A, before inserting the clamp into a port or cannula for endoscopic access (e.g., laparoscopic access or other minimally invasive surgery type), the clamp is configured so that the flexible band lies flat over the distal end of the elongate surface member, the balloon is deflated and the band tension/loosen switch is adjusted to its up position 23b. In this position, the clamp portion and sheath portion can be inserted through the port, while the handle remains outside of the port for manipulation of the flexible band and balloon.

The precise location of the port by which the band clamp is introduced is dependent on the particular target or organ that is to be compartmentalized for delivery of the nucleic acid. For example, laparoscopic procedures can be employed for clamping tissue or organs in the abdomen, including for example, the liver, pancreas, gallbladder, spleen, stomach or reproductive organs. As an example, FIGS. 8A-8C depict an exemplary laparoscopic surgical scheme for clamping the liver or portion thereof. As shown in FIGS. 8A-8C, the band clamp device 10 and injection device can be used in multi-port laparoscopic procedures. For example, the laparoscopic procedure can be a multi-port laparoscopic procedure that uses four ports, represented as black circles in FIGS. 8A-8C. The four ports can be located in various abdominal regions depending on the particular target tissue sought to be compartmentalized for delivery of the nucleic acid molecule. As an example, for compartmentalization and delivery of a nucleic acid molecule to the liver, the four ports can be located in the epigastric region, the umbilical region, the proximal left lumbar region and the distal left lumbar region (see e.g., FIGS. 8A-8C). The location of the four ports illustrated in FIGS. 8A-8C is a general depiction of an area where the port can be located. Exact position and location can vary and will depend upon any one or more factors, including, but not limited to, the type of procedure, the location of the tissue, and the amount of laparoscopic instruments to be used.

In particular, FIG. 8A-8C illustrate, in various schematic depictions, the abdominal region illustrating the location of four laparoscopic ports with respect to the liver for an exemplary laparoscopic procedure for use with the band clamp device described herein. The procedures can be performed in conjunction with an injection device that is also configured for minimally invasive surgeries, such as laparoscopic procedures, as described further below. The port located in the epigastric region is positioned directly above the portion of liver to be clamped. The band clamp device provided herein can be inserted into the epigastric port during a laparoscopic procedure. The port located in the umbilical region, directly below the epigastric region, can be used, for example, for the laparoscope. The port located in the left lumbar region, proximal to the liver, is positioned near the liver and near the epigastric port. The proximal left lumbar port can be used for other surgical instruments required to perform the surgery. For example, it can be used for insertion of an injection device into the abdominal cavity, such as for example, any syringe or needle. The position of the proximal left lumbar port can be determined based on the size and length of the injection device and location of the clamped tissue. For example, the proximal left lumbar port can be positioned so that it is close enough to the target tissue, e.g., liver, for the injection device, such as the syringe injection device described herein, to deliver the therapeutic to the clamped region when inserted through the port. The port located in the left lumbar region, distal to the liver, can be used with a surgical tool capable of grabbing and moving the target tissue, e.g., liver, for example, a grasper or tweezers. The position of the distal left lumbar port can be determined based on the size and length of the grasping device and location of the clamped tissue.

The amount of the band clamp device that is inserted into the port can vary throughout the surgical procedure. For example, the surgeon can constantly adjust (in and out) the length of the device inside the abdominal cavity until appropriate visualization and clamping of the desired portion of the tissue or organ or portion thereof (e.g., liver or portion thereof) is accomplished. In addition, the amount of the device inside the body, for example the human abdomen during laparoscopic procedures, can vary depending on the anatomical dimensions of the subject undergoing the procedure (e.g., age, weight, stature). In addition, the surgeon can choose to adjust the amount of insufflation, such as abdominal insufflation, depending on how well the inside of the cavity can be visualized by the surgeon to position the devices, which can make it necessary to insert more or less of the device into the body cavity to achieve successful clamping and compartmentalization of the tissue or organ or portion thereof (e.g., liver or portion thereof).

Once inserted into the port, such as a laparoscopic port, near the tissue or organ or portion thereof that is to be clamped, the band clamp device can be adjusted to effect clamping of a tissue or portion thereof. For example, as described with reference to FIG. 6B, the band/tension loosen switch 23a can be moved to the down position to permit adjustment, e.g., loosening, of the flexible band. The tensioning wheel 21 can be turned or rotated clockwise to advance the band forward so that a loop is created in the clamp portion of the device at the distal end of the elongated surface member.

As described elsewhere herein, the extent of movement of the tensioning wheel, and hence the portion of the band that is advanced out of the sheath to form the loop, can be determined so that the loop fits over the tissue or organ or portion thereof to be clamped. For performing the method of gene delivery, the height of the loop is sufficient so that an area of tissue can be pulled through the loop that is sufficient to effect delivery and injection of the delivered agent. For example, the loop is adjusted so that between or between about 5 g and 50 g of tissue, such as liver 501, can be clamped. As exemplified for the liver, for example, a human adult liver, at or about 1 to 5 cm, typically, 2 cm, from the tip of the liver, the liver is or is about 5 cm to 10 cm wide, generally, 7 cm wide, and 1 cm to 2 cm thick, generally, 1.5 cm thick. The thickness of the liver increases the further away from the edge, i.e., the liver thickness increases towards the center of the liver. Typically, when the liver is or is about 10 cm wide, the liver is or is about 3 cm thick. Thus, to clamp between or between about 5 g and 50 g of liver 501, for example, a human adult liver, the height of the loop should be from or from about 3 cm to 4 cm in height, so that the widened loop can be placed at or about at 1 cm to 5 cm from the tip of the liver, typically at or about at 1 cm to 3 cm, generally at or about at 2 cm from the tip of the liver. In particular, the flexible band is adjusted to 3 to 4 cm in height so that the loop fits over the left median lobe of the liver.

As described herein with reference to FIG. 6C, after adjustment of the flexible band to form a loop of the desired size, the loop can be placed over the portion of the target tissue to be clamped. In some instances, it can be necessary to mobilize a portion of the tissue or organ to allow access to the region to permit clamping. For example, ligaments connected to the tissue or portion that is being clamped can be cut in order to expose a sufficient portion of the tissue or organ or portion thereof for access through the loop in the clamp. For example, due to the segmented anatomy of the liver into self-contained units, compartmentalization of a specific lobe, segment or portion thereof can be achieved, while maintaining blood flow to the other segments. Mobilization can require dividing the associated ligaments and/or other associated glands. Procedures and techniques for mobilizing or isolating the various lobes or segments of the liver are well known to one of skill in the art. For example, the caudate lobe, the left lobe, or the left median lobe, are all reasonably vascularly isolated and accessible. Differences in liver anatomy between mammalian species can render a particular region or lobe more amenable to isolation in one species than another. One of skill in the art would recognize comparable lobes in other animals, and could identify a lobe or segment suitable for mobilizing or isolating for compartmentalization using the methods herein.

In particular examples herein, the caudate lobe, left lobe or left median lobe, or portion thereof, is compartmentalized. If necessary, retraction and dissection of the liver lobe or segment from its surrounding attachments can be performed to permit access to a region that can be properly compartmentalized from the vasculature without damaging or affecting other regions of the tissue or organ or surrounding structures. For example, the caudate lobe lies posterior to segment IV and is closely associated to the inferior vena cava and portal veins. Mobilization of the caudate lobe can be achieved by division of the gastrohepatic omentum and dorsal caudate-caval ligament. The left lobe of the liver can be mobilized by dividing the left triangular ligament. Similar procedures can be used to mobilize the comparable lobe in the human or other subject.

If necessary, the tissue or organ or portion thereof can be pulled into the loop in the clamp using graspers or tweezers that can be accessed using laparoscopic instruments. In such a configuration, the deflated balloon is generally on the underside of the tissue and the flexible band extends over the top of the tissue or organ. Once contained in the loop of the clamp, the clamp can be sized to fit the portion of the tissue or organ by adjusting the sheath, for example using the sheath adjustment knob 31, as described herein with reference to FIG. 6D. As shown in FIG. 6E, clamping of the tissue or organ or portion thereof can be effected by moving the band tension/loosen switch 23b to the up position, and adjusting the tensioning wheel so that the flexible band is pulled to decrease the size of the loop around the tissue or organ or portion thereof. For example, the sheath can be moved and the flexible band tensioned so that it fits snug over the tissue, but does not provide too substantial or high of a clamping force.

If desired, the force of a clamp can be determined using procedures known in the art, such as by using a tension gauge. Any tension gauge can be used that directly or indirectly indicates the amount of tension being applied by the flexible band. The tension gauge can be mechanical or electronic, digital or analog. For example, the tension gauge can have a digital display that indicates quantitatively the amount of tensile force that is being applies by the flexible band. A linear analog indicator device also can be used where the readout is in the form of a needle moving in a linear fashion with a tension-marked scale on one side of the device. The indication also can be remoted to a computer by cable or wirelessly. The gauge can be introduced separately into a port during the minimally invasive surgery, or can be configured to be introduced with the band clamp device. For example, a tension gauge can be spliced into a segment of the band so that direct measurements of the tension in the belt can be made. As an alternative, the band clamp can be configured with a movable bearing in a manner in which the flexible band is routed over the bearing. In such a device, an indirect measurement of the tension of the flexible band on the tissue can be made based on the deflection of the bearing.

In order to effect uniform compression, of the tissue or portion thereof to effect compartmentalization of the entire region of the area being clamped, the balloon is generally also inflated. As described elsewhere herein, the balloon can be inflated through the balloon inflation line using any external source that is capable of filling the balloon to the desired size and/or balloon inflation pressure. As described herein with reference to FIG. 6F, inflation of the balloon conforms the balloon so that the balloon applies a uniform clamping pressure to the area of the tissue or organ or portion thereof that is being clamped.

The extent or amount of inflation, and hence uniform pressure applied to the tissue, can be any that achieves a pressure that stops or cuts off blood flow across the entire section or portion of the tissue or organ that is under clamping. It is within the level of one of skill in the art, such as a skilled surgeon, to determine the ideal pressure to achieve optimal compartmentalization of an organ or portion thereof while minimizing tissue damage or trauma. Based on normal physiologic blood pressure ranges between 120 mmHg (systolic pressure) and 80 mmHg (diastolic pressure), safe and effective compartmentalization of the tissue or organ can be achieved with a balloon inflation pressure range of from 50 mmHg to 300 mmHg, such as 120 mmHg to 250 mmHg, for example 200 to 250 mmHg. Typically, the pressure is above the systolic blood pressure of 120 mmHg so that blood flow is completely cut off, but is not so high that tissue damage occurs. The pressure in the balloon can be measured as an indication of the compression of the organ. The pressure in mmHg can be determined using a pressure gauge, such as a Cole Parmer digital pressure measuring device (e.g., Cole-Parmer®; Vernon Hills, Ill.) or other similar device known to a skilled artisan. The balloon pressure can be monitored or measured during the course of the surgical procedure. For example, changes in balloon pressure can indicate that the clamping device has moved in the subject, the balloon inflation has been compromised, or the tensioning band otherwise loosened. By monitoring the balloon pressure, the device can be adjusted during the surgical procedure to ensure that the balloon pressure is kept uniform.

The tension and pressure applied by the band clamp to ensure compartmentalization of the tissue or organ or portion thereof has been achieved also can be monitored by any method that can assess blood flow to the tissue or organ. For example, reduction or elimination of blood flow can be monitored based on the color of tissue; electron paramagnetic resonance (EPR) oximetry using India ink or other reportable dye; using a Tissue Spectroscope (TiSpec); perfusion magnetic resonance imaging, positron emission tomography, near-infrared (NIR) spectroscopy, optical Doppler tomography, ultrasound and other methods known to a skilled artisan.

After clamping, and hence, compartmentalization of the tissue or organ or portion thereof occurs, the delivered agent is administered directly to the area that is compartmentalized. Hence, clamping the tissue or organ or portion thereof to effect compartmentalization is initiated immediately prior to delivery of the delivered agent to the tissue. As discussed further below, after delivery of the nucleic acid, the compartmentalization of the area from the systemic circulation is maintained for a predetermined time before release of the band clamp.

b. Delivery of a Nucleic Acid Molecule

After clamping or compartmentalizing the tissue or organ, a delivered agent containing a nucleic acid molecule of interest can be delivered to the tissue parenchyma in the area of the tissue or organ that is compartmentalized. The delivered agent is generally administered immediately after initiating compartmentalization of an organ or portion thereof, such as within or no more than 10 minutes and generally no more than 5 minutes after initiating compartmentalization of an organ or portion thereof. For example, the delivered agent is delivered to a subject no more than 30 seconds, 1 minute, 2 minutes, 3 minutes, 4 minutes or 5 minutes, 6 minutes, 7 minutes, 8 minutes, 9 minutes or 10 minutes after initiating compartmentalization.

i. Parenchymal Injection of Delivered Agent

Typically, direct intraparenchymal administration of the delivered agent is employed. Any desired nucleic acid molecule or delivered agent containing a nucleic acid molecule can be delivered to the compartmentalized tissue or organ or portion thereof, and in particular any described in Section D. In particular, the delivered agent is administered by direct injection into the parenchyma of the tissue so that the nucleic acid is delivered directly to cells in the organ or tissue or portion thereof. For example, in the case of the liver, target parenchymal cells are hepatocytes, while non-parenchymal cells include vascular endothelial cells, Kupffer cells and supporting stromal cells. Direct injection into the parenchyma or interstitial space by coupled with the compartmentalization of the tissue cells (e.g., by vascular exclusion and isolation) described above, increases the frequency and efficiency of uptake of the delivered agent by the tissue cells while minimizing exposure to the general circulation. In addition to increasing the frequency and efficiency of uptake of the delivered agent by tissue cells, parenchymal delivery also can avoid exposure of the delivered agent to immune cells.

Typically, the delivered agent that is delivered is provided as a composition. Exemplary of such delivered agents and compositions are those described in Section D. The delivered agent can be delivered in a pharmaceutically acceptable liquid or aqueous carrier. The delivered agent can be introduced directly into the parenchyma of a tissue or an organ or a portion thereof, by injection using a needle or other similar device. The volume of the delivered agent in the carrier to be delivered is or is about 0.5 mL to 100 mL, such as 0.5 mL to 50 mL, 1 mL to 20 mL, 5 mL to 50 mL, or 5 mL to 20 mL.

For example, in any of the methods of delivering the delivered agent containing the nucleic acid to the compartmentalized area, an injection device containing the agent to be delivered and that is adapted for laparoscopic access can be used for delivery of the delivered agent containing the nucleic acid molecule (see FIG. 7 and FIGS. 8A-8C). The injection device can be configured as part of the band clamp device, or can be a separate device. For example, the band clamp device can be adapted or modified or made to be compatible with a delivery device in order to permit faster or more efficient delivery of the delivered agent following vascular isolation. Typically, a separate injection device is utilized, which provides for flexibility in the procedure so that the delivery of the nucleic acid into the tissue is not limited by the proximity of the injection device to the band clamp or the configuration of a combined device. For example, as shown in FIG. 7, the delivered agent containing the nucleic acid molecule can be administered by any injection device known to a skilled artisan that is capable of delivering an agent to a target tissue, for example, injection device 51. The device 51 typically contains a syringe barrel containing a fluid reservoir for the agent, a plunger to control release and loading of the agent and an injection needle to penetrate the target tissue. Typically, a separate injection device is utilized that is introduced during the minimally invasive surgery through a separate laparoscopic port. Hence, the injection device is configured for laparoscopic access. Exemplary of an injection device that can be used in the compartmentalized methods herein is the laparoscopic injection device described in Section E and any described in U.S. Provisional Application Ser. No. 61/863,888.

It is understood herein that the delivered agent that is delivered to a tissue or cell, discussed further below, is one that is capable of uptake by resident cells. If necessary, the delivered agent can be modified to increase or mediate entry by a particular cell. For example, fiber capsomer modifications of adenovirus are known in the art to permit attachment of the viral vector to cell targets for efficient virus entry (see e.g., Campos et al. (2007) *Curr. Gene Ther.*, 7:189-204; Russell, W. C., (2009) *J. Gen. Virol.*, 90:1-20).

The delivery of delivered agents by parenchymal injection can be aided by the use of imaging techniques that differentiate the parenchymal tissue and cells from the surrounding vasculature and associated architecture. The imaging can be performed immediately prior to injection, coincident with injection and/or subsequent to injection. Such imaging techniques include, but are not limited to, magnetic resonance imaging (MRI), ultrasound and sonography techniques, including Doppler sonography. For example, B-glow, 3-D imaging or color Doppler can be used. If necessary, contrast agents can be injected to facilitate imaging. For example, such methods also can be used to minimize the possibility of introduction of the agent into the lumen of the vascular or ductal systems.

If necessary, the efficacy of delivery agent uptake by tissue cells can be increased using various techniques known to one of skill in the art. It is understood that procedures that enhance delivery agent uptake can reduce the compartmentalization time (discussed above) because less time will be required to ensure sufficient delivered agent is taken up by the cells. The choice of particular procedure can be empirically determined by one of skill in the art and depends on the particular delivered agent that is delivered, the route of administration (e.g., particular tissue or organ) and the dosage or amount of agent administered. In one example, the delivered agent can be formulated with lipids, polymer transfection reagents, or other agents. In other examples, physical methods can be used to enhance delivery. Exemplary physical methods to enhance delivery of a delivered agent include, but are not limited to, "gene gun" method, electroporation, sonoporation, pressure or ultrasound. Alternatively to enhance in vivo gene delivery with minimal tissue damage the pharmaceutical composition can be administered using a femtosecond infrared laser (LBGT technology).

In one example, the uptake of delivered agents, and in particular delivered agents that are viruses or virus-like particles, such as adenovirus, can be enhanced by the presence of various agents. For example, the delivered agent can be administered with an agent or compound that is a transcriptional enhancer of the virus-specific cell surface receptor. Such agents or compounds include, for example, a histone deacetylase (HDAC) inhibitors. HDAC inhibitors include those of the class of hydroxamic acids, cyclic tetrapeptides, benzamides, electrophilic ketones or aliphatic acid compounds. For example, HDAC inhibitors include, but are not limited to, trischostatin A, vorinostat (SAHA), belionostat (PXD101), LAQ824, panobinostat (LBH589), entinostat (MS-275), C199, mocetinostat (MGCD0103), romidepsin (lstodax), valproic acid, PCI-24781, SB939, resminostat, givinostat, CUDC-101, AR-42, CHR-2845, CHR-3996, 4SC-202, CG200745, Kevetrin, or trichostatin A (TSA). Exemplary of an HDAC inhibitor is valproic acid, which is a transcriptional enhancer of the adenovirus receptor CAR and the therapeutic transgene. Studies have shown that adenoviral uptake is increased in the presence of valproic acid (Segura-Pancheco et al. (2007) *Genet. Vaccines Ther.*, 5:10). In such examples, the viral vector is formulated together or separately with the agent. In examples where the viral vector is formulated separately, the transcriptional enhancer agent or compound is delivered prior to delivery of the delivered agent. The transcriptional enhancer agent can be administered at or between about 1 mg/kg to 100 mg/kg, for example, at or about 20 mg/kg to 60 mg/kg, such as 40 mg/kg. The dosage can be divided and administered separately to achieve the total dose. For example, the cycle of administration can be 1 time a day, 2 times, 3 times, 4 times, or 5 times a day. The frequency of administration can be daily for at least 3 days, 4 days, 5 days, 6 days, 7 days, or 2 weeks. The agent can be administered by any route of administration, such as, subcutaneously, intravenously, orally or topically. In particular examples, the agent is administered by direct parenchymal administration.

In some examples, the delivered agent is formulated with an agent or delivery vehicle that binds to or complexes with the delivered agent and mediates its entry into cells. Exemplary agents include, but are not limited to, cationic liposomes and lipids, lipoproteins, synthetic polymers or polypeptides, mineral compounds or vitamins. Exemplary of polymers include polycations or polyanions. For example, a delivered agent can be formulated with polyamine, calcium phosphate precipitate, histone protein, protamine, polyethylenemine, polylysine, polyarginine, polyornithine, DEAE dextrane, polybrene, polyampholyte complex, spermine, spermidine, purtrescine, human serum albumin, DNA binding proteins, non-histone chromosomal proteins, coat proteins from DNA viruses and polymers of N-substituted glycines.

For example, the delivered agent can be encapsulated in lipids or packaged in liposomes prior to delivery to the subject or to cells derived therefrom. Lipid encapsulation is generally accomplished using liposomes that are able to stably bind or entrap and retain nucleic acid. The ratio of condensed nucleic acid delivered agent to lipid preparation can vary but will generally be around 1 mg DNA: 1 micromoles lipid) or more of lipid. Liposomal preparations include cationic (positively charged), anionic (negatively charged) and neutral preparations. Such preparations are well known to one of skill in the art and readily available. For example, exemplary cationic lipids include, but are not limited to, N[1-2,3-dioleyloxy)propyl]-N,N,N-triethyammonium (DOTMA; available under the product line Lipofectin®); DDAB/DOPE and DOTAP/DOPE. Anionic and neutral liposomes also are readily available and can be prepared from phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), such as the commercially available preparation Avanti Polar Lipids. The liposomes include multilamellar vesicles (MLVs), small unilamellar vesicles (SUVs), or large unilamellar vesicles (LUCs).

In some examples, the delivered agent can be a nanoparticle that contains a functional group or targeting agent to further assist and increase cellular delivery of the agent, for example, a targeting molecule that binds to receptors expressed in the cells to be targeted. Functional groups or targeting agents include, for example, a cell targeting moiety that enhances the association of the agent or complex with a cell. The cell targeting moiety can be, but is not limited to, a protein, peptide, lipid, steroid, sugar, carbohydrate, (non-expressing) polynucleic acid or synthetic compound. For example, cell targeting signals can include ligands that enhance cellular binding to receptors. Such ligands include, but are not limited to, insulin, growth factor (e.g., EGF or FGF), transferrin, peptides that include the RGD sequence. Other targeting moieties include, but are not limited to, chemical groups that react with thiol, sulfhydryl or disulfide groups on cells, folate and other vitamins.

ii. Dosages and Amounts

The amount or dosage of delivered agent that is administered can be empirically determined based on the particular application and the particular type of agent that is being delivered (e.g., a virus). Delivery of nucleic acid to a compartmentalized tissue or organ, such as achieved using the band clamp device provided herein, effects a linear dose-response kinetics. For example, there is a direct correlation between the amount of delivered agent, for example virus, such as adenovirus or adeno-associated virus or other virus, that is administered and the transgene product that is produced. Since 40 genomes of transduced virus is sufficient to produce a therapeutic amount of protein (see, e.g., Nathwani et al. (2002) *Blood*, 100:1662), lower amounts of virus can be administered using compartmentalized gene delivery. For example, the amount can be an amount that is sufficient to transduce cells with 40 genomes per cell or higher of virus. The compartmentalized methods of gene delivery can further increase the genome copy per cell, and thereby further increase sustained expression of product with a lower dosage than existing methods. Thus, using compartmentalized methods of gene delivery, it is possible to precisely correlate the amount of particle injected, the intracellular genomes and the amount of protein expressed.

Generally, using the compartmentalized method of nucleic acid delivery, a markedly reduced quantity of delivered agent can be administered compared to existing methods to achieve optimal delivery of a nucleic acid molecule, such as a therapeutic nucleic acid molecule. In addition, the amount of delivered agent that is administered can be controlled due to the linear relationship between the dose of delivered agent and the amount of therapeutic product that is produced. The result is that up to 100-fold or less of delivered agent can be administered using the compartmentalized method of nucleic acid delivery than is achieved by administration of the same delivered agent intravenously. For example, the amount of delivered agent that is administered using the compartmentalized method of gene delivery can be up to 10-fold, 100-fold, 200-fold, 300-fold, 400-fold, 500-fold, 600-fold, 700-fold, 800-fold, 900-fold, 1000-fold, 5000-fold, 10000-fold or less than the amount of the same delivered agent that is administered intravenously to the target organ or tissue. It is within the level of one of skill in the art to determine the particular amount of delivered agent that is administered, based on the particular delivered agent, the nucleic acid molecule, and the disease or condition that is treated.

In particular, the dose or amount of delivered agent that is administered to a compartmentalized tissue or organ is such that a level of protein product is produced that is capable of delivering a therapeutic or prophylactic effect. Typically, the amount is one such that using the compartmentalized method of nucleic acid delivery, the level is sustained for at least 6 months, 7 months, 8 months, 9 months, 10 month, 11 months, 12 months, 14 months, 16 months, 18 months, 20 months, 24 months, 36 months, 48 months, 60 months, 72 months, 84 months, 96 months, 10 years, 15 years or more. Since there is a linear relationship in administered delivered agent and the amount of product produced, such dosages can be determined by one of skill in the art. Considerations in determining the dosage can include the particular genetic therapy and the therapeutic product, half-life of the protein product, the promoter used to express the transgene product, the particular delivered agent and other similar factors.

Where the delivered agent is non-viral nucleic acid, an effective dosage amount of DNA or RNA is in the range of from about or from 0.005 mg/kg body weight to about or 50 mg/kg body weight. Generally, the dosage is from about or from 0.005 mg/kg to about or 20 mg/kg and more generally from about or from 0.05 mg/kg to about or 5 mg/kg. For example, for non-viral nucleic acid (e.g., plasmid, naked DNA, siRNA, shRNA or antisense nucleic acid), 0.01 mg to 2000 mg is delivered, such as 0.05 mg to 1500 mg, 1 mg to 1000 mg, 10 mg to 1500 mg, or 100 mg to 1000 mg.

Where the delivered agent is a virus, such as an adenovirus or an adeno-associated virus or other virus, dosages are typically provided by number of virus particles (vp) or plaque forming units (pfu) and dosages generally are less than $1 \times 10^{12}$ total particles or $1 \times 10^{12}$ pfu, and are generally in the range from about or from 10 to $1 \times 10^{12}$ particles, 10 to $1 \times 10^6$ particles, $1 \times 10^3$ to $1 \times 10^{12}$ particles, such as $1 \times 10^6$ to $1 \times 10^{10}$ particles, or $1 \times 10^7$ to $1 \times 10^9$ particles or in the range from about or from 10 to $1 \times 10^{12}$ pfu, 10 to $1 \times 10^6$ pfu, $1 \times 10^3$ to $1 \times 10^{12}$ pfu, such as $1 \times 10^6$ to $1 \times 10^{10}$ pfu, or $1 \times 10^7$ to $1 \times 10^9$ pfu. Lower or higher doses than those recited can be required. Specific dosage and treatment regimens for any particular subject or patient can depend upon a variety of factors, including the specific genetic therapy and its therapeutic product, the activity of the specific compound or agent, the age, body weight, general health status, sex, diet, time of administration, rate of excretion, drug combination, the severity and course of the disease, condition or symptoms, the subject or patient's disposition to the disease, conditions or symptoms, method of administration and the judgment of the treating physician. It is within the level of the treating physician skilled in the art to determine the exact dosage.

Methods of titering viruses for the purposes of preparing compositions thereof and/or determining dosage amounts are well known to one of skill in the art. For example, titers can be determined by an $OD_{260}$ assay, which measures the concentration of viral DNA and protein. To perform such an assay, stocks of purified virus are required, since serum and other factors in growth media can interfere with the absorbance reading. For example, virus can be purified by banding using a CsCl density-gradient or other methods known to one of skill in the art. Typically, dilutions of virus are made. The optical particle units (opu) or viral particle (vp) per mL can be determined from the absorbance. For example, for adenovirus, the vp/mL is determined by multiplying $1.1 \times 10^{12}$ with the $OD_{260}$ absorbance and viral dilution factor. $OD_{260}$ assay does not distinguish between live and dead virus. In another example, titer can be determined by performing a plaque assay using standard procedures known in the art. Typically, cells that can be grown in a monolayer, for example 293 cells, are plated at a moderately high density (e.g., at or about or above 70%) followed by infection with a viral stock at various dilutions. After sufficient time to allow infection and transduction of cells, an agarose solution is added to the cells. Plaques, which are formed by lysis of the cells, are visible in several days and up to 10 days can be counted (typically by using a dye that can differentiate the plaque areas). Titer is calculated as plaque forming units (pfu) per mL by dividing the number of plaques by the dilution factor. In an addition example, an end-point dilution assay can be used. This assay is similar to a plaque assay, except greater numbers of dilutions are made (generally from $10^{-3}$ to $10^{-10}$). Also, instead of an agarose overlay to identify plaques, the infected plate of cells is manually visualized under a microscope to identify wells for cytopathic effect (CPE). The wells of the plate can be scored to determine the end-point dilution based on the Spearman-Karber method.

Dosage treatment can be a single dose schedule or multiple dose schedule. Frequency of dosing can depend on the agent being administered, the progression of the disease or conditions in the subject, and other considerations known to those of skill in the art. For example, delivered agents or compositions can be delivered 1 time, or can be delivered in multiple administrations, such as at least or about or 2, 3, 4, 5, 6, 7 or 8 administrations. Treatment can also be at a single target locus, or at multiple target loci. For example, delivery of a delivered agent can be single injection per target site, or can be repeated injection of the target site. By way of example, in the treatment of a lung disease like cystic fibrosis, it can be necessary to target at least 25, 50, 75, 80, 85, 90, or 95% of the lung with multiple injections to achieve enough transgene product and/or functional improvement in the subject. Thus, multiple injection sites can be used. The repeat injections can be effected in succession, such as immediately following a prior injection, or can be delayed over the course of minutes, hours, days or years. In some examples, the delivered agent is administered to more than one locus in the organ or portion thereof, particularly where high levels of transduction or expression is sought. For example, in some embodiments, in addition to the first administration site, a composition containing a delivered agent is administered to another site or locus. The other site or locus can be at a site that is adjacent to or near the first site in the same region or portion of a target tissue, or can be at a site removed from the first locus while still in the same target organ (e.g., a different lobe or region of the liver or lung).

c. Termination/Release of Compartmentalization

After delivery of the delivered agent, the compartmentalization of the tissue or organ or portion thereof is maintained for a time period sufficient to allow sufficient uptake of the delivered agent and/or minimize exposure of the delivered agent to the systemic circulation. For example, compartmentalization is for a sufficient time to allow entrance of the delivered agent to the cell while avoiding systemic circulation. The effect of this compartmentalization means that toxicity and immune activation is minimized. Generally, the compartmentalization of the tissue or organ or portion thereof is maintained to limit, minimize or avoid toxicity and immune activation (e.g., as assessed by local or systemic cytokine expression, inflammatory infiltrates such as neutrophil and lymphocyte infiltrates, and/or tissue enzymes). It is within the level of one of skill in the art to empirically determine the precise time period to maintain the compartmentalization based on factors that include the particular delivered agent that is administered, the target tissue or organ or portion thereof, the subject being treated or the particular application.

The optimal duration of compartmentalization can vary depending on a variety of factors that include the particular target organ or tissue or portion thereof, the delivered agent, and the particular method used for delivery. For example, different tissue or organ resident cells exhibit different endocytic abilities and kinetics for intracellular uptake of a delivered agent. This endocytic function can be influenced or differ depending on the particular delivered agent. For example, for a delivered agent that is a viral vector such as adenovirus, the kinetics of adenovirus infection is initiated upon binding and interaction with its receptors, which for adenovirus subgroups A, C-F, is the Coxsackie virus B Ad receptor (CAR). Binding to the primary receptor mediates endocytosis of the associated virus. Within 1 minute post-transduction, generally about 2% of the virus is intracellular. Disassembled adenovirus escapes to the cytosol by release of the endosomal contents into the cytoplasm. Within or before 30 minutes post-transduction, about 80% of the virus is intracellular. Upon further disassembly, the capsid is transported through the cytoplasm where it finally delivers the viral DNA into the cellular nucleus. Within or before 60 minutes post-transduction, all of the transgene is delivered into the nucleus.

In addition, the optimal duration of vascular compartmentalization can depend on the tolerance of the organ or tissue or portion thereof, and resident cells therein, to ischemic conditions and is a consideration in the methods herein. Some organs or tissues exhibit less tolerance to ischemic conditions than others. For example, hepatocytes generally are viable longer than neurons or cardiomyocytes subject to vascular isolation. The liver generally tolerates interruption of blood flow for up or more than 60 minutes (Abdalla et al. (2004) *Surg. Clin. N. Am,* 84:563-585). For the kidney, vascular isolation can be performed for a predetermined time to permit virtually all of the nucleic acid to be taken up by tissue cells. The kidney typically tolerates periods of ischemia of up to 2 hours, but generally no more than 1 hour or no more than 30 minutes (Hoffman et al. (1974) *AMA Arch. Surg.,* 109:550-551; Thompson et al. (2006) *J. Urology,* 177:471-476). Muscle is tolerant to ischemia for up to 4 hours (Blaisdell F. W. (2002) *Cardiovascular Surgery,* 10:620-630). One of skill in the art can monitor and assess the tissue or organ to determine a time period that achieves sufficient cellular uptake, minimizes systemic exposure and results in no ischemia or acceptable ischemia to the organ or portion thereof that is reversible or recoverable. For example, digital light processing (DLP®) hyperspectral imaging (HSI) can be used to construct a "real time" tissue oxygenation map of the tissue or organ or portion thereof (Best et al. (2011) *Proc. SPIE,* 7932, 793202).

In particular examples, compartmentalization of a tissue or an organ or a portion thereof is for greater than 15 minutes. For example, the time period to maintain compartmentalization of a tissue or an organ or a portion thereof is for at least or at least about or up to 15, 20, 25, 30, 35, 40, 45, 50, 55, 60, 65, 70, 75, 80, 85, 90, 95, 100, 105, 110, 115, or 120 minutes subsequent to initiation of compartmentalization and/or the administration of the delivered agent. It is understood that the time period to maintain compartmentalization can be shorter than 15 minutes in the presence of agents that can facilitate uptake or entry. Thus, in examples herein, the time period to maintain compartmentalization of a tissue or an organ or a portion thereof is for at least or at least about or up to 5, 6, 7, 8, 9, 10, 11, 12, 13, 14, 15 minutes or more. In certain embodiments the compartmentalization is maintained for at least about or up to 30 minutes. Generally, in any of the methods herein, compartmentalization of a tissue or an organ or a portion thereof is for no longer than 60 minutes, such as greater than 15 minutes but less than 60 minutes.

For example, in examples herein where the liver or portion thereof is compartmentalized by the methods herein, the time period to maintain compartmentalization of the liver is at least or at least about or up to 15 minutes, 20 minutes, 25 minutes, 30 minutes, 35 minutes, 40 minutes, 45 minutes, 50 minutes or 60 minutes subsequent to initiation of compartmentalization and/or administration of the delivered agent. Generally, in any of the methods herein, compartmentalization of the liver or a portion thereof is for no longer than 60 minutes, such as at least or at least about 15 minutes, 20 minutes, 25 minutes, 30 minutes, 35 minutes, 40 minutes, 45 minutes, 50 minutes, but less than 60 minutes. For example, compartmentalization can be from or from about 15 minutes to 60 minutes, 15 minutes to 50 minutes, 15 minutes to 40 minutes, 15 minutes to 30 minutes, 20 minutes to 60 minutes, 20 minutes to 40 minutes, and generally is for about or approximately 30 minutes.

In some examples herein, the compartmentalized method of nucleic acid delivery can further include removing from the organ or portion thereof, or from the surgical field, extracellular delivered agent (i.e., that portion of the delivered agent administered but that was not taken up by the cells of the compartmentalized organ or portion thereof). The removal step can include absorbing, suctioning, or flushing so that, once the vascular circulation to the organ or portion thereof is restored, little to no delivered agent will reach the general circulation. Thus, the removal step is performed prior to restoring vascular circulation to the organ or portion thereof.

After the period of compartmentalization, compartmentalization to the organ or portion thereof is terminated. This is effected by restoring communication of the tissue or organ or portion thereof with the systemic circulation by removing the clamp. For example, compartmentalization achieved by the band clamp device can be terminated by deflating the balloon, moving the band tension/loosen switch to the down position to permit loosening of the tensioned flexible loop, and turning the tensioning wheel clockwise to loosen the flexible band its slack position. The tissue or organ then can be removed from the clamp portion and the entire clamp device can be removed from the port. It is within the level of a skilled physician to carefully remove the device, apparatus or process used to block blood flow to the tissue or organ or portion thereof so that damage to the underlying tissue, vessels, veins or arteries, or ducts does not occur. For example, the pressure of a clamp can be carefully released to control restoration of blood flow to the tissue, organ or portion thereof.

2. Resection and Transplantation

The band clamp device provided herein can be used during any laparoscopic surgical procedure, such as a tissue resection surgery or transplant surgery. Typically, resection surgery involves the surgical removal of all or a part of an organ, tissue or structure, including tumors, malignancies or other growths or anomalies, such as lesions, from the surrounding tissue. Tissue resection surgery can be performed on any tissue, organ or portion thereof where a portion of or the entire tissue or organ is desired to be removed. For example, tissue resection can be performed on the liver, prostate, kidney, intestines, lung, spleen, gut, stomach, pancreas, reproductive organs, and any other tissue or organ where a portion of or the entire tissue or organ is desired to be removed. For example, the clamp device provided herein can be used during liver resection. Liver resection can be the most effective mode of curative treatment for liver tumors and neoplasm.

The device provided herein can be used during laparoscopic transplant surgeries. Transplant surgeries typically involve the removal, i.e., resection, of all or a part of a tissue or organ from a donor, where the removed tissue or organ or portion thereof is relocated to a recipient. Transplantation can be performed on any tissue or organ where there is a donor and a recipient, including, but not limited to liver, prostate, kidney, intestines, lung, spleen, gut, stomach, pancreas, reproductive organs, and any other tissue or organ where a portion of or the entire tissue or organ is desired to be removed from a donor and relocated to a recipient. In one example, the device provided herein can be used during an organ transplant procedure, for example, a laparoscopic donor nephrectomy, e.g., a kidney transplant procedure, where the kidney is removed from a donor and transplanted into a recipient. Generally, during a resection surgery or transplant surgery, the clamp can be applied to any location on the desired tissue or organ and manipulated by the operator to allow resection of various sizes of the tissue or organ.

3. Other Procedures

The clamp device provided herein can be used in any other type of minimally invasive surgical procedure that requires clamping of a tissue or an organ or a portion thereof. Exemplary procedures include dissection, hysterectomy, appendectomy, cholecystectomy (to treat gallstones), bariatric surgery, e.g., gastric bypass surgery, lap band surgery, laparoscopic surgery for endometriosis, hernia repair, laparoscopic surgery to treat diseases of the gastrointestinal tract, such as Crohn's disease, colorectal cancer, diverticulitis, familial polyposis, bowel incontinence, rectal prolapse, ulcerative colitis, colon polyps, chronic severe constipation, and any other minimally invasive surgery where a tissue or an organ or a portion thereof can be clamped.

D. DELIVERED AGENTS AND COMPOSITIONS THEREOF

The delivered agent for use in delivering to a compartmentalized tissue or organ using the compartmentalized nucleic acid delivery method described in Section C can be any desired nucleic acid molecule, or a vehicle, construct or complex containing any nucleic acid molecule. In particular, the delivered agent is a nucleic acid molecule or includes a nucleic acid molecule that has a desired function or that encodes a selected polypeptide with a desired function. The delivered agent can be a DNA (e.g., double stranded circular or linear), RNA, a ribozyme, or an aptamer. Further the delivered agent can be in any form including, but not limited to, naked DNA, a microRNA, a small interfering RNA, or an antisense nucleic acid. The delivered agent can be provided as a construct containing a heterologous nucleic acid molecule. There are a number of constructs that are known to one of skill in the art for delivery of nucleic acid to cells, either in vitro or in vivo. Such constructs include viral based delivery systems and non-viral based deliver systems. For example, the delivered agent can be a construct containing a nucleic acid molecule that is delivered in a nanoparticle (e.g., a targeted or radiolabeled nanoparticle), a plasmid or a vector (e.g., a viral vector or an expression vector). Such constructs are well known in the art and readily adaptable for use with the compositions and methods described herein.

It is understood that the choice of delivered agent that is used is dependent on the target tissue or organ locus. It is within the level of one of skill in the art to empirically determine and identify a delivered agent and/or delivery method that is compatible with cell uptake by the target tissue or organ cells. For example, it is known to one of skill in the art that retrovirus-based vectors generally only transduce actively dividing cells. Liver cells are generally quiescent, and thus delivery of a retrovirus-based vector to liver cells requires procedures whereby the method includes steps of stimulating cell division (e.g., partial hepatectomy). In contrast, adenoviral-based vectors are capable of being delivered to non-dividing cells.

1. Nucleic Acid Molecule

The particular delivered agent that is used in the compartmentalized nucleic acid delivery method is or includes a nucleic acid molecule whereby delivery and/or expression thereof effects an activity or property that is useful when present in the target organ or when secreted into the bloodstream. For example, delivery and/or expression of a nucleic acid molecule effects replacement of a missing or defective (e.g., partially or non-functional) gene product, achieves overproduction of a gene product, acts as a DNA vaccine, encodes a polypeptide that has a desired effect or therapeutic activity, or inhibits gene expression. For example, the nucleic acid molecule can be one that is selected for that encodes a polypeptide for a desired effect or therapeutic outcome. In another example, the nucleic acid molecule is a nucleic acid-based inhibitor of a gene or of a gene product, such as an inhibitor of transcription or translation of a gene. For example, the delivered agent can be a short-interfering RNA (siRNA) sequence, antisense sequence or a microRNA (miRNA) sequence. In additional examples, the delivered agent can be used prophylactically to deliver prophylaxis proteins. In a further example, delivery and/or expression of the nucleic acid molecule can encode proteins for use in agriculture application, for example, to improve meat production (e.g., by blocking production of myostatin). It is within the level of one of skill in the art to select a nucleic acid molecule depending on the particular application or the particular disease or disorder that is being treated.

The nucleic acid molecule can be delivered as a naked DNA, or can be delivered in a vehicle or as a complex or construct. Hence, it is understood that the delivered agent is or includes the nucleic acid molecule. For example, the nucleic acid molecule can include a vector or plasmid containing the nucleic acid molecule, such as a viral vector or non-viral vector. The nucleic acid molecule can be encapsulated in liposomes. The nucleic acid molecule can be complexed to other agents, such as target ligands or other moieties and delivered as a nanoparticle.

The nucleic acid molecule can be driven by a promoter to enhancer to control or regulate expression. The promoter is operably linked to the coding region. Any strong promoter known to those skilled in the art can be used for driving the expression of DNA. The promoter can be a constitutive promoter, such as a CMV promoter, a tissue-specific promoter, an inducible or regulatable promoter. In a specific embodiment, the nucleic acid molecule to be introduced for purposes of gene therapy contains an inducible promoter operably linked to the coding region, such that expression of the nucleic acid is controllable by controlling the presence or absence of the appropriate inducer of transcription. Generally the promoter is a regulated promoter and transcription factor expression system, such as the published tetracycline-regulated systems or other regulatable systems (see, e.g., International PCT Publication No. WO 01/30843), to allow regulated expression of the encoded polypeptide. Exemplary of other promoters, are tissue-selective promoters, such as those described in U.S. Pat. No. 5,998,205, including, for example, a fetoprotein, DF3, tyrosinase, CEA, surfactant protein and ErbB2 promoters. An exemplary regulatable promoter system is the Tet-On (and Tet-Off) system available, for example, from Clontech (Palo Alto, Calif.). This promoter system allows the regulated expression of the transgene controlled by tetracycline or tetracycline derivatives, such as doxycycline. Other regulatable promoter systems are known (see e.g., U.S. Patent Publication No. 2002-0168714, entitled "Regulation of Gene Expression Using Single-Chain, Monomeric, Ligand Dependent Polypeptide Switches," which describes gene switches that contain ligand binding domains and transcriptional regulating domains, such as those from hormone receptors). Other suitable promoters that can be employed include, but are not limited to, adenoviral promoters, such as the adenoviral major late promoter and/or the E3 promoter; or heterologous promoters, such as the cytomegalovirus (CMV) promoter; the Rous Sarcoma Virus (RSV) promoter; inducible promoters, such as the MMT promoter, the metallothionein promoter; heat shock promoters; the albumin promoter; and the ApoAI promoter.

In some examples, the delivered agent is or includes a nucleic acid molecule that encodes a desired polypeptide. Upon delivery of the delivered agent in the compartmentalized nucleic acid delivery methods, the encoded polypeptide can be one that can be used as a biologic therapy or drug. The nucleic acid molecule can encode any desired gene product, such as a cytokine, clotting factor or coagulation factor, hormone, growth factor, enzyme, transport protein, regulatory protein, receptor, or antigen. The nucleic acid molecule can encode hormonal proteins to regulate cell growth, cell differentiation or metabolism. The choice of particular nucleic acid molecule encoding a desired therapeutic polypeptide depends on the particular disease or condition that is treated, and is within the level of one of skill in the art. For example, the nucleic acid molecule encodes insulin if the subject to be treated has Type I diabetes, a specific blood clotting factor if the subject has hemophilia, dopamine if the subject has Parkinson's Disease, or LDL receptor if the subject being treated has familial hypercholesterolemia. One of skill in the art would know how to select the needed polypeptide and the nucleic acid that encodes it based on the particular needs of the subject to be treated. Exemplary nucleic acid molecules encode immunomodulatory proteins, enzymes, hormones, cytokines, receptor, an antibody or an anti-angiogenic agent. The nucleic acid molecule can encode a protein that is a fusion protein.

The selected nucleic acid molecule can encode a polypeptide that is an immunostimulating protein or that exhibits immunomodulatory properties. Such nucleic acid molecules include, but are not limited to, genes that encode cytokines, for example, an interleukin, interferon, granulocyte colony stimulating factor or thereof, such as interleukin (IL)-1, IL-2, IL-4, IL-5, IFN-β, IFN-γ, IFN-α, TNF, IL-12, IL-18, and flt3; proteins that stimulate interactions with immune cells (B7, cluster of differentiation 28 (CD28), major histocompatibility complex class I (MHC class I), MHC class II, Transporter associated with antigen processing (TAPs)); tumor-associated antigens (immunogenic polypeptides from melanoma antigen recognized by T-cells 1 (MART-1), gp100 (Melanocyte protein pmel-17); tyrosinase, tyrosinase-related protein 1, tyrosinase-related protein 2, melanocyte-stimulating hormone receptor, melanoma-associated antigen 1 (MAGE1), MAGE2, MAGE3, MAGE12, B melanoma antigen (BAGE), cancer-germline antigens (GAGE), cancer-testis antigen NY-ESO-1, β-catenin, Mutated melanoma-associated antigen 1 (MUM-1), cyclin-dependent kinase 4 (CDK-4), caspase 8, antigen identified by monoclonal antibody Ki-67 (KIA) 0205, human leukocyte antigen (HLA)-A2R1701, α-fetoprotein, telomerase catalytic protein, G-250, mucin 1 (MUC-1), carcinoembryonic protein, p53, Her2/neu, triosephosphate isomerase, cell division control protein 27 (CDC-27), low density lipid receptor-GDP-1-fucose:β-d-galactoside 2-α-1-fucosyltransferase fusion protein (LDLR-FUT), telomerase reverse transcriptase, and prostate-specific membrane antigen (PSMA)), cDNA encoding antibodies that block inhibitory signals (Cytotoxic T-Lymphocyte Antigen 4 (CTLA4) blockade), chemokines (Macrophage inflammatory protein (MIP1), MIP3, CCR7 ligand, and calreticulin), and other proteins.

The nucleic acid molecule can encode a polypeptide that is a growth factor or portions thereof that bind to the receptor or a growth factor receptor or portions thereof that bind to ligand. Growth factors and growth factor receptors are known in the art. See e.g., Baxley and Serra, *Curr. Drug Targets* 11(9):1089-102 (2010); Lo, *Curr. Mol. Pharmacol.* 3(1):37-52 (2010); Barakat and Kaiser, *Expert Opin. Investig. Drugs* 18(5):637-46 (2009); Trojanowska and Varga, *Curr. Opin. Rheumatol.* 19(6):568-73 (2007); Jimeno and Hidalgo, *Biochim. Biophys. Acta* 1766(2):217-29 (2006); Finch and Rubin, *J. Natl. Cancer Inst.* 98(12):812-24 (2006); Lo et al., *Breast Canc. Res. Treat.* 95(3):211-8 (2006); Schilephake, *Int. J. Oral Maxillofac. Surg.* 31(5): 469-84 (2002); George, *Urology* 60(3 Suppl. 1):115-21 (2002). Growth factors include, for example, bone morphogenic protein (BMPs), epidermal growth factor (EGF), erythropoietin (EPO), fibroblast growth factor (FGF), granulocyte colony stimulating factor (G-CSF), granulocyte macrophage colony stimulating factor (GM-CSF), hepatocyte growth factor (HGF), insulin-like growth factor (IGF), platelet derived growth factor (PDGF), transforming growth factor α and β, and vascular endothelial growth factor (VEGF). Growth factor receptors include, for example, epidermal growth factor receptor (EGFR), fibroblast growth factor receptor (FGFR), or transforming growth factor receptor (TGFR).

The nucleic acid molecule can encode a polypeptide that is an antibody or antibody fragment, including a single chain antibody or an anti-idiopathic antibody. Antibodies are known in the art. See e.g., Brekke and Sandlie, *Nat. Rev. Drug. Discov.* 2(1):52-62 (2003); Mellstedt, *Drugs Today* 39(Supl. C):1-16 (2003); Therapeutic Antibodies: Methods and Protocols; Ed. Dimitrov, A. S., Humana Press, Springer, New York, N.Y. (2009); Zheng et al. (2007) *Cell Research,* 17:303-306. Non-limiting examples of encoded antibodies or fragments thereof include, for example, anti-thymocyte globulin, muromonab, Abciximab, Adalimumab, Alemtuzumab, Basiliximab, Bevacizumab, Cetuximab, Certolizumab, Daclizuma, Eculizumab, Efalizumab, Gemtuzumab, Ibritumomab tiuxetan, Infliximab, Muromonab-CD3, Natalizumab, Omalizumab, Palivizumab, Panitumumab, Ranibizumab, Rituximab, Tositumomab or Trastuzumab.

The nucleic acid molecule can encode a polypeptide that is, but is not limited to, an enzyme (e.g., galsulfase, laronidase, N-acetylgalactosamine 6-sulfatase, phenylalanine ammonia lyase, acid alpha glucosidase, imiglucerase, alglucosidase alpha), a hormone (e.g., thyrotropin, growth hormone, insulin, thyroid hormone, erythropoietin), an angiogenesis modulator, an immunomodulator (denileukin diftitox; interleukin-2), a pain modulator (e.g., NP2), a fusion protein (e.g., insulin-like growth factor 2 and acid alpha glucosidase (IGF2-GAA); abatacept; alefacept; etanercept), a poly (ADP-ribose) polymerase (PARP) inhibitor, a hylan or other derivative of hyaluronan, or an allergen (e.g., a peanut or other food allergen).

For example, the nucleic acid molecule can encode human erythropoietin or a variants thereof (see e.g., U.S. Pat. No. 4,703,008, Accession No. P01588), human G-CSF or variants thereof (see e.g., Accession No. P09919); human GM-CSF or variants thereof (see e.g., Cantrell et al. (1985) Proc. Natl. Acad. Sci, 82:6250-4; Accession No. P04141); plasminogen activator or variants thereof (see e.g., Accession No. P00750); urokinase or variants thereof (see e.g., Accession No. P00749); insulin or variants thereof (see e.g., U.S. Pat. Nos. 4,652,525, 4,431,740, Groskreutz et al. (1994) *J. Biol. Chem.*, 269:6241-5, Accession No. P01308); interleukins such as interleukin-1 or variants thereof (see e.g. Accession Nos. P01583, P01584), interleukin-2 or variants thereof (see e.g., Accession No. P60568, U.S. Pat. No. 4,738,927), interleukin-3 or variants thereof (see e.g., Accession No. P08700, EP Publ. EP275,598 or 282,185), interleukin-4 or variants thereof (see e.g., Accession No. P05112), interleukin 7 or variants thereof (see e.g., Accession No. P13232, U.S. Pat. No. 4,965,195), an interferon or variants thereof, a Factor VIII or variants thereof (see e.g., Accession No. P00451), Factor IX or variants thereof (see e.g., P00740), von Willebrand factor or variants thereof (see e.g., Accession No. P04275), or human growth hormone or variants thereof (see e.g., Accession No. P01241, P01242, U.S. Pat. No. 4,342,832).

Other nucleic acid molecules of interest, include those that encode anti-angiogenic or suicide proteins. Anti-angiogenic proteins include, for example, METH-1, METH-2, TrpRS fragments, proliferin-related protein, prolactin fragment, PEDF, vasostatin, various fragments of extracellular matrix proteins and growth factor/cytokine inhibitors. Various fragments of extracellular matrix proteins include, but are not limited to, angiostatin, endostatin, kininostatin, fibrinogen-E fragment, thrombospondin, tumstatin, canstatin, and restin. Growth factor/cytokine inhibitors include, but are not limited to, VEGF/VEGFR antagonist, sFlt-1, sFlk, sNRP1, angiopoietin/tie antagonist, sTie-2, chemokines (IP-10, PF-4, Gro-beta, IFN-gamma (Mig), IFN, FGF/FGFR antagonist (sFGFR), Ephrin/Eph antagonist (sEphB4 and sephrinB2), PDGF, TGF and IGF-1. A suicide protein is a protein that can lead to cell death, as with expression of diphtheria toxin A, or the expression of the protein can render cells selectively sensitive to certain drugs, e.g., expression of the herpes simplex thymidine kinase gene (HSV-TK) renders cells sensitive to antiviral compounds, such as acyclovir, ganciclovir and FIAU (1-(2-deoxy-2-fluoro-β-D-arabinofuranosil)-5-iodouracil). Other suicide proteins include carboxypeptidase G2 (CPG2), carboxylesterase (CA), cytosine deaminase (CD), cytochrome P450 (cyt-450), deoxycytidine kinase (dCK), nitroreductase (NR), purine nucleoside phosphorylase (PNP), thymidine phosphorylase (TP), varicella zoster virus thymidine kinase (VZV-TK), and xanthine-guanine phosphoribosyl transferase (XGPRT). Other encoded proteins, include, but are not limited to, herpes simplex virus thymidine kinase (HSV-TK), which is useful as a safety switch (see, U.S. patent application Ser. No. 08/974,391, filed Nov. 19, 1997, which published as PCT Publication No. WO 99/25860), Nos, FasL, and sFasR (soluble Fas receptor).

In other examples herein, the nucleic acid molecule is one that encodes a protein that is involved in a lysosomal storage disorder, and in particular an enzyme that is defective therein, including, but not limited to, Aspartylglucosaminidase, α-Galactosidase A, Palmitoyl Protein Thioesterase, Tripeptidyl Peptidase, Lysosomal transmembrane protein, cysteine transporter, Acid ceramidase, acid α-L-fucosidase, protective protein/cathepsin A, acid β-glucosidase or glucocerebrosidase, acid β-galactosidase, iduronate-2-sulfatase, α-L-Iduronidase, galactocerebrosidase, acid α-mannosidase, acid β-mannosidase, arylsulfatase B, arylsulfatase A, N-Acetylgalactosamine-6-sulfate sulfatase, N-Acetylglucosamine-1-phosphotransferase, Acid sphingomyelinase, Niemann-Pick disease, type C1 (NPC-1), β-Hexosaminidase B, Heparan N-sulfatase, α-N-Acetylglucosaminidase (Na-Glu), Acetyl-CoA:αglucosamininde N-acetyltransferase, N-Acetylglucosamine-6-sulfate sulfatase, β-Glucuronidase, and acid lipase. The role of such enzymes in various lysosomal storage diseases are known to one of skill in the art (see e.g., U.S. Patent Publication No. US2008/0025952; US20120009268). The choice of enzyme depends on the particular lysosomal disorder. Non-limiting examples of nucleic acid molecules of interest include any that encode: a β-glucuronidase for treatment of mucopolysaccharidosis disorder (e.g., Sly syndrome); α-L-iduronidase for treatment of Hurler Syndrome; α-L-iduronidase for treatment of Scheie Syndrome or Hurler-Scheie Syndrome; iduronate sulfatase for treatment of Hunter's Syndrome; heparin sulfamidase for treatment of Sanfilippo Syndrome A (MPSIIIA); N-acetylglucosaminidase for treatment of Sanfilippo Syndrome B (MPSIIIB); acetyl-CoA:α-glucosaminide acetyltransferase for treatment of Sanfilippo Syndrome C (MPSIIIC); N-acetylglucosamine-6-sulfatase for treatment of Sanfilippo Syndrome D (MPSIIID); galactose-6-sulfate sulfatase for treatment of Morquio Syndrome A; β-galactosidase for treatment of Morquio Syndrome B; N-acetylgalactosamine-4-sulfatase for treatment of Maroteaux-Lamy Syndrome; α-galactosidase for treatment of Fabry disease; glucocerebrosidase for treatment of Gaucher's disease, or lysosomal acid α-glucosidase for treatment of a glycogen storage disorder (e.g., Pompe disease).

Other exemplary nucleic acids molecules of interest include, but are not limited to, any that encode: a protein for treatment of Alzheimer's disease such as a metalloendopeptidase, for example, amyloid-beta degrading enzyme neprilysin, the insulin-degrading enzyme insulysin, or thimet oligopeptidase; a protein or peptide that can act as an anti-retroviral agent to treat virus infection such as infection by human immunodeficiency virus (HIV), for example, enfuvirtide (Fuzeon®); a protein for treatment of Amyotrophic Lateral Sclerosis (ALS) such as, but not limited to, insulin growth factor-1 (IGF-1), calbindin D28, parvalbumin, HIF1-alpha, SIRT-2, VEGF, SMN-1, SMN-2, GDNF or ciliary neurotrophic factor (CNF); a protein that is deficient in subjects having hemophilia, such as, but not limited to, Factor VIII or Factor IX; a protein for treatment of type I diabetes, such as the furin-cleavable insulin gene; a protein for treatment of familial hypercholesterolemia, such as low density lipoprotein receptor (LDLR); a protein for treatment of lipoprotein lipase deficiency (LPLD), such as lipoprotein lipase (LPL); a protein for treatment of Alpha-1-Antitrypsin (AAT) deficiency, such as AAT; a protein for the treatment of Crigler Najar Syndrome Type I or Type II, such as hepatic bilirubin UDP-glucuronyl-transferase or a functional variant thereof, for example, UGT1A1 (Gong et al. (2001) Pharmacogentics, 11:357-68); a protein for treatment of glycogen storage deficiency type 1A such as glucose-6 phosphatase; a protein for treatment of Pepck deficiency such as phosphoenolpyruvate-carboxykinase; protein associated with galactosemia such as galactose-1 phosphate uridyl transferase; protein associated with phenylketonuria such as phenylalanine hydroxylase, protein associated with maple syrup urine disease such as branched chain alpha-ketoacid dehydrogenase; protein associated with tyrosinemia type 1 such as fumarylacetoacetate hydrolase; protein associated with methylmalonic acidemia such as methylmalonyl-CoA mutase; protein associated with ornithine transcarbamylase deficiency such as ornithine transcarbamylase; protein associated with citrullinemia such as argininosuccinic acid synthetase; protein associated with severe combined immunodeficiency disease such as adenosine deaminase; protein associated with Gout and Lesch Nyan syndrome such as hyposanthine guanine phosphoribosyl transferase; protein associated with biotinidase deficiency such as biotinidase;

protein associated with Gaucher disease such as beta-glucocerebrosidase; protein associated with Sly syndrome such as beta-glucuronidase; protein associated with Zellweger syndrome such as peroxisome membrane protein 70 kDa; protein associated with acute intermittent porphyria such as porphobilinogen deaminase (PBDG); protein associated with alpha-1 antitrypsin deficiency (emphysema) such as alpha 1 antitrypsin, protein associated with cancer such as a tumor suppressor gene such as p53; protein encoding glutamic acid decarboxylase (GAD) for the treatment of Parkinson's disease; or a protein that is deficient in a lysosomal storage disease, and in particular Sanfilippo Syndrome (also called Mucopolysaccharidosis type III, MPSIII), such as lysosomal sulfamidase, and α-N-acetylglucosaminidase (NaGlu).

Other exemplary nucleic acids molecules of interest include, but are not limited to, any that encode: a protein for treatment of a cancer. For example, the cancer can be a solid tumor, including, but not limited to, breast cancer, melanoma, head and neck cancer, colon cancer, renal carcinoma and sarcoma. Such cancers can be treated with any molecule that inhibits angiogenesis. Hence, a nucleic acid molecule can encode a protein that inhibits angiogenesis, including, but not limited to, endostatin, angiostatin, vasculostatin, thrombospondin-1, tissue inhibitor of metalloprotease (TIMP), soluble vascular endothelial growth factor (VEGF) receptor and vasostatin (calreticulin fragment). Such anti-angiogenic agents also can be used in the treatment of other angiogenic diseases or conditions, such as ocular diseases.

Alternatively, a therapeutic nucleic acid can exert its effect at the level of RNA, for instance, by encoding an antisense message or ribozyme, a protein that affects splicing or 3' processing (e.g., polyadenylation), or a protein that affects the level of expression of another gene within the cell, e.g., by mediating an altered rate of mRNA accumulation, an alteration of mRNA transport, and/or a change in post-transcriptional regulation. These include RNA, such as RNAi and other double-stranded RNA, antisense and ribozymes, which among other capabilities can be directed to mRNAs encoding proteins essential for proliferation, such as structural proteins, transcription factors, polymerases, genes encoding cytotoxic proteins, genes that encode an engineered cytoplasmic variant of a nuclease (e.g., RNase A) or protease (e.g., trypsin, papain, proteinase K and carboxypeptidase).

For example, the nucleic acid molecule can be a nucleic acid-based inhibitor of a gene or of a gene product, such as an inhibitor of transcription or translation of a gene. The delivered agent can be a short-interfering RNA (siRNA) sequence, antisense sequence or a micro-RNA (miRNA) sequence. The RNA can be 10 to 30 nucleotides long, such as 19-25 or 21-25 nucleotides in length. siRNA-mediated gene silencing methods, where expression products of a gene are targeted by specific double stranded derived siRNA nucleotide sequences that are complementary a nucleotide segment of the target gene transcript (e.g., to at least a 19-25 nucleotide long segment), including the 5' untranslated (UT) region, the ORF, or the 3' UT region, are known in the art (see e.g., PCT International Patent Publication Nos. WO00/44895, WO01/75164, WO01/92513, or WO01/29058. A siRNA sequence typically binds a unique sequence within a target mRNA with exact complementarity and results in the degradation of the target mRNA molecule. A siRNA sequence can bind anywhere within the mRNA molecule. Sequences targeted by the siRNA include genes expressing a polypeptide of interest, or an upstream or downstream modulator of such a gene. Examples of upstream or downstream modulators of a gene include a transcription factor that binds a gene promoter, a kinase or phosphatase that interacts with a polypeptide of interest, and polypeptides involved in regulatory pathways capable of influencing the polypeptide of interest. A miRNA sequence typically binds a unique sequence within a target mRNA with exact or less than exact complementarity and results in the translational repression of the target mRNA molecule. A miRNA sequence can bind anywhere within mRNA sequence, but generally binds within the 3' untranslated region of the mRNA molecule.

A nucleotide siRNA or miRNA sequence (e.g., 21-25 nucleotides in length) can, for example, be produced from an expression vector by transcription of a short-hairpin RNA (shRNA) sequence, a longer (e.g., 60-80 nucleotide) precursor sequence, which is subsequently processed by the cellular RNAi machinery to produce either a siRNA or miRNA sequence. Alternatively, a nucleotide siRNA or miRNA sequence (e.g., 21-25 nucleotides in length) can, for example, be synthesized chemically. Chemical synthesis of siRNA or miRNA sequences is commercially available from such corporations as Dharmacon, Inc. (Lafayette, Colo.), Qiagen (Valencia, Calif.), and Ambion (Austin, Tex.). Methods of delivering siRNA or miRNA molecules are known in the art. See e.g., Oh and Park, *Adv. Drug. Deliv. Rev.* 61(10):850-62 (2009); Gondi and Rao, *J. Cell Physiol.* 220(2):285-91 (2009); and Whitehead et al., *Nat. Rev. Drug. Discov.* 8(2):129-38 (2009).

For example, the nucleic acid molecule can be an antisense nucleic acid sequence. By hybridization interactions, antisense nucleic acid block expression of a cellular or pathogen mRNA. Antisense nucleic acid molecules can, for example, be transcribed from an expression vector to produce an RNA which is complementary to at least a unique portion of the target mRNA and/or the endogenous gene which encodes the target. Hybridization of an antisense nucleic acid under specific cellular conditions results in inhibition of target protein expression by inhibiting transcription and/or translation. Examples of antisense nucleic acids include, but are not limited to, the following Isis Pharmaceuticals, Inc. products: Mipomersen for high cholesterol; ISIS-CRP$_{Rx}$ for coronary artery disease, inflammation, and renal disease; ISIS-APOCIII$_{Rx}$ for high triglycerides; ISIS-FXI$_{Rx}$ for clotting disorders; BMS-PCSK9$_{Rx}$ for coronary artery disease; ISIS-SGLT2$_{Rx}$, ISIS-PTP1B$_{Rx}$, ISIS-GCGR$_{Rx}$, and ISIS-GCCR$_{Rx}$ for Type 2 diabetes; ISIS-FGFR4$_{Rx}$ for obesity; OGX-011 f, LY2181308, ISIS-EIF4E$_{Rx}$, OGX-427, ISIS-STAT3$_{Rx}$ for cancer; ISIS-SOD1$_{Rx}$ for ALS; ISIS-TTR$_{Rx}$ for TTR amyloidosis; ISIS-SMN$_{Rx}$ for spinal muscular atrophy; Vitravene for CMV retinitis; Alicaforsen for ulcerative colitis; ACHN-490 for severe bacterial infection; ATL1102 for multiple sclerosis; EXC 001 for local fibrosis; iCo-007 for ocular disease; and ATL1103 for acromegaly. Examples of microRNAs that can be administered using the methods taught herein include, but are not limited to, the following Santaris Pharma products: Miravirsen for Hepatitis C; EZN-2968 for solid tumors; EZN-3042 for cancer; EZN-4176 for androgen receptor; SPC 4955 and SPC 5001 for high cholesterol. Additional therapeutic microRNAs include the following Mirna Therapeutics, Inc. products for the treatment of cancer: let-7, miR-34, miR-Rx02, miR-16, miR-Rx-01, miR-Rx-03, miR-Rx-06, and miR-Rx-07.

In other examples, the nucleic acid molecule can be a ribozyme (e.g., a hammerhead or a hairpin-based ribozyme) designed either to repair a defective cellular RNA or to destroy an undesired cellular or pathogen-encoded RNA (see, e.g., Sullenger (1995) *Chem. Biol.*, 2:249-253; Czubayko et al. (1997) *Gene Therapy*, 4:943-9; Rossi (1997) *Ciba Found. Symp.*, 209:195-204; James and Gibson (1998) *Blood*, 91:371-82; Sullenger (1996) *Cytokines Mol. Ther.*, 2:201-5; Hampel (1998) *Prog. Nucleic Acid Res. Mol. Biol.*, 58:1-39; or Curcio et al. (1997) *Pharmacol Therapy*, 74:317-32).

2. Vehicles and Constructs Containing the Nucleic Acid Molecule

The nucleic acid molecule can be provided in a vector, construct or other vehicle of delivery. Exemplary of such are viral vectors, non-viral vectors, nanoparticles or whole cells. Methods of generating such constructs or vehicles for delivery are well-known to a skilled artisan. For example, nucleic acid molecules can be inserted into non-viral or viral vectors using standard methods well-known to one of skill in the art. In some instances, routine molecular biology and recombinant DNA techniques can be used (see, e.g., Ausubel et al., Current Protocols in Molecular Biology, John Wiley & Sons, New York, N.Y., 1998, Sambrook et al., Molecular Cloning: A Laboratory Manual, Cold Spring Harbor, N.Y. (1989). In other instances, the nucleic acid molecule can be inserted so it is under the control of any appropriate regulatory sequence or sequences. In other examples, the nucleic acid molecules are inserted as part of an expression cassette that includes regulatory elements, such as promoters or enhancers. Appropriate regulatory elements can be selected by one of ordinary skill in the art based on, for example, the desired level of expression. In particular examples, the regulatory elements can be selected to include tissue-specific promoters, such as liver-specific promoters, to limit gene expression to tissue-specific cells.

a. Virus and Viral Vectors

A virus can be used as a delivered agent in the compartmentalized nucleic acid delivery methods as the delivered agent, whereby an exogenous nucleic acid sequence is inserted into a viral vector. Viruses are useful in delivering nucleic acid molecules in vivo because they are efficient at transferring viral DNA into host cells, they can infect and be taken up by specific target cells depending on the viral attachment proteins (e.g., capsid or glycoproteins), and they can be manipulated to remove non-essential genes and add heterologous nucleic acid molecules. Many viral vectors are known to those skilled in the art. Examples of viruses that can be used in the methods herein include, but are not limited to, adenoviruses, adeno-associated viruses, alphaviruses, baculoviruses, hepadenaviruses, baculoviruses, poxviruses, herpesviruses, retroviruses, lentiviruses, orthomyxoviruses, papovaviruses, paramyxoviruses, and paroviruses. In particular examples, the virus is an adenovirus. The choice of virus is within the level of one of skill in the art and is dependent on a number of factors, such as the desire for replication or integration of viral DNA, the tropism of the virus, and/or the immunogenicity of the virus. Such viruses and derivatives thereof, are well-known and available to one of skill in the art. For example, many are available from the American Type Culture Collection (ATCC, Rockville, Md.) or from commercial vendors (e.g., Vector Biolabs, Philadelphia, Pa.; Applied Biological Materials, Inc., Richmond, British Columbia, Canada).

Viral vectors for use in generating recombinant viruses include replication-competent viruses and replication-defective viruses. In replication-defective viruses, the virus typically lacks one or more genes associated with viral replication and cannot replicate beyond the first cycle of infection. In some cases, in order to produce replication-defective viruses, transfer vectors, packaging vectors or helper virus are required. For example, a packaging vector can be provided as a cosmid or in a cell line that provides the viral structural proteins for packaging of the defective vector.

The viral vectors also can contain expression cassettes that include regulatory elements, such as promoters and enhancers, operably linked to a transgene of choice. As discussed above, any suitable promoter can be used. Suitable promoters and enhancers are widely available in the art for use in the viral vector of choice. Typically the promoter is constitutive promoter. Exemplary promoters include, but are not limited to, a CMV promoter, a truncated CMV promoter, a human serum albumin promoter or an α-1-antitrypsin promoter. For example, the promoter is a truncated CMV promoter in which binding sites for known transcriptional repressors have been deleted. In other examples, the promoter is an inducible promoter. For example, the promoter is the inducible ecdysone promoter. Other examples of promoters include steroid promoters, such as estrogen and androgen promoters, and metallothionein promoters. The enhancer can be a tissue specific- or non-specific enhancer. For example, the enhancer is a liver-specific enhancer element. Exemplary enhancer elements include, but are not limited to, human serum albumin (HSA) enhancers, human prothrombin (HPrT) enhancers, α-1-microglobulin enhancers, intronic aldolase enhancers and apolipoprotein E hepatic control region.

i. Adenovirus

Adenoviruses are viral vectors that can be used as delivered agents containing a nucleic acid molecule of interest. Adenovirus is a nuclear DNA virus with a genome of about 36 kb, which has been well-characterized through studies in classical genetics and molecular biology (Horwitz, M. S., "Adenoviridae and Their Replication," in Virology, 2nd edition, Fields, B. N., et al., eds., Raven Press, New York, 1990). The genome is classified into early (known as E1-E4) and late (known as L1-L5) transcriptional units, referring to the generation of two temporal classes of viral proteins. The demarcation between these events is viral DNA replication.

Adenoviruses exhibit a natural tropism for epithelial cells of the respiratory and gastrointestinal tract. Adenovirus also can infect liver cells, such as hepatocytes and endothelial cells, which can occur upon clearance of the virus into the liver after systemic administration. In particular, in the methods herein, direct injection into the parenchyma facilitates selective liver cell uptake by hepatocytes. Penton base and fiber proteins on the surface of the virus are responsible for the virus tropism. Multiple interactions between adenoviral particles and the host cell are required to promote efficient cell entry (Nemerow (2000) *Virology* 274:1-4). For subgroup C adenoviruses, such as adenovirus 2 and 5 (Ad2 or Ad5), the viral entry pathway has been well characterized and is believed to involve two separate cell surface events. First, a high affinity interaction between the adenoviral fiber knob and coxsackie-adenovirus receptor (CAR) mediates the attachment of the adenovirus particle to the cell surface. A subsequent association of penton with the cell surface integrins $\alpha_v\beta_3$ and $\alpha_v\beta_5$, which act as co-receptors, potentiates virus internalization. CAR, which is expressed in many human tissues including lung epithelial cells (Bergelson et al., (1997) *Science* 275: 1320-1323), appears to function as a cellular receptor for most adenoviral subgroups, except subgroup B (Bergelson et al., (1997) *Science* 275: 1320-1323; Roelvink et al., (1998) *J. Virol.* 72: 7909-7915).

Adenovirus includes over 50 serotypes that are grouped into six distinct subgroups, A to F. Any of these adenovirus serotypes, which are available from the American Type Culture Collection (ATCC, Rockville, Md.) and other commercial and non-commercial providers can be used in the methods herein or used as a source for further modification as is known in the art. Also, any other serotype of adenovirus available from any other source can be used or further modified. For instance, an adenovirus can be of subgroup A (e.g., serotypes 12, 18, 31), subgroup B (e.g., serotypes 3, 7, 11a, 11p, 14, 16, 21, 34, 35, 50), subgroup C (e.g., serotypes 1, 2, 5, 6), subgroup D (e.g., serotypes 8, 9, 10, 13, 15, 17, 19, 19p, 20, 22-30, 32, 33, 36-39, 42-49, 51), subgroup E (e.g., serotype 4), subgroup F (e.g., serotypes 40, 41), or any other adenoviral serotype. In certain embodiments, the adenovirus is a subgroup C adenovirus or derived from a subgroup C adenovirus. Subgroup C adenoviruses, include, but are not limited to, Ad2 and Ad5.

Adenoviral vectors are available in the art (e.g., available from the American Type Culture Collection (ATCC, Rockville, Md.), and the sequences of the wild-type adenovirus proteins from many different adenovirus serotypes are well known in the art (see e.g., Roberts et al. (1984) *J. Biol. Chem.*, 259:13968-13975; Chroboczek et al. (1992) *Virology*, 186:280-285; Sprengel et al. (1994) *J. Virol.*, 68:379-389; Chillon et al. (1999) *J. Virol.*, 73:2537-2540; Davison et al. (1993) *J. Mol. Biol.*, 234:1308-1316; www.binf.gmu.edu/wiki/index.php/Human_Adenovirus_Genome_Sequences_and_Annotations). The adenoviral vectors are widely available to the skilled artisan, for example from the American Type Culture Collection (ATCC) or other commercial or non-commercial provider. From the ATCC, adenoviruses are available as ATCC numbers VR-1 to VR-1616. For example, wild type adenovirus type 2 is available from the ATCC as VR-846 and type 5 is available as VR-5 and VR-1082. Any of a number of recombinant or modified adenoviruses can be generated that are derived from any of the above serotypes, as described in the art and herein or by any suitable method known to one of skill in the art.

Adenoviral vectors have several advantages for use as gene delivery vehicles, including tropism for both dividing and non-dividing cells, minimal pathogenic potential, ability to replicate to high titer for preparation of vector stocks, and the potential to carry large inserts (see, e.g., Berkner (1992) *Curr. Top. Micro. Immunol.*, 158:39-66; Jolly et al. (1994) *Cancer Gene Therapy*, 1:51-64).

For example, adenovirus vectors include defective adenovirus vector containing at least one deletion in the first early gene region (E1-E4). Modifications to adenoviral vectors include deletions known in the art, such as deletions in one or more of the E1, E2a, E2b, E3, or E4 coding regions. For example, adenovirus vectors for gene therapy can be prepared by substitution of a heterologous nucleic acid molecule in place of the E1, E2a, E2b, E3 and/or E4 genes. Deletion can be effected using restriction endonucleases. For example, the E1a region can be deleted using convenient restriction endonuclease sites within the E1a region. Often, a portion of E3 is also deleted by restriction endonuclease addition so as to permit the insertion of a larger piece of foreign DNA while still satisfying the size constraints required for packaging into new viral particles. Due to deletion of these regions, the cloning capacity of an adenovirus vector can be about 8 kb. Such adenoviral vectors are typically referred to as replication defective adenovirus due to the at least one deletion in the first viral early gene region, such as E1, which includes the E1a and E1b regions.

Deletion of the early genes, such as viral E1 region, renders the recombinant adenovirus defective for replication and incapable of producing infectious viral particles in subsequently infected target cells. Thus, to permit early gene-deleted adenovirus genome replication, such as E1-deleted adenovirus genome replication, and to produce virus particles requires a system of complementation which provides the missing gene product. For example, E1 complementation is typically provided by a cell line expressing E1, such as the human embryonic kidney packaging cell line, i.e. an epithelial cell line, called 293 (deposited with the ATCC under Accession No. CRL-1573). Cell line 293 contains the E1 region of adenovirus, which provides E1 gene region products to "support" the growth of E1-deleted virus in the cell line (see e.g., Graham et al., *J. Gen. Virol.* 36: 59-71, 1977). Additionally, cell lines that are usable for production of defective adenovirus having a portion of the adenovirus E4 region have been reported (see, e.g., International published Appl. No. WO 96/22378). E3 also can be deleted from the vector, but since it is not required for vector production, it can be omitted from the complementing producer cell.

The benefit of the use of replication deficient viruses as vectors is that they are limited in the extent to which they can spread to other cell types, since they can replicate within an initial infected cell, but are unable to form new infectious viral particles. Multiple deficient adenoviral vectors and complementing cell lines have also been described (see, e.g., International PCT Publication Nos. WO 95/34671, U.S. Pat. No. 5,994,106). The construction of replication-defective adenoviruses has been described (Berkner et al., *J. Virol.* 61:1213-20 (1987); Massie et al., *Mol. Cell. Biol.* 6:2872-83 (1986); Haj-Ahmad et al., *J. Virol.* 57:267-74 (1986); Davidson et al., *J. Virol.* 61:1226-39 (1987); Zhang et al., *BioTechniques* 15:868-72 (1993); Berkner (1983) *Nuc. Acids Res.* 11:6003; Ghosh-Choudhury (1987) *Biochem. Biophys. Res. Commun.*, 147:964; Gilardi et al. (1990) *FEBS* 267:60; Mittal (1993) *Virus Res.* 28:67; Yang (1993) *Proc. Natl. Acad. Sci. USA* 90:4601; and International published PCT WO1995/026411).

Adenovirus vectors also include "gutless" or "gutted" vectors in which all viral genes are removed leaving only the ITRs necessary for vector propagation and the Ψ. Such adenoviral vectors are designated pseudoadenoviral vectors (PAVs) because they are derived from the genome of an adenovirus that contain minimal cis-acting nucleotide sequences required for the replication and packaging of the vector genome. PAVs vectors contain the 5' inverted terminal repeat (ITR) and the 3' ITR nucleotide sequences that contain the origin of replication, and the cis-acting nucleotide sequences required for packaging of the PAV genome. They can be modified to contain one more transgenes with appropriate regulatory elements (e.g., promoter or enhancers). PAVs have a carrying capacity of far more than 8 kb in size and up to 36 kb in size, since they contain deletions of most viral coding sequences. (see e.g., U.S. Pat. No. 5,882,887 or 5,670,488; PCT Publication No. WO96/40955, WO97/25466, WO95/29993, WO97/00326; Morral et al. (1998) *Hum. Gene Ther.*, 10:2709-2716, Kochanek et al. (1996) *Proc. Natl. Acad. Sci.*, 93:5731-5736; Parks et al. (1996) *Proc. Natl. Acad. Sci.*, 93:13565-13570; Lieber et al. (1996) *J. Virol.*, 70:8944-8960 or Fisher et al. (1996) *J. Virol.*, 217:11-22).

PAVs are grown by co-infection of the producing cells with a "helper" virus (such as using an E1-deleted adenovirus vector), where the packaging cells express the E1 gene products. The helper virus trans-complements the missing adenovirus functions, including production of the viral structural proteins needed for particle assembly. For example, a helper adenovirus vector genome and a gutless adenoviral vector genome are delivered to packaging cells.

The cells are maintained under standard cell maintenance or growth conditions, whereby the helper vector genome and the packaging cell together provide the complementing proteins for the packaging of the adenoviral vector particle. Such gutless adenoviral vector particles are recovered by standard techniques. The helper vector genome can be delivered in the form of a plasmid or similar construct by standard transfection techniques, or it can be delivered through infection by a viral particle containing the genome. Such viral particle is commonly called a helper virus. Similarly, the gutless adenoviral vector genome can be delivered to the cell by transfection or viral infection.

Adenoviruses also include replication-conditional adenoviruses, which are viruses that replicate in certain types of cells or tissues but not in other types as a result of placing adenoviral genes essential for replication under control of a heterologous promoter (discussed above; see, also U.S. Pat. Nos. 5,998,205, 5,801,029 and U.S. application Ser. No. 10/081,969, published as U.S. 2003-0104625 and corresponding International PCT Publication No. WO 2002/067861).

Adenoviruses also include those that have been modified to contain a targeting ligand to increase infection of specific target cells that express receptors (proteins, lipids, carbohydrates, or portions thereof) for the targeting ligand, for example, to alter the tropism of the virus. While adenoviral vectors and others, hold much promise for therapeutic applications, their usefulness is limited by the widespread tissue distribution of CAR, which restricts delivery of adenoviral vectors to specific cell types. Furthermore, the absence of CAR and/or $\alpha_v$ integrin receptors on certain cells in vivo restricts the cell or tissue types that can be targeted by adenoviral vectors. Thus, adenovirus also include those that have been modified by reducing or ablating binding to native receptors and/or engineering capsid proteins, such as the HI loop, C terminus of fiber, the L1 loop of hexon or the RGD loop of penton base, or the capsid protein IX, to incorporate target ligands for a desired cell receptor or tissue-specific receptor (see, e.g., Krasnykh et al. (2000) *Mol. Ther.*, 1:391-405; Wickham et al. (2000) *Gene Ther.*, 7:110-4; Dmitriev et al. (1998) *J. Virol.*, 72:9706-12; Mizuguchi et al. (2004) *Hum. Gene Ther.*, 15:1034-44; Wickham et al. (1997) *J. Virol.*, 71:8221-9; Curiel (1999) *Ann NY Acad. Sci.*, 886:158-71). A capsid protein can be modified, for example, by addition of a target ligand or substitution of the fiber with other types of adenovirus fiber. The target ligand can be any protein, or portion thereof, that binds to a moiety in or on a cell, such as a cell surface protein, lipid, carbohydrate or other moiety. For example, the target ligand includes, but is not limited to, growth factors, adhesion molecules, cytokines, protein hormones, neuropeptides (neurotransmitters) and single-chain antibodies, or a suitable portion thereof. In other examples, adenovirus vectors can be conjugated with adaptor molecules, such as antibody and fusion protein containing an anti-Ad single-chain antibody (scFv) or the extracellular domain of CAR with the targeting ligand, or chemically modified with polymers, e.g., polyethylene glycol (PEG) moieties, that contain the targeting ligands (see e.g., Mizuguchi et al. (2004) *Hum. Gene Ther.*, 15:1034-44; Eto et al. (2008) *Int. J. Pharm.*, 354:3-8).

Any of the above adenoviruses, or any known in the art, can be modified to contain a desired heterologous nucleic acid molecule for use as a delivered agent herein. The adenovirus containing the desired heterologous nucleic acid sequence can be prepared by any technique known to persons skilled in the art (Levrero et al., *Gene* 101 (1991) 195, EP 185 573; Graham, *EMBO J.* 3 (1984) 2917; International PCT Publication No. WO95/26411). In particular, such viruses can be prepared by homologous recombination between an adenoviral vector and a plasmid carrying the heterologous DNA sequence. The homologous recombination can occur after cotransfection of the adenovirus vector and plasmid into an appropriate cell line. The cell line used is generally one that is transformable. The transfection can be performed in the presence of a reagent that directs adenoviral particle entry into producer cells. Such reagents include, but are not limited to, polycations and bifunctional reagent. In some examples, if the adenovirus is a defective adenovirus (due to deletion of an early gene or fiber protein), the cell line also contains the sequences capable of complementing the defective adenovirus genome part, such as in integrated form in order to avoid risks of recombination. Examples of complementing cell lines include, but are not limited to, the human embryonic kidney line 293 (Graham et al., *J. Gen. Virol.* 36 (1977) 59) which contains the left-hand part of the genome of an Ad5 adenovirus. A complementing cell also includes, for example, a cell of the PER.C6 cell line, which contains the adenoviral E1 gene (PER.C6 is available, for example, from Crucell, The Netherlands; deposited under ECACC accession no. 96022940; see, also Fallaux et al. (1998) *Hum. Gene Ther.* 9:1909-1907; see, also, U.S. Pat. No. 5,994,128) or an AE1-2a cell (see, Gorziglia et al. (1996) *J. Virology* 70:4173-4178; and Von Seggern et al. (1998) *J. Gen. Virol.* 79:1461-1468)). Then, the adenoviruses which have multiplied are recovered and purified according to conventional molecular biology techniques.

References illustrating the use of adenoviruses in gene therapy include, but are not limited to, Vorburger and Hunt (2002) *The Oncologist*, 7:46-59; Breyer et al. (2001) *Current Gene Therapy*, 1:149-162; Shirakawa (2009) *Drugs News Perspectives*, 22:140-5; Wang et al. (2005) *Gene Therapy and Mol. Biology*, 9:291-300; and Sheridan (2011) *Nature Biotechnology*, 29:121)

ii. Adeno-Associated Virus (AAV)

Viral vectors for use as a delivered agents include adeno-associated virus (AAV). AAV is a single-stranded human DNA parvovirus whose genome has a size of 4.6 kb. The AAV genome contains two major genes: the rep gene and the cap gene. The rep gene codes for the rep proteins (Rep 76, Rep 68, Rep 52 and Rep 40). The cap gene codes for AAV replication, rescue, transcription and integration, while the cap proteins form the AAV viral particle. AAV derives its name from its dependence on an adenovirus or other helper viruses (e.g., herpesviruses) to supply essential gene products that permit AAV to undergo a productive infection (i.e. reproduce itself in the host cell). In the absence of helper virus, AAV integrates as a provirus into the host cell's chromosome until it is rescued by superinfection of the host cell with a helper virus, usually adenovirus (Muzyczka (1992) *Curr. Top. Micro. Immunol.*, 158:97-129).

AAV viruses can be integrated into the cellular genome. The mechanism of integration is mediated by the presence of inverted terminal repeat (ITRs) at both ends of the AAV genome, which contain cis-acting nucleotide sequences required for virus replication, rescue, packaging and integration. The integration function of the ITR mediated by the rep protein in trans permits the AAV genome to integrate into a cellular chromosome after infection in the absence of helper virus. The site of integration for AAV is well-established and has been localized to chromosome 19 of humans (Kotin et al. (1990) *Proc. Natl. Acad. Sci.*, 87:2211-2215). Knowledge of the integration site reduces the danger of random insertional events into the cellular genome that can activate or inactivate host genes or interrupt coding sequences. AAV also is useful for gene therapy applications because its host range is broad, exhibiting tropism for many cell types. AAV also can infect both non-dividing and dividing cells.

AAV vectors can be derived from any naturally occurring AAV serotype, including AAV-1, AAV-2, AAV-3, AAV-4, AAV-5, AAV-6, AAV-7, AAV-8 or AAV-9. Such viruses are well known and available to one of skill in the art (see e.g. Grimm et al. (2003) Current Gene Therapy, 3:281-304; Muramatsu et al. (1996) Virol., 221:208-217; Chiorini et al. (1997) J. Virol., 71:6823-6833; Chiorini (1999) J. Virol., 73:1309-1319; Rutledge et al. (1998) J. Virol, 72:309-319; Xiao et al. (1999) J. Virol., 73:3994-4003; Gao et al. (2002) Proc Natl. Acad. Sci., 99:11854-11859; Kotin (1994) Human Gene Therapy, 5:793-801). Other serotypes also are known and available and include AAV-8 to AAV-12. For example, many AAV vectors are available from American Type Culture Collection (ATCC, Rockville, Md.; see e.g. VR-197, VR-645, VR-646, VR-680, VR-681, VR-1449, VR-1523, VR-1616). Also available are compatible host cells and helper virus. AAV vectors also include "pseudotyped" AAV vectors, in which the AAV-2 vector genome is cross-packaged into the capsids of the other AAV serotypes (Burger et al. (2004) Mol. Ther., 10:302-17; U.S. Pat. No. 7,094,604). Such pseudotyped AAV vectors overcome limitations of AAV-2-derived serotypes, such as their inefficiency at transducing some cells, such as liver or muscle cells.

Many AAV vectors exhibit widespread transduction throughout multiple tissues, such as skeletal and cardiac muscles, following delivery methods that achieve systemic expression. These include, for example, AAV serotypes-6, -8 and -9. In particular, AAV vectors include an adenovirus-associated serotype 9 (AAV-9; GenBank Accession No. AY530629.1; Gao et al. (2004) J. Virol., 78:6381-6388). AAV-9 is a vector that can bypass the blood brain barrier to target the central nervous system (CNS) (see e.g. Foust et al., (2009) Nature Biotechnology, 27:59-65; Duque et al. (2009) Mol. Ther., 17:1187-1196). Hence, in examples of neurodegenerative diseases or other diseases herein that affect or are associated with the brain or CNS, AAV-9 can be used as the delivered agent to encode a protein of interest for delivery systemically (e.g. delivery to the liver or portion thereof for expression in the blood).

AAV vectors include recombinant AAV vectors that contain a heterologous nucleic acid of interest. Procedures for generating such vectors are known to one of skill in the art. For example, standard approaches to the generation of AAV vectors requires transfection of a host cell with an AAV vector genome containing a nucleic acid molecule of interest flanked by the AAV ITR sequences, transfection of the host cell by a plasmid encoding the genes for the AAV rep and cap proteins that are required in trans, and infection of the transfected cell with a helper virus to supply the non-AAV helper functions required in trans (Muzyczka (1992) Curr. Top. Micro. Immunol., 158:97-129; U.S. Pat. No. 5,139, 941). The helper virus can be an adenovirus or other helper virus. The helper virus proteins activate transcription of the AAV rep gene, and the rep proteins then activate transcription of the AAV cap genes. The cap proteins then utilize the ITR sequences to package the AAV genome into a viral particle.

Alternatively, recombination of AAV virions can be helped using a plasmid containing helper function genes, in combination with infection by one of the well-known helper viruses that can be used as the source of replicative functions (see e.g. U.S. Pat. Nos. 5,622,856 and 5,139,941). Similarly, the skilled artisan can make use of a plasmid containing accessory function genes, in combination with infection by wt AAV, to provide the necessary replicative functions. A triple transfection method also can be used to produce rAAV virions, which is a method that does not require helper virus (see e.g., U.S. Pat. No. 6,001,650). This is accomplished by use of three vectors for rAAV virion production: an AAV helper function vector, an accessory function vector, and a rAAV vector.

References illustrating the use of AAV viruses in gene therapy include, but are not limited to, Sheridan (2011) Nature Biotechnology, 29:121 iii. Retrovirus

Viral vectors for use as a delivered agent include a retroviral vector (see e.g., Miller (1992) Nature, 357:455-460). Retroviral vectors are well suited for delivering nucleic acid into cells because of their ability to deliver an unrearranged, single copy gene into a broad range or rodent, primate and human somatic cells. Retroviral vectors integrate into the genome of host cells. Unlike other viral vectors, they only infect dividing cells.

Retroviruses are RNA viruses such that the viral genome is RNA. When a host cell is infected with a retrovirus, the genomic RNA is reverse transcribed into a DNA intermediate, which is integrated very efficiently into the chromosomal DNA of infected cells. This integrated DNA intermediate is referred to as a provirus. Transcription of the provirus and assembly into infectious virus occurs in the presence of an appropriate helper virus or in a cell line containing appropriate sequences permitting encapsulation without coincident production of a contaminating helper virus. A helper virus is not required for the production of the recombinant retrovirus if the sequences for encapsulation are provided by co-transfection with appropriate vectors.

The retroviral genome and the proviral DNA have three genes: the gag, the pol and the env, which are flanked by two long terminal repeat (LTR) sequences. The gag gene encodes the internal structural (matrix, capsid, and nucleocapsid) proteins and the env gene encodes viral envelope glycoproteins. The pol gene encodes products that include the RNA-directed DNA polymerase reverse transcriptase that transcribes the viral RNA into double-stranded DNA, integrase that integrate the DNA produced by reverse transcriptase into host chromosomal DNA, and protease that acts to process the encoded gag and pol genes. The 5' and 3' LTRs serve to promote transcription and polyadenylation of the virion RNAs. The LTR contains all other cis-acting sequences necessary for viral replication.

Retroviral vectors are described by Coffin et al., Retoviruses, Cold Spring Harbor Laboratory Press (1997). Exemplary of a retrovirus is Moloney murine leukemia virus (MMLV) or the murine stem cell virus (MSCV). Retroviral vectors can be replication-competent or replication-defective. Typically, a retroviral vector is replication-defective in which the coding regions for genes necessary for additional rounds of virion replication and packaging are deleted or replaced with other genes. Consequently, the viruses are not able to continue their typical lytic pathway once an initial target cell is infected. Such retroviral vectors, and the necessary agents to produce such viruses (e.g. packaging cell line) are commercially available (see e.g. retroviral vectors and systems available from Clontech, such as Catalog number 634401, 631503, 631501, and others, Clontech, Mountain View, Calif.).

Such retroviral vectors can be produced as delivered agents by replacing the viral genes required for replication with the nucleic acid molecule to be delivered. The resulting genome contains an LTR at each end with the desired gene or genes in between. Methods of producing retrovirus are known to one of skill in the art (see e.g. International PCT Publication No. WO1995/26411). The retroviral vector can be produced in a packaging cell line containing a helper plasmid or plasmids. The packaging cell lines provides the viral proteins required for capsid production and the virion maturation of the vector (e.g. gag, pol and env genes). Typically, at least two separate helper plasmids (separately containing the gag and pol genes; and the env gene) are used so that recombination between the vector plasmid cannot occur. For example, the retroviral vector can be transferred into a packaging cell line using standard methods of transfection, such as calcium phosphate mediated transfection. Packaging cell lines are well known to one of skill in the art, and are commercially available. An exemplary packaging cell line is GP2-293 packaging cell line (Catalog Numbers 631505, 631507, 631512, Clontech). After sufficient time for virion product, the virus is harvested. If desired, the harvested virus can be used to infect a second packaging cell line, for example, to produce a virus with varied host tropism. The end result is a replicative incompetent recombinant retrovirus that includes the nucleic acid of interest but lacks the other structural genes such that a new virus cannot be formed in the host cell.

References illustrating the use of retroviral vectors in gene therapy include: Clowes et al., (1994) *J. Clin. Invest.* 93:644-651; Kiem et al., (1994) *Blood* 83:1467-1473; Salmons and Gunzberg (1993) *Human Gene Therapy* 4:129-141; Grossman and Wilson (1993) *Curr. Opin. in Genetics and Devel.* 3:110-114; Sheridan (2011) *Nature Biotechnology*, 29:121; Cassani et al. (2009) *Blood*, 114:3546-3556.

iv. Lentivirus

Lentiviruses are a subclass of retroviruses. Exemplary of lentiviruses are HIV, SIV and FIV. Unlike other retroviruses, lentiviruses are able to integrate into the genome of non-dividing cells. Thus, for example, lentiviral vectors have been reported to deliver genes to primary livers cells efficiently and permanently, integrating into the genome of non-dividing primary liver cells (Lewis and Emerman (1994) *J. Virol.*, 68:510-6). Lentiviral vectors also do not suffer from the same transcription silencing mechanism as MMLV retroviral vectors. Lentiviruses differ from other retroviruses in that they have karyophilic determinants contained in several virion proteins, such as matrix or VPR, which interact with the nuclear import machinery and mediate active transportation of the viral pre-integration complex through the nucleopore. Therefore, lentiviral integration into the genome of the host cells is not dependent on cell division.

Similar to other retroviruses, lentiviruses contain gag, pol and env genes that are the main genes coding for viral proteins. In addition, there also are other accessory genes that are involved in regulation of synthesis, processing of viral RNA and other replicative functions (e.g. Tat and Rev in HIV). These are flanked by two long terminal repeat (LTR) sequences. The replication cycle is initiated by binding of a viral glycoprotein to a host cell receptor, fusion of the membranes, and entry of the virus into the cell. Upon entry the virus is uncoated and reverse transcription takes place leading to the formation of a pre-integration complex (PIC). It is the other accessory genes that play a role in the formation of a PIC and the ability of lentiviruses to infect non-dividing cells by actively entering the nucleus of a cell through the nuclear envelope via the PIC. Once the provirus enters the nuclear envelope, it integrates itself into the host genome.

Exemplary lentivirus vectors are based on HIV-1, HIV-2, SIV or FIV. In order to generate safe lentiviral vectors, packaging cell lines are created that contain several plasmid vectors, for example a four plasmid vector system. For example, a first plasmid contains accessory proteins (e.g. tat, brf, vpr and nef) deleted such that it contains only the promoter, gag and pol and the Psi packaging sequence that allows the transcribed viral RNA to be incorporated into the assembly of new virus, a second plasmid contains the reverse transcriptase, a third plasmid contains the env gene replaced with the Vesicular Stomatitis Virus Envelope Protein (VSV-G), and a fourth plasmid is the vector of interest by replacing the viral genes required for replication with the nucleic acid molecule to be delivered.

Such lentiviral vectors, and systems and methods of producing lentivirus, are known in the art (see e.g. Buchsacher and Wong-Staal (2000) *Blood*, 95:2499-2504; Blomer et al. (1997) *J. Virol.*, 71:6641-9; Choi et al. (2001) *Stem Cells*, 19:236-46; U.S. Pat. No. 6,218,186). The lentiviral vectors are replication defective and do not contain the genes required for replication. To produce a lentivirus, several packaging plasmids are transfected into a packaging cell line, generally derivatives of HEK 293 or other similar cell line (e.g. 293FT cells, Catalog number R700-07, Invitrogen, Life Technologies, Carlsbad, Calif.); 293LTV cell line, catalog number LTV-100, Cell Biolabs, Inc., San Diego, Calif.; Lenti-Pac 293Ta Cell Line, Catalog Number CLv-PK-01, GeneCopoeia, Rockville, Md.). The packaging plasmids separately encode virion proteins (e.g. capsid and reverse transcriptase) and the nucleic acid molecule to be delivered by the vector (which can be transfected into the packaging cell lines). A single-stranded RNA viral genome is transcribed, which is packaged into the virion. Methods of generating lentiviral vectors are well known to one of skill in the art (see e.g. Naldine et al. (1996) *Science*, 272:263-267). Lentiviral vectors and systems for producing virus are commercially available (see e.g., Lentiviral expression vectors such as pSMPUW Lentiviral vector and derivatives thereof and Lentiviral Expression and Packaging Systems available from Cell Biolabs, Inc.).

Lentiviral vectors have been used in gene therapy applications (see e.g. Manilla et al. (2005) *Human Gene Therapy*, 16:17-25; Sheridan (2011) *Nature Biotechnology*, 29:121). In particular, lentiviral vectors have been used for the delivery of short-interfering RNA (siRNA) (Sachdeva et al. (2007) *Journal of Medical Virology*, 79:118-26).

b. Non-Viral Vectors

Non-viral based agents can be used as delivered agents. These include non-viral expression vectors. Non-viral expression vectors contain a nucleic acid of interest, e.g. a nucleic acid encoding a polypeptide, an antisense DNA or an siRNA, wherein the nucleic acids are operably linked to an expression control sequence (e.g. promoter). Suitable vector backbones include, for example, those routinely used in the art such as plasmids, minicircles, and artificial chromosomes (e.g. mammalian artificial chromosomes (MACs), bacterial artificial chromosomes (BACs), yeast artificial chromosomes (YACs), or plant artificial chromosomes (PACs). Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

Vectors typically contain one or more regulatory regions, which are functionally inked to the encoding region. Regulatory regions include, without limitation, promoter sequences, enhancer sequences, SMARS (scaffold matrix attachment regions), insulators, response elements, protein recognition sites, inducible elements, protein binding sequences, 5' and 3' untranslated regions (UTRs), transcriptional start sites, termination sequences, polyadenylation sequences, and introns.

Promoters controlling transcription from vectors in mammalian host cells may be obtained from various sources, for example, the genomes of viruses such as polyoma, Simian Virus 40 (SV40), adenovirus, retroviruses, hepatitis B virus, and most preferably cytomegalovirus (CMV), or from heterologous mammalian promoters, e.g. β-actin promoter or EF1α promoter, or from hybrid or chimeric promoters (e.g., CMV promoter fused to the β-actin promoter). Promoters from the host cell or related species are also useful herein.

Enhancer generally refers to a sequence of DNA that functions at no fixed distance from the transcription start site and can be either 5' or 3' to the transcription unit. Furthermore, enhancers can be within an intron as well as within the coding sequence itself. They are usually between 10 and 300 base pairs (bp) in length, and they function in cis. Enhancers usually function to increase transcription from nearby promoters. Enhancers can also contain response elements that mediate the regulation of transcription. While many enhancer sequences are known from mammalian genes (globin, elastase, albumin, fetoprotein, and insulin), typically, one will use an enhancer from a eukaryotic cell virus for general expression. Examples are the SV40 enhancer on the late side of the replication origin, the cytomegalovirus early promoter enhancer, the polyoma enhancer on the late side of the replication origin, and adenovirus enhancers.

The promoter and/or the enhancer can be inducible (e.g. chemically or physically regulated). A chemically regulated promoter and/or enhancer can, for example, be regulated by the presence of alcohol, tetracycline, a steroid, or a metal. A physically regulated promoter and/or enhancer can, for example, be regulated by environmental factors, such as temperature and light. Optionally, the promoter and/or enhancer region can act as a constitutive promoter and/or enhancer to maximize the expression of the region of the transcription unit to be transcribed. In certain vectors, the promoter and/or enhancer region can be active in a cell type specific manner. Optionally, in certain vectors, the promoter and/or enhancer region can be active in all eukaryotic cells, independent of cell type. Examples of promoters of this type are the CMV promoter, the SV40 promoter, the β-actin promoter, the EF1α promoter, and the retroviral long terminal repeat (LTR).

The vectors also can include, for example, origins of replication and/or markers. A marker gene can confer a selectable phenotype on a cell (e.g., antibiotic resistance) or be otherwise detectable. Examples of detectable markers include the E. coli lacZ gene, green fluorescent protein (GFP), and luciferase. In addition, an expression vector can include a tag sequence designed to facilitate manipulation or detection (e.g., localization) of the expressed polypeptide. Tag sequences, such as GFP, glutathione S-transferase (GST), polyhistidine, c-myc, hemagglutinin, or FLAG™ tag (Kodak; New Haven, Conn.) sequences typically are expressed as a fusion polypeptide, including the encoded polypeptide and the marker. Such tags can be inserted anywhere within the encoded polypeptide including at either the carboxyl or amino terminus.

In particular, a desired nucleic acid molecule expression vector containing a desired nucleic acid molecule of interest, for example, encoding a gene of interest, antisense DNA or siRNA or other nucleic acid molecule, can be delivered as naked DNA can be used as a delivered agent. The efficiency of delivery of the naked DNA in the methods herein can be increased by using various methods well-known to one of skill in the art (see e.g. Li and Huang (2006) *Gene Therapy*, 13:1313-1319). Such methods include, for example, such as electroporation, sonoporation or "gene gun" approaches as described elsewhere herein and known to one of skill in the art. Also, the efficiency of delivery can be increased by encapsulation in liposomes or complexing with polymers as described herein. In a particular example, the nucleic acid can be delivered as a nanoparticle.

References illustrating the use of non-vectors in gene therapy include: Sheridan (2011) *Nature Biotechnology*, 29:121.

Non-viral-based delivered agents include nanoparticles (generally of 3-200 nm) where the nucleic acid molecule is encapsulated or conjugated to a particular carrier that contain a targeting molecule for specific targeting to cells of interest. The generation of nanoparticles for gene therapy is well known in the art (see e.g. Cho et al. (2008) *Clin. Cancer. Res.*, 14:1310; Jin et al. (2007) *Biotechnol. Prog.*, 23:32-41). The nanoparticle can be made as a polymer, such as by using polymer carriers (e.g. polylactic acid, polysaccharides, poly(cyanoactylates, poly(lactide-co-glycolide)) or branched polymers to generate dendrimers, such as by growth polymerization steps from poly(L-glutamic acid (PGA), polyamidoamine (PAMAM), poly(ethylene glycol) (PEG) and polyethylenimine (PEI). Biodegradable polymers can be used which include, for example, polylactic acid, polyglycolic acid, polylactic-glycolic acid (PLGA) or poly (methyl methacrylate) (PMMA). Other types of nanoparticles can be generated as a liposome using various lipid mixtures; as a magnetic nanoparticle using iron oxide, as a silica nanoparticle using $SiO_2$ or as a gold nanoparticle using chlorauric acid or sodium citrate. Nanoparticle systems are well known to one of skill in the art.

The nanoparticles can be functionalized by conjugating or coating a targeting molecule onto the surface, for example, a targeting molecule that is a ligand for or otherwise binds to receptors expressed in the cells to be targeted. Such targeting molecules include, but are not limited to, ligands, antibodies, or peptides. In particular examples, a dual-ligand approach can be used to increase the selectivity for a cell. An example of a targeting molecule could be a growth factor, e.g., a fibroblast growth factor, that targets a fibroblast growth factor receptor. The choice of targeting molecule depends on the particular application, including the tissue or organ to be targeted, and can be empirically determined by one of skill in the art. Targeted nanoparticles are known in the art (see e.g., Franzen (2011) *Expert Opin. Drug. Deliv.* 8(3):281-98; Faraji and Wipf (2009) *Bioorg. Med. Chem.* 17(8):2950-62; Sajja et al., (2009) *Curr. Drug. Discov. Technol.* 6(1):43-51). In particular, methods for tissue-specific gene delivery of nanoparticles are known in the art (see e.g. Harris et al. (2010) *Biomaterials*, 31:998-1006. For example, parenchymal hepatocytes express asialoglycoprotein receptor (ASGP-R) and hepatic lectins. Thus, liver-specific nanoparticles are known in the art and can include functionalization with agents that recognize the asialoglycoprotein receptor (ASGP-R) and other receptors including, for example, asialo-feutin, asialo-transferrin, asialo-ceruloplasmin, asialo-lactoferrin, asialo-orosomucoid, lac-BSA, hepatoglobulin, antibodies and galactose (see e.g. Pathak et al. (2008) *Int. J. Nanomedicine*, 3:31-49).

3. Exemplary Gene Therapy Agents

The delivered agent containing a nucleic acid molecule can be any viral or non-viral vector encoding a nucleic acid of interest, such as any gene therapy agent that is known to the skilled artisan. It is within the level of a skilled artisan to choose an appropriate gene therapy agent depending on the particular disease or condition that is being treating. Hundreds of gene therapy agents are in clinical trials, and several have received market approval in Europe (e.g. Glybera®, AdLPL) and China (e.g. rAd53, Gendicine®) (see e.g. Sheridan (2011) Nature Biotechnology, 29:121).

For example, exemplary gene therapy vectors include adenovirus- or AAV-based therapeutics. Non-limiting examples of adenovirus-based or AAV-based therapeutics for use in the methods, uses or compositions herein include, but are not limited to: rAd-p53, which is a recombinant adenoviral vector encoding the wild-type human tumor suppressor protein p53, for example, for the use in treating a cancer (also known as Gendicine®, Genkaxin®, Qi et al. (2006) *Modern Oncology*, 14:1295-1297); Ad5_d11520, which is an adenovirus lacking the E1B gene for inactivating host p53 (also called H101 or ONYX-015; see e.g. Russell et al. (2012) *Nature Biotechnology*, 30:658-670); AD5-D24-GM-CSF, an adenovirus containing the cytokine GM-CSF, for example, for the use in treating a cancer (Cerullo et al. (2010) *Cancer Res.*, 70:4297); rAd-HSVtk, a replication deficient adenovirus with HSV thymidine kinase gene, for example, for the treatment of cancer (developed as Cerepro®, Ark Therapeutics, see e.g. U.S. Pat. No. 6,579,855; developed as ProstAtak™ by Advantagene; International PCT Publication No. WO2005/049094); rAd-TNFα, a replication-deficient adenoviral vector expressing human tumor necrosis factor alpha (TNF-α) under the control of the chemoradiation-inducible EGR-1 promoter, for example, for the treatment of cancer (TNFerade™, GenVec; Rasmussen et al. (2002) *Cancer Gene Ther.*, 9:951-7; rAd-FGF4, an adenoviral vector serotype 5 encoding FGF-4, for example, for the treatment of angiogenesis and coronary artery disease (GENERX, *BioDrugs*, 2002, 16:75-6; U.S. Pat. No. 5,792,453); rAd-VEGF-D, an adenoviral vector 5 containing a gene encoding vascular endothelial growth factor (VEGF-D), for example, for use in treating angiogenesis-related diseases and conditions (Trinam®, Ark Therapeutics; U.S. Patent Publication No. US20120308522); rAd-PDGF, an adenoviral vector 5 containing a gene encoding PDGF-B, for example, for the treatment of wounds (Excellarate, GAM501 Tissue Repair Co.; Blume et al. (2011) *Wound Repair Regen.*, 19:302-308); Ad-IFNβ, an adenovirus serotype 5 vector from which the E1 and E3 genes have been deleted expressing the human interferon-beta gene under the direction of the cytomegalovirus (CMV) immediate-early promoter, for example for treating cancers (BG00001 and H5.110CMVhIFN-beta, Biogen; Sterman et al. (2010) *Mol. Ther.*, 18:852-860); an AAV containing a gene encoding the lipoprotein lipase deficiency (LPLD) gene, for example, for treatment of subjects with LPLD or familial hyperchylomicronemia (alipogene tiparvovec, Glybera®, Amsterdam Molecular Therapeutics; see e.g. International PCT Publication No. WO2010/134806; WO2001000220, Yla-Herttuala (2012) *Mol. Ther.*, 20:1831-2); AMT-021, an AAV containing a gene encoding the enzyme porphobilinogen deaminase (PBGD), for example, for treatment of subjects with Acute Intermittent Porphyria (AIP) (see e.g. U.S. Patent Publication No. US2011/0262399; European Patent No. EP1049487); rAAV9-CMV-hNaGlu, an AAV-9 containing a gene encoding NaGlu under the control of the CMV promoter (see e.g. Fu et al. (2011) *Mol. Ther.*, 19:1025-33).

Other exemplary gene therapy agents for use in the methods, uses and compositions herein include, but are not limited to, rAd-H1F1α (Genzyme/Sunway), V930/V932 (Merck), NLX-P101 (Neurologix), Toca-511 (Tocagen, San Diego), LentiGlobin (Bluebird Bio), ProSavin (Oxford Bio- Medica), rAAV-1-CB-hAAT (Applied Genetic Technologies), rAAV2-CB-human retinal pigment epithelium specific 65 dalton protein (RPE65) (Applied Genetic Technologies), AMT-101 (Amsterdam Molecular), Ad5CMV-p53 (Aventis), CERE-120 (Ceregene, San Diego), CERE-110 (Ceregene, San Diego), SERCA-2a (Celladon, La Jolla), AAV2-sFLT01 (Genzyme), tgAAG76 (Targeted Genetics, Seattle), tgAAC94 (Targeted Genetics, Seattle), GX-12 (Genexine, Seoul, Korea), SC1B1 (ScanCell, Nottingham, UK), Allovectin-7 (Vical, San Diego), VM202 (ViroMed, Minnetonka, Minn.) or Rexin-G nanoparticle (Epeius Biotechnologies, San Marino, Calif.).

4. Compositions

The delivered agents can be provided as compositions, such as pharmaceutical compositions. The compositions are suitable for administration in vivo. The compositions are formulated for parenchymal administration. Typically, the compositions herein are provided as injectables, and can be delivered using any injection device such as the laparoscopic injection device provided herein. Injectables can be prepared in conventional forms, either as liquid solutions or suspensions, solid forms suitable for solution or suspension in liquid prior to injection, or as emulsions. Generally, the delivered agent compositions provided herein are in liquid form.

The compositions can contain a pharmaceutically acceptable carrier. For injection, the carrier will typically be a liquid. In particular, the pharmaceutical carrier is any carrier that is not biologically or otherwise undesirable, i.e. the composition is administered to a subject without causing undesirable side effects or interacting in a deleterious manner with the other components of the pharmaceutical composition in which it is contained. The carrier is selected to minimize degradation of the active ingredient and to minimize adverse side effects to the subject. For example, pharmaceutically acceptable carriers for administration to cells typically is a carrier acceptable for delivery by injection, and do not include agents such as detergents or other compounds that could damage cells.

Suitable carriers and their formulations are described in *Remington: The Science and Practice of Pharmacy*, 21$^{st}$ Edition, David B. Troy, ed., Lippicott Williams & Wilkins (2005). Compositions for administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. As an injection medium, it is general carriers include water that contains additives usual for injection solutions, such as stabilizing agents, salts or saline, and/or buffers. Exemplary physiologically acceptable carriers include sterile water, saline, buffered solutions or dextrose solution. For example, exemplary physiological carriers include physiological saline, phosphate buffered saline, balanced salt solution (BSS), or Ringer's solution and solutions containing thickening and solubilizing agents, such as glucose, polyethylene glycol, and polypropylene glycol and mixtures thereof. The pH of the solution is generally about 5 to about 8 or from about 7 to 7.5. If necessary, the pH of the formulation can be adjusted with pharmaceutically acceptable acids, bases or buffers to enhance the stability of the formulated compound or its delivery form.

The delivered agent (that is the nucleic acid molecule or contains the nucleic acid molecule) can be formulated as the sole pharmaceutically active ingredient in the composition or can be combined with other active agents for the particular disorder treated. Optionally, other medicinal agents, pharmaceutical agents, carriers, adjuvants, diluents can be included in the compositions provided herein. For example, any one or more of a wetting agents, emulsifiers and lubricants, such as sodium lauryl sulfate and magnesium stearate, as well as coloring agents, release agents, coating agents, sweetening, flavoring and perfuming agents, preservatives, antioxidants, chelating agents and inert gases also can be present in the compositions. Exemplary other agents and excipients that can be included in the compositions include, for example, water soluble antioxidants, such as ascorbic acid, cysteine hydrochloride, sodium bisulfate, sodium metabisulfite, sodium sulfite; oil-soluble antioxidants, such as ascorbyl palmitate, butylated hydroxyanisole (BHA), butylated hydroxytoluene (BHT), lecithin, propyl gallate, $\alpha$-tocopherol; and metal chelating agents, such as citric acid, ethylenediamine tetraacetic acid (EDTA), sorbitol, tartaric acid and phosphoric acid.

The compositions also can be formulated for sustained release formulations, such as adsorbed to biodegradable supports, including collagen sponges, or in liposomes. Sustained release formulations can be formulated for multiple dosage administration, so that during a selected period of time, such as a month or up to about a year, several dosages are administered. Thus, for example, liposomes can be prepared such that a total of about two to up to about five or more times the single dosage is administered in one injection.

The compositions can be prepared with carriers that protect them against rapid elimination from the body, such as time release formulations or coatings. Such carriers include controlled release formulations, such as, but not limited to, microencapsulated delivery systems, and biodegradable, biocompatible polymers, such as ethylene vinyl acetate, polyanhydrides, polyglycolic acid, polyorthoesters, polylactic acid and other types of implants that can be placed directly into the body. The compositions also can be administered in pellets, such as ELVAX pellets (ethylene-vinyl acetate copolymer resin).

Liposomal suspensions, including tissue-targeted liposomes, also can be suitable as pharmaceutically acceptable carriers. For example, liposome formulations can be prepared by methods known to those of skill in the art (see e.g., Kim et al. (1983) *Bioch. Bioph. Acta* 728:339-348; Assil et al. (1987) *Arch Ophthalmol.* 105:400; and U.S. Pat. No. 4,522,811). The delivered agent can be encapsulated into the aqueous phase of liposome systems.

The active materials also can be mixed with other active materials, that do not impair the desired action, or with materials that supplement the desired action or have other actions, including viscoelastic materials, such as hyaluronic acid, which is sold under the trademark HEALON, which is a solution of a high molecular weight (MW) of about 3 millions fraction of sodium hyaluronate (manufactured by Pharmacia, Inc; see e.g., U.S. Pat. Nos. 5,292,362, 5,282, 851, 5,273,056, 5,229,127, 4,517,295 and 4,328,803). Additional active agents can be included.

The composition can be formulated for single or multiple dosage administration. For example, the amount of adenovirus in a composition for single dosage administration is 10 plaque forming unit (pfu) to $1 \times 10^{12}$ pfu, $1 \times 10^2$ pfu to $1 \times 10^{10}$, $1 \times 10^3$ pfu to $1 \times 10^{10}$ pfu, $1 \times 10^3$ pfu to $1 \times 10^9$ pfu, $1 \times 10^3$ pfu to $1 \times 10^8$ pfu, or $1 \times 10^3$ pfu to $1 \times 10^9$ pfu, or is 10 particles to $1 \times 10^{12}$ particles, $1 \times 10^2$ particles to $1 \times 10^{10}$ particles, $1 \times 10^3$ particles to $1 \times 10^{10}$ particles, $1 \times 10^3$ particles to $1 \times 10^9$ particles, $1 \times 10^3$ particles to $1 \times 10^8$ particles, or $1 \times 10^6$ particles to $1 \times 10^9$ particles. Generally, the amount of adenovirus in the composition for single dosage administration is 10 virus particles (vp) to $1 \times 10^{12}$ vp, $1 \times 10^2$ vp to $1 \times 10^{10}$ vp, $1 \times 10^3$ vp to $1 \times 10^{12}$ vp, $1 \times 10^3$ vp to $1 \times 10^{10}$ vp, $1 \times 10^3$ vp to $1 \times 10^9$ vp, $1 \times 10^3$ vp to $1 \times 10^8$ vp, $1 \times 10^3$ vp to $1 \times 10^6$ vp, $1 \times 10^6$ vp to $1 \times 10^{12}$ vp, $1 \times 10^6$ vp to $1 \times 10^{10}$ vp, or is less than or about less than $1 \times 10^{12}$ vp, $1 \times 10^{11}$ vp, $1 \times 10^{10}$ vp, $1 \times 10^9$ vp, $1 \times 10^8$ vp, $1 \times 10^7$ vp, $1 \times 10^6$ vp, $1 \times 10^5$ vp, $1 \times 10^4$ vp, $1 \times 10^3$ vp, $1 \times 10^2$ vp, 10 vp or less. In other examples, the amount of adenovirus in the composition for single dosage administration is 10 pfu to $1 \times 10^{12}$ pfu, $1 \times 10^2$ pfu to $1 \times 10^{10}$ pfu, $1 \times 10^3$ pfu to $1 \times 10^{12}$ pfu, $1 \times 10^3$ pfu to $1 \times 10^{10}$ pfu, $1 \times 10^3$ pfu to $1 \times 10^9$ pfu, $1 \times 10^3$ pfu to $1 \times 10^8$ pfu, $1 \times 10^3$ pfu to $1 \times 10^6$ pfu, $1 \times 10^6$ pfu to $1 \times 10^{12}$ pfu, $1 \times 10^6$ pfu to $1 \times 10^{10}$ pfu, or is less than or about less than $1 \times 10^{12}$ pfu, $1 \times 10^{11}$ pfu, $1 \times 10^{10}$ pfu, $1 \times 10^9$ pfu, $1 \times 10^8$ pfu, $1 \times 10^7$ pfu, $1 \times 10^6$ pfu, $1 \times 10^5$ pfu, $1 \times 10^4$ pfu, $1 \times 10^3$ pfu, $1 \times 10^2$ pfu, 10 pfu or less. The composition can be formulated in 10 µL to 5 mL, such as 20 µL to 1 mL or 50 µL to 500 µL. In such compositions, the adenovirus is formulated for parenchymal administration. In particular examples, the adenovirus is formulated for parenchymal administration to the liver.

The compositions can be packaged for storage and/or use. The packaging material for use in packaging the agents are well known to those of skill in the art. Examples of packaging materials include ampoules, bottles, tubes, vials, containers, syringes, and any packaging material suitable for a selected formulation and parenchymal administration. For example, the compositions can be enclosed in ampoules, disposable syringes or multiple or single dose vials made of glass, plastic or other suitable material. The packaging material can include a needle or other injection device so as to facilitate administration for parenchymal administration purposes. For example, the composition can be packaged in a syringe barrel for use in an injection device described in Section E. The choice of package depends on the particular delivered agent. In general, the packaging is non-reactive with the compositions contained therein. Also, the composition and packaging material is sterile.

For example, the composition containing a delivered agent can be provided in a container, such as a sealed sterile vial or syringe barrel (e.g. one that is adaptable with an injection device described in Section E) containing an amount such that upon administration a sufficient amount of delivered agent (e.g. viral particles) is delivered. The amount of delivered agent, such as an adenovirus or adeno-associated virus, in the composition is from or from about 10 pfu to $1 \times 10^{12}$ pfu, $1 \times 10^2$ pfu to $1 \times 10^{10}$, $1 \times 10^3$ pfu to $1 \times 10^{10}$ pfu, $1 \times 10^3$ pfu to $1 \times 10^9$ pfu, $1 \times 10^3$ pfu to $1 \times 10^8$ pfu, or $1 \times 10^6$ pfu to $1 \times 10^9$ pfu; or is from or from about 10 particles to $1 \times 10^{12}$ particles, $1 \times 10^2$ particles to $1 \times 10^{10}$ particles, $1 \times 10^3$ particles to $1 \times 10^{10}$ particles, $1 \times 10^3$ particles to $1 \times 10^9$ particles, $1 \times 10^3$ particles to $1 \times 10^8$ particles, or $1 \times 10^6$ particles to $1 \times 10^9$ particles. The volume of the composition in the container can be 50 µL to 50 mL, 50 µL to 5 mL, 50 µL to 500 µL, 100 µL to 10 mL, 100 µL to 5 mL, 100 µL to 2 mL, 100 µL to 1 mL, 200 µL to 4 mL, 200 µL to 2 mL, 1 mL to 10 mL or 1 mL to 2 mL. For example, the container can be provided for single use or for multiple use administration. The volume of agent in the container can be 100 µL to 10 mL, where about 20 to 5 mL, such as 20 to 500 µL, 50 to 150 µL, 100 µL to 10 mL or 200 µl to 2 mL, containing at least about 10 to $10^{10}$ plaque forming units (pfu) or particles, such as $10^2$ to $10^6$ plaque forming units (pfu) or particles in such volume are delivered.

E. INJECTION DEVICE

Provided herein are injection devices that can be used in minimally invasive procedures, such as laparoscopic procedures, for use in delivering fluids, such as therapeutics, by direct injection into a target locus, such as by direct injection into a target tissue. The device has an elongated needle sheath with a small diameter, and can be inserted through an endoscopic port, such as a laparoscopic ports, trocars or cannulas, to reach the internal target site. The device provided herein can deliver small and accurate doses of the fluid directly into the target tissue, without the need of large standard syringes and open surgery. The device can optionally deliver multiple doses to the same or different target sites.

The device can be used in any method that requires direct injection of an agent into a target site, in which access to the target site is limited, such as in minimally invasive procedures. For example, in addition to laparoscopic surgeries, the device provided herein can also be used for direct injection of a fluid, such as a therapeutic, during other minimally invasive medical or surgical procedures, such as thoracoscopic surgery. As described elsewhere herein, any fluid, such as a therapeutic, can be administered, including but not limited to, protein, nucleic acid, small molecule, virus, antibodies or other fluids. The device can be used in conjunction with other minimally invasive surgical devices using single-port or multi-port endoscopic (e.g., laparoscopic) surgery. The device can also be used to deliver multiple discrete doses to the same or different sites of injection without removing or after removing the device from the laparoscopic port.

The device, including exemplary embodiments of the device, will be described with reference to the accompanying drawings. As indicated, the use of a prime (') designation with a number indicates that the element shown or described is the same as the non-prime element, except as shown or described differently. A lowercase reference numeral (e.g. a, b, etc.) refers to the same part but in different positions or states.

The device generally has two ends, the needle tip end and the plunger end. For clarity of description, it should be noted that the exemplary devices are depicted with the needle tip end generally towards the right side in the drawings, and the plunger end generally towards the left side of the drawing. The needle tip end will be generally described as the "distal end," and the plunger end will be generally described as the "proximal end." The term "distal end" is intended to refer to the end of the injection device furthest from the person holding the device, and the term "proximal end" is intended to refer to the end of the device closest to the holder of the device. If a component is described to be more "proximal" to another component, the component is closer to the proximal (plunger) end. If a component is described to be more "distal" to another component, the component is closer to the distal (needle tip) end.

Some components of the injection device can move in two general directions along the longitudinal axis relative to other components. For example, components can generally move towards the proximal end or distal end, or move in the proximal direction or the distal direction. Components that move towards the distal direction (needle tip) are described as moving forward, and components that move toward the proximal direction (plunger) are described as moving rearward/backward. The exemplary devices are also generally depicted with needle sheath controller positioned so that the positioner is pointing upward, with the exception of FIGS. 12A-12C, which are birds-eye views looking down on the device. Some of the components, such as the positioner, can move parallel to the vertical axis. The components can move in the upward direction or the downward direction. Pressing of the positioner toward the needle sheath controller will be described as pressing "downward" and releasing the positioner will be described as the positioner moving "upward."

In a general embodiment, the injection device, or apparatus, provided herein, includes a needle sheath and needle sheath controller, an injection needle with a needle tip that can be sheathed and unsheathed, a syringe barrel used as a reservoir for the fluid, such as a therapeutic, that is being delivered to the target tissue and a plunger that controls loading and release of the fluid. The needle sheath generally is a rigid shaft, but a flexible or steerable shaft can also be used depending on the purpose of use.

Figure 9A:
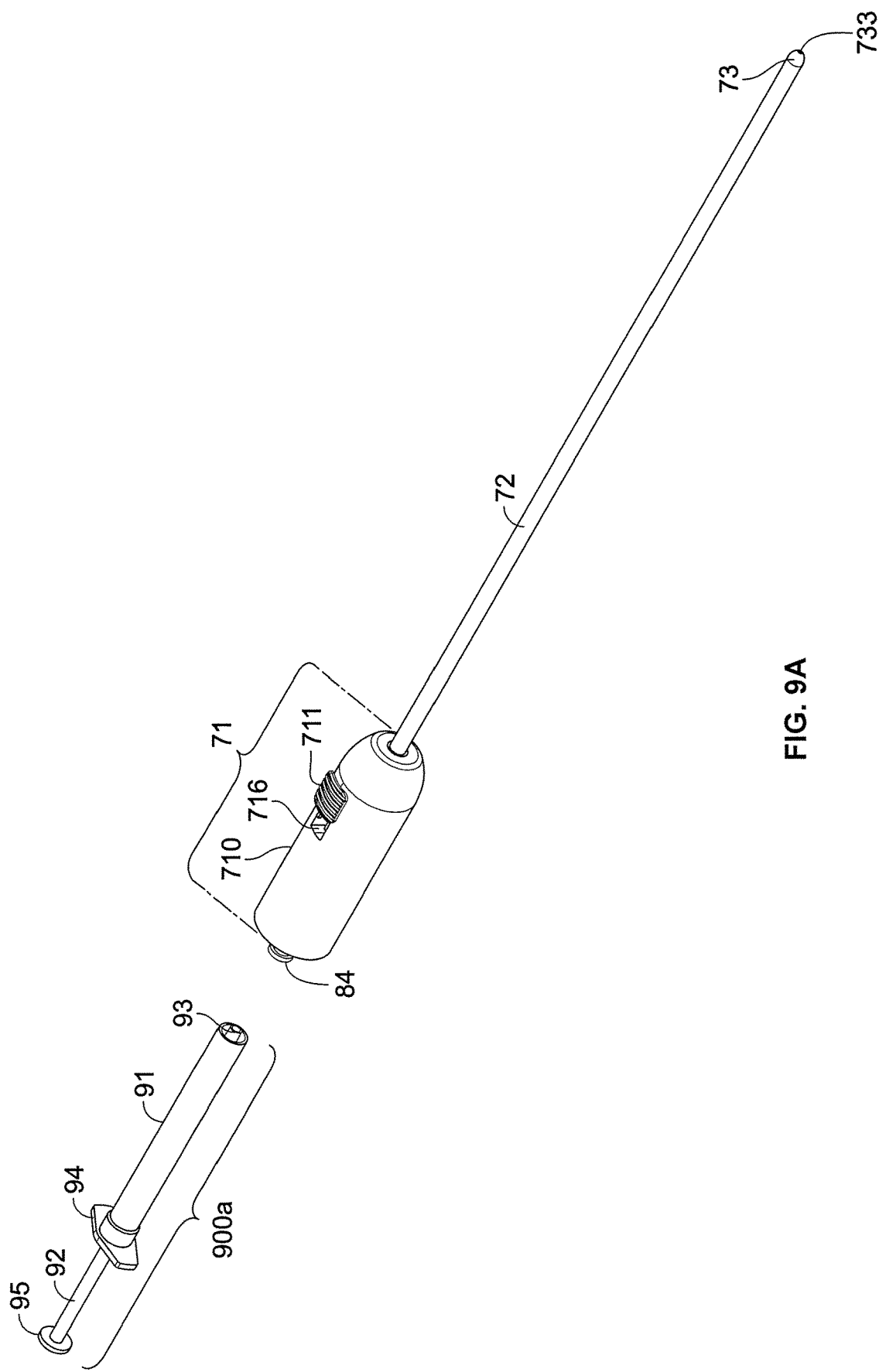
FIGS. 9A and 9B illustrate a standard syringe injection device.
Figure 9B:
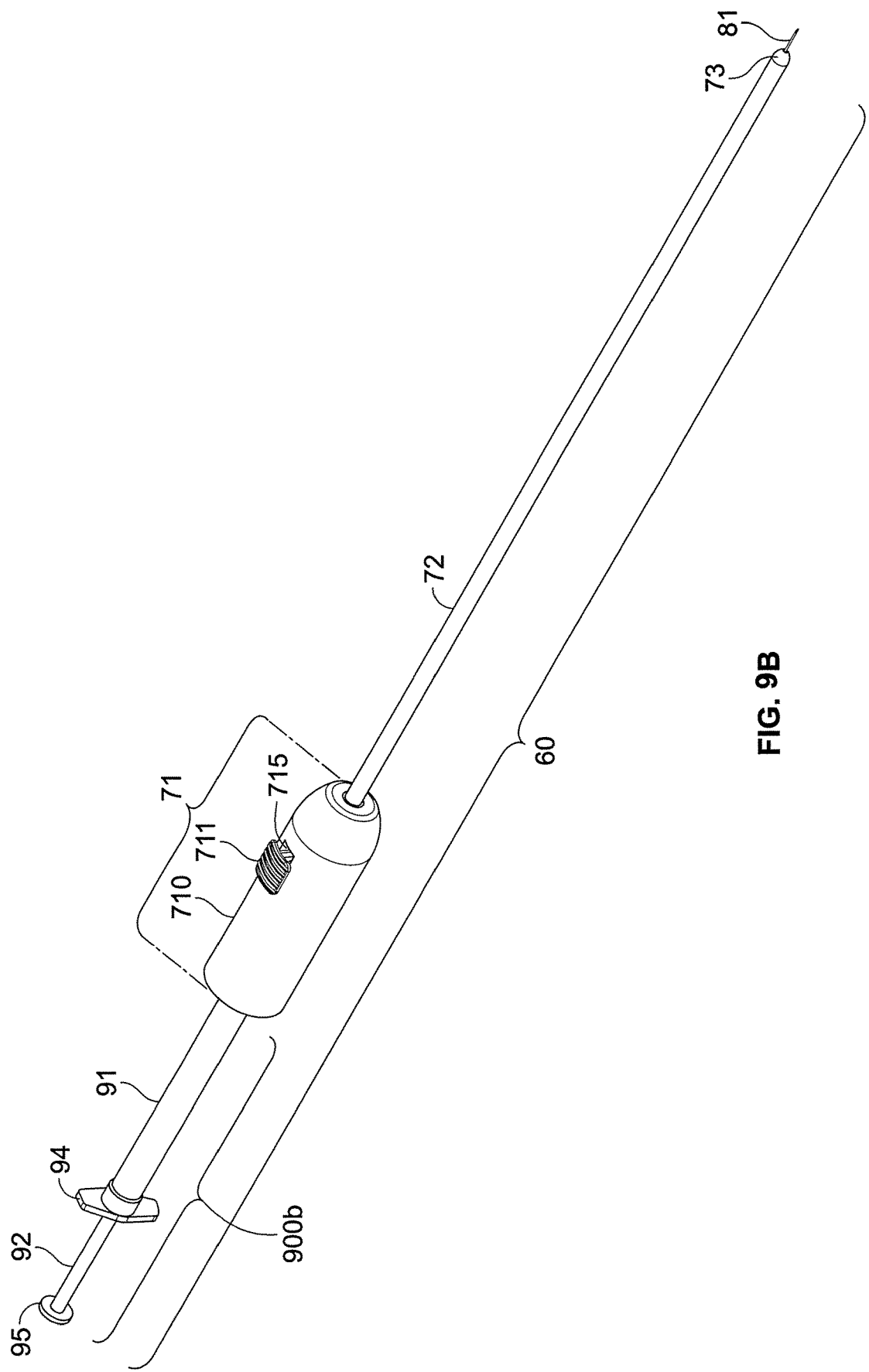
Figure 10:
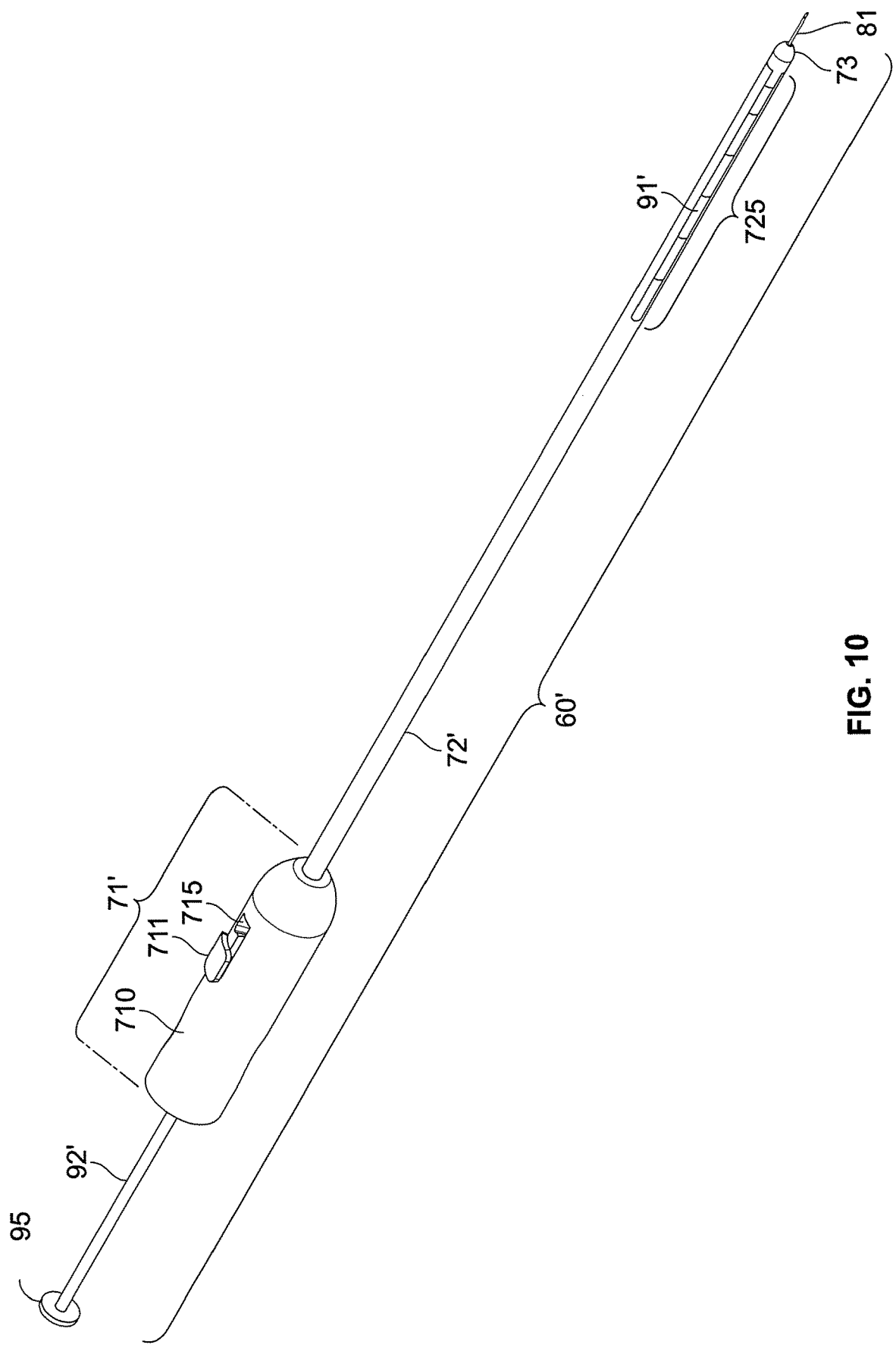
FIG. 10 shows a perspective view of an exemplary embodiment of an integrated syringe injection device in which a syringe barrel is integrated into the needle sheath lumen at the distal end of the device.
Figure 11:
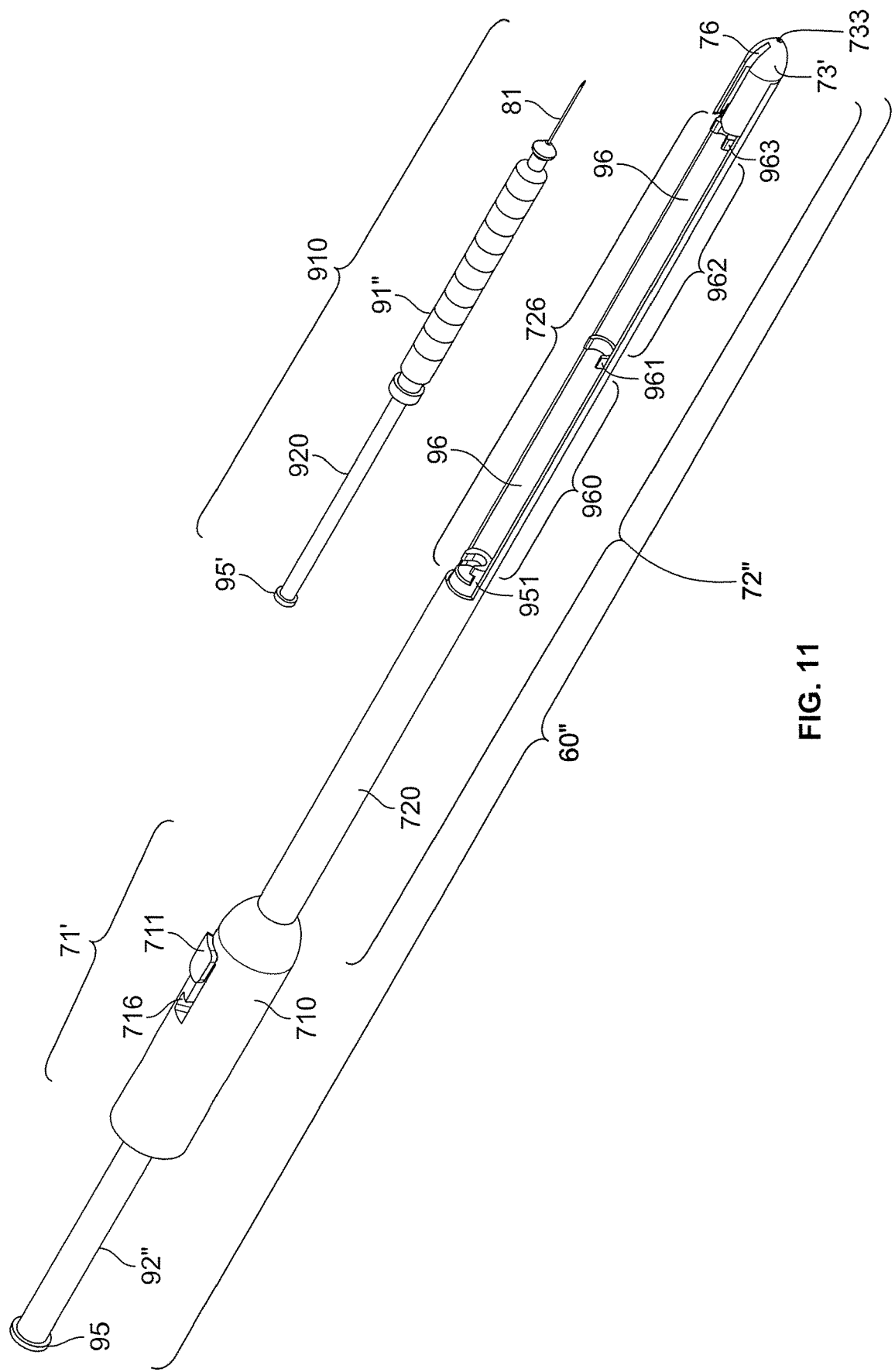
FIG. 11 shows a perspective view of an exemplary embodiment of a dockable syringe injection device in which a syringe containing an auxiliary plunger, barrel and injection needle are adapted to be docked onto a syringe adaptor within the needle sheath lumen at the distal end of the device

For example, with reference to FIGS. 9A and 9B, which illustrate a first exemplary embodiments provided herein, the syringe injection device is indicated generally by the reference numeral 60, and includes the needle sheath 72 and needle sheath controller 71, the injection needle 81, the syringe barrel 91 and the plunger 92. Other embodiments of the syringe device are described in FIG. 10 and FIG. 11, and other Figures as described below. For example, FIG. 10 shows a further embodiment indicated generally by the reference numeral 60', and includes the needle sheath 72', needle sheath controller 71', the injection needle 81, the syringe barrel 91' and the plunger 92'. In this embodiment, the needle sheath 72', needle sheath controller 71', syringe barrel 91' and the plunger 92' are substantially the same as the embodiment of FIGS. 9A and 9B, except that that the syringe barrel 91' is located at the distal end of the device and is integrated with the needle sheath 72' and therefore the plunger 92' traverses through the needle control sheath controller 71'. FIG. 11 shows a further embodiment indicated generally by the reference numeral 60", and includes the needle sheath 72", the needle sheath controller 71', the injection needle 81, the syringe barrel 91" and the plunger 92". In this embodiment, the needle sheath 72", needle sheath controller 71', syringe barrel 91" and plunger 92" are substantially the same as the embodiment of FIGS. 9A and 9B, except that the syringe barrel 91" is located at the distal end of the device and is adapted so that it is dockable into the needle sheath 72". Further, the plunger 92" traverses the needle sheath controller 71', and is further adapted to associate with an auxiliary plunger 920 located distal to the needle sheath controller 71' where the auxiliary plunger 920 is adapted to move within the syringe barrel 91".

In all embodiments of the laparoscopic device provided herein, the dimensions of the laparoscopic device permits its use through typical ports for laparoscopic surgery or other minimally invasive surgical procedures. For example, typical ports for laparoscopic surgery, through which the instruments or devices enter the patient, is about 5 to 10 mm in diameter. The device is used to reach and inject into the target tissue, which is typically an internal tissue or organ of the body, including the parenchyma of an organ. The length of the device is sufficiently long to permit access to the particular desired target tissue through a laparoscopic port, while not being so unwieldy that it is difficult to control. The choice of dimension of the device is dependent on the particular user, the target tissue, the subject being treated, the agent being administered, and other factors within the level of a skilled artisan. Generally, the needle sheath 72, 72' or 72" of the injection device is of a sufficient length to permit laparoscopic access to the target of interest, and is generally a length of 200 mm to 600 mm, such as 250 to 400 mm, and generally at least or about at least or 300 mm.

In all aspects of the device provided herein, the syringe barrel 91, 91' or 91" is cylindrical in shape with a hollow center that can fit the plunger 92, 92' or 92" so that the plunger can move back and forth inside the syringe barrel. The syringe can be made out of plastic or glass or other suitable material. Generally, the syringe is made out of glass or plastic, such as polypropylene, polyethylene, or polycarbonate. Other types of biocompatible materials may also be used. The syringe barrel can contain calibrations or markings on the outer surface in order to measure or detect the volume of solution. The calibrations can be marked in any measurement such as in cubic centimeters (cc), milliliters (mL), tenths of a milliliter, hundredths of a milliliter or other measurement. The volume of the syringe barrel can be selected by the operator depending on the particular application, the agent being administered, the type of device that is being used and other similar factors. For example, the volume of the syringe barrel can depend on the desired amount of fluid, such as a therapeutic, to be delivered, which is generally between 200 µL and 10 mL, more typically 500 µL to 2.5 mL, such as at least 500 µL, 1 milliliter (mL), 2 mL, 2.5 mL, 3 mL, 4 mL, 5 mL, 6 mL, 7 mL, 8 mL, 9 mL, 10 mL or more. For example, the syringe barrel can be 0.5 mL to 20 mL (i.e. 0.5 cc to 20 cc), and generally is 0.5 mL to 3 mL (i.e. 0.5 cc to 3 cc), such as at least or about a 1 mL (i.e. 1 cc) syringe. The syringe barrel also can have unit calibrations, such as present on standard insulin syringes (e.g. 100 units correlates to 1 mL). Typically, 200 µL to 600 µL of the fluid, such as a therapeutic, is delivered to the target locus, and the volume of syringe barrel is 1 mL.

The syringe barrel 91, 91' or 91" is always positioned on the proximal side of the injection needle, but can be positioned on either side of the needle sheath controller and in a manner that is on the proximal or distal side of the needle sheath controller. For example, the syringe barrel can be positioned on the proximal side of the needle sheath controller, or inside the needle sheath 72, 72' or 72". In particular aspects, with reference to the Figures and description below, FIGS. 9A and 9B depict a device 60 where the syringe barrel 91 is proximal to the needle sheath controller 71. In contrast, FIG. 10 depicts a device 60' where the syringe barrel 91' is distal to the needle sheath controller 71' and is integrated with the needle sheath at its distal end. FIG. 11 depicts a device 60" where the syringe barrel 91" is distal to the needle sheath controller 71' and is dockable, and hence removable from, the needle sheath at the distal end.

In cases where sterile injections are required, the syringe barrel can be loaded with the fluid, such as a therapeutic, in a sterile environment, such as a sterile operating room, or a sterile pre-loaded syringe can be used. For example, a sterile standard or dockable syringe can be connected to the device after loading with the fluid, such as a therapeutic, in a sterile environment. In other cases, the entire device is loaded, manipulated and operated in a sterile environment.

The plunger is located at the proximal end of the device and is movable so that it can be pulled and pushed along the inside the syringe barrel. Portions of the plunger travel within the syringe barrel along the longitudinal axis of the device. The plunger is cylindrical to move through the syringe barrel, and is made of a material that permits ease of movement through the syringe barrel. For example, the plunger generally is made of a plastic, such as polypropylene or polyethylene. The plunger also contains a head at the proximal end of the device that can be conveniently grasped by the operator to manipulate the plunger. The plunger head can transmit axial force from the operator in both the distal or proximal directions, leading to depression and drawing back, respectively, of the plunger. The plunger can be drawn back to load the syringe barrel with the fluid, such as a therapeutic, or depressed to inject the fluid, such as a therapeutic, in the target tissue. Pulling back on the plunger draws in the fluid, such as a therapeutic, or air into the syringe barrel. Pushing in the plunger forces air or the fluid or air out of the syringe barrel. The plunger can also be pulled back at the site of injection to test needle placement.

The length of the plunger is sufficiently long to permit its association with the inside of the syringe barrel directly or indirectly in order to effect dispelling of the fluid, such as a therapeutic, or composition or solution through the distal end of the syringe (and into a needle or tube if connected thereto). For example, in some aspects herein, a control plunger that is accessible to the operator can be adapted to be used with an auxiliary plunger when the syringe barrel is distally located. The length of the plunger can be 5 mm to 500 mm, such as 10 mm to 300 mm, 10 mm to 200 mm or 10 mm to 100 mm. Depending on the positioning of the syringe barrel with reference to the needle sheath controller, in some aspects the plunger also traverses through the needle sheath controller. In particular aspects, with reference to the Figures and description below, FIGS. 9A and 9B depict a device 60 where the plunger 92 is a standard plunger that is sized to move only within the syringe barrel 91 located at the proximal end of the device relative to the needle sheath controller. In contrast, FIG. 10 depicts a device 60' where the plunger 92' is elongated to traverse through the needle sheath controller 71' and hollow lumen of the needle sheath before traveling through the syringe barrel 91' at the distal end of the device. In another aspect, FIG. 11 depicts a device 60" where the plunger 92" is elongated to traverse through the needle sheath controller 71' and hollow lumen of the needle sheath, but does not travel through the syringe barrel 92" at the distal end of the device. Instead, the plunger is adaptable with an auxiliary plunger 920 that is sized to move only with the syringe barrel located at the distal end of the device.

The plunger 92, 92' or 92" can be manually depressed or pulled back, or an automatic controller can be used to control the plunger. An automatic or mechanical plunger mechanism can deliver several fixed or variable doses of the fluid, such as a therapeutic, with or without having to remove the injection device from the laparoscopic port. For example, a means of depressing the plunger 92, 92' or 92" can include hydraulic components, such as mechanically or electronically actuated piston and cylinder assemblies operatively connected, via hydraulic fluid lines, to the respective plunger 92, 92' or 92" elements. The device can be used to deliver a single dose of the fluid, such as a therapeutic, or multiple injections to the same patient without withdrawing the device from the laparoscopic port. Multiple doses can be delivered at different injection sites, if the multiple sites are reasonably close to each other that removal from the laparoscopic port is not necessary. The injection of several discrete doses can be achieved using different controls, such as mechanical controls and hydraulic mechanisms. For example, hydraulic components, such as mechanically and/or electronically actuated piston/cylinder assemblies or hydraulic plunger actuators can be used to control the plunger, which permits the use of a stroke or a force multiplier, and also permits a flexible shaft for the plunger mechanism, to transmit axial force. For multiple injections, an indexed injection trigger is used to deliver discrete doses of the fluid, such as a therapeutic, for example 100 microliter (µL), upon each pull of the trigger. The doses for multiple injections can be fixed or variable, and a volume control or a feedback mechanism for dose control for multiple injections can be used. Multiple doses provide an advantage over a single large dose in that they can be manipulated by parameters such as the location of the tissue, geometrical parameters and temporal parameters.

In all aspects of the devices provided herein, the device contains an injection needle 81 that is located inside the sheath at the proximal end of the needle and can be sheathed and unsheathed at its distal tip. The injection needle typically contains a beveled tip sufficient to penetrate or pierce a tissue or organ. The injection needle 81 can be directly or indirectly connected to the distal end of the syringe barrel in a manner that permits passage of a fluid or solution in the syringe barrel through the needle to its distal tip. For example, in some aspects, the injection needle 81 can be indirectly connected to the syringe barrel by an intermediary tube 83 that, together with the injection needle, form a continuous sealed fluid pathway for solution to move through. The intermediary tube can be a plastic or metal tube that is coupled directly or indirectly to the injection needle 81 by welding, bonding or molding. The intermediary injection tube 83 can be indirectly coupled to the injection tube 81 by a needle coupler 85. The needle coupler 85 can be made of any biocompatible and drug compatible rigid material, including metals, plastics, and ceramics, and is typically made of plastics such as polycarbonate or Acrylonitrile butadiene styrene (ABS). An optional coupling member 82 can be present inside the cavity of the needle coupler 85. The needle coupler 85 is coupled to each of the intermediary injection tube 83 and injection tube 81 by welding, bonding, molding or other procedure that creates a secure and reliable seal.

In some variations, the distal end of the syringe barrel can contain an adaptor that is compatible with a needle hub on the proximal end of the injection needle 81 or other intermediary tube 83 that itself is coupled to the injection needle 81. For example, with reference to FIG. 9A, and as described further below, the distal end of the syringe barrel 91 can contain a Luer fit adaptor 93 that is compatible with a needle hub 84 on the proximal end of intermediary injection tube 83, which itself is directly or indirectly connected to the injection needle 81. In other variations of the devices herein, the proximal portion of the injection needle 81 or other intermediary tube 83 that couples to the injection needle is directly affixed to the distal end of the syringe barrel and extends out of the syringe barrel. For example, with reference to FIGS. 10 and 11, the injection needle 81 is directly connected to the syringe barrel.

The size and diameter of the injection needle 81 is selected depending on the ease of insertion into tissue, damage to tissue that can be tolerated, shear/flow parameters of the fluid such as viscosity, injection force and injection rate required for the fluid, properties of the target tissue, amount of dead volume that remains in the device after injection, and other factors considered by persons skilled in the art. Typically, a small diameter needle 81 is employed to reduce the force required to insert the needle into the target tissue or organ, and to reduce trauma to the target tissue or organ. Generally, injection needle 81 is between 25 and 34 gauge, such as 25 gauge, 26 gauge, 27 gauge, 28 gauge, 29 gauge, 30 gauge or 31 gauge, and typically is 27 gauge.

The length of the injection needle 81 is dependent on the configuration of the syringe barrel in the device (i.e., whether the syringe barrel is located at the proximal or distal end of the device). The length of the injection needle 81 also is dependent on whether the needle is coupled directly to an intermediary injection tube 83 or is indirectly coupled to an intermediary injection tube 83 by a needle coupler 85. Such parameters can be related to the pressure drop that can be tolerated, the viscosity of fluid, the dead volume that can be tolerated, and other similar factors. For example, factors that influence pressure drop include the length of the needle, the diameter of the needle, and the viscosity of the fluid. A certain amount of injection pressure can be needed to deliver a fluid, such as a therapeutic, to a specific tissue. A specific injection pressure can be needed for delivery of certain fluid compositions. The injection pressure required can depend on factors such as parameters of the fluid being delivered such as viscosity, injection rate, and target tissue pressure.

For example, in some variations of the device, the injection needle 81 can be long and extend from the distal tip of the device through the sheath controller 71 where it is connected to syringe barrel 91 at the proximal end of the device. Hence, the length of the injection needle can range from 5 mm to 500 mm or more, such as 10 mm to 300 mm. Generally, in examples of the devices herein, the injection needle is shorter, which avoids problems in pressure drop that can occur when a solution is injected through a long needle. For example, the length of the injection needle generally can range from 5 mm and 40 mm, such as 10 mm to 40 mm. For example, common needle lengths that are widely available include for example, 12.7 mm, 25.4 mm or 38.1 mm needles. If a longer path is required for solution or fluid to travel (i.e., the syringe barrel is located at the proximal end of the device, e.g. FIGS. 9A and 9B), a smaller injection needle 81 can still be employed, but a pressure drop can be avoided by directly or indirectly coupling a smaller diameter injection needle 81 to an intermediary injection tube 83 of a greater diameter. For example, if the injection needle 81 is 27 gauge, the intermediary injection tube can be 15 gauge to 25 gauge, such as generally 20 gauge to 25 gauge, for example 21 gauge.

The injection needle 81 of the device is protected by a blunt, elongated needle sheath, which can sheathe and protect the needle prior to injection and unsheathe the needle at the site of injection. Hence, in all embodiments of the laparoscopic injection device provided herein, such as devices set forth in FIG. 9A, 9B, 10 or 11, the needle sheath 72, 72' or 72" is adapted so that the injection needle 81 can be sheathed and unsheathed. The ability to sheathe or unsheathe the injection needle 81 permits the operator of the device to control when the injection needle is exposed or when the injection needle is protected. For example, sheathing of the needle can prevent accidental injections or penetrations, damages to the patient's tissue, including the target tissue and non-target tissues, damages to the laparoscopic surgical instruments, such as damages to the elastomeric seals and valves of the laparoscopic port, damage to the needle, and accidental drip of the fluid, such as a therapeutic, during the insertion of the device into the laparoscopic port or removal of the device from the laparoscopic port. At the site of injection, the needle can be unsheathed, exposing the injection needle 81 to allow the needle tip to penetrate the target site and deliver the agent to the target site, such as the parenchyma of a target organ. The injection needle 81 can be sheathed again after injection to prevent accidental needle puncture of tissue other than the injection site.

In particular, the needle sheath 72, 72' or 72" is adapted to be controlled by the needle sheath controller 71 or 71'. The needle sheath controller 71 or 71' contains the components that control movement of the needle sheath 72, 72' or 72", connects the proximal and distal ends of the device, and is the conduit by which inner tubings, plungers or other components can travel between the proximal and distal ends of the device. The needle sheath controller 71 or 71' includes a controller housing 710 that encloses components internal to the needle sheath controller 71 or 71', and the proximal end of the needle sheath 72, 72' or 72". The needle sheath controller housing 710 can be made of any suitably resilient and rigid material, such as any polymeric material, including plastics, or rubber, metals, ceramics, composites, or other suitable material known to one of skill in the art. Typically, the needle sheath controller housing 710 is made from a plastic, including medical-grade plastics such as polypropylene, polystyrene, polyethylene, polyvinyl chloride, polyurethane, or silicone, rubber or acrylic. The needle sheath controller housing 710 can be molded using any technique known in the art, including compression-molding, thermoforming or injection-molding. The housing 710 can be made of one singular piece, using methods such as by an injection molding. Alternatively, the housing 710 can include multiple pieces that are separately manufactured and attached in a secondary process, such as with adhesive, locking joints, or other fasteners.

As shown in FIGS. 9A, 9B, 10 and 11, the needle sheath controller 71 or 71' is positioned on the proximal side of the needle sheath 72, 72' or 72". The needle sheath controller 71 or 71' is configured to be held and manipulated by an operator, such as a surgeon. The needle sheath controller 71 or 71' can be any shape and size that is convenient to permit the operator to hold and manipulate the device. Generally, the needle sheath controller 71 or 71' is cylindrical and can fit into the palm of an average person. The diameter of the needle sheath controller 71 or 71' is larger than the diameter of the needle sheath 72, 72' or 72" in order to accommodate the proximal end of the needle sheath 72, 72' or 72". For example, the diameter can be 15 mm to 100 mm, and is generally 20 to 35 mm. The diameter can be uniform or variable. For example, the outside of the needle sheath controller 71 or 71' can be graduated, contoured, beveled or grooved. The needle sheath controller 71 or 71' generally has a length of 30 mm to 225 mm, such as 50 mm to 75 mm. On the outside of the needle sheath controller 71 or 71', an optional grip can be present to facilitate the manipulation and handling of the device.

The needle sheath controller 71 or 71' contains an externally accessible positioner 711, which controls the position of the needle sheath 72 relative to the injection needle 81. As can be seen in FIGS. 9A, 9B, 10 and 11, the needle sheath controller 71 or 71' is a cylindrical ring having a positioner 711 extending out of the needle sheath controller 71 or 71' so that it is accessible to the operator. The positioner 711 can be integrally formed with the housing 710, or alternatively can be a separate piece coupled to the housing during assembly.

The positioner 711 is configured in the needle sheath controller 71 or 71' so that it is movable both forward and rearward relative to the needle sheath controller 71 or 71'. Movement of the positioner 711 forward or rearward controls movement of the needle sheath 72, 72' or 72" between two fixed or locked positions, the sheathed position 72a and unsheathed positions 72c. When sheathed, the injection needle 81 is hidden inside the needle sheath, and when unsheathed, the injection needle 81 is exposed outside of the needle sheath. The injection needle 81, however, is fixed and does not move relative to the needle sheath controller 71 or 71'. Thus, the positioner 711 only controls the movement of the needle sheath 72, 72' or 72", while the position of the injection needle 81 and other components of the device are stationary regardless of the position of the positioner 711. The relative position of the injection needle 81, however, changes with the movement of the needle sheath 72, 72' or 72", as the needle sheath 71 or 71' moves in the distal direction or the proximal direction, hiding or exposing the injection needle 81.

Figure 12A:
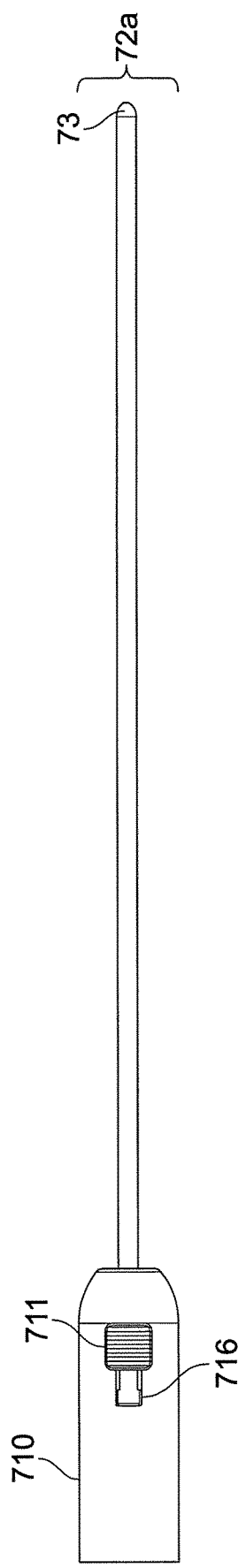
FIGS. 12A-12C illustrate the movement of the needle sheath of the injection device between the sheathed and unsheathed position as controlled by the positioner.
Figure 12B:
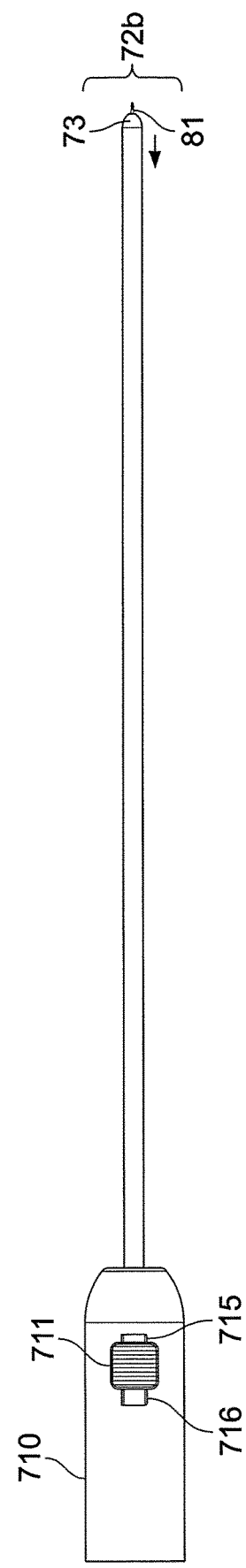

As shown in FIG. 12A, positioning of the positioner in a forward 711a position moves the needle sheath over the injection needle in the sheathed position 72a so that the injection needle is hidden inside the shaft of the needle sheath. As shown in FIG. 12B, positioning or moving the positioner to an intermediate position 711b, that is not fully locked forward or rearward, transitions the needle from outside of the needle sheath shaft to a transitional position 72b that exposes less of the needle than its maximum extent or length. As show in FIG. 12C, positioning of the positioner in the rearward 711c position moves the needle sheath proximally towards the needle sheath controller to its fully unsheathed position 72c, thereby permitting maximum exposure of the injection needle 81.

Figure 13:
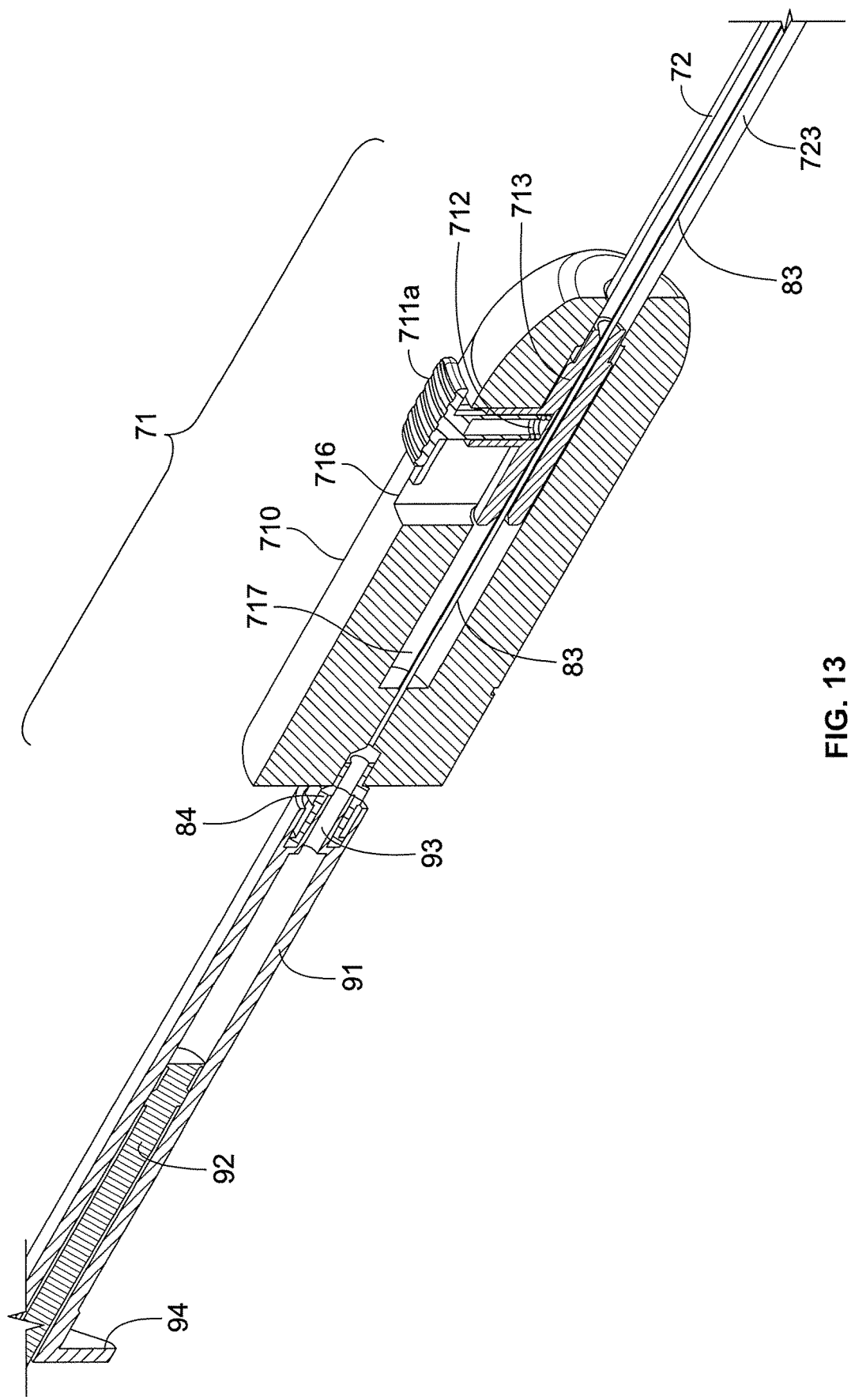
FIG. 13 is an enlarged sectional view of the needle sheath controller of the device depicted in FIGS. 9A and 9B.
Figure 14:
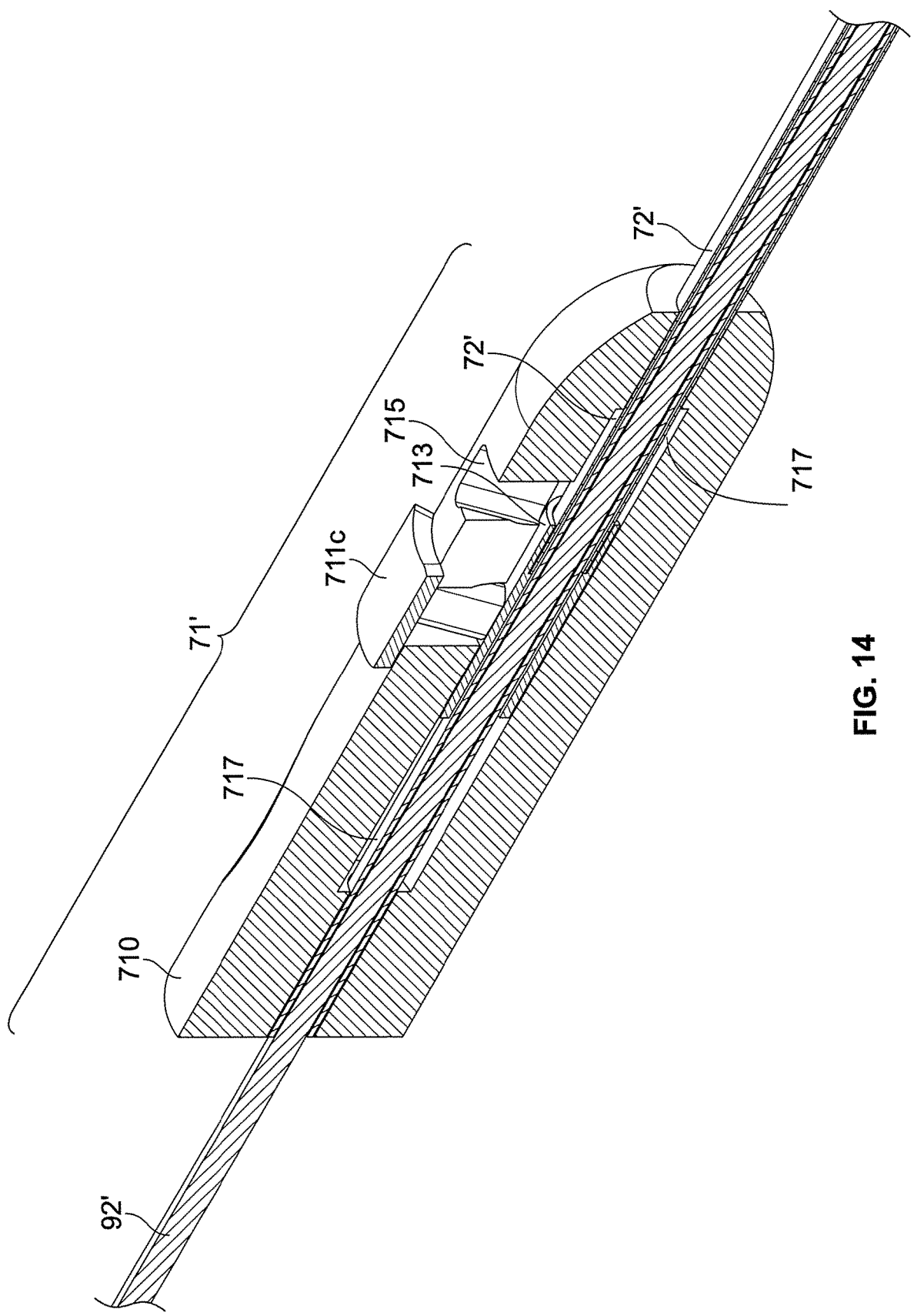
FIG. 14 is an enlarged sectional view of the needle sheath controller of the device depicted in FIG. 10.
Figure 15:
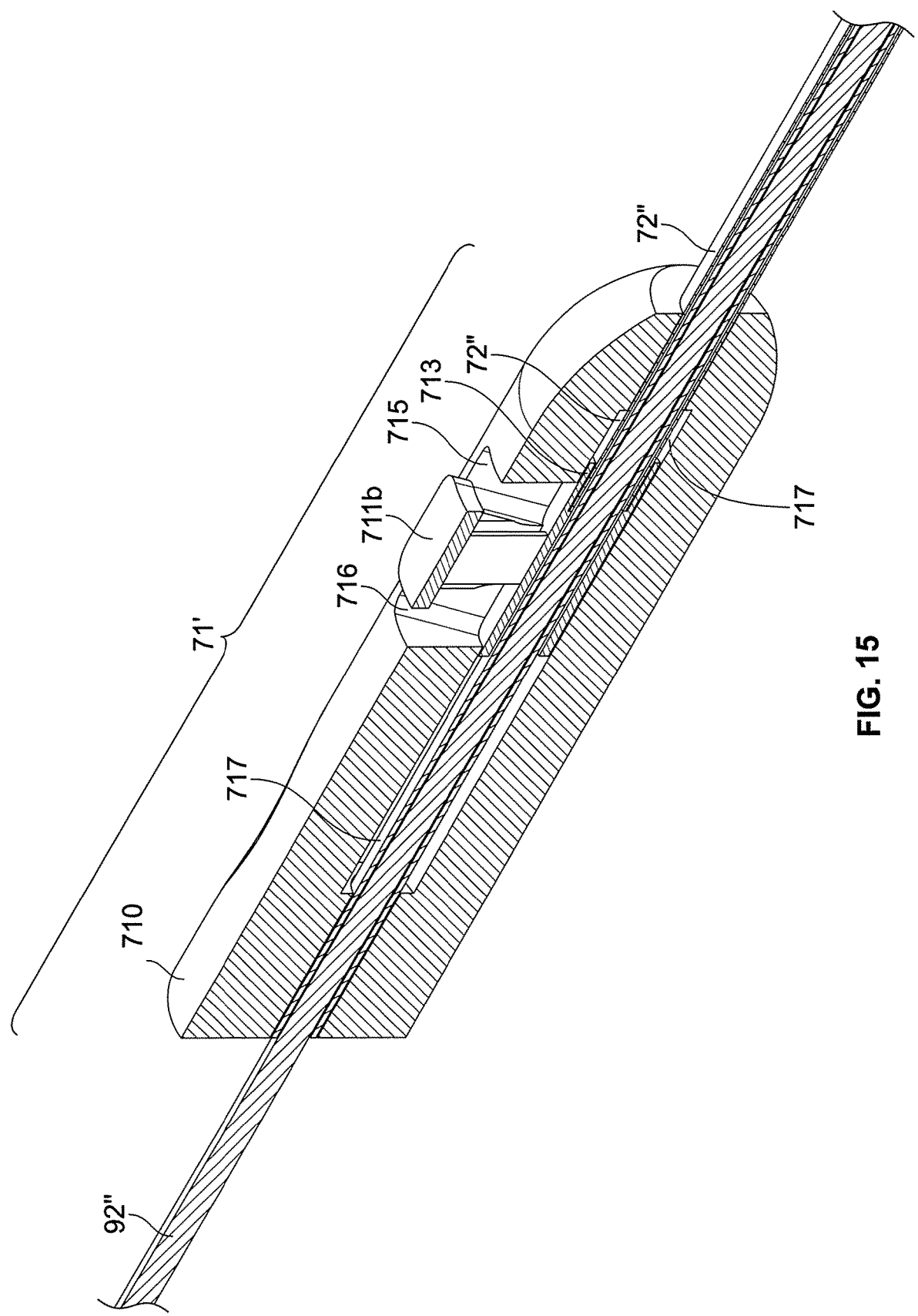
FIG. 15 is an enlarged sectional view of the needle sheath controller of the device depicted in FIG. 11.

The positioner 711 is engaged with the needle sheath and slides the needle sheath. As can be seen in FIGS. 13-15, the movement of the needle sheath 72, 72' or 72" by the positioner 711 is facilitated by a connection member 713. The connection member 713 is connected to the proximal end of the needle sheath 72, 72' or 72" and the lower part of the positioner 711. The positioner 711 and the needle sheath connector 713 can be connected to each other by welding, adhesive, locking joints, fasteners or other suitable means. The distal end of the connection member 713 is connected to the proximal end of the needle sheath 72, 72' or 72", such that the sheath is longitudinally movable relative to the controller housing 710 and the injection needle 81. In particular, the distal end of the outside of the connection member 713 is engaged with the proximal inside lumen 723 of the needle sheath around its circumference. The needle sheath 72, 72' or 72" can be connected to the connection member 713 by welding, adhesive, locking joints, fasteners or other suitable means.

The lower portion of the positioner 711, the connection member 713 and proximal end of the needle sheath 72, 72' or 72" are enclosed by the controller housing 710. With reference to FIGS. 13-15, the needle sheath controller housing 710 is molded with an internal needle sheath controller lumen 717 that is a hollow cavity inside the needle sheath controller 71 or 71' of a sufficient length and diameter to accommodate forward and rearward movement of the connection member 713. The length and diameter of the controller lumen 717, however, is always less than the total length and diameter of the needle sheath controller 71 or 71", thereby restricting movement of the needle sheath connector 713 within the inside of the needle sheath controller 71 or 71'. The controller lumen 717 is generally longitudinal along the housing body. The shape of the internal or central lumen 717 of the controller can be any of a variety of shapes and configurations, so long as it provides a tracking means along which the connection member 713 slides. For example, the controller lumen 717 can be cylindrical or rectangular. The controller lumen 717 also can be uniform or non-uniform in shape, size or diameter. For example, the distal and proximal ends can be the same diameter or different diameters.

The needle sheath controller housing 710 also contains cut-out grooves to serve as sheath stops 715 and 716 that provide a means to engage with the positioner 711. As shown in FIGS. 13-15, the positioner 711 contains a projected top portion or head that juts out of the needle sheath controller 71 or 71' where it can be moved forward or rearward by the operator. Internal to the needle sheath controller 71 or 71', the body of the positioner 711 is notched on its sides or is otherwise configured to engage with sheath stops. The sheath stops 715 and 716 are grooves in the needle sheath controller housing 710 that fit the notched body of the positioner and trap the positioner 711 so that it cannot be moved without external force.

The positioner 711 is configured to be lockable and releasable in the sheath stops 715 and 716, such that when the positioner is engaged in a sheath stop it is secure to prevent the sheath from moving, but can be conveniently repositioned to control the movement of the sheath. For example, the sheath stops can be configured in a manner that creates a cradle for the positioner so that the positioner 711 is secured within the sheath stop and is not able to fall out of the cradle in the stop. To move the positioner 711 out of the cradle in the stop, the positioner must be physically moved outward from the cradle, so that the positioner 711 can be repositioned. To lock the positioner, the positioner must be physically moved inward (towards the grooves or cradle in the stop) to engage with the cradle created in the stop. Thus, the positioner 711 can also be pivoted to move outward (away from the grooves or cradle in the stop) to unlock from the sheath stops 715 and 716, then slid along the longitudinal axis to change positions, and pivoted again to move inward (towards the grooves or cradle in the stop) to engage with and lock into the sheath stops 715 and 716 to lock the positioner 711 and the needle sheath 72.

As an alternative, the positioner 711 can contain a lock and release element that facilitates lock and release of the positioner with the grooves of the sheath stops. FIG. 13 depicts an optional lock and release element 712 that can be contained in the positioner to facilitate lock and release of the positioner 711 with the grooves of the sheath stops. For example, the lock and release element 712 can be a spring or other resilient means. When the positioner 711 is moved or fit into the grooves of a stop it is locked into place by a vertically upward force against the positioner 711 and a downward force against the connection member 713. Pressing the positioner 711 vertically downwards releases the vertically upward force applied by the lock and release element 712, and releases the positioner from the stops.

Because the positioner 711 and the connection member 713 are connected, the movement of the positioner 711 can control the movement of the connection member 713 and the connected needle sheath 72, 72' or 72". Therefore, movement of the positioner 711 between the sheath stops 715 and 716 moves the needle sheath 72, 72' or 72" between the sheathed and unsheathed positions. In other variations, the lock and release mechanism can be a latch or switch that can be selectively engaged or disengaged according to its mechanical nature, for example, by sliding a latch or pivoting a lever attached to the head of the positioner 711, thereby moving it out of the way of a notch or other fastening mechanisms in the groove of the sheath stops.

For example, with reference to FIGS. 13-15, the needle sheath controller housing 710 contains two stop sheath stops 715 and 716 that are arranged into the needle sheath controller housing 710 on the proximal and distal sides of the positioner 711. With reference to FIG. 13, when the positioner 711 is engaged in either of the sheath stops 715 or 716, the lock and release element 712, such as a spring, can exert a force against the positioner 711 in the vertically upward direction, and the connection member 713 in the downward direction. Unless force is applied against the lock and release element 712 by pressing the positioner 711 down, the positioner 711 and connection member 713 have a tendency to be pushed away from each other in the vertical direction, due to the force exerted by the lock and release element 712. The force that pushes the positioner 711 in the upward direction permits the positioner 711 to be locked in place in either the distal sheath stop 715 or the proximal sheath stop 716. If the positioner 711 is pressed vertically downward, the positioner 711 is freed from the grooves and can move in the forward or rearward direction longitudinally.

FIGS. 13-15 demonstrate the alternative positions of the positioner 711 relative to the sheath stops. For example, FIG. 13 depicts the positioner 711 in the forward position 711a where it is engaged or fit into the distal sheath stop 715. When the positioner 711 is engaged with distal stop 715, the connection member 713 is longitudinally moved to the furthest distal position within the controller lumen 717 and the sheath is in the extended position hiding the needle tip. FIG. 14 depicts the positioner 711 in the rearward position 711c where it is engaged or fit into the proximal sheath stop 716. When the positioner 711 is engaged with proximal stop 716, the connection member is longitudinally moved towards the proximal end of the needle sheath lumen, thereby exposing the injection needle. FIG. 15 depicts the positioner 711 in an intermediate position 711b after releasing the positioner from its locked position in either sheath stop and sliding the positioner along the longitudinal axis. In this position, the injection needle 81 is in an intermediate unsheathed position, but is not fully exposed.

The extent or length of the injection needle 81 that can be exposed or unsheathed at the distal end of the device is related to the distance along the longitudinal axis between a first sheath stop and a second sheath stop, which is the distance that the positioner 711, and hence connection member 713 controlling the position of the sheath, moves between locked positions. For example, with reference to FIGS. 13-15, the extent or length of the injection needle 81 that can be exposed or unsheathed at the distal end of the device can be substantially the same as the distance between the distal sheath stop 715 and the proximal sheath stop 716. It is understood, however, that the extent or length of the injection needle that is exposed can be somewhat longer or shorter than the distance between the first and second groove stop due to a slight recess of the distal tip of the injection needle in the distal tip of the needle sheath when it is unsheathed. For example, if the distal tip of the injection needle 81 is recessed from the distal tip of the needle sheath 73 in the fully sheathed position 72c, the extent or length the injection needle that can be exposed is shorter than the distance between a first sheath stop and a second sheath stop. A needle that is exposed substantially the same as the distance between the sheath stops is recessed only slightly and no more than 1 mm, such that the difference in the distance of the sheath stop and the length that the injection needle that can be exposed is less than 1 mm or 0.5 mm or less. As an example, if the distal tip of the injection needle 81 is slightly recessed from the distal tip of the needle sheath 73 in the fully sheathed position 72c, the maximum extent or length of the injection needle that can be exposed or unsheathed at the distal end of the device is the distance between the distal sheath stop 715 and the proximal sheath stop 716, minus the slight distance between the tip of the injection needle 81 and the distal tip of the needle sheath 73 in the fully sheathed position.

In other examples, the length of the injection needle that is exposed or extended is appreciably shorter than the distance between the sheath stops. In this case, the injection needle can be positioned so that it is recessed inside the distal tip of the needle sheath 73 in the unsheathed position 72c more than 1 mm, and generally 2 mm to 5 mm, from the distal tip of the needle sheath 73 in the unsheathed position 72c. Thus, if the distal tip of the injection needle 81 is recessed from the distal tip of the needle sheath 73 in the fully sheathed position 72c, the maximum extent or length of the injection needle that can be exposed or unsheathed at the distal end of the device is the distance between the distal sheath stop 715 and the proximal sheath stop 716, minus the distance between the tip of the injection needle 81 and the distal tip of the needle sheath 73 in the fully sheathed position.

The extent or length of the injection needle 81 that is exposed when unsheathed can be empirically determined, and is a function of the target tissue, the particular subject being treated, the agent being administered and other factors within the level of a skilled artisan. For example, the extent of the injection needle that is unsheathed is of a sufficient length so that the needle tip can penetrate the parenchyma of the target tissue of interest, but not so long that it can easily pass through or puncture the target tissue through to the other side. Typically, the desired length of the exposed injection needle when unsheathed is from or from about 2 mm to 10 mm, such as generally 5 mm to 10 mm. For example, general adult tissues, such as the liver, have a thickness of 10 mm to 30 mm. The thickness of the tissue can vary depending on the anatomical dimensions of the subject, such as age, height, weight, and/or the type of tissue or organ. Hence, the distance between the distal sheath stop 715 and the proximal sheath stop 716 is 2 mm to 15 mm, such as 2 mm to 12 mm, 2 mm to 10 mm, such as generally 5 mm to 10 mm.

In variations of the injection devices herein, more than two sheath stops, such as 3, 4, 5 or more sheath stops, can be configured into the needle sheath controlling housing 710 that can each engage separately with the positioner 711 to lock the sheath. Engagement of the positioner with the most distal sheath stop locks the sheath in its fullest extended position to completely hide the injection needle inside the needle sheath. Engagement of the positioner with the most proximal sheath stop locks the sheath in its fullest retracted or opened position to maximally expose the injection needle outside of the needle sheath. The other sheath stops provide means to vary the length of the exposed injection needle from its fully sheathed or unsheathed positions. Hence, the length of the exposed injection needle 81 can be varied with use of multiple needle sheath lock grooves. For example, in addition to the proximal 715 and distal 716 needle sheath stops, several additional sheath stops can be present, between the proximal and distal stops, permitting the positioner 711 and the needle sheath 72, 72' or 72" to be locked in several different positions, with different lengths of the injection needle 81 exposed. As an example, the controller housing 710 can contain four sheath stops that are separated along the longitudinal axis by a distance of 2 mm. Thus, the positioner 711 can be locked in four different positions, resulting in positioning of the injection needle so that it can be sheathed, or exposed by 2 mm, 4 mm or 6 mm.

The connection member 713 contains a central cavity that is also longitudinal along the housing body and is of a sufficient size to slide around and independently from components of the device that traverse through the needle sheath controller 71, 71' or 71". For example in FIGS. 13-15, an injection tube or plunger can traverse through the inside of the needle sheath controller across its longitudinal axis. In particular, FIG. 13 shows an intermediary injection tube 83 that traverses through the inside of the needle sheath controller, and the connection member 713 contains a central cavity that slides around and independently from the injection tube 83. The injection tube 83 is fixed to the needle sheath controller 71 at its proximal end. As shown in FIGS. 14-15, the plunger 92' or 92", respectively, longitudinally traverses through the inside of the needle sheath controller 71', and the connection member 713 contains a central cavity that accommodates and slides around and independently from the plunger 92' or 92". The plunger is movable within the needle sheath controller 71' and is not fixed thereto. The particular width or size of the cavity is dependent on the particular component that traverses through it. The connection member 713 is disengaged from and moves independently with respect to the components (e.g. injection tube or plunger) that run through its internal central cavity.

In aspects of the injection device provided herein, the needle sheath optionally has a visibility window, allowing visualization of the drawback fluids to test needle placement in target organs. For injections into the parenchyma of a target organ that has extensive vasculature, the drawback fluid can be used to confirm needle placement into the parenchyma, and avoid injections into the vasculature or the bile duct. At the site of injection, the plunger can be pulled back slightly to draw a small amount of fluids, in order to determine whether the needle was placed at a blood vessel or the target organ. Once the needle 81 is positioned and has penetrated the target injection site, the plunger 92, 92' or 92" can be depressed to deliver the fluid, such as a therapeutic, contained in the syringe barrel to the target site.

The syringe barrel 91, 91' or 91" and/or the device can be disposable or reusable. For example, except if the syringe is integrated with the device, the syringe barrel can be removed after injection or exhaustion of the fluid, such as a therapeutic, replaced with a new loaded syringe, or reloaded and re-connected. If the syringe barrel is at the outside the laparoscopic port, such as described with device 60, this can be achieved without the need to withdraw the device from the laparoscopic port. In some cases, the device can be withdrawn from the laparoscopic port and disposed of after one use. The method of loading and the type of syringe and syringe format employed can be empirically determined and is a function of factors considered by persons of skill in the art, such as the objective of the injection, target tissue or organ, dose and frequency of injections needed, properties of the fluid, such as a therapeutic, composition, and surgical environment.

For clarity of description, exemplary embodiments of the injection device are described below. It is understood that for the described embodiments, general aspects and components of the device are the same, and that different aspects or components are so described. Thus, except as noted, the description of the various exemplary embodiments and the structures of the embodiments described above apply to all embodiments of the injection device. Additionally, the methods of using the injection device, for example for injection of a fluid, such as a therapeutic, to a target tissue during a minimally invasive surgery, apply to all embodiments as well. The particular injection device employed can be empirically determined and is a function of factors considered by persons of skill in the art, such as the objective of the injection, target tissue or organ, dose and frequency of injections needed, properties of the fluid, such as a therapeutic, composition, and surgical environment.

1. Standard Injection Device

FIGS. 9A-B, 13, 16A-B, and 17A-D depict the injection device 60 and components and features thereof. The injection device as shown in FIGS. 9A and 9B includes needle sheath 72, needle sheath controller 71, injection needle 81, syringe barrel 91 and plunger 92. With reference to FIG. 9A, generally, the needle sheath 72 of the injection device is of a sufficient length to permit laparoscopic access to the target of interest, and is generally a length of 200 mm to 600 mm, such as 250 to 400 mm, and generally at least or about at least or 300 mm. The device is generally cylindrical around the longitudinal axis, generally having a smaller diameter in the needle sheath 72 region and the plunger 92 region, and a larger diameter in the needle controller 71 region. The needle sheath 72 portion of the device is typically inserted through the laparoscopic port. The diameter of the needle sheath 72 is typically between 3 mm to 12 mm in size, and typically from 5 mm to 10 mm. It is understood that the portions of the device external to the laparoscopic port can have a diameter greater than 10 mm. For example, the needle sheath controller body 71 can have a diameter sufficiently large, so long as it can be easily gripped or handled by the operator. The needle sheath controller body 71 is held by the operator, typically a surgeon, to manipulate and position the device 60, control the needle sheath 72, and support the device while manipulating the plunger 92.

The syringe barrel 91 is cylindrical in shape with a hollow center that can fit plunger 92 so that the plunger can move back and forth inside the syringe barrel. The syringe barrel is generally clear and transparent. The syringe barrel 91 can be made out of plastic or glass or other suitable material, and in particular is made out of plastic such as polypropylene, polyethylene, polycarbonate or other clear material. As described above, the syringe barrel 91 can contain calibrations or marking on the outer surface to indicate the volume of the agent within the barrel. As described above, the syringe barrel 91 can have a volume capacity that is from the range of 0.5 mL to 20 mL (i.e. 0.5 cc to 20 cc), and generally is 0.5 mL to 3 mL (i.e. 0.5 cc to 3 cc), such as at least or about a 1 mL (i.e. 1 cc) syringe. Typically, 200 µL to 600 µL of the fluid, such as a therapeutic, is delivered to the target locus, and the volume of syringe barrel is 1 mL.

The syringe barrel 91 is positioned proximal to the injection needle 81, and on the proximal side of the needle sheath controller 71. As shown in FIG. 9A, the distal end of the syringe barrel 91 contains a Luer fit adaptor 93 that is compatible with a needle hub 84 on the proximal side of the needle sheath controller 71. The syringe barrel 91 is removable and attachable with the needle sheath controller 71 and the connected needle sheath 72 by manipulation of the Luer fit locking mechanisms. FIG. 9A shows the syringe in the detached position 900a. Thus, a sterile syringe barrel 91 can conveniently be used when drawing up or loading the syringe with a fluid, such as a therapeutic, compositions or other solutions into the syringe barrel. If desired, a separately sterile needle can be fitted on the Luer fit adaptor 93 to permit loading of the syringe barrel 91 with a fluid, such as a therapeutic. After the agent is drawn up into the syringe, the syringe barrel 91 (without needle) can be secured to the needle sheath controller 71 through the Luer fit adaptor 93 on the distal end of the syringe barrel 91 and the needle hub 84 on the proximal end of the needle sheath controller 71. In some cases, a pre-loaded syringe a with standard Luer fit adaptor 93 can be connected. FIG. 9B shows injection device 60 with the syringe barrel 91 secured to the needle sheath controller, in the connected position 900b. Advantages of device 60 having a removable and attachable syringe barrel 91 include the ease of loading the syringe barrel and exchange of loaded syringe. Since standard syringes can be used to connect to the needle sheath control 71, a variety of syringe types can be used, and several different types of syringes can be used for one patient, if necessary. In cases where the syringe must be re-loaded or additional fluid is needed, new or re-loaded syringes can easily be connected.

The plunger 92 is located on the proximal end of the device 60 and is movable so that it can be pulled and pushed along the inside of the syringe barrel 91. The plunger 92 can be drawn back to load the syringe barrel 91 with the fluid or depressed to inject the fluid in the target tissue. The plunger 92 can also be pulled back at the site of injection to test needle placement. The plunger is cylindrical to move through the syringe barrel 91, and is made of a material that permits ease of movement through the syringe barrel, such as a plastic, for example polypropylene or polyethylene. The plunger contains a head 95 at the proximal end of the device that can be conveniently grasped by the operator to manipulate the plunger. The plunger head 95 also is generally made of plastic. The distal tip of the plunger 92 is generally made of silicone or other natural or synthetic rubber to provide a tight seal within the syringe barrel 91 when traveling within the syringe barrel 91.

The plunger 92 is long enough in length to permit its association with the inside of the syringe barrel 91 in order to dispel the fluid through the distal end of the syringe (and into a needle or tube if connected thereto). For example, the plunger is 5 cm to 50 cm, such as 5 cm to 30 cm or 10 cm to 20 cm. Pulling back on the plunger 92 draws in the fluid, such as a therapeutic, or air, and pushing the plunger 92 forces the fluid, such as a therapeutic, or air out of the syringe barrel. Optionally, the plunger can contain syringe barrel base 94 that can aid manipulation of the syringe barrel 91 with respect to the plunger 92.

The syringe barrel 91 and/or the device 60 can be disposable or reusable. For example, the syringe barrel 91 connected to the proximal side of the needle sheath controller 71 through a Luer fit adaptor 93, can be removed after injection of the fluid, such as a therapeutic, replaced with a new loaded syringe, or reloaded and re-connected, with or without the need to withdraw the device from the laparoscopic port. The device 60 can be withdrawn from the laparoscopic port and disposed of after one use.

The device 60 contains an injection needle 81 that is located inside the needle sheath 72 that can be sheathed and unsheathed at the distal tip of the needle 81. With reference to FIG. 9A, the distal tip of the needle sheath 73 contains a needle channel 733 that guides the needle outside of the needle sheath 72 when it is unsheathed as shown in FIG. 9B. As shown in FIG. 9B, the injection needle 81 contains a beveled tip sufficient to penetrate or pierce a tissue or organ.

FIG. 13 depicts an enlarged cross section view of the distal end of the syringe barrel 91 and the needle sheath controller 71. As shown in FIG. 13, the plunger 92 is contained within the syringe barrel 91, which optionally can contain a syringe base 94, where it can movably travel. The needle sheath controller 71 is positioned on the proximal side of the needle sheath 72. The needle sheath controller 71 contains the components that control movement of the needle sheath 72, connect the proximal and distal ends of the device, and is the conduit by which the injection needle 81, directly or indirectly connected to an intermediary injection tube 83, travel between the proximal and distal ends of the device. The needle sheath controller 71 is configured to be held and manipulated by an operator, such as a surgeon. As discussed above, the needle sheath controller 71 can be any shape and size that is convenient to permit the operator to hold and manipulate the device, and typically is cylindrical in shape. The diameter of the needle sheath controller 71 is such that it can be held in the palm of an average adult, and is generally 20 mm to 100 mm in diameter with a length of 50 mm to 225 mm. The needle sheath controller 71 optionally can contain an outside grip for handling.

As shown in FIGS. 9A-B and FIG. 13, the needle sheath controller 71 includes a controller housing 710 that encloses components internal to the needle sheath controller 71, and the proximal end of the needle sheath 72. As discussed above, the needle sheath controller housing 710 can be made of any suitably resilient and rigid material, such as any polymeric material, including plastics, or rubber, metals, ceramics, composites, or other suitable material known to one of skill in the art. The controller housing 710 is typically made of polypropylene, polystyrene, polyethylene, polyvinyl chloride, polyurethane, silicone, rubber or acrylic. As discussed above, the housing 710 can be made by any manufacturing known to a skilled artisan, and can be made as one singular piece or can be made of two or more pieces that are attached together, such as with adhesive, locking joints or fasteners.

As shown in FIGS. 9A and 9B, the needle sheath controller 71 contains an externally accessible positioner 711. As described above, the positioner 711 is configured in the needle sheath controller 71 so that it is movable both forward and rearward relative to the needle sheath controller 71. As described above, the positioner 711 is engaged with the needle sheath 72 through a connection member 713, and can be used to slide the needle sheath 72. This connection permits movement of the positioner 711 between the forward or rearward positions to control movement of the needle sheath between two fixed or locked positions, the sheathed and unsheathed positions. The sheathed position protects or hides the injection needle, while the unsheathed position exposes the needle.

With reference to FIG. 13, the connection member 713 is connected to the proximal end of the needle sheath 72, and the lower part of the positioner 711. The connection of the connection member 713 with the proximal end of the needle sheath is such that the needle sheath 72 is longitudinally movable relative to the controller housing 710 and the injection needle 81. For example, the distal end of the outside of the connection member 713 is engaged with the proximal inside cavity of the needle sheath 72 around its circumference. The connections of the control member 713 with the positioner 711 and needle sheath 72 can be by welding, adhesive, locking joints, fasteners or other suitable means.

As described above generally, the connection member 713 moves inside a hollow cavity or lumen 717 contained inside the housing 710 of the needle sheath controller 71 that is closed at both ends relative to the housing 710. The controller lumen 717 accommodates the connection member 713 such that the connection member 713 can easily glide or move forward or rearward in a restricted manner. For example, the connection member 713 can be cylindrical and fit inside a cylindrical hollow lumen cavity 717. As shown in FIG. 13, and discussed further below, the connection member 713 contains an internal hollow cavity to fit the injection tube 83 that passes through.

Movement of the connection member 713 is controlled by the positioner 711. As shown in FIGS. 9A, 9B and 13, the positioner 711 contains a projected top portion or head that juts out of the needle sheath controller 71 where it can be moved forward or rearward by the operator. As shown in FIG. 13, internal to the needle sheath controller 71, the body of the positioner 711 is notched on its sides or is otherwise configured to engage with sheath stops 715 or 716. Sheath stops 715 and 716 are grooves in the needle sheath controller housing 710 that fit the notched body of the positioner and trap the positioner 711 so that it cannot be moved.

FIG. 13 depicts the optional lock and release element 712 configured in the positioner 711 to facilitate lock and release of the positioner with the grooves of the sheath stop 715 or 716. For example, the lock and release element 712 can be a spring or other resilient means. The mechanism controlling lock and release of the positioner 711 with the grooves of the sheath stop 715 or 716 by the lock and release element 712 is as described above, whereby downward, vertical or lateral forces release or lock the positioner 711 from the sheath stops 715 or 716. Pushing downward on the positioner 711 permits the positioner to slide and to fit it into either of sheath stops 715 or 716.

Movement of the positioner 711 between the sheath stops 715 and 716 moves the connection member 713, and thereby also moves the needle sheath 72 so that it can transition from the sheathed and unsheathed positions by control of the positioner by the operator. When the positioner is in the forward position 711*a* as exemplified in FIG. 13, proximal sheath stop 716 is free and the positioner 711 is fit into the distal sheath stop 715, thereby sheathing the injection needle so that it is protected. While not shown in FIG. 13, the positioner 711 also can be in the rearward position 711*c* as exemplified in FIG. 14, where the distal sheath stop 715 is free and the positioner 711 is fit into the proximal sheath stop 716, thereby unsheathing the injection needle so that it is exposed. As a further position, the positioner 711 also can be in an intermediate position 711*b* as exemplified in FIG. 15, where both the distal sheath stop 715 and the proximal sheath stop 716 are free and not engaged with the positioner 711.

The injection needle 81 shown in FIG. 9B is indirectly connected to the syringe barrel 91 through an intermediary injection tube 83 as shown in FIGS. 9A and 5. The injection tube 83 contains a proximal needle hub 84 that is secured with the Luer fit adaptor 93 of the syringe barrel 91. The injection tube 83 is fixed directly to the needle sheath controller housing 710 so that the injection tube, and hence injection needle coupled thereto at the distal end of the device, is not movable.

As shown in FIG. 13, the injection tube 83 passes through the inside lumen 717 of the needle sheath controller 71 and passes through a central cavity of the connection member 713, but is not directly attached to the connection member. Hence, the connection member 713 can move independently around the fixed injection tube 83. As discussed above, because the needle sheath 72 is directly connected to the connection member 713 contained in the controller lumen 717, the injection tube 83 enters the lumen 723 of the needle sheath 72 inside the needle sheath controller 71. The injection tube 83 exits the distal end of the needle sheath controller 71 where it is contained within the hollow cavity of the needle sheath 72.

Figure 16A:
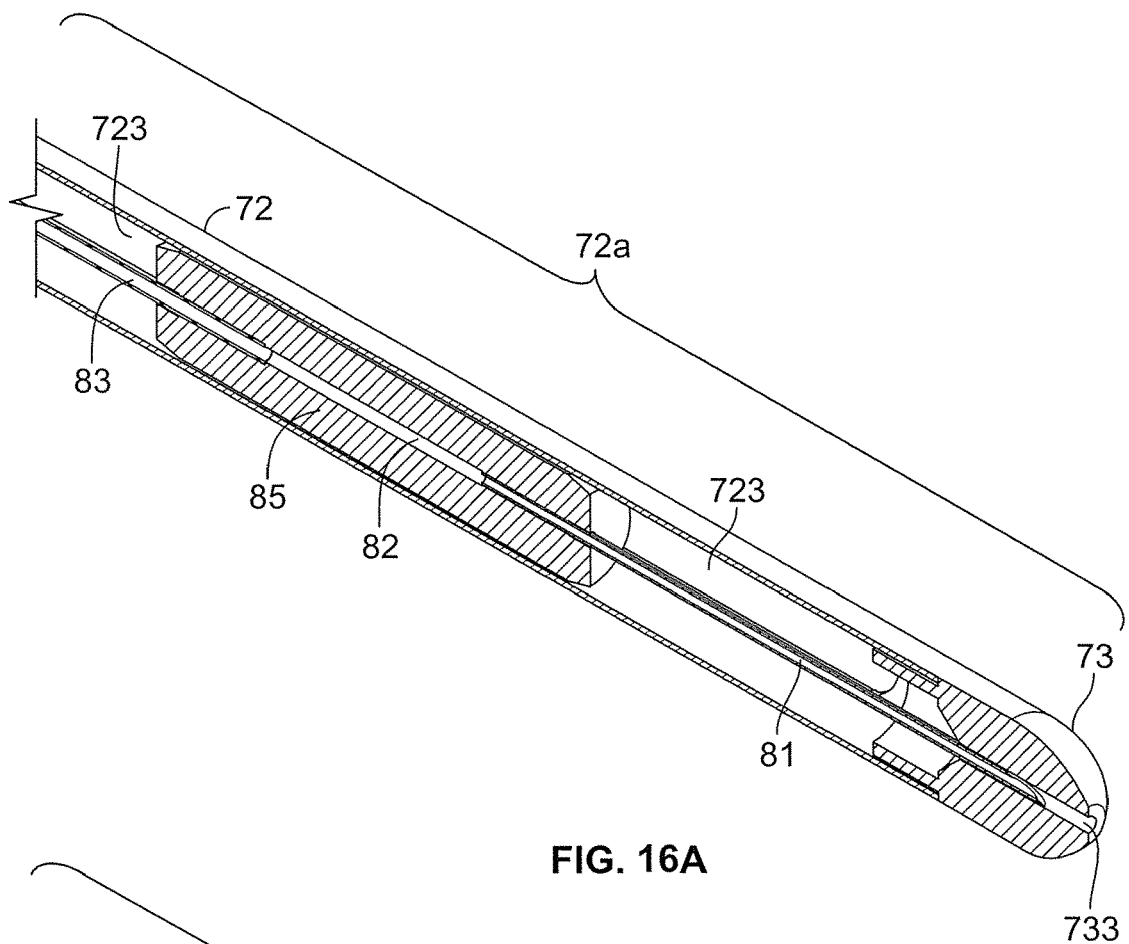
FIGS. 16A-16B show an enlarged sectional view of the tip of the needle sheath in the device shown in FIGS. 9A and 9B.
Figure 16B:
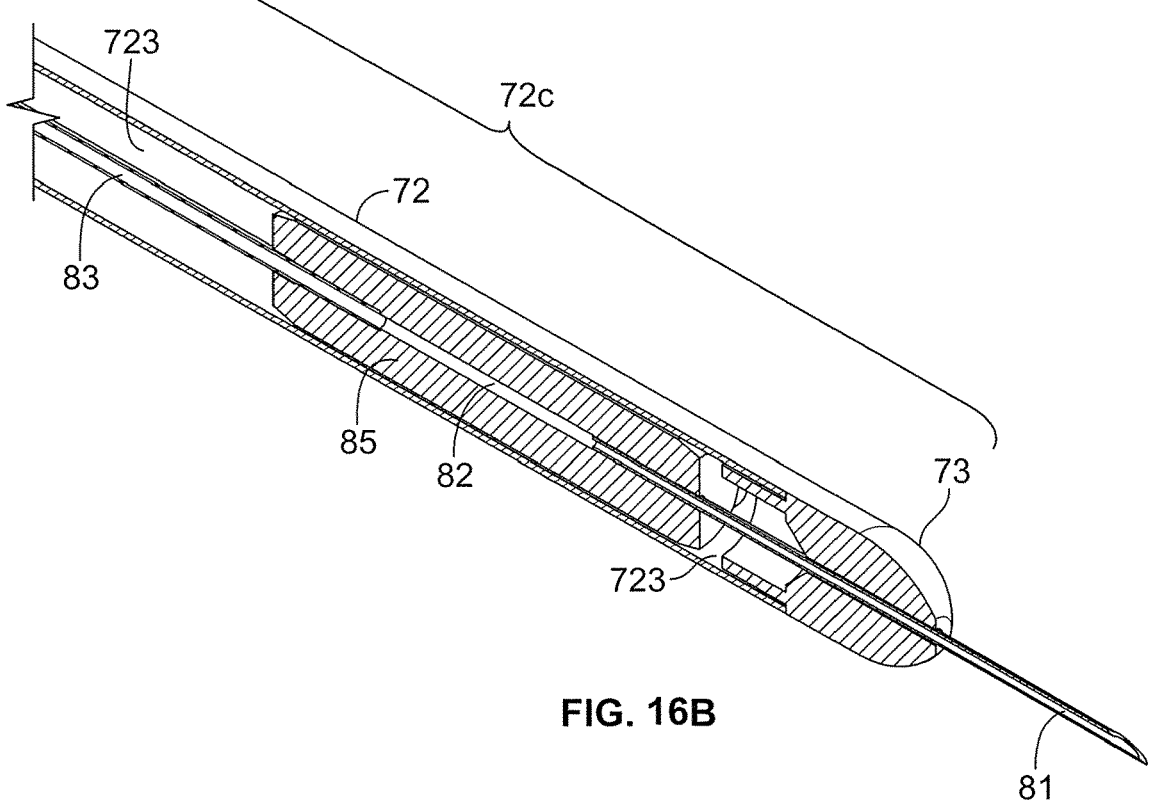

With reference to FIGS. 16A and 16B, the injection tube 83 runs distally and longitudinally through the needle sheath 72 where it is connected to the injection needle 81. The injection tube 83 and the injection needle 81 can be made of one piece, or made of more than one separate pieces. When the injection tube and injection needle 81 are made of one piece, the injection tube 83 can also be an elongated tapered needle, having a larger diameter in the proximal region, and a smaller diameter in the distal region near the injection needle 81. Optionally, a needle coupler 85, made of the same or different material, can be used to indirectly connect the two parts. The injection tube 83 and injection needle 81 can be made of the same material, or of different material. The injection tube 83 and the injection needle 81 have the same diameter, or a different diameter.

As shown in FIGS. 16A and 16B, the injection tube 83 is indirectly coupled to the injection needle 81 through a needle coupler 85. The coupler 85 connects the injection tube 83 to the injection needle 81 to form a continuous sealed fluid pathway for solution to move through. The connection can be by welding, bonding, molding or other procedure that creates a secure and reliable seal. The coupler 85 can be made of any biocompatible and drug compatible material suitable to provide a seal, and generally is made of a plastic. The coupler 85 can be clear or transparent or opaque. For example, the coupler 85 can be made of polycarbonate or other clear material. As discussed further below, in embodiments where the needle sheath 72 contains an optional visibility window 724 to view drawn up fluids, the needle coupler 85 generally is clear or transparent to permit visualization of the fluid or solution through the window.

The injection needle 81 contains a beveled tip sufficient to penetrate or pierce a tissue or organ. The injection needle 81 is typically made of metal or alloy, such as surgical stainless steel or other medical grade metal. The size and diameter of the injection needle 81 is selected based on parameters described above. As described above, typically a small diameter needle 81 is employed to reduce the force required to insert the needle into the target tissue or organ, and to reduce trauma to the target tissue or organ. For example, the injection needle 81 is between 25 and 34 gauge, such as a 25 gauge, 26 gauge, 27 gauge, 28 gauge, 29 gauge, 30 gauge or 31 gauge needle, and typically is 27 gauge.

The gauge of the injection tube 83 can be the same or different than the injection needle 81. The device provided herein is generally designed, however, to minimize pressure drop throughout the path that the fluid traverses. Factors that influence the pressure within the column of fluid includes the length of the needle, viscosity of the fluid contained within, rate of delivery of the fluid, and the gauge of the needle. The device is designed to have reasonable axial force requirements to depress the plunger 92, thereby permitting delivery of the fluid in a laparoscopic manner with sufficient injection pressure. For example, the axial force required to depress the plunger 92 in order to inject the fluid to the target organ is typically less than 2 pounds of force (lbf), preferably less than 1 lbf. The axial force required to depress the plunger 92 can also depend on the desired rate of delivery of the fluid, and the optimal pressure can also depend on the operator. In some cases, a significant injection force can be required to inject the fluid through a long needle of the laparoscopic device. To prevent an immediate significant pressure drop when the fluid traverses the injection tube 83, a larger gauge injection tube can be used. Thus, in order to reduce pressure drops that can occur due to the long path created by the continuous sealed fluid pathway made up of the injection tube 83, coupler 85 and injection needle 81, the injection tube 83 generally has a larger diameter than the injection needle 81.

For example, if the syringe barrel 91 is positioned at least 300 mm proximal to the injection needle 81, and the fluid, such as a therapeutic, must traverse a long path through the needle sheath shaft 72, a significant pressure drop can occur. In this case, an injection tube 83 of a larger diameter can be used, coupled to an injection needle 81 with a smaller diameter, to prevent the large pressure drop when traversing through a narrow needle 80. An optional needle coupler 85 can be used to join the injection tube 83 with the injection needle 81. The needle coupler 85 contains a recess by which the injection tube 83 and the injection needle 81 can be press fit to stably hold the position of the needle components in place within the needle sheath lumen 723. The needle coupler 85, can optionally contain a coupling member 82 to facilitate coupling of the injection tube 83 and the injection needle 81 in the recess of the needle coupler 85.

If the gauge of the injection tube 83 and injection needle 81 are different, the coupler 85 can be sized to fit the opposing diameters, for example, it can be beveled on its proximal or distal end. In particular examples, the injection tube 83 is 15 gauge to 25 gauge, and the injection needle 81 is 25 gauge to 34 gauge. For example, the injection tube 83 is 21 gauge and the injection needle 81 is 27 gauge. The injection tube 83 can be made of metal or plastic, such as any surgical grade materials. The combined length of the injection tube 83, coupler 85 and injection needle 81 is sufficiently long to pass from the distal end of the syringe barrel 91 to the distal end of the needle sheath 72, for example is 100 mm to 600 mm long, and generally at least or about at least 300 mm. The particular size of the injection tube 83, coupler 85 and injection needle 81 can be chosen by the user and can depend, for example, on the convenience of available injection needles. For example, commonly used injection needles are sized as 12.7 mm, 25.4 mm or 38.1 mm needles.

The continuous sealed fluid pathway formed by the injection tube 83, coupler 85 and injection needle 81 pass through and traverse the central inside hollow cavity or lumen 723 of the needle sheath 72. The needle coupler 85 also holds the injection tube 83, and injection needle 81, so that the needle sheath 72 can slide over the injection tube 83, needle coupler 85 and injection needle 81 when the sheath is moved between the sheathed position 72a and unsheathed position 72c. For example, the needle coupler 85 is loosely fit into the hollow circular sheath lumen 723. Thus, the needle sheath 72 moves independently from the needle coupler 85. The needle coupler 85 can be made of any biocompatible and drug compatible rigid material, including metals, plastics, and ceramics, and is typically made of plastics such as polycarbonate or Acrylonitrile butadiene styrene (ABS). The injection tube 83 and injection needle 81 can be press fit into the recess of the needle coupler to create a stable fixed relationship with the needle coupler 85, and hence also the housing 710. An optional coupling member 82 can be present inside the recess of the needle coupler 85 and can be connected to the injection tube 83 and injection needle 81. The coupling member 82 is coupled to each of the intermediary injection tube 83 and injection tube 81 by welding, bonding, molding or other procedure that creates a secure and reliable seal. The coupling member 82 can be made of any biocompatible and drug compatible rigid material, including metals, plastics, and ceramics, and is typically made of plastics such as polycarbonate or Acrylonitrile butadiene styrene (ABS).

Figure 12C:
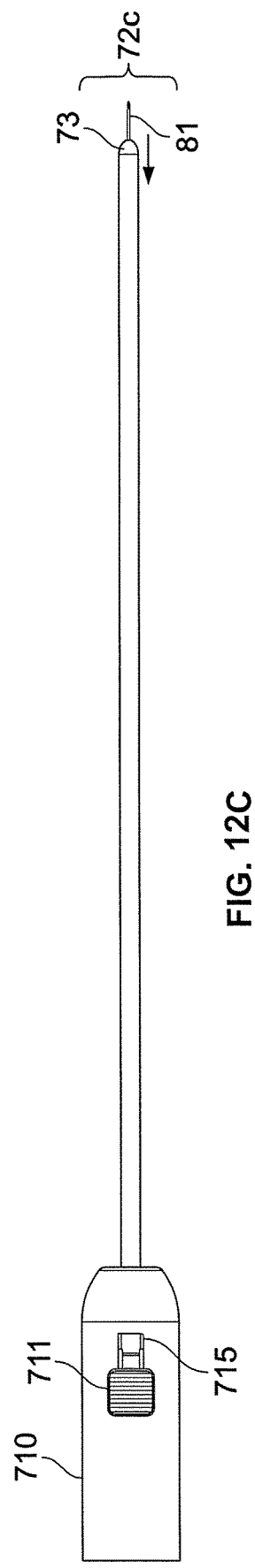

At the distal end of the device 60, the needle sheath 72 ends in a distal tip of the needle sheath 73 that contains a needle channel 733. The needle channel 733 is sufficiently sized to fit the injection needle 81 so that the injection needle can extend and retract through the needle channel 733 as the needle sheath 72 moves. In FIG. 16A, the injection needle 81 is covered by the needle sheath 72 and does not traverse through the distal portion of the needle channel 733. With reference to FIG. 12A, the device 60 in FIG. 16A is in the sheathed position 72a. In FIG. 16B, the injection needle 81 is extended out of the needle sheath 72 and does traverse through the distal portion of the needle channel 733. With reference to FIG. 12C, the device 60 in FIG. 16B is in the unsheathed position 72c.

In the unsheathed position, the needle sheath 72 is pulled back, but the injection tube 83, needle coupler 85 and injection needle 81 are fixed and do not move. For example, as shown in FIG. 16B, because the needle sheath 72 is pulled back, the size of the sheath lumen 723 between the distal end of the needle coupler 85 and the distal tip 73 of the device is shortened compared to the size of the corresponding sheath lumen shown in FIG. 16A. This demonstrates that movement of the sheath, as described with reference to FIG. 13 above using the positioner 711, only controls the movement of the needle sheath 72, while the position of the injection needle 81 and other components of the device are stationary regardless of the position of the positioner 711.

As described above, in the unsheathed position, the extent by which the injection needle 81 is extended or exposed out of the device 60 is a function of the distance between the sheath stops 715 and 716 as shown in FIG. 13. This distance is a function of the particular application of the device, the particular target tissue, the subject being treated and other considerations. For example, unsheathed needle that is exposed should not be so long that it can easily penetrate through to the other side of a target tissue. Generally, with reference to most target tissues (e.g. liver), the portion of the injection needle 81 shown in FIGS. 16B, 17B and 17D that can be unsheathed or exposed is generally less than 1 cm, such as 2 mm to 10 mm, and generally no more than 5 mm. For a child, the length can be smaller, and is generally less than 4 mm. For applications in utero, the length can be 2 mm to 3 mm.

The needle sheath 72 can be solid or can be transparent or clear. In some cases, the needle sheath 72 contains an optional visibility window 724. As described above, the presence of the visibility window 724 allows visualization of the administered agent or solution as well as the drawback fluids. For example, since some applications require injection directly into the parenchyma, and not into a vessel or bile duct, the ability to drawback and visualize fluid from the area the needle has penetrated can be used to confirm needle placement into the parenchyma, while avoiding injections into the vasculature or bile ducts. Since device 60 is long and the plunger 92 is outside of the body it is helpful to visualize the fluid path closer to the injection site and within the view of the laparoscope. To achieve this, a visibility window 724 can optionally be present in the needle sheath 72 to visualize the fluid path through a clear or transparent needle coupler 85. FIGS. 17A and 17C provide corresponding perspective views of the needle sheath shown in FIG. 16A in the sheathed position 72a. In FIG. 17A, the needle sheath 72 is solid and the injection needle inside the sheath cannot be visualized. In FIG. 17C, the needle sheath 72 contains a visibility window 724 that permits visualization of the inside components of the needle sheath 72, including the injection needle. Likewise, FIGS. 17B and 17D provide corresponding perspective views of the needle sheath shown in FIG. 16B in the unsheathed position 72c. In FIG. 17B, the needle sheath 72 is solid and the injection needle 81 inside the sheath is extended, but otherwise cannot be visualized inside the needle sheath 72. In FIG. 17D, the needle sheath 72 contains a visibility window 724 that permits visualization of the inside components of the needle sheath 72, including the portion of the injection needle 81 that is not extended out of the sheath. It is understood that the visualization window 724 in FIGS. 17B and 17D is for exemplification only, and that the visualization window can be any desired size. For example, the visualization window can extend the entire sheath. It also can extend distally and include portions of the distal tip of the needle sheath 73. Other variations also are contemplated and can be easily envisioned by a skilled artisan in view of this description.

The syringe barrel and/or the device can be disposable or reusable. For example, the syringe barrel 91 connected to the proximal side of the needle sheath controller 71 through a Luer fit adaptor 93, can be removed after injection or exhaustion of the fluid, such as a therapeutic, replaced with a new loaded syringe, or reloaded and re-connected, without the need to withdraw the device from the laparoscopic port. In some cases, the device 60 can be withdrawn from the laparoscopic port and disposed of after one use, or can be re-used.

With reference to the above Figures, exemplary of the mode of operation of the injection device 60 involves loading a standard syringe (e.g. 1 mL insulin syringe) containing a syringe barrel 91 and plunger 92 with a fluid, such as a therapeutic, prior to connecting the syringe to the needle sheath controller 71 via the Luer fit adaptor 93 of the syringe barrel 91 and the needle hub 84 connected to the injection tube 83. Once the syringe barrel 91 is loaded and connected to the needle sheath controller 71, the needle sheath 72 can be positioned in the sheathed position 72a, and the device can be inserted into a laparoscopic port to be placed near the site of injection. At the site of injection (target tissue), the needle sheath 72 can be unsheathed 72c, and the injection needle 81 can be exposed for injection. If necessary, the plunger 92 can be pulled back to draw fluids from the site of injection, to test the placement of the injection needle 81 at the injection site. The optional visibility window 724 can be used to visualize the drawback fluid from the injection site. Once the site of needle placement is determined, the plunger 92 can be depressed, to inject the fluid, such as a therapeutic, at the target tissue. After injection, the needle sheath 72 can be positioned in the sheathed position 72a, to protect the non-target organs and prevent accidental needle puncture, prior to removing the laparoscopic device from the injection site and through the laparoscopic port.

2. Integrated Injection Device

FIGS. 10, 14 and 18A-D depict the injection device 60' and components and features thereof. The injection device as shown in FIG. 10 includes needle sheath 72', needle sheath controller 71', injection needle 81, syringe barrel 91' and plunger 92'. The needle sheath 72' of the injection device is of a sufficient length to permit laparoscopic access to the target of interest, and is generally a length of 200 mm to 600 mm, such as 250 to 400 mm, and generally at least or about at least or 300 mm. The device is generally cylindrical around the longitudinal axis, generally having a smaller diameter in the needle sheath 72' region and the plunger 92' region and a larger diameter in the sheath controller 71' region. The needle sheath 72' of the device is typically inserted through the port (e.g. laparoscopic port). The diameter of the needle sheath 72' is typically from 3 mm to 12 mm in size, and typically from 5 mm to 10 mm. It is understood that portions of the device external to the laparoscopic port can have a diameter greater than 10 mm. For example, the needle sheath controller body 71' can have a diameter sufficiently large, so long as it can be easily gripped or handled by the operator. The needle sheath controller body 71' is held by the operator, typically a surgeon, to manipulate and position the device 60', control the needle sheath 72' and support the device while manipulating the plunger 92'.

The syringe barrel 91' is cylindrical in shape with a hollow center that can fit plunger 92' so that the plunger can move back and forth inside the syringe barrel. The syringe barrel is generally clear and transparent. The syringe barrel can be made out of plastic or glass or other suitable material, and in particular is made of plastic such as polypropylene, polyethylene, polycarbonate or other clear material. As described generally above, the syringe barrel 91' can contain calibrations or markings on the outer surface to indicate the volume of the agent within the barrel. As described above, the syringe barrel 91' can have a volume capacity that is from the range of 0.5 mL to 20 mL (i.e. 0.5 cc to 20 cc), and generally is 0.5 mL to 3 mL (i.e. 0.5 cc to 3 cc), such as at least or about a 1 mL (i.e. 1 cc) syringe. Typically, 200 µL to 600 µL of the fluid, such as a therapeutic, is delivered to the target locus, and the volume of syringe barrel is 1 mL.

Figure 18A:
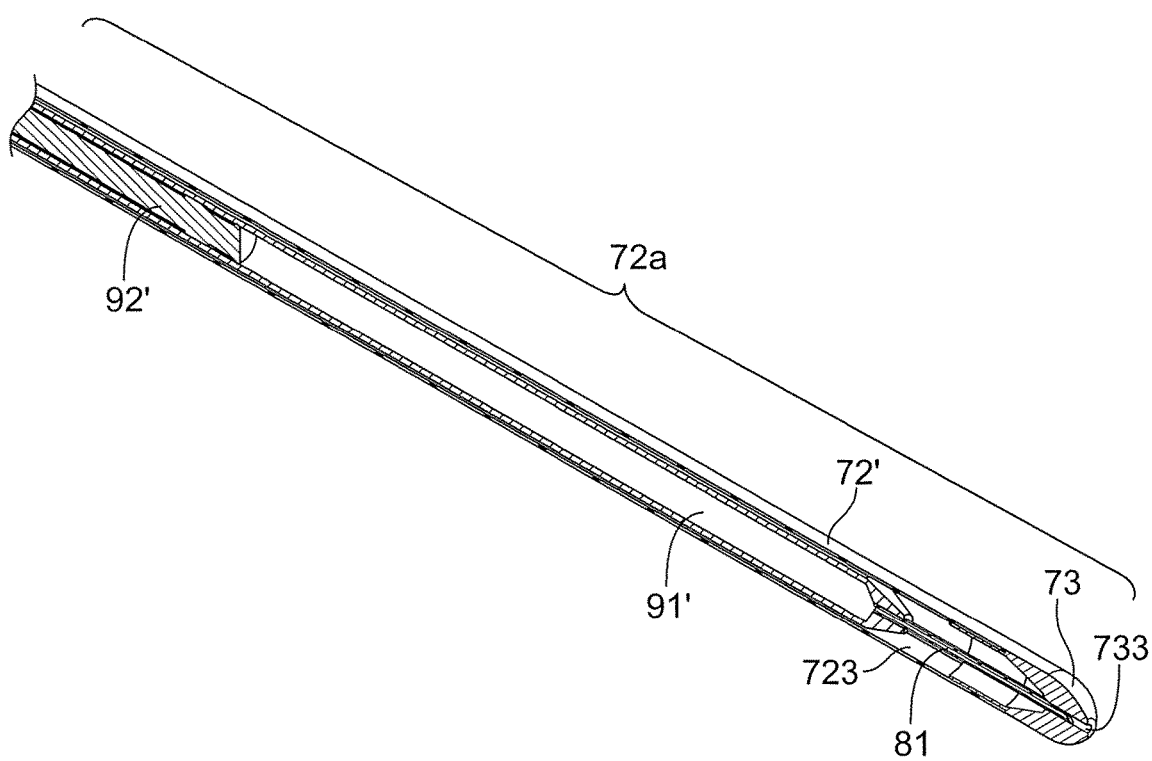
FIGS. 18A-18D illustrate enlarged views of the device shown in FIG. 10.
Figure 18B:
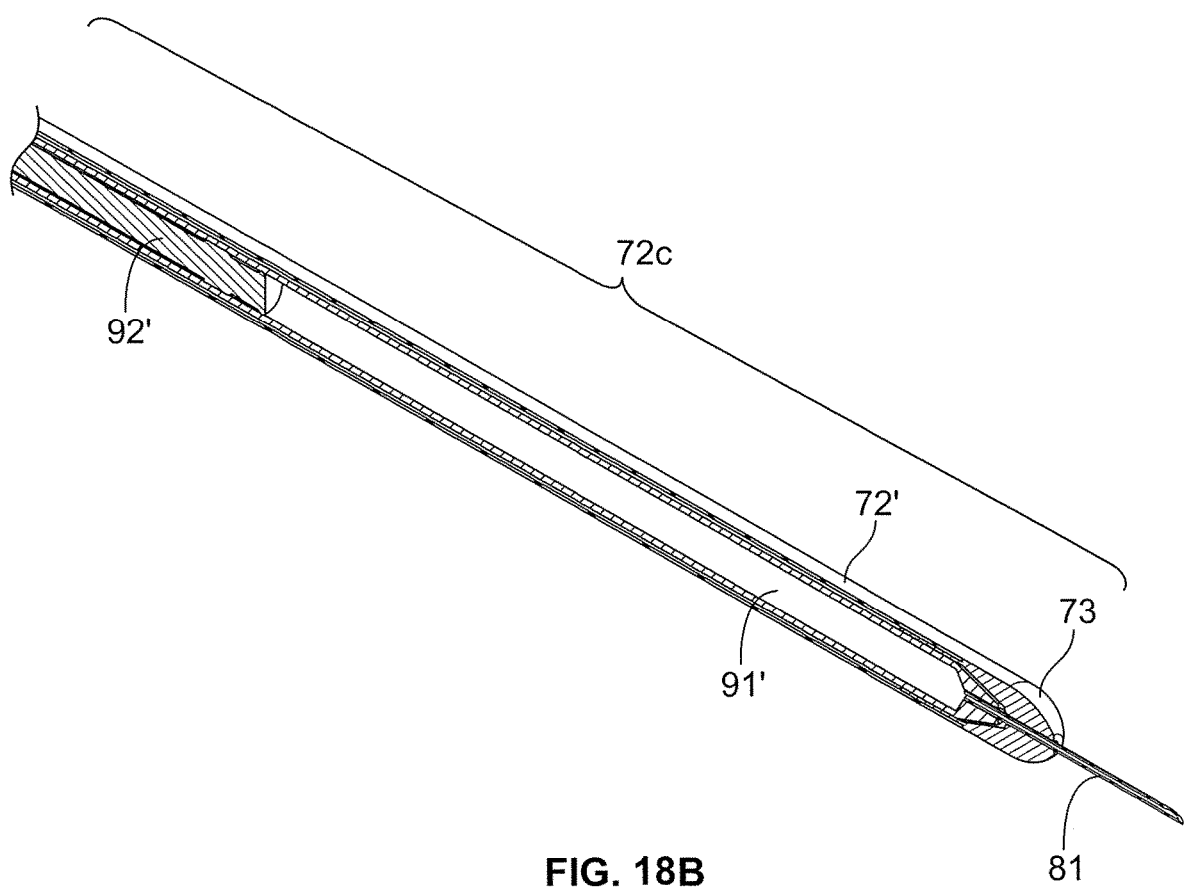

The syringe barrel 91' is positioned on the distal side of the needle sheath controller 71'. As shown in FIG. 10, the syringe barrel 91' is integrated and contained within the distal most lumen end of the needle sheath 72'. Thus, the syringe barrel is enclosed by the needle sheath 72'. As shown in FIGS. 18A and 18B, described in more detail below, the syringe barrel 91' is not directly connected to the lumen 723 of the sheath cavity, but is positioned so that it is immovable in relation to the needle sheath controller 71'. Thus, in this embodiment, the syringe barrel 91' is not removable from the needle sheath 72'.

The needle sheath 72' can be opaque or can be transparent or clear. Generally, the needle sheath 72' is opaque, but contains a visibility window 725 for visualization of the integrated syringe barrel 91'. Since device 60' contains a syringe barrel 91' that is enclosed within the needle sheath 72', and that would not otherwise be visible, the presence of the visibility window 725 permits visualization of the graduated markings on the syringe barrel to aid in drawing up agents or solutions. In addition to permitting visualization of the administered agent or solutions, the presence of the visibility window 725 allows visualization of drawback fluids. For example, since some applications require injection directly into the parenchyma, and not into a vessel or bile duct, the ability to drawback and visualize fluid from the area the needle has penetrated can be used to confirm needle placement into the parenchyma, while avoiding injections into the vasculature or bile ducts. The visibility window 725 can be made of glass or clear plastic such as polycarbonate. The visibility window 725 is integrated directly into the body of the needle sheath 72'. The visibility window can surround the entire circumference of the needle sheath 72' or can partially surround the circumference of needle sheath 72'. The visibility window 725 can be any desired length, and located anywhere along the needle sheath 72' so long as a portion of the syringe barrel 91' is exposed under the visibility window 725. Generally, the visibility window 725 exposes the distal portion of the syringe barrel 91', but can expose the entire syringe barrel 91. The visibility window 725 can be 10 cm to 300 mm, and generally is 20 mm to 100 mm in length.

The plunger 92' is located on the proximal end of the device 60' and passes through the needle sheath controller 71' and the needle sheath 72' where it can engage with and pass into the syringe barrel 91'. The plunger 92' is movable through the needle sheath controller 71', needle sheath 72' and syringe barrel 91' so that it can be pulled and pushed along inside the syringe barrel 91'. The plunger 92' can be drawn back to load the syringe barrel 91' with the fluid, such as a therapeutic, or depressed to inject the fluid, such as a therapeutic, in the target tissue. The plunger 92' also can be pulled back at the site of injection to test needle placement. The plunger is cylindrical to move through the syringe barrel 91', and is made of material that permits ease of movement through the needle sheath controller 71', needle sheath 72' and syringe barrel 91'. Typically, the plunger 92' is made of plastic, for example polypropylene or polyethylene. The plunger contains a head 95 at the proximal end of the device that can be conveniently grasped by the operator to manipulate the plunger. The plunger head 95 also is generally made of plastic. The distal tip of the plunger 92' is generally made of silicone or other natural or synthetic rubber to provide a tight seal within the syringe barrel 91' when traveling within the syringe barrel 91'.

The plunger 92' is long enough in length to permit its association with the inside of the syringe barrel 91' in order to dispel the fluid, such as a therapeutic through the distal end of the syringe and into the needle 81 connected thereto. Since the plunger essentially extends the length of the device, the plunger is generally at least as long as the sheath, and generally longer since it extends outside of the laparoscopic port. For example, the plunger 92' can be 200 mm to 800 mm, such as 300 to 600 mm, and generally at least or about at least or 300 to 400 mm. Pulling back on the plunger 92' draws in the fluid, such as a therapeutic, or air, and pushing the plunger 92' forces the fluid, such as a therapeutic, or air out of the syringe barrel.

The device 60' contains an injection needle 81 that is located inside the needle sheath 72' that can be sheathed and unsheathed at the distal tip of the needle 81. With reference to FIG. 18A, described in more detail below, the distal tip of the needle sheath 73 contains a needle channel 733 that guides the needle outside of the needle sheath 72' when it is unsheathed as shown in FIG. 10. As shown in FIG. 10, the injection needle contains a beveled tip sufficient to penetrate or pierce a tissue or organ.

As discussed further below, because the injection needle 81 is directly attached to the syringe barrel 91' at the distal end of the device, the injection needle is relatively short. This avoids problems in pressure drop that can occur with longer needles. This also means that the dead volume in the device 60', which is the volume of fluid that is loaded into the syringe barrel 91', but cannot be expelled from the device and injected into the tissue, is generally small. Since therapeutics are often costly or limited, an injection device that minimizes amount of dead volume is advantageous. Factors that influence the amount of dead volume include the length of the needle, the diameter of the needle, and the diameter of the syringe barrel. In case of a long needle, the amount of air in the needle often is not tolerable in the patient and the target tissue and/or organ. Hence, the air needs to be removed from the needle and the needle is sometimes "primed." After the injection, the amount of fluid remaining in the fluid path between the tip of the plunger and the tip of the injection needle 81 cannot be expelled completely, and thus results in dead volume. In case of a long needle, the amount of dead volume is thus larger. In device 60', the syringe barrel 91' is located close to the tip of the needle sheath 72', and the dead volume occurs only in the tip of the syringe barrel 91' and the injection needle 81.

FIG. 14 depicts an enlarged cross section view of the needle sheath controller 71' and the plunger 92' extended through the needle sheath controller 71'. The needle sheath controller 71' is positioned on the proximal side of the needle sheath 72'. The needle sheath controller 71' contains components that control movement of the needle sheath 72', connect the proximal and distal end of the device, and is the conduit by which the plunger 92' travels between the proximal and distal ends of the device. The needle sheath controller 71' is configured to be held and manipulated by an operator, such as a surgeon. As discussed above, the needle sheath controller 71' can be any shape and size that is convenient to permit the operator to hold and manipulate the device, and typically is cylindrical in shape. The diameter of the needle sheath controller 71' is such that it can be held in the palm of an average adult, and is generally 20 mm to 100 mm in diameter with a length of 50 mm to 225 mm. The needle sheath controller optionally can contain an outside grip for handling.

As shown in FIG. 10 and FIG. 14, the needle sheath controller 71' includes a controller housing 710 that encloses components internal to the needle sheath controller 71', and the proximal end of the needle sheath 72'. As discussed above, the needle sheath controller housing 710 can be made of any suitably resilient and rigid material, such as any polymeric material, including plastics, or rubber, metals, ceramics, composites, or other suitable material known to one of skill in the art. The controller housing 710 is typically made of polypropylene, polystyrene, polyethylene, polyvinyl chloride, polyurethane, silicone, rubber or acrylic. As discussed above, the housing 710 can be made by any manufacturing known to a skilled artisan, and can be made as one singular piece or can be made of two or more pieces that are attached together, such as with adhesive, locking joints or fasteners.

As shown in FIG. 10 and FIG. 14, the needle sheath controller 71' contains an externally accessible positioner 711. As described above, the positioner 711 is configured in the needle sheath controller 71' so that it is movable both forward and rearward relative to the needle sheath controller 71'. As described above, the positioner 711 is engaged with the needle sheath 72' through a connection member 713, and can be used to slide the needle sheath 72'. This connection permits movement of the positioner 711 between the forward or rearward positions to control movement of the needle sheath between two fixed or locked positions, the sheathed and unsheathed positions. The sheathed position protects or hides the injection needle, while the unsheathed position exposes the needle.

With reference to FIG. 14, the connection member 713 is connected to the proximal end of the needle sheath 72', and the lower part of the positioner 711. The connection of the connection member 713 with the proximal end of the needle sheath is such that the needle sheath 72' is longitudinally movable relative to the controller housing 710 and the injection needle 81. For example, the distal end of the outside of the connection member 713 is engaged with the proximal inside cavity of the needle sheath 72' around its circumference. The connections of the control member with the positioner 711 and needle sheath 72' can be by welding, adhesive, locking joints, fasteners or other suitable means.

As described above generally, the connection member 713 moves inside a hollow cavity or lumen 717 contained inside the housing 710 of the needle sheath controller 71' that is closed at both ends relative to the housing 710. The controller lumen 717 accommodates the connection member 713 such that the connection member 713 can easily glide or move forward or rearward in a restricted manner. For example, the connection member 713 can be cylindrical and fit inside a cylindrical hollow lumen cavity 717. As shown in FIG. 14, and discussed further below, the connection member 713 contains an internal hollow cavity sized to fit the plunger 92' that passes through.

Movement of the connection member 713 is controlled by the positioner 711. As shown in FIGS. 10 and 14, the positioner 711 contains a projected top portion or head that juts out of the needle sheath controller 71' where it can be moved forward or rearward by the operator. As shown in FIG. 14, internal to the needle sheath controller 71', the body of the positioner 711 is notched on its sides or is otherwise configured to engage with sheath stops 715 or 716. Sheath stops 715 and 716 are grooves in the needle sheath controller housing 710 that fit the notched body of the positioner and trap the positioner 711 so that it cannot be moved.

As exemplified in FIG. 13 with the exemplary device 60, device 60' also contains an optional lock and release element 712 configured in the positioner 711 to facilitate lock and release of the positioner with the grooves of the sheath stop 715 or 716. For example, the lock and release element 712 can be a spring or other resilient means. The mechanism controlling lock and release of the positioner 711 with the grooves of the sheath stop 715 or 716 by the lock and release element 712 is as described above, whereby downward, vertical or lateral forces release or lock the positioner 711 from the sheath stops 715 or 716. Pushing downward on the positioner 711 permits the positioner to slide and to fit it into either of sheath stops 715 or 716.

Movement of the positioner 711 between the sheath stops 715 and 716 moves the connection member 713, and thereby also moves the needle sheath 72' so that it can transition from the sheathed and unsheathed positions by control of the positioner by the operator. When the positioner is in the rearward position 711c as exemplified in FIG. 14, distal sheath stop 715 is free and the positioner 711 is fit into the proximal sheath stop 716, thereby unsheathing the injection needle so that it is exposed. While not shown in FIG. 14, the positioner 711 also can be in the forward position 711a as exemplified in FIG. 13, where the proximal sheath stop 716 is free and the positioner 711 is fit into the distal sheath stop 715, thereby sheathing the injection needle so that it is protected. As a further position, the positioner 711 also can be in an intermediate position 711b as exemplified in FIG. 15, where both the distal sheath stop 715 and the proximal sheath stop 716 are free and not engaged with the positioner 711.

As shown in FIG. 14, the plunger 92' passes through the inside lumen 717 of the needle sheath controller 71' and passes through a central cavity of the connection member 713, but is not directly attached to the needle sheath controller 71' or connection member 713. Hence, the connection member 713 can move independently around the plunger 92', and the plunger 92' can move independently through the connection member 713. As discussed above, because the needle sheath 72' is directly connected to the connection member 713 contained in the controller lumen 717, the plunger 92' enters the inside cavity of the needle sheath 72' inside the needle sheath controller 71'. The plunger 92' exists the distal end of the needle sheath controller 71' where it is contained within the lumen 723 of the needle sheath 72'.

With reference to FIGS. 18A and 18B, the plunger 92' runs distally and longitudinally through the needle sheath 72' where it engages with the proximal end of the syringe barrel 91'. The injection needle 81 is directly connected to the inside of the syringe barrel 91' at the distal end of the syringe barrel 91'. The injection needle 81 contains a beveled tip sufficient to penetrate or pierce a tissue or organ. The injection needle 81 is typically made of metal or alloy, such as surgical stainless steel or other medical grade metal. The size and diameter of the injection needle 81 is selected based on parameters generally describe above. As described above, typically a small diameter needle 81 is employed to reduce the force required to insert the needle into the target tissue or organ, and to reduce trauma to the target tissue or organ. For example, the injection needle 81 is between 25 and 34 gauge, such as a 25 gauge, 26 gauge, 27 gauge, 28 gauge, 29 gauge, 30 gauge or 31 gauge needle, and typically is 27 gauge.

At the distal end of the device 60', the needle sheath 72' ends in a distal tip 73 that contains a needle channel 733. The needle channel 733 is sufficiently sized to fit the injection needle 81 so the injection needle can extend and retract through the needle channel 733 as the needle sheath 72' moves. In FIG. 18A, the injection needle 81 is covered by the needle sheath 72' and does not traverse through needle channel 733. With reference to FIG. 12A, the device 60' in FIG. 18A is in the sheathed position 72a. In FIG. 18B, the injection needle 81 is extended out of the needle sheath 72' and does traverse through needle channel 733. With reference to FIG. 12C, the device 60' in FIG. 18B is in the unsheathed position 72c.

As shown in FIGS. 18A and 18B, because the syringe barrel 91' is not connected to the needle sheath 72', the needle sheath 72' moves independently around the syringe 91'. In the unsheathed position, the needle sheath 72' is pulled back, but the syringe barrel 91' and injection needle 81 are fixed and do not move. For example, as shown in FIG. 18B, because the needle sheath 72' is pulled back, the size of the sheath lumen 723 is shortened compared to FIG. 18A when the needle sheath 72' is not pulled back. In the unsheathed position shown in FIG. 18B, the distal end of the syringe barrel 91' touches the distal tip of the sheath 73. A notch can be configured in the distal tip 73 in order to accommodate the syringe barrel 91' as it is positioned in the unsheathed position 72c. This demonstrates that movement of the sheath, as described with reference to FIG. 14 above using the positioner 711, only controls the movement of the needle sheath 72', while the position of the syringe barrel 91' and injection needle 81 of the device are stationary regardless of the position of the positioner 711.

As described above, in the unsheathed position, the extent by which the injection needle 81 is extended or exposed out of the device 60' is a function of the distance between the sheath stops 715 and 716 as shown in FIG. 14. This distance is a function of the particular application of the device, the particular target tissue, the subject being treated and other considerations. For example, unsheathed needle that is exposed should not be so long that it can easily penetrate through to the other side of a target tissue. Generally, with reference to most target tissues (e.g. liver), the portion of the injection needle 81 shown in FIG. 18B that can be unsheathed or exposed is generally less than 1 cm, such as 2 mm to 10 mm, and generally no more than 5 mm. For a child, the length can be smaller, and is generally less than 4 mm. For applications in utero, the length can be 2 mm to 3 mm. Generally, the total length of the injection needle 81 in device 60' is slightly longer than the unsheathed needle tip that extends out of the device. As shown in FIG. 18B, the extent of the extra length is sufficient to account for the distance of the distal sheath tip 73 and the extent to which the proximal end of the needle is connected to syringe barrel 91'. For example, the total length of the injection needle 81 can range from 5 mm to 40 mm, such as 10 mm to 40 mm, such as a 12.7 mm, 25.4 mm or 38.1 mm needle.

Figure 18C:
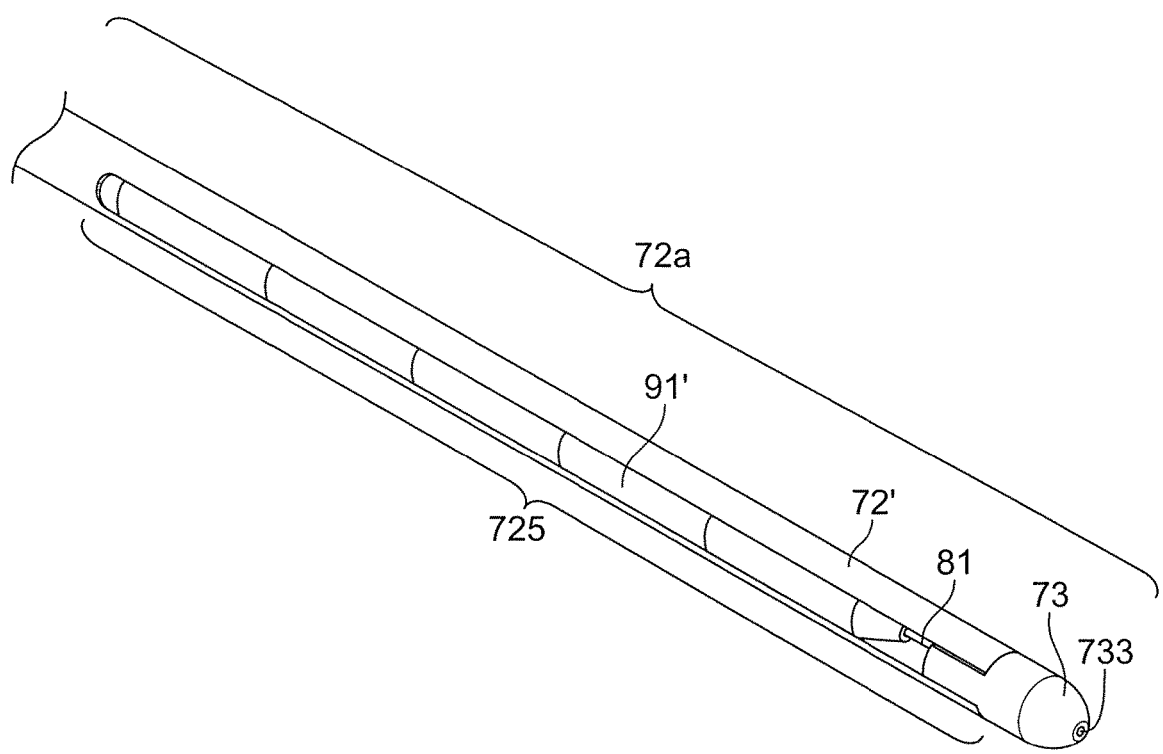
Figure 18D:
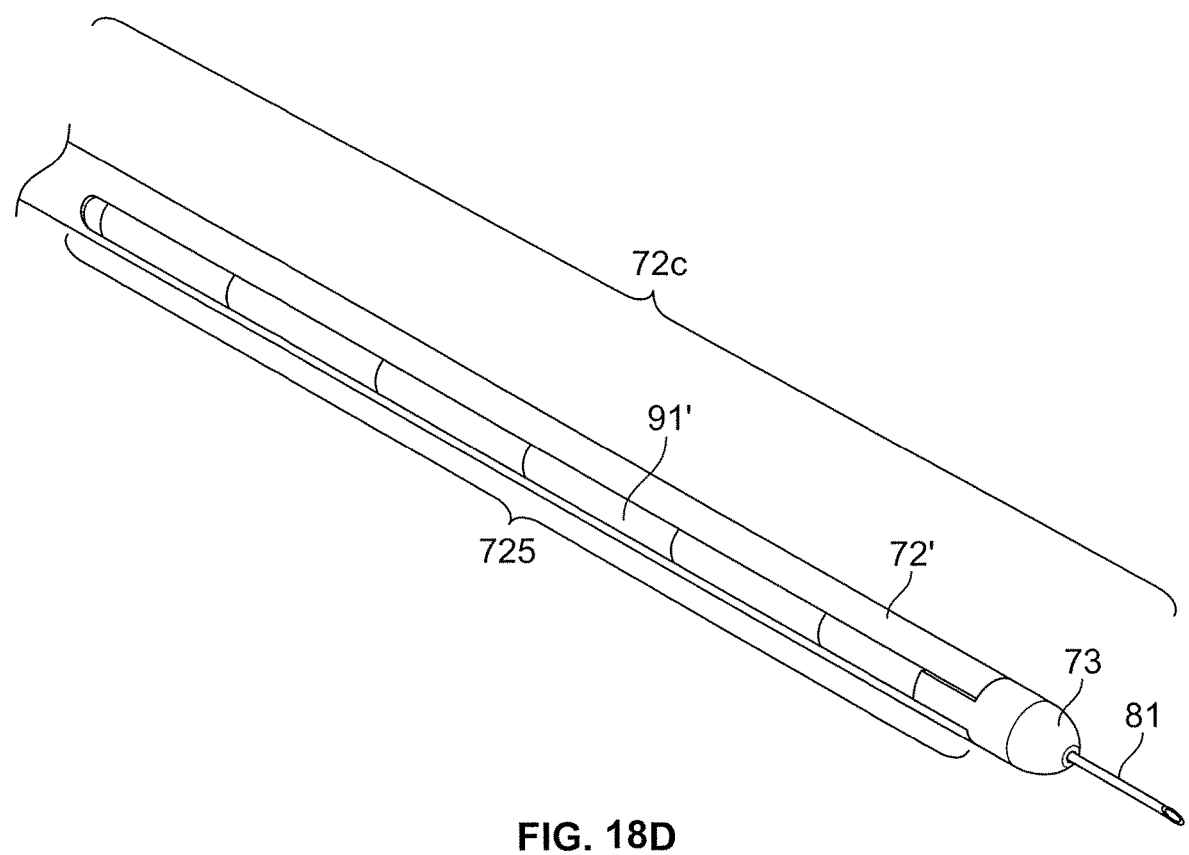

FIG. 18C provides a corresponding perspective view of the needle sheath shown in FIG. 18A in the sheathed position 72a. FIG. 18D provides a corresponding perspective view of the needle sheath shown in FIG. 18B in the unsheathed position 72c. In FIGS. 18A and D, the needle sheath 72' is opaque, but contains a visibility window 725 in order to view the syringe barrel 91' and injection needle 81 whether sheathed or unsheathed.

The device 60' can be disposable or reusable. For example, the device 60' can be withdrawn from the laparoscopic port and disposed of, or reloaded and reused. The device 60' also can be a sterile device. For example, the device 60' can be loaded through the injection needle 81 in a sterile environment, such as a sterile operating room. The device 60' can be pre-loaded with the fluid, such as a therapeutic, and provided as a sterile pre-loaded syringe. Furthermore, distribution of sterile disposable pre-loaded devices is easily achieved using this device 60' due to the complete integration of the syringe barrel into the needle shaft, thereby minimizing contamination that can occur when the syringe barrel and device must be packaged or stored separately. Alternatively, the injection needle 81 can be inserted into a container with the fluid, such as a therapeutic, composition, and the plunger 92' can be pulled back to load the fluid, such as a therapeutic, in the syringe barrel 91'.

With reference to the above Figures and description, exemplary of the mode of operation of the injection device 60' involves first loading the device 60' with a fluid, such as a therapeutic. With the needle sheath 72' in the unsheathed position 72c, the injection needle 81 can be inserted into a vial or a container of fluid, such as a therapeutic, and the integrated syringe plunger 92' can be pulled back to load the syringe with the fluid, such as a therapeutic. Optionally, a vial adaptor can be used when loading the syringe with the therapeutic compound, such that the long device can be stabilized over a vial or container of fluid, such as a therapeutic, loading the syringe barrel 92'. Once the syringe is loaded, the needle sheath 72' can be positioned in the sheathed position 72a, and the device can be inserted into a laparoscopic port to place the device near the site of injection. At the site of injection (target tissue), the needle sheath 72' can be unsheathed 72c, and the injection needle 81 can be exposed for injection. If necessary, the integrated syringe plunger 92' can be pulled back to draw fluids from the site of injection, to test the placement of the injection needle 81 at the injection site. The syringe visibility window 725 can be used to visualize the drawback and the movement of the plunger 92'. Once the site of needle placement is determined, the plunger 92' can be depressed, to inject the fluid, such as a therapeutic, at the target tissue. After injection, the needle sheath 72' can be positioned in the sheathed position 72a, to protect the non-target organs and prevent accidental needle puncture, prior to removing the laparoscopic device from the injection site and through the laparoscopic port.

3. Dockable Injection Device

FIGS. 11, 15 and 19A-D depict the injection device 60" and components and features thereof. The injection device as shown in FIG. 11 includes needle sheath 72", needle sheath controller 71', plunger 92" and a dockable syringe 910 containing injection needle 81, syringe barrel 91", and associated auxiliary plunger 920. The needle sheath 72" of the injection device is of a sufficient length to permit laparoscopic access to the target of interest, and is generally a length of 200 mm to 600 mm, such as 250 to 400 mm, and generally at least or about at least or 300 mm. The device is generally cylindrical around the longitudinal axis, generally having a smaller diameter in the needle sheath region 72" and the plunger region 92" and a larger diameter in the needle controller region 71'. The needle sheath 72" of the device is typically inserted through the port (e.g. laparoscopic port). The diameter of the needle sheath 72" is typically between 3 mm to 12 mm in size, and typically from 5 mm to 10 mm. It is understood that portions of the device external to the laparoscopic port can have a diameter greater than 10 mm. For example, the needle sheath controller body 71' can have a diameter sufficiently large, so long as it can be easily gripped or handled by the operator. The needle sheath controller body 71' is held by the operator, typically a surgeon, to manipulate and position the device 60", control the needle sheath 72" and support the device while manipulating the plunger 92".

Injection device 60" is adapted so that a dockable syringe 910 containing injection needle 81, syringe barrel 91" and associated auxiliary plunger 920 can be temporarily docked therewith. As shown in FIG. 11, the syringe barrel 91" is cylindrical in shape with a hollow center that can fit auxiliary plunger 920 so that the plunger can move back and forth inside the syringe barrel. The auxiliary plunger 920 is located on the proximal side of the syringe barrel 91" and is movable so that it can be pulled and pushed along inside of the syringe barrel 91". The auxiliary plunger 920 can be drawn back to load the syringe barrel 91" with the fluid, such as a therapeutic, or depressed to dispel or inject the fluid in the target tissue. The auxiliary plunger 920 can also be pulled back at the site of injection to test needle placement. As discussed below, movement of the auxiliary plunger 920 when docked in the device is controlled by the plunger 92". The auxiliary plunger 920 is cylindrical to move through the syringe barrel 91", and is made of material that permits ease of movement through the syringe barrel, such as a plastic, for example, polypropylene or polyethylene.

The auxiliary plunger 920 contains a plunger head 95 at the proximal end of the plunger that can be conveniently grasped by the operator to manipulate the plunger, or otherwise configured to control movement of auxiliary plunger 920. For example, the auxiliary plunger 920 can be independently moved and controlled, for example, when the dockable syringe 910 is in the undocked position (discussed further below). In other instances, when the dockable syringe 910 is docked in device 60", movement of the auxiliary plunger 920 is controlled by plunger 92" at the proximal end of device 60" through a plunger adaptor 951 (discussed further below). The plunger head 95 also is generally made of plastic. The distal tip of the auxiliary plunger 920 is generally made of silicone or other natural or synthetic rubber to provide a tight seal within the syringe barrel 91" when traveling within the syringe barrel 91".

The auxiliary plunger 920 is long enough in length to permit its association with the inside of syringe barrel 91" in order to dispel the fluid, such as a therapeutic, through the distal end of the syringe barrel 91" and into injection needle 81 connected thereto. For example, the auxiliary plunger 920 can have a length between 50 mm and 100 mm, typically 70 mm to 90 mm. Pulling back on the auxiliary plunger 920 draws in the fluid or air, and pushing the auxiliary plunger 920 forces the fluid or air out of the syringe barrel.

The syringe barrel 91" is generally clear and transparent. The syringe barrel 91" can be made out of plastic or glass or other suitable material, and in particular is made out of plastic such as polypropylene, polyethylene, polycarbonate or other clear material. As described above, the syringe barrel 91" can contain calibrations or marking on the outer surface to indicate the volume of the agent within the barrel. As described above, the syringe barrel 91" can have a volume capacity that is from the range of 0.5 mL to 20 mL (i.e. 0.5 cc to 20 cc), and generally is 0.5 mL to 3 mL (i.e. 0.5 cc to 3 cc), such as at least or about a 1 mL (i.e. 1 cc) syringe. Typically, 200 µL to 600 µL of the fluid, such as a therapeutic, is delivered to the target locus, and the volume of syringe barrel is 1 mL.

The dockable syringe 910 of device 60" contains an injection needle 81 that is located on the distal end of the syringe barrel 91", and hence the distal end of the device 60" when the dockable syringe 910 is docked into device 60" (discussed further below). The injection needle 81 can be connected directly or indirectly to syringe barrel 91". For example, the injection needle 81 can be directly affixed, such as by an adhesive, bonding or molding, to the inside of syringe barrel 91" at the distal end of syringe barrel 91". In other examples, the distal end of syringe barrel 91" can contain a Luer fit or other adaptor that is compatible with a hub on the proximal end of injection needle 81.

As shown FIG. 11, the injection needle contains a beveled tip sufficient to penetrate or pierce a tissue or organ. The injection needle 81 is typically made of metal or alloy, such as surgical stainless steel or other medical grade metal. The size and diameter of the injection needle 81 is selected based on parameters generally describe above. As described above, typically a small diameter needle 81 is employed to reduce the force required to insert the needle into the target tissue or organ, and to reduce trauma to the target tissue or organ. For example, the injection needle 81 is between 25 and 34 gauge, such as a 25 gauge, 26 gauge, 27 gauge, 28 gauge, 29 gauge, 30 gauge or 31 gauge needle, and typically is 27 gauge.

Because the injection needle 81 is directly attached to the syringe barrel 91", the injection needle is relatively short. This avoids problems in pressure drop that can occur with longer needles. Similar to device 60' discussed above, this also means that there is generally a small dead volume created by device 60". For example, the total length of the injection needle 81 can range from 5 mm to 40 mm, such as 10 mm to 40 mm, such as a 12.7 mm, 25.4 mm or 38.1 mm needle. Generally, the use of shorter needle is desired in order to avoid problems related to dead volume and pressure drops.

Figure 19A:
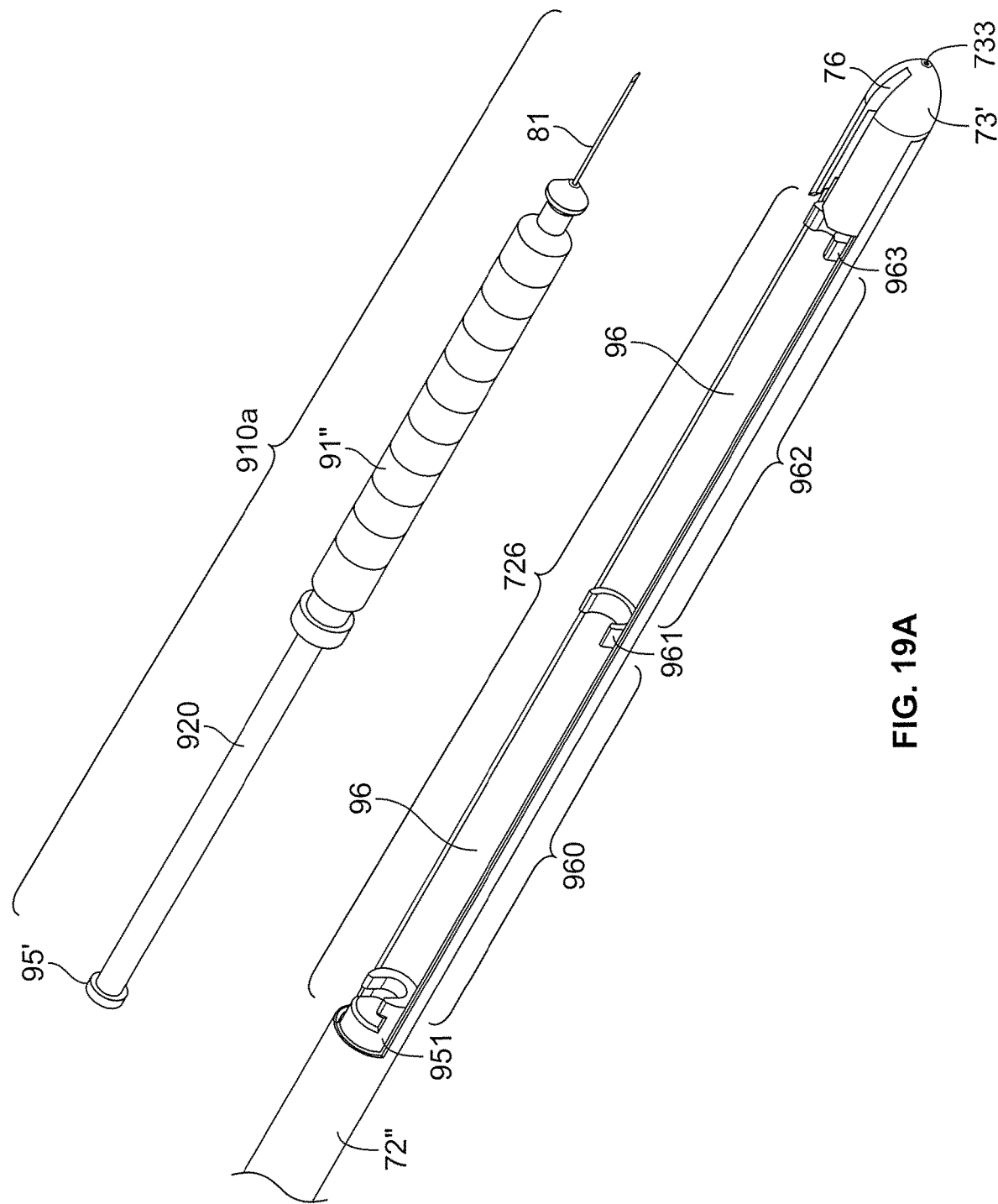
FIGS. 19A-19D illustrate enlarged views of the device shown in FIG. 11.

The needle sheath 72" can be opaque or can be transparent or clear. The needle sheath 72" is generally solid at the proximal portion of the needle sheath 720, but contains an open cavity 726 at its distal portion. The dockable syringe 910 containing auxiliary plunger 920, syringe barrel 91" and injection needle 81 is configured so that it can be docked and undocked in the open cavity of the sheath, and in a manner in which the needle sheath 72" is movable around the dockable syringe 910. As shown in FIG. 11 and FIG. 19A, the open cavity 726 is a cut out in the top half of the needle sheath 72". The inner side of the open cavity 726 of the sheath can be lined with a syringe adaptor lining 96 in a manner so that the sheath moves independently from the syringe adaptor lining 96. The syringe adaptor lining 96 also has an open cavity of substantially similar size.

Figure 19B:
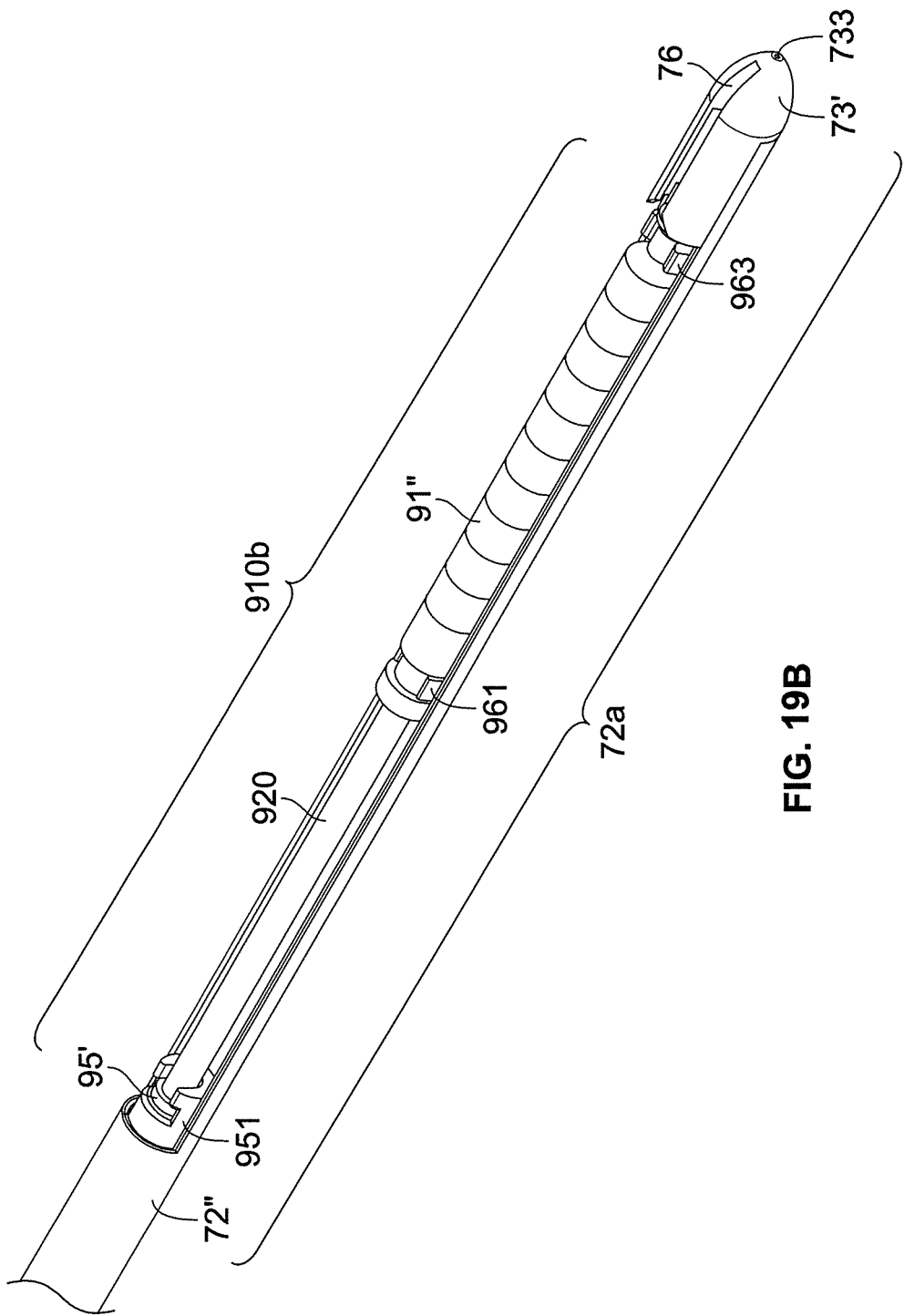

For example, as shown in FIGS. 19A and 19B, a syringe adaptor lining 96 can run through the sheath, such that the sheath moves independently around the syringe adaptor lining 96. The syringe adaptor lining 96 can be connected or fixed at its proximal end to the needle sheath controller 71' and have an open cavity at its distal end to form a nest for the dockable syringe. For example, the syringe adaptor lining 96 can be a hypodermic tubing that has a distal section removed to form a nest for the dockable syringe. The tubing can have a diameter smaller than the inside portion of the needle sheath 72" so that the tubing can run into and through the sheath where it can be connected to the needle sheath controller 71' in a fixed position.

The open cavity of the syringe adaptor lining 96 can contain a plunger rest cavity 960, a barrel rest cavity 962, and two barrel docks 961 and 963. The barrel rest cavity 962 is flanked by two barrel docks 961 and 963, which are clasps or fitting that are adapted to seat or secure the syringe barrel 91" at its proximal and distal end, respectively. The size of the barrel rest cavity 962 and the distance between the two barrel docks 961 and 963 permit engagement with the syringe barrel 91". If the syringe barrel 91" contains grooves to fit into the barrel docks 961 and 963, the length between the two barrel docks 961 and 963 is the same as the length between the corresponding grooves in the syringe barrel 91". The portion of the syringe barrel 91" that can dock with barrel docks 961 and 963 can be restricted by configuring syringe barrel 91" with narrow grooves at its proximal and distal ends that fit dock 961 and 963, respectively. This ensures that the syringe barrel 91", when fitted in the open cavity 726, is properly lined up for sheathing and unsheathing injection needle 81. The barrel docks 961 and 963 can be similarly sized, or can be different sizes depending on the particular size and configuration of syringe barrel 91". The barrel docks 961 or 963 can be rigid or flexible, and can be made out of metal or polymeric materials such as plastics. The barrel docks 961 and 963 can be features extruding from the syringe adaptor lining 96, or can be separate parts that are attached to the exposed part of the syringe adaptor lining 96. The barrel rest cavity 962 and the docks 961 and 963 are not directly connected to the needle sheath so that the needle sheath 72" moves around and independently from the syringe adaptor lining 96, including the barrel rest cavity and docks.

A plunger adaptor 951 that is part of the distal end of plunger 92" is located at the proximal end of the cavity 726. The plunger adaptor 951 rests inside open cavity of the syringe adaptor lining 96 when the plunger 92" is pulled back in an extended position. As discussed below, the plunger 92" is movable within the lumen of the syringe adaptor lining 96 in order to control movement of auxiliary plunger 920. The distance between barrel dock 961 and plunger adaptor 951 when the plunger 92" is in its extended position (i.e. pulled out to maximum length outside of syringe barrel) creates a plunger rest cavity 960 within the syringe adaptor lining 96 sufficiently sized to fit the auxiliary plunger 920 in its extended position.

Hence, the length of the open cavity 726 of the needle sheath 72" and the open cavity of the syringe adaptor lining 96 is sufficient to fit dockable syringe 910. In some instances, the cavity can span the entire length of the needle sheath 72", except for the distal tip of the needle sheath 73' discussed below. Typically, the open cavity 726 is 50 mm to 250 mm in length. Accordingly, the open cavity of the syringe adaptor lining 96, which has a substantially similar length to the open cavity 726 of the needle sheath, is 50 mm to 250 mm in length. The length of the open cavities also depends on the diameter of the needle sheath 72", the volume, length and diameter of the dockable syringe 910. If a larger volume of syringe barrel 91" is needed for a specific injection, the length of the syringe barrel 91" and the open cavities can be made larger. However, the stroke length of the auxiliary plunger 920 is limited to less than half of the entire length of the needle sheath 72", as both the fully extended auxiliary plunger 920 and the syringe barrel 91" must fit in the length of the needle sheath 72" and the open cavities. The stroke length of the plunger 92" is also limited to the maximum stroke length of the auxiliary plunger 920. Hence, if a larger volume of syringe barrel 91" is needed, the diameter of the needle sheath 72" can be larger. The optimal length and diameter of the syringe barrel 91" in relation to the stroke length and the length of the needle sheath 72", including the length of the proximal portion of the needle sheath 720, can be empirically determined based on the diameter of the laparoscopic ports, type of surgery, and the volume of syringe barrel required.

The open cavities terminate at the distal tip of the needle sheath 73'. The distal tip of the needle sheath 73' is solid, except that it contains an open needle groover 76 on its top side. The needle groover 76 is a narrow opening sufficient for injection needle 81 to drop into the distal tip of needle sheath 73' where it can line up with needle channel 733 to guide the injection needle 81 outside when unsheathed. The length and diameter of the groover 76 is sufficient to fit injection needle 81. For example, the needle groover 76 is 5 mm to 40 mm long, such as 10 mm to 40 mm. The width of the needle groove is 0.2 to 2 mm, such as 0.3 to 1 mm.

FIGS. 19A and 19B depict the dockable and undocked configurations of dockable syringe 910 with the syringe adaptor lining 96 and the needle sheath 72". For example, FIG. 19A shows the dockable syringe 910 in the undocked position 910a. As shown in FIG. 19A, a syringe adaptor lining 96 is inside the needle sheath 72". An open cavity of the syringe adaptor lining 96 configured into the open cavity 726 of the needle sheath 72" is configured to fit the dockable syringe 910 as described above. FIG. 19B shows the dockable syringe 910 in the docked position 910b. In the docked position 910b, the dockable syringe 910 is positioned on the distal side of the needle sheath controller 71'. When in the docked position 910b, the injection needle 81 is located inside the needle sheath 72" and can be sheathed and unsheathed at the distal tip of the needle 81 as discussed below.

The ability to dock into the syringe dock accessible by the open cavity 726 of the needle sheath 72" and the open cavity of the syringe adaptor lining 96 permits visualization of the syringe barrel in device 60" so that the administered agent or drawback fluids can be visualized. For example, as discussed above, since some applications require injection directly into the parenchyma, and not into a vessel or bile duct, the ability to drawback and visualize fluid from the area the needle has penetrated can be used to confirm needle placement into the parenchyma, while avoiding injections into the vasculature or bile ducts.

In addition, the ability to remove or dock the syringe 910 in injection device 60" also provides advantages, including the ease of loading the syringe barrel, exchange of loaded syringe, and sterility of syringe. For example, a sterile syringe barrel 91" can conveniently be used when drawing up or loading the syringe with a fluid, such as a therapeutic, compositions or other solutions into the syringe barrel. If desired, a separately sterile needle 81 can be fitted to the syringe barrel 91", such as by a Luer fit adaptor, to permit loading of the syringe barrel 91" with a fluid, such as a therapeutic. Syringe barrel 91" also can be separately loaded prior to use of device 60", or a pre-loaded syringe barrel 91" can used. Also, a variety of syringe types and sizes can be used so long as they are dockable with the device 60". In some cases, several different types of syringes can be used for one patient, if necessary. In cases where the syringe must be re-loaded or additional fluid, such as a therapeutic, is needed, new or re-loaded syringes can be docked.

As shown in FIG. 11, plunger 92" is located on the proximal end of the device 60" where it can be controlled and operated by the operator outside of the laparoscopic port. Plunger 92" passes through the needle sheath controller 71' and the proximal portion of the needle sheath 72". The plunger 92" is generally cylindrical and movable within needle sheath controller 71' and needle sheath 72". The plunger 92" is made of material that permits ease of movement through the needle sheath controller 71' and needle sheath 72". Typically, the plunger 92" is made of plastic, for example polypropylene or polyethylene. The distal end of the plunger 92" contains a plunger adaptor 951 that is exposed through open cavity 726 in the needle sheath 72" where it associates with auxiliary plunger 920. The plunger 92" is long enough in length to permits its association with auxiliary plunger 920 in needle sheath 72" when auxiliary plunger 920 is docked in cavity 726. For example, the length of plunger 92" can range from 50 mm to 500 mm, such as 100 mm to 400 mm or 100 mm to 200 mm. Plunger 92" is generally longer than auxiliary plunger 920.

The plunger adaptor 951 contains a groove or notch to connect with auxiliary plunger 920 through plunger head 95' of auxiliary plunger 920. The plunger adaptor 951 is of a sufficient size and shape so that plunger head 95' of auxiliary plunger 920 can be seated or secured in the plunger rest cavity 960. As shown in FIG. 19B, when plunger head 95' of auxiliary plunger 920 is fitted or secured in plunger adaptor 951, the auxiliary plunger 920 and the plunger 92" are connected, such that movement of the plunger 92" controls movement of auxiliary plunger 920. The plunger 92" also contains a plunger head 95 at the proximal end of the device that can be conveniently grasped by the operator to manipulate plunger 92", and thus also auxiliary plunger 920. For example, pushing the plunger 92" also pushes the auxiliary plunger 920 and forces the fluid or air out of the syringe barrel 91".

FIG. 15 depicts an enlarged cross section view of the needle sheath controller 71' and the plunger 92" extended through the needle sheath controller 71'. The needle sheath controller 71' is positioned on the proximal side of the needle sheath 72". The needle sheath controller 71' contains the components that control movement of the needle sheath 72", connect the proximal and distal end of the device, and is the conduit by which the plunger 92" travels between the proximal and distal ends of the device. The needle sheath controller 71' is configured to be held and manipulated by an operator, such as a surgeon. As discussed above, the needle sheath controller 71' can be any shape and size that is convenient to permit the operator to hold and manipulate the device, and typically is cylindrical in shape. The diameter of the needle sheath controller 71' is such that it can be held in the palm of an average adult, and is generally 20 mm to 100 mm in diameter with a length of 50 mm to 225 mm. The needle sheath controller optionally can contain an outside grip for handling.

As shown in FIG. 11 and FIG. 15, the needle sheath controller 71' includes a controller housing 710 that encloses components internal to the needle sheath controller 71', and the proximal end of the needle sheath 72". As discussed above, the needle sheath controller housing 710 can be made of any suitably resilient and rigid material, such as any polymeric material, including plastics, or rubber, metals, ceramics, composites, or other suitable material known to one of skill in the art. The controller housing 710 is typically made of polypropylene, polystyrene, polyethylene, polyvinyl chloride, polyurethane, silicone, rubber or acrylic. As discussed above, the housing 710 can be made by any manufacturing known to a skilled artisan, and can be made as one singular piece or can be made of two or more pieces that are attached together, such as with adhesive, locking joints or fasteners.

As shown in FIG. 11 and FIG. 15, the needle sheath controller 71' contains an externally accessible positioner 711. As described above, the positioner 711 is configured in the needle sheath controller 71' so that it is movable both forward and rearward relative to the needle sheath controller 71'. As described above, the positioner 711 is engaged with the needle sheath 72" through a connection member 713, and can be used to slide the needle sheath 72". This connection permits movement of the positioner 711 between the forward or rearward positions to control movement of the needle sheath 72" between two fixed or locked positions, the sheathed and unsheathed positions. The sheathed position protects or hides the injection needle, while the unsheathed position exposes the needle.

With reference to FIG. 15, the connection member 713 is connected to the proximal end of the needle sheath 72", and the lower part of the positioner 711. The connection of the connection member 713 with the proximal end of the needle sheath is such that the needle sheath 72" is longitudinally movable relative to the controller housing 710 and the injection needle 81. For example, the distal end of the outside of the connection member 713 is engaged with the proximal inside lumen 723 of the needle sheath 72" around its circumference. The connections of the control member with the positioner 711 and needle sheath 72" can be by welding, adhesive, locking joints, fasteners or other suitable means.

As described above generally, the connection member 713 moves inside a hollow cavity or lumen 717 contained inside the housing 710 of the needle sheath controller 71' that is closed at both ends relative to the housing 710. The controller lumen 717 accommodates the connection member 713 such that the connection member 713 can easily glide or move forward or rearward in a restricted manner. For example, the connection member 713 can be cylindrical and fit inside a cylindrical hollow lumen cavity 717. As shown in FIG. 15, and discussed further below, the connection member 713 contains an internal hollow cavity sized to fit the plunger 92" that passes through.

Movement of the connection member 713 is controlled by the positioner 711. As shown in FIGS. 11 and 15, the positioner 711 contains a projected top portion or head that juts out of the needle sheath controller 71' where it can be moved forward or rearward by the operator. As shown in FIG. 15, internal to the needle sheath controller 71', the body of the positioner 711 is notched on its sides or is otherwise configured to engage with sheath stops 715 or 716. Sheath stops 715 and 716 are grooves in the needle sheath controller housing 710 that fit the notched body of the positioner and trap the positioner 711 so that it cannot be moved.

As exemplified in FIG. 13 with the exemplary device 60, device 60" also contains an optional lock and release element 712 configured in the positioner 711 to facilitate lock and release of the positioner with the grooves of the sheath stops 715 or 716. For example, the lock and release element 712 can be a spring or other resilient means. The mechanism controlling lock and release of the positioner 711 with the grooves of the sheath stops 715 or 716 by the lock and release element 712 is as described above, whereby downward, vertical or lateral forces release or lock the positioner 711 from the sheath stops 715 or 716. Pushing downward on the positioner 711 permits the positioner to slide and to fit it into either of sheath stops 715 or 716.

Movement of the positioner 711 between the sheath stops 715 and 716 moves the connection member 713, and thereby also moves the needle sheath 72" so that it can transition from the sheathed and unsheathed positions by control of the positioner by the operator. When the positioner is in the intermediate position as exemplified in FIG. 15, both distal sheath stop 715 and the proximal sheath stop 716 are free and not engaged with the positioner 711. While not shown in FIG. 15, the positioner 711 also can be in the forward position 711*a* as exemplified in FIG. 13, where the proximal sheath stop 716 is free and the positioner 711 is fit into the distal sheath stop 715, thereby sheathing the injection needle so that it is protected. As a further position, while not shown in FIG. 15, the positioner also can be in the rearward position 711*c* as shown in FIG. 14, where distal sheath stop 715 is free and the positioner 711 is fit into the proximal sheath stop 716, thereby unsheathing the injection needle so that it is exposed.

As shown in FIG. 15, the plunger 92" passes through the inside lumen 717 of the needle sheath controller 71' and passes through a central cavity of the connection member 713, but is not directly attached to the needle sheath controller 71' or connection member 713. Hence, the connection member 713 can move independently around the plunger 92", and the plunger 92" can move independently through the connection member 713. As discussed above, because the needle sheath 72" is directly connected to the connection member 713 contained in the controller lumen 717, the plunger 92" enters the inside cavity of the needle sheath 72" inside the needle sheath controller 71'. The plunger 92" exits the distal end of the needle sheath controller 71' where it is contained within the hollow cavity of the needle sheath 72".

Figure 19C:
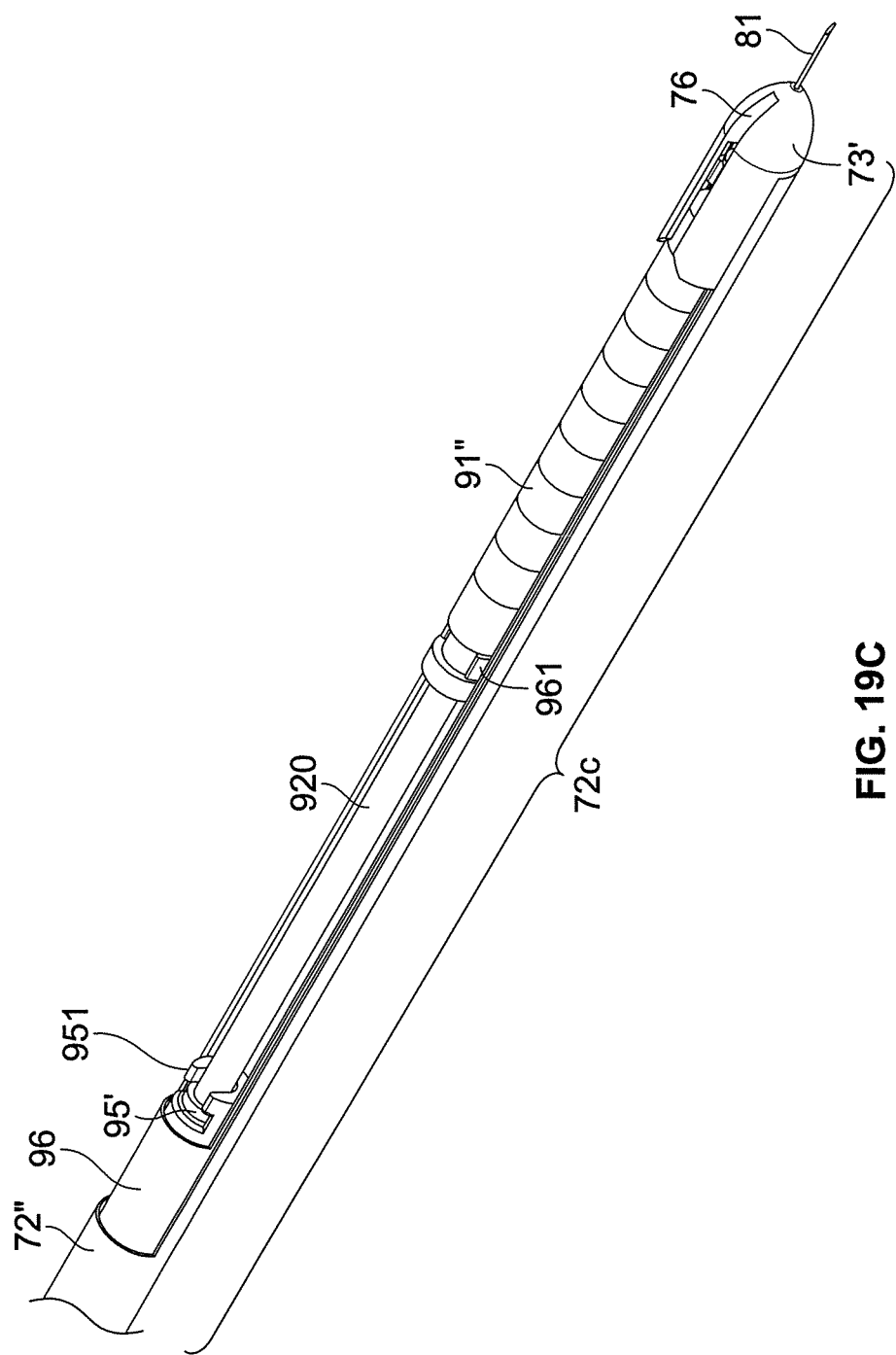
Figure 19D:
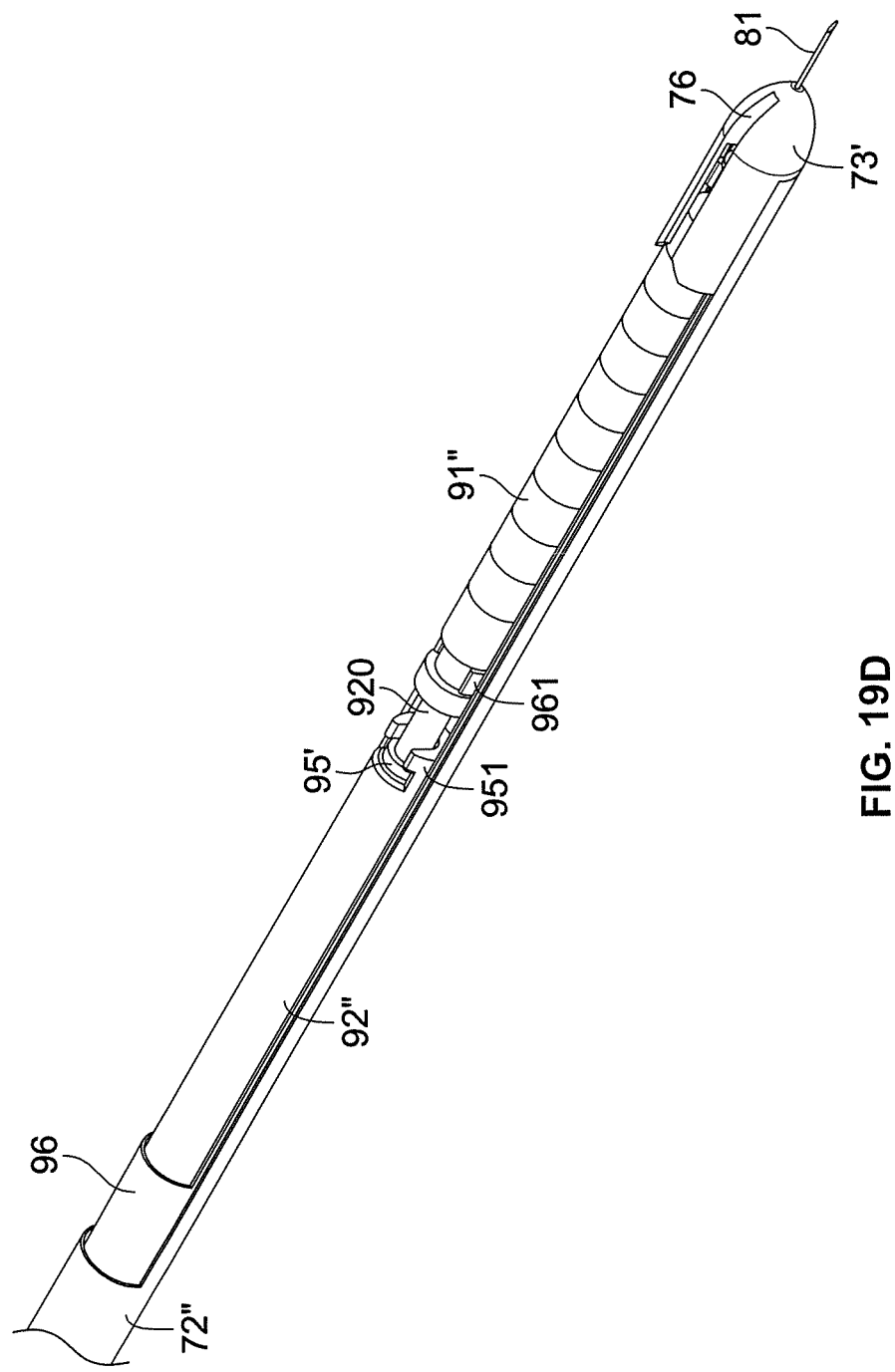

At the distal end of the device 60", the needle sheath 72" ends in a distal tip of the needle sheath 73' that contains a needle channel 733 that is sufficiently sized to fit injection needle 81. When the dockable syringe 910 is docked in the device in the docked position 910*b* as shown in FIGS. 19B-D, injection needle 81 fits through groover 76 where it is lined up to pass through needle channel 733 so that injection needle 81 can extend and retract through needle channel 733 as the needle sheath 72" moves. In FIG. 19B, injection needle 81 is fit into the groover 76 and contained in needle sheath 72", but does not traverse through the distal portion of needle channel 733. With reference to FIG. 12A, the device 60" in FIG. 19B is in the sheathed position 72*a*. In FIG. 19C, injection needle 81 is extended out of needle sheath 72" and does traverse through the distal portion through needle channel 733. With reference to FIG. 12C, the device 60" in FIG. 19C is in the unsheathed position.

As shown in FIGS. 19B and 19C, because syringe barrel 91" is not connected to needle sheath 72", the needle sheath 72" moves independently around syringe barrel 91". In the unsheathed position 72*c* as shown in FIG. 19C, the needle sheath 72" is pulled back, but the syringe barrel 91" and injection needle 81 are fixed and do not move. For example, as shown in FIG. 19C, because the needle sheath 72" is pulled back, the distal portion of the syringe barrel 91" is covered up by the distal tip of the needle sheath 73. In contrast, in the sheathed position 72*a* as shown in FIG. 19B, the sheath is not pulled back, such that the distal end of the syringe barrel 91" is not covered up by the distal tip of needle sheath 73. Hence, movement of the needle sheath 72" between sheathed and unsheathed positions, shortens the amount of syringe barrel 91" that is exposed in the docked cavity of device 60".

As described above, in the unsheathed position 72*c* as shown in FIG. 19C, the extent by which injection needle 81 is extended or exposed out of the device 60" is a function of the distance between sheath stops 715 and 716 as shown in FIG. 15 (and related FIGS. 13 and 14). This distance is a function of the particular application of the device, the particular target tissue, the subject being treated and other considerations. For example, unsheathed needle that is exposed should not be so long that it can easily penetrate through to the other side of a target tissue. Generally, with reference to most target tissues (e.g. liver), the portion of the injection needle 81 shown in FIG. 19C that can be unsheathed or exposed is generally less than 1 cm, such as 2 mm to 10 mm, and generally no more than 5 mm. For a child, the length can be smaller, and is generally less than 4 mm. For applications in utero, the length can be 2 mm to 3 mm. Generally, the total length of the injection needle 81 in device 60" is slightly longer than the unsheathed needle tip that can extend out of the device in the fully unsheathed position. As shown in FIG. 19C, the extent of the extra length is sufficient to account for the portion of the proximal end of the injection needle 81 still contained in the distal tip of sheath 73' and distal end of syringe barrel 91" when device is in the unsheathed position. For example, as described above, the total length of the injection needle 81 can range from 5 mm to 40 mm, such as 10 mm to 40 mm, such as a 12.7 mm, 25.4 mm or 38.1 mm needle.

Dispelling or ejecting a fluid, such as a therapeutic, or other solution through the injection needle is controlled by depressing plunger 92", which effects depression of auxiliary plunger 920 because of the connection achieved by plunger adaptor 951. With reference to FIG. 19C, plunger 92" is in an extended position, such that auxiliary plunger 920 also is in an extended position. In contrast, FIG. 19D illustrates plunger 92" in the depressed position, such that auxiliary plunger 920 also is in the depressed position. This allows the delivery of the fluid, such as a therapeutic, to the target tissue. The plunger 92" also can be used to control draw back of fluids from the injection site if drawback is required to test the needle placement. This is achieved by pulling or drawing back on plunger 92", which, through its connection with auxiliary plunger 920, also draws back auxiliary plunger 920. The drawback fluid can be visible in syringe barrel 91" where it is not covered by needle sheath 72".

The dockable syringe 910 (containing auxiliary plunger 920, syringe barrel 91" and injection needle 81) and/or the device 60" can be disposable or reusable. For example, after injection or exhaustion of the fluid, such as a therapeutic, from the syringe barrel 91", or when otherwise desirable, dockable syringe 910 can be withdrawn from the laparoscopic port. A newly loaded dockable syringe 910 can be docked into device 60". The newly loaded dockable syringe 910 can contain the previously used dockable syringe barrel 91" that can be re-loaded, or it can be new pre-loaded dockable syringe 910. Alternatively, the device 60" can be withdrawn from the laparoscopic port and disposed of after one use. In cases where sterile injections are required, the syringe barrel 91" can be loaded with the fluid, such as a therapeutic, in a sterile environment, such as a sterile operating room, and then docked into device 60". Alternatively, a sterile pre-loaded dockable syringe 910 can be used, which can be docked into device 60".

With reference to the above Figures and description, exemplary of the mode of operation of the injection device 60" involves first loading dockable syringe 910 with fluid, such as a therapeutic, prior to docking the syringe into the syringe adaptor in the syringe adaptor lining 96 located inside the needle sheath 72". Once the dockable syringe 910 is loaded, the syringe is docked into the syringe dock by engagement with barrel docks 961 and 963 and plunger adaptor 951. The needle sheath 72" can be positioned in the sheathed position 72*a*, and the device can be inserted into a laparoscopic port to be positioned close to the target site. At the site of injection (target tissue), the needle sheath 72" can be unsheathed 72c, and the injection needle 81 can be exposed for injection. If necessary, the control plunger 92" can be pulled back to draw fluids from the site of injection, for example, to test the placement of injection needle 81 at the injection site. The drawback fluid is visible at the distal end of syringe barrel 91" in needle sheath 72". The control plunger 92" can be depressed, to inject the fluid, such as a therapeutic, at the target tissue. After injection, the needle sheath 72" can be positioned in the sheathed position 72a, to protect the non-target organs and prevent accidental needle puncture, prior to removing the laparoscopic device from the injection site and through the laparoscopic port.

F. SYSTEMS AND KITS

The band clamp device can be provided as systems or kits in combination with other medical materials that can be used in conjunction with the particular medical procedure employing the band clamp device. For example, the band clamp device can be provided as systems in combination with other surgical instruments or tools, in particular other tools used for minimally invasive surgeries. In particular, the band clamp device can be provided as systems in combination with graspers, tweezer, injection devices, pumps, pressure gauges, tension gauges, laparoscope or medical devices or instruments that are routinely employed in conjunction with the band clamp device. The systems and kits also can be provided in combination with a pharmaceutical composition or other drug agent that can be employed in the clamping procedure.

In particular examples, the band clamp device is provided as a system in combination with an injection device that can be used in methods and procedures employing the band clamp device. In particular, the injection device can be one that is capable of holding or storing for direct injection a fluid, such as a therapeutic, for example a biologic, chemotherapeutic or gene therapy (i.e., nucleic acid molecule) into a target tissue. For example, the injection device can be one that can be used in combination with the band clamp device in the compartmentalized nucleic acid delivery method described herein to deliver a nucleic acid agent to a tissue or an organ or a portion thereof that has been compartmentalized using the band clamp device. Typically, the injection device is a laparoscopic injection device. In particular, provided herein is a system or kit provided as a combination containing a band clamp described herein in Section B and the injection device described herein in Section E. Such a system or kit can be used in the compartmentalized nucleic acid delivery method.

The system or kit can optionally be supplied to contain a pharmaceutical composition to be employed with the injection device. For example, any of the compositions described herein in Section D.4 containing a nucleic acid or a delivered agent containing a nucleic acid molecule can be provided to be included in a combination containing an injection device. The compositions can be contained in the injection device for administration or can be provided separately to be added later. The kit can, optionally, include instructions for application including instructions for use of the device or devices, dosages, dosing regimens and instructions for administration. Other reagents also can be provided. For example, the kits can optionally include implements for effecting mobilization of a tissue or organ, a timer in order to monitor compartmentalization and other reagents for use in practice of the method.

G. EXAMPLES

The following examples are included for illustrative purposes only and are not intended to limit the scope of the invention.

Example 1

Construction of Band Clamp Device

A band clamp device of the type depicted in FIGS. 1-5 and as described in the detailed description was constructed. To permit laparoscopic access to a portion of the liver, the diameter of the sheath component 30 was 10 mm and the length of the sheath component 30 and clamp portion 40 was 300 mm (see, e.g., FIG. 1). The flexible upper band 42 was made of polyurethane reinforced with fiber (Stock Drive Products, Hyde Park, N.Y.) (see, e.g., FIG. 1). The balloon 43 was a medical balloon made of medium-durometer polyurethane (Advanced Polymers, Salem, N.H.) and was approximately 10 cm in length to fit in the cradle groover 44 formed in the elongate surface member 41 of the clamp portion 40 (see, e.g., FIG. 1). A 20 mL standard syringe (Becton & Dickinson Corp., Franklin, N.J.) filled with air was connected to the balloon inflation line 25 to control inflation of the balloon 43 (see, e.g., FIG. 1).

Before insertion in the cannula of a laparoscopic port, the balloon was left deflated 43a and the first band tensioning wheel 21 was turned towards the handle (i.e., counter-clockwise) so that the flexible band laid flat 42a over the deflated balloon 43a (see, e.g., FIG. 4A). The band tension/loosen switch 23 was positioned up (23b) to prevent the first band tensioning wheel 21 from turning towards the clamp end (i.e., clockwise) to pay out or loosen the flexible band 42 (see, e.g., FIG. 3B).

Example 2

Ex-Vivo Clamping Studies on Cadaver Pig Liver Using the Band Clamp Device

Fresh whole/complete livers from a cadaver pig were obtained from a local butchery. Using the band clamp device described in Example 1, the band tension/loosen switch 23 was positioned in the down position 23a, and the first band tensioning wheel 21 was turned clockwise to pay out the flexible band to generate a slack loop 42b of 3 to 4 cm in height to fit the liver (see, e.g., FIG. 6B). The left median lobe of the liver 501 was identified, grasped and 20 cm of the lobe were cut/sectioned from the liver. The clamp portion 40 was placed over the sectioned portion of the liver 501 (see, e.g., FIG. 6C). The sheath adjustment knob 31 was turned to advance the sheath to reduce the size of the clamp portion 40 in order to fit the anatomy and size of the liver portion being clamped (see, e.g., FIG. 6D). The first band tensioning wheel 21 was turned counter-clockwise to reduce the size of the slack loop 42b to generate a tensioned loop 42c fitted snug against the anatomy of the liver (see, e.g., FIG. 6E). The balloon 43 was filled with air by engaging the syringe connected to the balloon line 25, resulting in an inflated balloon 43b that conformed to the anatomy of the underside of the liver 501 held in the clamp portion 40 (see, e.g., FIG. 6F).

Once the device was positioned and fitted over the portion of the sectioned liver, the switch was positioned in the up position 23b to prevent the first band tensioning wheel 21 from moving clockwise to pay out or loosen the tensioned flexible loop 42c. A major vessel was identified on the sectioned aspect of the clamped liver portion and a cannula tube was inserted 3 cm into the sectioned liver. Fifty (50) mLs of bromphenol blue were infused into the parenchyma of the clamped liver via the cannulated vessel. Once the 50 mLs had been infused, the balloon 43 was deflated by retrieving air from the syringe connected to the balloon line 25, the switch was moved to the down position 23a to permit loosening of the tensioned flexible loop 42c, and the first band tensioning wheel 21 was turned clockwise to loosen the flexible band its slack position 42b. The liver 501 was removed from the clamp portion 40.

The tissue on both sides of where the clamp had been placed were visualized and analyzed for the presence of the blue dye. The blue dye was localized only to the proximal half side of the cannulated clamped liver portion and did not penetrate the other side of the clamped tissue. Thus, the results show that the band clamp device was able to simulate circulation cut-off and hence achieved successful compartmentalization by preventing circulation of the blue dye solution into the distal side of the clamped liver portion.

Example 3

Prolonged Soluble Reporter Protein Expression of Injected Adenovirus Following Compartmentalization of a Liver Using the Band Clamp Device To assess the extent of long term gene expression achievable by the compartmentalized gene delivery method, adenovirus expressing a secretable protein, alpha-fetoprotein (AFP), was injected to the parenchyma of a liver that had been compartmentalized from the systemic circulation for 30 minutes using the band clamp device. The presence of soluble protein was assessed over time post-injection in peripheral blood to determine prolonged gene expression.

A. Methods

The adenovirus designated Ad-pALB.AFP was derived from human adenovirus type 5 and encodes the porcine (Sus scrofa) alpha-fetoprotein (AFP) cDNA (Genbank accession number AF517770.1) driven by a Sus scrofa serum albumin gene, promoter region (Genbank accession number AY033476.1). The adenovirus was made replication deficient by deleting the E1 region. Into this deleted E1 region, the reporter gene alpha fetoprotein (AFP) was cloned and constructed to be driven by the porcine albumin (ALB) promoter for specificity to the liver. The Sus scrofa AFP cDNA under control of the ALB promoter was synthesized by Genscript (Piscataway, N.J.) and cloned into the pUC57 plasmid. The AFP expression cassette in the pUC57 plasmid was subcloned into the Dual-Basic adeno-viral shuttle vector and recombined with Ad5 (DE1/DE3) vector (Vector Biolabs, Philadelphia, Pa.). The adenovirus designated Ad.pALB.AFP was packaged in HEK293 cells, purified with cesium chloride ultracentrifugation and titered using the conventional HEK293 plaque assay.

Briefly, under general anesthesia, 20 kilogram (kg) vietnamese pigs (n=3) were placed in the supine position. Asepsis and antisepsis was performed and the abdominal region was dressed using sterile surgical sheets. A 10 cm supra-umbilical medial incision was performed exposing the abdominal cavity and the liver. Carefully, 10 centimeters (cms) of the left medial lobe of the liver was extracted from the abdominal cavity.

Approximately five centimeters (5 cms) of the distal portion of the left medial lobe was compartmentalized using the band clamp device described in Example 1. Using the band clamp device described in Example 1, the band tension/loosen switch 23 was positioned in the down position 23a, and the first band tensioning wheel 21 was turned towards the clamp end (i.e., clockwise) to pay out the flexible band to generate a slack loop 42b of 3 to 4 cm in height to fit the liver (see, e.g., FIG. 6B). The left median lobe of the liver 501 was grasped with tweezers and the clamp portion 40 was placed over the liver 501 (see, e.g., FIG. 6C). The sheath adjustment knob 31 was turned to advance the sheath 32 to reduce the size of the clamp portion 40 in order to fit the anatomy and size of the liver portion being clamped (see, e.g., FIG. 6D). The first band tensioning wheel 21 was turned towards the handle (i.e., counter-clockwise) to reduce the size of the slack loop 42b to generate a tensioned loop 42c fitted snug against the anatomy of the liver (see, e.g., FIG. 6E). The balloon 43 was filled with air by engaging the syringe connected to the balloon line 25, resulting in an inflated balloon 43b that conformed to the anatomy of the underside of the liver 501 held in the clamp portion 40.

Once the device was positioned and fitted over the liver, the band tension/loosen switch was positioned in the up position 23b to prevent the first band tensioning wheel 21 from turning towards the clamp end (i.e., clockwise) to pay out or loosen the tensioned flexible loop 42c. Using a standard 1 mL insulin syringe, 0.500 mL (500 μL) of solution containing $1.2 \times 10^5$ pfus of Ad.pALB.AFP were injected directly into the compartmentalized liver parenchyma (n=2). As a negative control, the third pig was not injected with adenovirus (n=1).

The laparoscopic liver clamp was held in position for 30 minutes and then released from the liver. To release the clamp, the band tension/loosen switch was moved to the down position to permit loosening of the tensioned flexible loop 42c, and the first band tensioning wheel 21 was turned towards the clamp end (i.e., clockwise) to loosen the flexible band its slack position 42b. The liver 501 was removed from the clamp portion 40. The site of injection was observed for 1 minute for hemorrhage, after which the lobe was carefully reintroduced into the abdominal cavity. The abdominal muscle incision was sutured using Vycril 1. The skin was then closed with standard surgical staples. The incision was dressed and the pigs were carefully carried to their cages where they were allowed to recover. The negative control pig (n=1) was submitted to the same surgical procedure including clamping of the lobe for 30 minutes but was injected with PBS.

Ten milliliters (10 mLs) of peripheral blood were drawn from the right jugular vein during the surgical procedure before adenoviral injection and sixty days post-injection and surgery. The blood was processed using a serum separator tube (Becton Dickinson Corp., Franklin, N.J.) and samples were allowed to clot for 30 minutes before centrifugation at 1,000 g for 15 minutes. Serum was removed, aliquoted and stored at −80° C. AFP was detected in the serum using the PIG Alpha-fetoprotein, AFP ELISA Kit (Cusabio Biotech Co., Ltd., Wuhan China) according to the manufacturer's protocol.

One pig from the adenovirus injected group and one PBS injected control were subsequently followed up for 12 months and AFP levels of each pig were assessed. Serum was sampled and processed as described above. Due to problems in sensitivity with the AFP ELISA kit, AFP was detected using a solid-phase two-site sequential chemiluminescent immunometric assay kit, IMMULITE 2000 AFP (Siemens Healthcare, Gwynedd, United Kingdom) according to the manufacturer's protocol.

B. Results

1. Initial Sixty Day

The results of the sixty day follow up show that an average basal or background levels of AFP of 0.4 ng/mL was detected in the peripheral serum of animals before adenoviral injection. In animals injected with adenovirus Ad.pALB.AFP as described above, an average of 36 ng/ml of AFP were detected in pigs 60 days post-adenovirus administration. In contrast, basal levels of AFP were detected in control pigs that did not receive adenovirus (0.4 ng/ml). These results demonstrate that delivery of adenovirus to a liver compartmentalized with the band-clamp device achieves sustained transgene expression for at least sixty days (2 months) post-adenoviral transduction.

2. 12-Month Follow Up

Table 1 sets forth the results of the 12-month follow up where the AFP level was detected using the solid-phase two-site sequential chemiluminescent immunometric assay. In the animal injected with Ad.pALB.AFP, at all time points tested post-administration, serum AFP levels were detected that were substantially greater than control, which were sustained throughout the 12 month follow-up. These results demonstrate that delivery of adenovirus to a liver compartmentalized with the band-clamp device achieves sustained transgene expression for at least a year (12 months) post-adenoviral transduction.

TABLE 1

AFP Levels in the 12-month Followup Study

| Month(s) following Injection | AFP level (ng/mL) of 6E6DFA3 (PBS injected control pig) | AFP level (ng/mL) of 6E6DBFA (Ad.pALB.AFP injected pig) |
| --- | --- | --- |
| 0 | 6 | 7 |
| 1 | 4 | 10.3 |
| 2 | 4 | 65.1 |
| 3 | 4.8 | 36 |
| 4 | 3.6 | 38 |
| 5 | 8.2 | 48.5 |
| 6 | 2.8 | 35 |
| 7 | 4.5 | 40 |
| 8 | 2 | 36 |
| 9 | 5.8 | 32 |
| 10 | 7 | 42 |
| 11 | 15 | 28 |
| 12 | 4.2 | 24 |

Example 4

Systemic Detection of Injected Adenovirus During & Following Compartmentalization of a Liver Using the Band Clamp Device Adenovirus was injected to the parenchyma of a liver that had been compartmentalized from the systemic circulation for 30 minutes using the band clamp device, and its presence in the blood stream during and following clamping was assessed using quantitative PCR to determine if viremia occurs. The adenovirus designated Ad.pALB.AFP described in Example 3 was used in these experiments.

Briefly, under general anesthesia, 20 kilogram (kg) pigs (n=3) were placed in the supine position. Asepsis and antisepsis was performed and the abdominal region was dressed using sterile surgical sheets. A 10 cm supra-umbilical medial incision was performed exposing the abdominal cavity and the liver. Carefully, 10 centimeters (cms) of the left medial lobe of the liver was extracted from the abdominal cavity. Pig liver was compartmentalized with the band clamp device and injected with a dose of $1.2 \times 10^{10}$ pfus of Ad.pALB-AFP (n=2) as described in Example 3. As a negative control, the third pig was not injected with adenovirus. At 1, 3 and 5 minutes post adenoviral injection (post-injection), 5 mL of peripheral blood were drawn from the jugular vein.

The laparoscopic liver clamp was held in position for 30 minutes and then released from the liver. To release the clamp, the band tension/loosen switch was moved to the down position to permit loosening of the tensioned flexible loop 42c, and the first band tensioning wheel 21 was turned towards the clamp end (i.e., clockwise) to loosen the flexible band its slack position 42b. The liver 501 was removed from the clamp portion 40. Then, at 1, 3 and 5 minutes post clamp release (post-clamp release), 5 mL of peripheral blood were drawn from the jugular vein. The site of injection was observed for 1 minute for hemorrhage, after which the lobe was carefully reintroduced into the abdominal cavity. The abdominal muscle incision was sutured using Vycril 1. The skin was then closed with standard surgical staples. The incision was dressed and the pigs were carefully carried to their cages where they were allowed to recover. The negative control pig (n=1) was submitted to the same surgical procedure including clamping of the lobe for 30 minutes but was injected with PBS.

Obtained blood samples were processed using a serum separator tube (Becton Dickinson Corp., Franklin, N.J.), samples were allowed to clot for 30 minutes before centrifugation at 1,000 g for 15 minutes. Serum was removed, aliquoted and samples stored at −80° C. Serum samples were analyzed for the presence of adenoviral DNA by amplifying the E4 adenovirus 5 gene by quantitative PCR. DNA was purified from 500 µl of serum samples using the Wizard Genomic DNA purification Kit (Promega) as described by the manufacturer. Using 10 ng of DNA per PCR reaction, Adenoviral genome copy numbers were determined by amplification of the E4 Human Adenoviral 5 region (GenBank AB685372.1) using SYBR Green Master Mix (Applied Biosystems) and the Step One Plus System (Applied Biosystems). The cycles for PCR were as follows: one cycle at 95° C. for 10 minutes, 40 cycles of 15 seconds at 95° C., 1 minute at 60° C. followed by dissociation protocol. The primers used for amplification were: forward 5'-GGAGTGCGCCGAGACAAC-3' (SEQ ID NO:1) and reverse 5'-ACTACGTCCGGCGTTCCAT-3' (SEQ ID NO:2) (Kanerva et al, Molecular Therapy Vol. 5, No. 6, 2002). For quantification of Adenoviral genomes, sample readings were compared with a standard curve created by amplifying known numbers of Adenoviral genome copies ($10^6$, $10^5$, $10^4$, $10^3$, $10^2$, 10 and 1).

The results are set forth in Table 2. The results showed that no genomes were detected at any of the tested time points, indicating that viremia did not occur and that there was no release of the virus into the peripheral circulation immediately post-Adenoviral injection and post-clamp release.

TABLE 2

Systemic Detection of Injected Adenovirus

| Pig | Post-Injection (copies/μg DNA) | | | Post-clamp release (copies/μg DNA) | | |
|---|---|---|---|---|---|---|
| (chip No.) | 1 min | 3 min | 5 min | 1 min | 3 min | 5 min |
| 6E6F371 | (—) | (—) | (—) | (—) | (—) | (—) |
| 6E6DD9C | (—) | (—) | (—) | (—) | (—) | (—) |
| 6E6DFA3 (PBS ctrl) | (—) | (—) | (—) | (—) | (—) | (—) |

Example 5

Detection of Injected Adenovirus in Peripheral Organs Following Compartmentalization of a Liver Using the Band Clamp Device To further confirm the finding that viremia of injected virus did not occur as described in Example 3, the presence of virus in peripheral organs was assessed after injection of adenovirus to the parenchyma of a compartmentalized liver. Pig liver (n=2) was compartmentalized with the band clamp device and injected with a dose of $1.2 \times 10^{10}$ pfus of Ad.pALB-AFP as described in Example 3. As a negative control, a pig (n=1) was submitted to the same surgical procedure including clamping of the lobe for 30 minutes but was injected with PBS.

The clamp was released after 30 minutes and the pigs were sutured as described in Example 3 and allowed to recover. Eight days post-compartmentalized liver transduction, the pigs were euthanized and three random samples of tissue were obtained from liver at site of injection, liver tissue distal to the injection site, heart, lung, kidney, muscle, small intestine, spleen, bladder, aortic tissue, and testicles. Obtained tissue samples were stored at −80° C. until processed. DNA was purified from tissue samples using the Wizard Genomic DNA purification Kit (Promega) as described by the manufacturer.

Purified DNA from the tissue samples was analyzed for the presence of adenoviral DNA by amplifying the E4 adenovirus 5 gene by quantitative PCR as described in Example 3. The results are shown in Table 3. The results show that viral genomes were present in the liver at the site of injection in animals injected with adenovirus, but not in the control animal. The results further show that no viral genomes were detected on any of the other analyzed organs/tissue. Thus, the results show that the band-clamp device achieves compartmentalization of the liver, and that the compartmentalized transduction of the liver avoids the viral transduction of non-desired organs/tissue.

TABLE 3

Presence of Viral Genomes in organs/tissue

| Tissue/Organ | | Animal Chip | | |
|---|---|---|---|---|
| | | 6E6F371 | 6E6DD9C | 6E6DFA3 (PBS Control) |
| Liver - site of injection | sample 1 | (—) | 126 ± 29 | (—) |
| | sample 2 | 142.5 ± 3.1 | (—) | (—) |
| | sample 3 | 329 ± 47 | 234 ± 32 | (—) |
| liver - distal site | | (—) | (—) | (—) |
| Heart | | (—) | (—) | (—) |
| Lung | | (—) | (—) | (—) |
| Aorta | | (—) | (—) | (—) |

TABLE 3-continued

Presence of Viral Genomes in organs/tissue

| Tissue/Organ | Animal Chip | | |
|---|---|---|---|
| | 6E6F371 | 6E6DD9C | 6E6DFA3 (PBS Control) |
| Kidney | (—) | (—) | (—) |
| Muscle | (—) | (—) | (—) |
| Testicles | (—) | (—) | (—) |
| Small Intestine | (—) | (—) | (—) |
| Spleen | (—) | (—) | (—) |
| Bladder | (—) | (—) | (—) |

Example 6

Assessment of Liver Tissue Damage Following Compartmentalization with the Band-Clamp Device and Delivery of an Adenoviral Vector Tissue damage as assessed by histology and the levels of liver injury biomarkers aspartate aminotransferase (AST) and alanine aminotransferase (ALT) were determined following compartmentalization of the liver with the band-clamp device and delivery of an adenoviral vector.

A. Method

To document the extent of liver injury, the left median lobe of pigs were compartmentalized with the band clamp device and injected with a dose of $1.2 \times 10^{10}$ pfu, $1.2 \times 10^{5}$ pfu or $1.2 \times 10^{2}$ pfu Ad.pALB.AFP in 500 μL essentially as described in Example 3 (n=3 per dose). A negative control group of pigs (n=2) were submitted to the same surgical procedure, including clamping of the liver with the band-clamp device for 30 minutes, but were injected with PBS. The clamp was released after 30 minutes and the pigs were sutured as described in Example 3 and allowed to recover. Peripheral blood was drawn from animals before clamping, and at 24, 48, 72, 96, 120 and 144 hours post-clamping and transduction. Eight days post-compartmentalized liver transduction, the pigs that received $1.2 \times 10^{10}$ pfus were euthanized.

One pig that received $1.2 \times 10^{5}$ pfu Ad.pALB.AFP and one PBS injected control were subsequently followed up monthly for 12 months and the serum levels of liver injury biomarkers aspartate aminotransferase (AST) and alanine aminotransferase (ALT) were determined.

The blood samples were processed using a serum separator tube (Becton Dickinson Corp., Franklin, N.J.), and samples were allowed to clot for 30 minutes before centrifugation at 1,000 g for 15 minutes. Serum was removed, aliquoted, refrigerated and sent to The National University of Mexico's (UNAM) Veterinary School for determination of blood levels of aspartate aminotransferase (AST) and alanine aminotransferase (ALT) using commercial kits (Sigma Chemicals, St. Louis, Mo.) in a Hitachi Automatic Analyzer (Boehringer Mannheim, Indianapolis, Ind.).

B. Results

1. Liver Injury Biomarkers a. Alanine Aminotransferase (ALT)

The results of the initial study showed that the average level of ALT in the control animals subjected to compartmentalization with the band-clamp device for 30 minutes ranged between about 55-80 U/L, which was slightly higher on average than the normal range of ALT levels of 21-46 U/L. In animals injected with adenovirus, the adenoviral liver transduction did not significantly increase the level of ALT compared to that observed in control animals at any of the doses tested.

Table 4 sets forth the results of the ALT level determination of the 12-month followup study with one pig that received $1.2 \times 10^5$ pfu Ad.pALB.AFP liver transduction and one PBS injected control. As shown in Table 4, for the first 6 days, the ALT levels of the Ad.pALB.AFP injected pig ranged from approximately 60-80 U/L. In the PBS injected pig, also subjected to the compartmentalization method using the band clamp device, the values ranged from approximately 55-60 U/L. These results indicate slightly higher ALT levels than the normal range of 21-46 U/L in both groups. The ALT levels generally gradually decreased to fall within the normal range (21-46 U/L) within approximately five months (150 days) for both Ad.pALB.AFP injected and control pigs.

TABLE 4

ALT Levels in the 12-month Followup Study

| Day(s) following Injection | ALT Level (U/L) of 6E6DFA3 (PBS injected control pig) | ALT Level (U/L) of 6E6DBFA (Ad.pALB.AFP injected pig) |
|---|---|---|
| 0 | 33 | 53 |
| 1 | 55 | 62 |
| 2 | 53 | 64 |
| 3 | 50 | 80 |
| 4 | 59 | 75 |
| 5 | 60 | 75 |
| 6 | 60 | 73 |
| 30 | 50 | 57 |
| 60 | 52 | 51 |
| 90 | 48 | 47 |
| 120 | 49 | 49 |
| 150 | 37 | 46 |
| 180 | 29 | 48 |
| 210 | 46 | 46 |
| 240 | 31 | 43 |
| 270 | 22 | 37 |
| 300 | 22 | 25 |
| 330 | 35 | 30 |
| 365 | 25 | 24 | b. Aspartate Aminotransferase (AST)

The results of the initial study showed that the average measured levels of AST in the control animals compartmentalized with the band-clamp device for 30 minutes were about 60 U/L (80 U/L to 100 U/L in one animal), which was also a slight increase in AST levels above the normal range of 15-55 U/L. In animals injected with adenovirus, the adenoviral liver transduction did not significantly increase the level of AST compared to that observed in control animals at any of the doses tested.

Table 5 sets forth the results of the AST level determination of the 12-month followup study with one pig that received $1.2 \times 10^5$ pfu Ad.pALB.AFP liver transduction and one PBS injected control. As shown in Table 5, for the first 6 days, the AST levels of the Ad.pALB.AFP injected pig ranged from approximately 60-100 U/L. In the PBS injected pig, the values ranged from approximately 30-60 U/L. These results indicate slightly higher AST levels than the normal range of 15-55 U/L in the Ad.pALB.AFP injected pig. In the subsequent followup, the AST levels fell within the normal range (15-55 U/L) in one month (30 days), and the levels stayed within the normal range for up to the 12 month time point for both groups.

TABLE 5

AST Levels in the 12-month Followup Study

| Day(s) following Injection | AST Level (U/L) of 6E6DFA3 (PBS injected control pig) | AST Level (U/L) of 6E6DBFA (Ad.pALB.AFP injected pig) |
|---|---|---|
| 0 | 33 | 60 |
| 1 | 55 | 58 |
| 2 | 53 | 80 |
| 3 | 50 | 97 |
| 4 | 59 | 64 |
| 5 | 60 | 62 |
| 6 | 60 | 57 |
| 30 | 50 | 30 |
| 60 | 32 | 35 |
| 90 | 35 | 33 |
| 120 | 33 | 35 |
| 150 | 55 | 24 |
| 180 | 27 | 52 |
| 210 | 33 | 52 |
| 240 | 55 | 41 |
| 270 | 22 | 40 |
| 300 | 22 | 32 |
| 330 | 30 | 35 |
| 365 | 32 | 38 | c. Conclusion

The results demonstrate that in the short term (e.g., 1-6 days after compartmentalization with the band-clamp device and adenovirus transduction), the ALT and AST levels were slightly above the normal range in the adenovirus injected group. However, a slight increase was also observed in the negative control group, indicating that the surgical procedure is likely the cause of the slight increase.

The ALT and AST levels were not significantly higher in the adenovirus injected group. Over long term (up to 12 months), the ALT and AST levels were restored to within the normal range for both the adenovirus injected and control groups. These results show that the compartmentalized adenoviral transduction of the liver did not trigger immune-activation events or other responses that damages the hepatic tissue with the concomitant increase in liver injury markers.

2. Histology

At eight days post-compartmentalized liver transduction, the livers of the euthanized pigs were harvested and the left medial lobe processed. The tissue was fixed in 4% paraformaldehyde and embedded in Tissue Path media (Fisher Scientific, Pittsburgh, Pa.). Four micrometer (4 μm) thick tissue sections were prepared and mounted on tissue glass slides, counterstained with hematoxylin and eosin and observed under light microscopy at a magnification of 60× and 190×. These results demonstrate that compartmentalized Adenoviral liver transduction does not generate hepatic tissue damage in the form of a polymorphonuclear leukocyte infiltrate. This further evidences that the compartmentalized adenoviral transduction of the liver did not trigger immune-activation events or other responses that damages the hepatic tissue.

Example 7

Construction of Syringe Injection Device

A syringe injection device of the type depicted in FIG. 9A and as described in the detailed description was constructed. The device contained a plunger 92 and syringe barrel 91, a needle sheath controller 71, a needle sheath 72, an injection tube 83 and injection needle 81. To permit laparoscopic access to a portion of the liver, the diameter of the needle sheath 72 was 5 mm and the length of the needle sheath 72 was 300 mm (see, e.g., FIG. 9A).

The device was constructed so that a needle sheath lumen 723 inside the needle sheath 72 housed the injection tube 83 and injection needle 81 when in the sheathed position (see, e.g., FIG. 9A). The injection needle was a standard 27 gauge of 10 mm in length and was connected directly to a 27 gauge injection tube 83. The injection tube 83 and injection needle 81 were made of stainless steel. The injection tube 83 was affixed to the needle hub 84 and needle sheath controller 71 at the proximal end of the inside of the needle sheath controller 71 (see, e.g., FIG. 9A). The injection needle 81 was sheathed and locked by sliding the needle lock button 711 forward. A standard 1 cc insulin syringe containing a syringe barrel 91 and plunger 92, but without a needle, was filled with 0.7 mL solution and purged. The syringe was attached to the proximal end of the needle hub 84 outside of the needle sheath controller 71 using a Luer fit adaptor 93 (see FIG. 9A).

Example 8

Compartmentalized Transduction of the Liver in a Laparoscopic Simulator

The band-clamp device 10 described in Example 1 and the laparoscopic injection device 60 described in Example 7 were utilized in a laparoscopic simulator by a skilled surgeon/physician to effect compartmentalization of a portion of the left median lobe of a liver for delivery of an injectable solution. The laparoscopic simulator (Lapa-Pro, Mexico) was positioned at a 35° to 45° angle inclination to simulate the Semi-Fowlers position of a subject. The Semi-Fowlers position facilitates the access to the distal portion of the left lobe of the human liver using gravity to distally displace the abdominal organs. With respect to a subject, the entry ports of the simulator were positioned as follows: one entry port in the epigastric abdominal region; one entry port in the umbilical abdominal region; and two entry ports in the left lumbar abdominal region.

A freshly obtained cadaveric pig liver was positioned inside the laparoscopic simulator. The laparoscope was inserted through the umbilical entry port. The sheath component 30 and clamp portion 40 of the band-clamp device 10 as described in Example 1 was inserted through the epigastric entry port. As described in Example 1, for insertion into the cannula of the laparoscopic port, the device was positioned with the balloon deflated 43a, the first band tensioning wheel 21 turned towards the handle end (i.e., counter-clockwise) so that the flexible band laid flat 42a over the deflated balloon 43a, and the first band tension/loosen switch 23 positioned up (23b) to prevent the first band tensioning wheel 21 from moving clockwise to pay out or loosen the flexible band 42. A grasper was inserted through the distal left lumbar entry port.

The band tension/loosen switch 23 was positioned in the down position 23a, and the first band tensioning wheel 21 was turned toward the clamp end (i.e., clockwise) to pay out the flexible band to generate a slack loop 42b of 3 to 4 cm in height to fit the liver (see, e.g., FIG. 6B). The distal portion of the left median lobe of the cadaveric pig liver was located. At least 5 cm of the left median lobe of the liver 501 was carefully manipulated into the payed-out loop 42b of the band-clamp device using the graspers so that the portion of the liver laid flat on the elongate surface member 41 of the clamp portion 40 (see, e.g., FIG. 6C). The sheath adjustment knob 31 was turned to advance the sheath 32 to reduce the size of the clamp portion 40 in order to fit the anatomy and size of the liver portion being clamped (see, e.g., FIG. 6D). The first band tensioning wheel 21 was turned towards the handle end (i.e., counter-clockwise) to reduce the size of the slack loop 42b to generate a tensioned loop 42c fitted snug against the anatomy of the liver in order to simulate circulation cut-off or compartmentalization of the liver portion (see, e.g., FIG. 6E). The balloon 43 was filled with air by engaging the syringe connected to the balloon line 25, resulting in an inflated balloon 43b that conformed to the anatomy of the underside of the liver 501 held in the clamp portion 40 (see, e.g., FIG. 6F).

A standard 1 cc insulin syringe was filled with 0.7 mL tap water solution and purged. The filled syringe containing a syringe barrel 91 and plunger 92 was attached needle hub 84 on the proximal end of the needle sheath controller 71. The needle lock button 711 on the needle sheath controller 71 was slid backward to unlock the needle lock button 711 and to un-sheathe the needle. The entire syringe injection device was purged by pressing the plunger until liquid was observed at the tip of the needle (approximately 200 µL). The needle lock button 711 on the needle sheath controller 71 was then slid forward to lock the needle lock button 711 in the forward position 711a and to sheathe the injection needle 81. The syringe injection device with the needle sheathed was introduced into the simulator through the proximal left lumbar entry port. Using the laparoscope monitor, the tip of the injection device was positioned close to the site of injection. The injection needle 81 on the laparoscopic injection device was un-sheathed by sliding the needle lock button 711 backward and locking the button in the rearward position 711c. The tip of the injection needle 81 was introduced into the parenchymal tissue making sure that it did not go through the tissue. Once the tip of the injection needle 81 was carefully positioned inside the parenchyma, the plunger 92 was pressed until 500 µL of liquid was injected.

The needle lock button 711 on the needle sheath controller 71 was slid forward to lock the needle lock button 711 in the forward position 711a and to sheathe the needle. The laparoscopic injection device 60 was removed from the simulator. To release the clamp from the liver, the balloon 43 was deflated by retrieving air from the syringe connected to the balloon line 25, the band tension/loosen switch 23 was moved to the down position 23a to permit loosening of the tensioned flexible loop 42c, and the first band tensioning wheel 21 was turned clockwise to loosen the flexible band its slack position 42b. Once released, the procedure was over. The liver 501 was removed from the clamp portion 40. The band-clamp device 10 was removed from the simulator.

Since modifications will be apparent to those of skill in the art, it is intended that this invention be limited only by the scope of the appended claims.

The invention claimed is:

1. A clamp device for uniformly compressing a tissue, an organ, or a portion of the tissue or organ during minimally invasive surgery, comprising:
   a) an elongate surface member that has a concave surface with a proximal end and a distal end;
   b) a biocompatible deformable article that rests on the distal end of the surface member in a cradle formed by the concave surface member, and, when clamped, conforms to the shape of the tissue, organ, or portion of the tissue or organ that is clamped; and
   c) a flexible band that has a proximal end and a distal end, wherein:
      the distal end of the flexible band is connected to the distal end of the surface member;
      the flexible band forms a closed loop with the biocompatible deformable article on the surface member;
      the proximal end of the flexible band is configured to be adjustably tensioned so that the portion of the flexible band that forms a closed loop with the biocompatible deformable article can be shortened or lengthened, whereby the closed loop fits and clamps the tissue, organ, or portion thereof during minimally invasive surgery; and
      when the flexible band is tensioned, the biocompatible deformable article conforms to the shape of the tissue or organ or portion thereof, thereby filling any voids where the tissue or organ or portion thereof otherwise would not be contacted with the clamp portion, to thereby clamp and uniformly compress the tissue, or organ, or portion thereof to isolate the tissue, organ or a portion thereof from systemic circulation.

2. The clamp device of claim 1, further comprising a sheath having a lumen comprising a proximal end and a distal end, wherein:
   the lumen of the sheath encloses a portion of the elongate surface member and flexible band; and
   the surface member is longer than the sheath, whereby the lumen of the sheath does not enclose the biocompatible deformable article resting in the cradle at the distal end of the surface member.

3. The clamp device of claim 2, wherein the sheath is configured to be linearly movable along the surface member to shorten or lengthen the portion of the surface member that is not enclosed by the sheath.

4. The clamp device of claim 2, wherein the sheath is at least about or is about 3 mm, 4 mm, 5 mm, 6 mm, 7 mm, 8 mm, 9 mm, 10 mm, 11 mm, 12 mm, 13 mm, 14 mm or 15 mm in diameter.

5. The clamp device of claim 1, wherein the biocompatible deformable article is made from a material selected from among an elastomeric foam, a silicone, an elastomer, silicone rubber, a visco-elastic gel, a hydrogel and a non-elastomeric film material.

6. The clamp device of claim 5, wherein the material is selected from among polyurethane, polyethylene, polyethylene terephthalate (PET), polyethylene terephthalate glycol-modified (PETG), ethylene vinyl acetate (EVA) and silicone.

7. The clamp device of claim 1, wherein the biocompatible deformable article is made from a material with a durometer of 5 A to 95 A, 10 A to 95 A, 20 A to 95 A, 20 A to 85 A, 20 A to 70 A, 20 A to 60 A, 20 A to 50 A, 20 A to 40 A, 30 A to 85 A, 30 A to 70 A, 30 A to 60 A, 30 A to 50 A, 30 A to 40 A, 40 A to 85 A, 40 A to 70 A, 40 A to 60 A, 40 A to 50 A, 50 A to 85 A, 50 A to 70 A, 50 A to 60 A, 60 A to 85 A, 60 A to 70 A or 70 A to 85 A.

8. The clamp device of claim 1, wherein the biocompatible deformable article is an inflatable balloon.

9. The clamp device of claim 8, further comprising a sheath having a lumen comprising a proximal end and a distal end, wherein:
   the lumen of the sheath contains a balloon inflation line having a proximal end and a distal end, the distal end in communication with the proximal end of the inflatable balloon to control inflation of the balloon;
   the lumen of the sheath encloses a portion of the elongate surface member, flexible band and balloon inflation line; and
   the surface member is longer than the sheath, whereby the lumen of the sheath does not enclose the inflatable balloon resting in the cradle at the distal end of the surface member.

10. The clamp device of claim 9, wherein:
the device further comprises a handle connected to the proximal end of the surface member;
the proximal end of the balloon inflation line extends from the bottom of the handle and is operably connected to an external source of fluid or gas; and
the external source of fluid or gas inflates and deflates the inflatable balloon through the balloon inflation line.

11. The clamp device of claim 8, wherein the inflatable balloon is made of a medium durometer material.

12. The clamp device of claim 11, wherein the medium durometer material is a polyurethane or polyethylene material.

13. The clamp device of claim 1, further comprising a handle connected to the proximal end of the surface member, wherein the handle comprises:
a case comprising an inside and an outside;
a first tensioning wheel mounted in the case for access by an operator to adjustably tension the flexible band; and
the proximal end of the flexible band operably engaged with the first tensioning wheel, whereby movement of the tensioning wheel shortens or lengthens the portion of the flexible band that forms a closed loop with the biocompatible deformable article in the distal end of the elongate surface member.

14. The clamp device of claim 1, wherein the elongate surface member is of a sufficient length and diameter to access a tissue or an organ or a portion thereof through an endoscopic port during the minimally invasive surgery.

15. The clamp device of claim 14, wherein the minimally invasive surgery is laparoscopy.

16. The clamp device of claim 14, wherein the tissue or organ or portion thereof is selected from among the liver, pancreas, gallbladder, spleen, stomach, reproductive organs and portions thereof.

17. The clamp device of claim 16, wherein the tissue or organ is the liver or portion thereof.

18. The clamp device of claim 14, wherein the elongate surface member has a length from its proximal end to its distal end of from or from about 100 mm to 600 mm.

19. The clamp device of claim 1, wherein:
the biocompatible deformable article is an inflatable balloon; and
the flexible band is comprised of material whereby the closed loop has an open area between the balloon and the flexible band in the absence of any clamped tissue, whereby tensioning or loosening the flexible band increases or decreases the space formed in the open area between the balloon and the flexible band.

20. The clamp device of claim 1, wherein the flexible band can be loosened to lengthen the flexible band to achieve a height of the closed loop that is greater than the thickness of the tissue or organ or portion thereof to fit the tissue or organ or portion thereof in the closed loop.

21. The clamp device of claim 20, wherein the flexible band can be loosened to lengthen the flexible band to achieve a height of the closed loop of from 1 cm to 10 cm.

22. The clamp device of claim 1, wherein:
the distal end of the flexible band is configured to be adjustably tensioned proximal to the distal end of the elongate surface member; and
the flexible band is longer than the elongate surface member by an amount that is greater than the thickness of the tissue or organ or portion thereof to be clamped.

23. The clamp device of claim 1, wherein the biocompatible deformable article is attached to the flexible band at the distal end of the flexible band near the connection of the flexible band with the surface member.

24. The clamp device of claim 1, wherein:
the distal end of the surface member has a notch; and
the distal end of the flexible band is connected to the distal end of the surface member at the notch to form the closed loop.

25. The clamp device of claim 1, wherein the biocompatible deformable article is made of a low or medium durometer material for clamping and conforming to the shape of the tissue, organ, or portion thereof.

26. A system for performing a minimally invasive surgery, comprising:
the device of claim 1; and
an injection device configured to access an endoscopic port for the minimally invasive surgery.

27. A clamp device for uniformly compressing a tissue, organ, or portion of the tissue or organ during minimally invasive surgery, comprising:
a) an elongate surface member that has a proximal end and a distal end;
b) a biocompatible deformable article that rests on the surface member at the distal end of the surface member, wherein the distal end of the elongate surface member is concave and forms a cradle upon which the biocompatible deformable article rests;
c) a flexible band that has a proximal end and a distal end, wherein:
the distal end of the flexible band is connected to the distal end of the surface member;
the flexible band forms a closed loop with the biocompatible deformable article on the surface member, the closed loop is able to fit a tissue or an organ or a portion thereof during minimally invasive surgery, to thereby uniformly compress the tissue, or organ or portion thereof;
the proximal end of the flexible band is configured to be adjustably tensioned so that the portion of the flexible band that forms a closed loop with the biocompatible deformable article can be shortened or lengthened, whereby the closed loop clamps the tissue or organ or portion thereof; and
the biocompatible deformable article conforms to the shape of the tissue or organ or portion thereof;
d) a sheath having a lumen comprising a proximal end and a distal end, wherein the lumen of the sheath encloses a portion of the elongate surface member; and
e) an adjustable knob to control movement of the sheath linearly along the surface member, wherein:
the adjustable knob is operably connected to the sheath; and
the adjustable knob is configured on the device so that axial rotation of the adjustable knob with respect to the sheath linearly moves the sheath with respect to the surface member to advance or retract the sheath into the adjustable knob, thereby shortening or lengthening the portion of the surface member enclosed by the lumen of the sheath.

28. The clamp device of claim 27, wherein:
the sheath comprises male threads on the outside surface at the proximal end; and
the adjustable knob is a hollow cylinder and comprises female threads on the inside surface of the distal end of the adjustable knob, whereby axial rotation of the adjustable knob with respect to the sheath around the sheath moves the sheath linearly with respect to the surface member to advance or retract the sheath into the adjustable knob, thereby shortening or lengthening the portion of the surface member enclosed by the lumen of the sheath.

29. A clamp device for uniformly compressing a tissue, organ, or portion of the tissue or organ during minimally invasive surgery, comprising:
   a) an elongate surface member that has a proximal end and a distal end;
   b) a biocompatible deformable article that rests on the surface member at the distal end of the surface member, wherein the distal end of the elongate surface member is concave and forms a cradle upon which the biocompatible deformable article rests;
   c) a flexible band that has a proximal end and a distal end, wherein:
      the distal end of the flexible band is connected to the distal end of the surface member;
      the flexible band forms a closed loop with the biocompatible deformable article on the surface member, the closed loop is able to fit a tissue or an organ or a portion thereof during minimally invasive surgery, to thereby uniformly compress the tissue, or organ or portion thereof;
      the proximal end of the flexible band is configured to be adjustably tensioned so that the portion of the flexible band that forms a closed loop with the biocompatible deformable article can be shortened or lengthened, whereby the closed loop clamps the tissue or organ or portion thereof; and
      the biocompatible deformable article conforms to the shape of the tissue or organ or portion thereof; and
   d) a handle connected to the proximal end of the surface member that comprises:
      a case comprising an inside and an outside;
      a first tensioning wheel mounted in the case for access by an operator to adjustably tension the flexible band; and
      the proximal end of the flexible band operably engaged with the first tensioning wheel, whereby movement of the tensioning wheel shortens or lengthens the portion of the flexible band that forms a closed loop with the biocompatible deformable article in the distal end of the elongate surface member;
      wherein the first tensioning wheel is operably connected to a second tensioning wheel so that movement of the first tensioning wheel effects simultaneous movement of the second tensioning wheel in the same direction; and
      the second tensioning wheel is configured to hold the flexible band around its exterior circumference, whereby movement of the first tensioning wheel shortens or lengthens the portion of the flexible band that forms a closed loop with the biocompatible deformable article in the distal end of the elongate surface member.

30. The clamp device of claim 29, wherein:
   the handle further comprises a movable switch mounted on the handle that controls the direction of movement of the first tensioning wheel.

31. A clamp device for uniformly compressing a tissue, organ, or portion of the tissue or organ during minimally invasive surgery, comprising:
   a) an elongate surface member that has a proximal end and a distal end;
   b) a biocompatible deformable article that is an inflatable balloon, and that rests on the surface member at the distal end of the surface member, wherein the distal end of the elongate surface member is concave and forms a cradle upon which the biocompatible deformable article rests;
   c) a flexible band that has a proximal end and a distal end, wherein:
      the distal end of the flexible band is connected to the distal end of the surface member;
      the flexible band forms a closed loop with the inflatable balloon on the surface member, the closed loop is able to fit a tissue or an organ or a portion thereof during minimally invasive surgery, to thereby uniformly compress the tissue, or organ or portion thereof;
      the proximal end of the flexible band is configured to be adjustably tensioned so that the portion of the flexible band that forms a closed loop with the inflatable balloon can be shortened or lengthened, whereby the closed loop clamps the tissue or organ or portion thereof; and
      the inflatable balloon conforms to the shape of the tissue or organ or portion thereof;
   d) a sheath having a lumen comprising a proximal end and a distal end, wherein:
      the lumen of the sheath contains a balloon inflation line having a proximal end and a distal end;
      the inflatable balloon has a proximal end and a distal end;
      the distal end of the sheath is in communication with the proximal end of the inflatable balloon to control inflation of the balloon;
      the lumen of the sheath encloses a portion of the elongate surface member, flexible band and balloon inflation line, the balloon inflation line resting in the cradle of the surface member between the flexible band and surface member;
      the surface member is longer than the sheath, whereby the lumen of the sheath does not enclose the inflatable balloon resting in the cradle at the distal end of the surface member; and
      the sheath is configured to be linearly movable along the surface member to shorten or lengthen the portion of the surface member that is not enclosed by the sheath;
   e) an adjustable knob to control movement of the sheath linearly along the surface member, wherein:
      the adjustable knob is operably connected to the proximal end of the sheath; and
      the adjustable knob is configured on the device so that axial rotation of the adjustable knob with respect to the sheath moves the sheath linearly with respect to the surface member to advance or retract the sheath into the adjustable knob, thereby shortening or lengthening the portion of the surface member enclosed by the lumen of the sheath; and
   f) a handle positioned proximal to the adjustable knob and connected to the proximal end of the surface member, wherein the handle comprises:
      a case comprising an inside and an outside;
      a first tensioning wheel mounted in the case for access by an operator to adjustably tension the flexible band;
      a second tensioning wheel that is operably connected to the first tensioning wheel so that movement of the first tensioning wheel effects simultaneous movement of the second tensioning wheel in the same direction, the second tensioning wheel configured to hold the proximal end of the flexible band around its exterior circumference;

a ratchet that is configured inside the case and capable of being operably connected to the first tensioning wheel, whereby movement of the ratchet engages the first tensioning wheel; and a movable switch mounted on the handle that controls the direction of movement of the first tensioning wheel, the switch is mounted to have a portion outside of the case that is accessible by an operator and a portion inside the case that is operably coupled to the ratchet located in proximity to the inner portion of the switch, whereby movement of the switch moves the ratchet, thereby engaging the first tensioning wheel to shorten or lengthen the portion of the flexible band that forms the closed loop with the balloon in the distal end of the elongate surface member, whereby the size of the closed loop is adjustable for clamping a tissue or organ or portion thereof during minimally invasive surgery.

32. A clamp device for uniformly compressing a tissue, organ, or portion of the tissue or organ during minimally invasive surgery, comprising:
 a) an elongate surface member that has a proximal end and a distal end;
 b) a biocompatible inflatable balloon that rests on the surface member at the distal end of the surface member; and
 c) a flexible band that has a proximal end and a distal end, wherein:

the distal end of the flexible band is connected to the distal end of the surface member;

the flexible band forms a closed loop with the balloon on the surface member, wherein the proximal end of the flexible band is configured to be adjustably tensioned so that the portion of the flexible band that forms a closed loop with the balloon can be shortened or lengthened, whereby the closed loop can uniformly compress and clamp a tissue or an organ or a portion thereof during minimally invasive surgery;

the proximal end of the flexible band is configured to be adjustably tensioned so that the portion of the flexible band that forms a closed loop with the balloon can be shortened or lengthened, whereby the closed loop fits around and uniformly compresses the tissue, organ, or portion thereof during minimally invasive surgery;

when the flexible band is tensioned and the balloon is inflated, the loop clamps around the tissue or organ or portion thereof and the balloon conforms to the shape of the tissue or organ or portion thereof filling any voids where the tissue or organ or portion thereof otherwise would not be contacted with the clamp portion, to thereby clamp and uniformly compress the tissue, or organ, or portion thereof to isolate the tissue, organ or a portion thereof from systemic circulation;

the clamp device is configured to access an endoscopic port for the minimally invasive surgery.

* * * * *